US011376314B2

(12) United States Patent
Faridmoayer et al.

(10) Patent No.: US 11,376,314 B2
(45) Date of Patent: Jul. 5, 2022

(54) IMMUNOGENIC COMPOSITION

(71) Applicant: GLAXOSMITHKLINE BIOLOGICALS SA, Rixensart (BE)

(72) Inventors: Amirreza Faridmoayer, Schlieren (CH); Rainer Follador, Schlieren (CH); Stefan Jochen Kemmler, Schlieren (CH); Michael Thomas Kowarik, Schlieren (CH); Gerald Johann Posch, Schlieren (CH); Fabio Serventi, Schlieren (CH)

(73) Assignee: GlaxoSmithKline Biologicals SA

( * ) Notice: Subject to any disclaimer, the term of this patent is extended or adjusted under 35 U.S.C. 154(b) by 0 days.

(21) Appl. No.: 16/620,921

(22) PCT Filed: Jul. 17, 2018

(86) PCT No.: PCT/EP2018/069355
§ 371 (c)(1),
(2) Date: Dec. 10, 2019

(87) PCT Pub. No.: WO2019/016188
PCT Pub. Date: Jan. 24, 2019

(65) Prior Publication Data
US 2020/0188502 A1 Jun. 18, 2020

(30) Foreign Application Priority Data
Jul. 19, 2017 (GB) .................................. 1711637

(51) Int. Cl.
*A61K 39/09* (2006.01)
*C08B 37/00* (2006.01)
*A61K 39/102* (2006.01)
*A61K 38/00* (2006.01)
*C07K 14/315* (2006.01)
*A61K 35/74* (2015.01)
*A61K 47/36* (2006.01)
*C07K 9/00* (2006.01)
*B01J 20/32* (2006.01)

(52) U.S. Cl.
CPC .......... *A61K 39/092* (2013.01); *A61K 39/102* (2013.01); *C08B 37/006* (2013.01); *A61K 35/74* (2013.01); *A61K 38/00* (2013.01); *A61K 47/36* (2013.01); *B01J 20/32* (2013.01); *C07K 9/005* (2013.01); *C07K 14/315* (2013.01)

(58) Field of Classification Search
None
See application file for complete search history.

(56) References Cited

U.S. PATENT DOCUMENTS

2015/0238588 A1* 8/2015 Kowarik ............... C07K 14/21
424/190.1
2016/0067325 A1* 3/2016 Damotharan ............ C12N 9/96
424/197.11

FOREIGN PATENT DOCUMENTS

| WO | 2015/121783 A1 | 8/2015 | |
|---|---|---|---|
| WO | 2016/020499 A2 | 2/2016 | |
| WO | WO-2016020499 A2 * | 2/2016 | ........... A61K 47/646 |
| WO | WO-2017173415 A2 * | 10/2017 | .............. A61P 37/04 |

OTHER PUBLICATIONS

Ravenscroft, N., Omar, A., Hlozek, J., Edmonds-Smith, C., Follador, R., Serventi, F., . . . & Faridmoayer, A. (2017). Genetic and structural elucidation of capsular polysaccharides from *Streptococcus pneumoniae* serotype 23A and 23B, and comparison to serotype 23F. Carbohydrate research, 450, 19-29. (Year: 2017).*
Statens Serum Institut: "Diagnostic Products Catalogue 2016 2 Table of Contents" diagnostic product catalogue 2016; 2016; retrieved from the Internet: URL:https:www.medica.de/vis-content/event-medcom2016.MEDICA/exh-medcom2016.2487572/MEDICA-2016-SSI-Diagnostica-Paper-medcom2016.2487572-XLPH7wV2RwuIDbTYynVtZA.pdf [retrieved on Oct. 8, 2018; Product No. 76969, purified polysaccharide type 23A; p. 10.
Ravenscroft, et al., "Genetic and structural elucidation of capsular polysaccharides from *Streptococcus pneumoniae* serotype 23A and 23B, and comparison to serotype 23F" Carbohydrate Research; 2017; pp. 19-29; vol. 450.
Park, et al., "L-Rhamnose Is Often an Important Part of Immunodominant Epitope for Pneumococcal Serotype 23F Polysaccharide Antibodies in Human Sera Immunized with PPV23" PLOS One; 2013; pp. e83810; vol. 8(12).
Bentley et al., "Genetic analysis of the capsular biosynthetic locus from all 90 pneumococcal serotypes" PLOS Genetics, Public Library of Science; 2006; pp. e31-e0262; vol. 2(3).

* cited by examiner

*Primary Examiner* — Dale R Miller
(74) *Attorney, Agent, or Firm* — Dana L. Broughton

(57) ABSTRACT

The disclosure provides synthetic (e.g. recombinant) pneumococcal saccharides comprising one or more repeat unit(s) →4)-β-D-Glcp-(1→4)-[Gro-(2→P→3)]-β-D-Galp-(1→4)-β-L-Rhap-(1→. Also provided are conjugates comprising a →4)-β-D-Glcp-(1→4)-[Gro-(2→P→3)]-β-D-Galp-(1→4)-β-L-Rhap-(1→, immunogenic compositions, vaccines and their use in preventing or treating infection by *Streptococcus pneumoniae*.

16 Claims, 15 Drawing Sheets
Specification includes a Sequence Listing.

IMMUNOGENIC COMPOSITION

CROSS-REFERENCE TO RELATED APPLICATIONS

This application is filed pursuant to 35 U.S.C. § 371 as a United States National Phase Application of International Application No. PCT/EP2018/069355 filed Jul. 17, 2018 which claims priority from GB 1711637.7 filed Jul. 19, 2017.

TECHNICAL FIELD

The present invention relates to the field of immunogenic compositions and vaccines, their manufacture and the use of such compositions in medicine. More particularly, it relates to a saccharide from *Streptococcus pneumoniae* comprising one or more repeat units having the structure →4)-β-D-Glcp-(1→4)-[Gro-(2→P→3)]-β-D-Galp-(1→4)-β-L-Rhap-(1→. The pneumococcal saccharide can be synthesized (e.g. recombinantly) and used either on its own or as conjugate, coupled to a carrier protein, for use in an immunogenic composition or vaccine.

BACKGROUND

*Streptococcus pneumoniae* is a globally important encapsulated human pathogen [van Tonder, A. J.; Bray, J. E.; Quirk, S. J.; Haraldsson, G.; Jolley, K. A.; Maiden, M. C.; Hoffmann, S.; Bentley, S. D.; Haraldsson, Á.; Erlendsdóttir, H.; Kristinsson, K. G. Microb. Genom. 2016, 2(10).]. *Streptococcus pneumoniae* (*S. pneumoniae*, pneumococcus) is a Gram-positive bacterium responsible for considerable morbidity and mortality (particularly in infants and the elderly), causing invasive diseases such as bacteraemia and meningitis, pneumonia and other non-invasive diseases, such as acute otitis media. About 800,000 children die annually due to pneumococcal disease, especially in emerging countries (O-Brien et al. 2009 Lancet 374:893-902). The increasing number of antibiotic-resistant strains (Linares et al. 2010 Cin. Microbiol. Infect. 16:402-410) and the severity of pneumococcal diseases make vaccination the most effective intervention. The major clinical syndromes caused by *S. pneumoniae* are widely recognized and discussed in standard medical textbooks (Fedson D S, Muscher D M. In: Plotkin S A, Orenstein W A, editors. Vaccines. 4th edition. Philadelphia WB Saunders Co, 2004a: 529-588). For instance, Invasive Pneumococcal Disease (IPD) is defined as any infection in which *S. pneumoniae* is isolated from the blood or another normally sterile site (Musher D M. *Streptococcus pneumoniae*. In Mandell G L, Bennett J E, Dolin R (eds). Principles and Practice of Infectious diseases (5th ed.). New York, Churchill Livingstone, 2001, p 2128-2147).

*S. pneumoniae* is encapsulated with a covalently linked polysaccharide which confers serotype specificity. There are more than 90 known serotypes of pneumococci, and the capsule is the principle virulence determinant for pneumococci, as the capsule not only protects the inner surface of the bacteria from complement, but is itself poorly immunogenic. Certain serotypes are more abundant than others, to be associated with clinically apparent infections, to cause severe invasive infections and to acquire resistance to one or more classes of antibacterial agents (Rueda, A. M. M. MSc; Serpa, José A. MD; Matloobi, Mahsa M D; Mushtaq, Mahwish M D; Musher, Daniel M. MD. 2010. The spectrum of invasive pneumococcal disease at an adult tertiary care hospital in the early 21st century. Medicine (Baltimore) 89:331-336). According to previous analyses approximately 10 or 11 serotypes account for over 70% of invasive pediatric infections in all regions of the world (Hausdorff W P, Bryant J, Paradiso P R, Siber G R: Which pneumococcal serogroups cause the most invasive disease: implications for conjugate vaccine formulation and use, part I. Clinical infectious diseases: an official publication of the *Infectious Diseases Society of America* 2000, 30(1):100-121). The distribution of serotypes causing disease varies by age, disease syndrome, disease severity, geographic region, and over time. Pneumococci that are resistant to penicillin, erythromycin, co-trimoxazole or multiple drugs are common in many regions (Evolving trends in *Streptococcus pneumoniae* resistance: implications for therapy of community-acquired bacterial pneumonia. Jones R N, Jacobs M R, Sader H S. *Int J Antimicrob Agents*. 2010 September; 36(3):197-204).

Bacterial polysaccharides may elicit a long-lasting immune response in humans if they are coupled to a protein carrier that contains T-cell epitopes. This concept was elaborated almost 100 years ago (Avery, O. T. and W. F. Goebel, 1929, *J. Exp. Med.* 50:521-533), and proven later for the polysaccharide of *Haemophilus influenzae* type B (HIB) coupled to the protein carrier diphtheria toxin (Anderson, P. 1983, *Infect Immun* 39:233-8; Schneerson, R. O. Barrera, A. Sutton, and J. B. Robbins. 1980, *J Exp Med* 152:361-76). This glycoconjugate was also the first conjugated vaccine to be licensed in the USA in 1987 and introduced into the US infant immunization schedule shortly thereafter. Besides HIB, conjugated vaccines have been successfully developed against the encapsulated human pathogens *Neisseria meningitidis* and *S. pneumoniae*. After initial licensure of a 7-valent conjugate vaccine containing serotypes 4, 6B, 9V, 14, 18C, 19F, 23F (PCV7), two pneumococcal conjugate vaccines (PCVs) designed to broaden coverage have been licensed. The 10-valent pneumococcal *Haemophilus influenzae* protein D conjugate vaccine (PCV10) contains serotypes 1, 4, 5, 6B, 7F, 9V, 14 and 23F conjugated to nontypeable *H. influenzae* protein D, plus serotype 18C conjugated to tetanus toxoid and serotype 19F conjugated to diphtheria toxoid. The 13-valent pneumococcal conjugate vaccine (PCV13) contains the PCV7 (4, 6B, 9V, 14, 18C, 19F, 23F) serotypes plus serotypes 1, 3, 5, 6A, 7F and 19A, conjugated to cross-reactive material CRM197 (a genetically detoxified form of diphtheria toxin).

T-independent antigens, for example saccharides, are antigens that elicit antibody production via B lymphocytes without involvement of T-cells. Conjugation of T-independent antigens to carrier proteins has long been established as a way of enabling T-cell help to become part of the immune response for a normally T-independent antigen. In this way, an immune response can be enhanced by allowing the development of immune memory and boostability of the response. Successful conjugate vaccines which have been developed by conjugating bacterial capsular saccharides to carrier proteins are known in the art; the carrier protein having the known effect of turning the T-independent saccharide antigen into a T-dependent antigen capable of triggering an immune memory response. Several carrier proteins are known in the art with tetanus toxoid, diphtheria toxoid, CRM197 and protein D from *Haemophilus influenzae* being used as carrier protein in commercialised vaccines. CRM197 is currently used in the *Streptococcus pneumoniae* capsular polysaccharide conjugate vaccine PREVENAR (Pfizer) and protein D, tetanus toxoid and diphtheria toxoid are currently used as carriers for capsular polysaccharides in the *Streptococcus pneumoniae* capsular polysaccharide conjugate vaccine SYNFLORIX (GlaxoSmithKline). Other carrier proteins known in the art include EPA (exotoxin A of *P. aeruginosa*) (Wacker et al. J Infect. Dis, 2014 May 15: 209(10):1551-1561) and Outer Membrane Protein (OMP) (Wu et al. Infect. Imun. 1999 October 67(1): 5508-5513). In an embodiment, the carrier protein is detoxified Exotoxin A from *Pseudomonas aeruginosa*.

While development of vaccines against such infection is ongoing, there remains a major need for effective vaccines against *Streptococcus pneumoniae* infection that can safely be produced in high quantities.

Despite extensive genetic and serological studies, the polysaccharide structures of several serotypes have yet to be determined. Serogroup 23 consists of serotypes 23F, 23A and 23 B for which only the structure of polysaccharide 23F has been published [Richards, J. C.; Perry, M. B. *Biochem. Cell Biol.* 1988, 66(7), 758-771.]. Furthermore, only polysaccharide 23F has been included in commercially available vaccines to date. The capsule biosynthetic genes and repeat units for all 90 serotypes are described in Bentley et al. (2006) [Bentley, S. D.; Aanensen, D. M.; Mavroidi, A.; Saunders, D.; Rabbinowitsch, E.; Collins, M.; Donohoe, K.; Harris, D.; Murphy, L.; Quail, M. A.; Samuel, G. *PLoS Genet.* 2006, 2(3), e31] together with the repeat unit structure for 23F, but not 23A or 23B. Based on the epidemiology at the time, serotype 23F was chosen for inclusion in the 23-valent polysaccharide vaccine (PPV23) [Robbins, J. B.; Austrian. R.; Lee, C. J.; Rastogi, S. C.; Schiffman, G.; Henrichsen, J.; Mäkelä, P. H.; Broome, C. V.; Facklam, R. R; Tiesjema, R. H.; Parke, J. C. *J. Infect. Dis.* 1983, 148(6), 1136-1159] and 23F is currently present in all licensed conjugate vaccines. Epitope specificity studies on synthetic conjugates and killed *S. pneumoniae* 23F in animals showed that the terminal α-Rha is immunodominant [De Velasco, E. A.; Verheul, A. F.; Van Steijn, A. M.; Dekker, H. A.; Feldman, R. G.; Fernandez, I. M.; Kamerling, J. P.; Vliegenthart, J. F.; Verhoef, J.; Snippe, H. *Infect. Immun.* 1994, 62(3), 799-808]; this has also been observed in human sera from subjects immunized with PPV23 [Park, S.; Nahm, M. H. *PLoS One.* 2013, 8(12), e83810]. Early studies showed that typing antiserum prepared in rabbits with type 23F bacteria reacts only slightly with serotype 23A and hardly at all with serotype 23B [Robbins, J. B.; Austrian. R.; Lee, C. J.; Rastogi, S. C.; Schiffman, G.; Henrichsen, J.; Mäkelä, P. H.; Broome, C. V.; Facklam, R. R; Tiesjema, R. H.; Parke, J. C. *J. Infect. Dis.* 1983, 148(6), 1136-1159.] and therefore crossprotection from the 23F polysaccharide and conjugate vaccines is not expected. It is therefore unsurprising that serotype 23A and 23B have been identified as emerging pathogens due to a combination of serotype replacement and antimicrobial resistance.

The genes required for pneumococcal capsular polysaccharide (CPS) synthesis are generally encoded on the cps locus [Bentley, S. D.; Aanensen, D. M.; Mavroidi, A.; Saunders, D.; Rabbinowitsch, E.; Collins, M.; Donohoe, K.; Harris, D.; Murphy, L.; Quail, M. A.; Samuel, G. *PLoS Genet.* 2006, 2(3), e31]. The locus contains three types of enzymes: those responsible for (i) biosynthesis of nucleotide-activated sugars, (ii) polysaccharide repeat-unit synthesis and (iii) assembly of the repeat units and transport across the membrane. In 23F, WchA initiates the repeat-unit synthesis by catalysing the production of an undecaprenyl pyrophosphate-linked D-Glucose (UndPP)-D-Glucose. In successive steps, WchF adds a L-rhamnose to the UndPP-Glucose, followed by WchV linking a D-galactose. This D-galactose is extended by WchW and WchX adding a L-rhamnose and a glycerol-2-phosphate, respectively. Wzx flips a single repeat unit into the periplasm, where the Wzy polymerase links the D-glucose at reducing end of the growing chain to the position 4 of the single repeat units' D-galactose, resulting in the mature polysaccharide [Morona, J. K.; Miller, D. C.; Coffey, T. J.; Vindurampulle, C. J.; Spratt, B. G.; Morona, R.; Paton, J. C. *Microbiology.* 1999, 145(4), 781-789]. Wzg, Wzh, Wzd, and Wze are involved in the modulation of capsule synthesis [Yother, *J. Annu. Rev. Microbiol.* 2011, 65, 563-581]. Biosynthesis of dTDP-L-rhamnose is achieved via the RmlACBD genes, while CDP-2-glycerol biosynthesis requires Gtp123 [Wang, Q.; Xu, Y.; Perepelov, A. V.; Xiong, W.; Wei, D.; Shashkov, A. S.; Knirel, Y. A.; Feng, L.; Wang, L. *J. Bacteriol.* 2010, 192(20), 5506-5514]. The serogroup 23 cps loci sequences share the same 18 genes with a varying degree of similarity.

The published structure for the 23F polysaccharide was elucidated by use of chemical and spectroscopic analysis performed on the native and de-phosphorylated polysaccharide and fragments generated by partial hydrolysis and periodate treatment [Richards, J. C.; Perry, M. B. *Biochem. Cell Biol.* 1988, 66(7), 758-771.]. $^1$H NMR assignments were presented for the native and de-phosphorylated polysaccharide, however, the $^{13}$C NMR spectrum was not assigned. As described in the present patent application, detailed $^1$D and $^2$D $^1$H, $^{13}$C and $^{31}$P NMR experiments on the 23F polysaccharide were performed in order to make full NMR assignments that were used to facilitate the structural elucidation of the structurally related serotype 23B polysaccharide.

SUMMARY OF THE INVENTION

Serogroup 23 consists of serotypes 23F, 23A and 23 The structure of the pneumococcal capsular polysaccharide serotype 23B was determined using genetic analysis, composition analysis and NMR spectroscopy of polysaccharide 23B. The structure was compared to the serologically and genetically related serotype 23F for which full NMR assignments have been made.

The published structure of the serotype 23F capsular polysaccharide is:

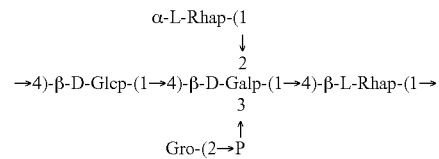

The structure of the serotype 23B capsular polysaccharide of the present invention is:

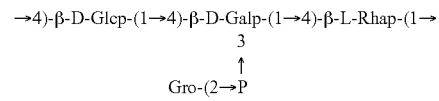

The rhamnosyltransferase WchW, which in 23F and 23A is responsible for the addition of the terminal α-Rha, is present in the 23B cps biosynthesis locus, but apparently inactive. The immunodominant terminal α-Rha of 23F is more sterically crowded in 23A compared to 23F and absent in 23B, which may explain the reported typing cross reactions for serotype 23F: slight with 23A and none with 23B.

Determination of the 23B pneumococcal saccharide structure enables the verification of synthetically (e.g. recombinantly)-produced saccharide and allows the design of a glycoengineering strategy which might be needed for bioconjugation. The present invention is directed to synthetic (e.g. recombinant) pneumococcal saccharide comprising one or more repeat unit(s) of the 23B pneumococcal saccharide.

Thus, the present invention provides a synthetic (e.g. recombinant) pneumococcal saccharide comprising one or more repeat unit(s) →4)-β-D-Glcp-(1→4)-[Gro-(2→P→3)]-β-D-Galp-(1→4)-β-L-Rhap-(1→.

According to a further aspect of the invention, there is provided a bioconjugate comprising a recombinant pneumococcal saccharide of the present invention conjugated to a carrier protein.

According to a further aspect of the invention, there is provided a host cell comprising:
  (i) one or more nucleic acids that encode glycosyltransferase(s) sufficient for synthesis of the repeat unit →4)-β-D-Glcp-(1→4)-[Gro-(2→P→3)]-β-D-Galp-(1→4)-β-L-Rhap-(1→;
  (ii) nucleic acid that encodes an oligosaccharyl transferase; and optionally
  (iii) nucleic acid that encodes a carrier protein comprising an N-glycosylation consensus sequence (e.g. detoxified exotoxin A from *P. aeruginosa*, CRM197, Diphtheria toxoid, tetanus toxoid, detoxified hemolysin A of *S. aureus*, clumping factor A, clumping factor B, *E. coli* FimH, *E. coli* FimHC, *E. coli* heat labile enterotoxin, detoxified variants of *E. coli* heat labile enterotoxin, Cholera toxin B subunit (CTB), cholera toxin, detoxified variants of cholera toxin, *E. coli* sat protein, the passenger domain of *E. coli* sat protein, *C. jejuni* AcrA, *C. jejuni* natural glycoproteins, *S. pneumoniae* pneumolysin, *S. pneumoniae* NOX, *S. pneumoniae* PspA, *S. pneumoniae* PcpA, *S. pneumoniae* PhtD, *S. pneumoniae* PhtE, *S. pneumoniae* ply (e.g. detoxified ply), or *S. pneumoniae* LytB); and optionally
  (iv) nucleic acid that encodes a polymerase (e.g. wzy).

According to a further aspect of the invention, there is provided a process of producing a bioconjugate that comprises a recombinant pneumococcal saccharide linked to a carrier protein, said process comprising (i) culturing the host cell of the present invention under conditions suitable for the production of glycoproteins and (ii) isolating the bioconjugate. There is further provided a bioconjugate produced by this process.

According to a further aspect of the invention, there is provided an immunogenic composition comprising a pneumococcal saccharide comprising one or more repeat unit(s) →4)-β-D-Glcp-(1→4)-[Gro-(2→P→3-β-D-Galp-(1→4)]-β-L-Rhap-(1→. There is also provided an immunogenic composition comprising a pneumococcal saccharide of the present invention, or a bioconjugate of the present invention. There is also provided an immunogenic composition comprising a pneumococcal saccharide comprising one or more repeat unit(s) →4)-β-D-Glcp-(1→4)-[Gro-(2→P→3-β-D-Galp-(1→4)]-β-L-Rhap-(1→ conjugated to a carrier protein (e.g. selected from detoxified exotoxin A from *P. aeruginosa* (EPA), TT, DT, CRM197, PhtD, detoxified pneumolysin and protein D, suitably exotoxin A from *P. aeruginosa* (EPA)).

According to a further aspect of the invention, there is provided a process of making the immunogenic composition of the present invention, which process comprises the step of mixing the pneumococcal saccharide or the bioconjugate with a pharmaceutically acceptable carrier, diluent or adjuvant.

According to a further aspect of the invention, there is provided a vaccine comprising an immunogenic composition of the present invention.

According to a further aspect of the invention, there is provided a kit comprising a pneumococcal saccharide of the present invention, a bioconjugate of the present invention, or an immunogenic composition of the present invention or a vaccine of the present invention and instructions for the use thereof.

According to a further aspect of the invention, there is provided a pneumococcal saccharide of the present invention, a bioconjugate of the present invention, an immunogenic composition of the present invention or a vaccine of the present invention, for use in the treatment or prevention of a disease caused by *Streptococcus pneumoniae* infection, e.g. pneumonia, invasive pneumococcal disease (IPD), exacerbations of chronic obstructive pulmonary disease (COPD), otitis media, meningitis, bacteraemia, pneumonia and/or conjunctivitis.

According to a further aspect of the invention, there is provided an pneumococcal saccharide of the present invention, a bioconjugate of the present invention, an immunogenic composition of the present invention, or a vaccine of the present invention for use in immunizing against infection by *Streptococcus pneumoniae*.

According to a further aspect of the invention, there is provided a pneumococcal saccharide of the present invention, a bioconjugate of the present invention, an immunogenic composition of the present invention, or a vaccine of the present invention, for inducing an immune response against *Streptococcus pneumoniae*.

According to a further aspect of the invention, there is provided the use of a pneumococcal saccharide of the present invention, a bioconjugate of the present invention, an immunogenic composition of the present invention, or a vaccine of the present invention in the manufacture of a medicament for the treatment or prevention of a disease caused by *Streptococcus pneumoniae* infection, e.g. pneumonia, invasive pneumococcal disease (IPD), exacerbations of chronic obstructive pulmonary disease (COPD), otitis media, meningitis, bacteraemia, pneumonia and/or conjunctivitis.

According to a further aspect of the invention, there is provided the use of a pneumococcal saccharide of the present invention, a bioconjugate of the present invention, an immunogenic composition of the present invention, or a vaccine of the present invention in the manufacture of a medicament for immunizing against infection by *Streptococcus pneumoniae*.

DETAILED DESCRIPTION

Terminology

Figure 1:
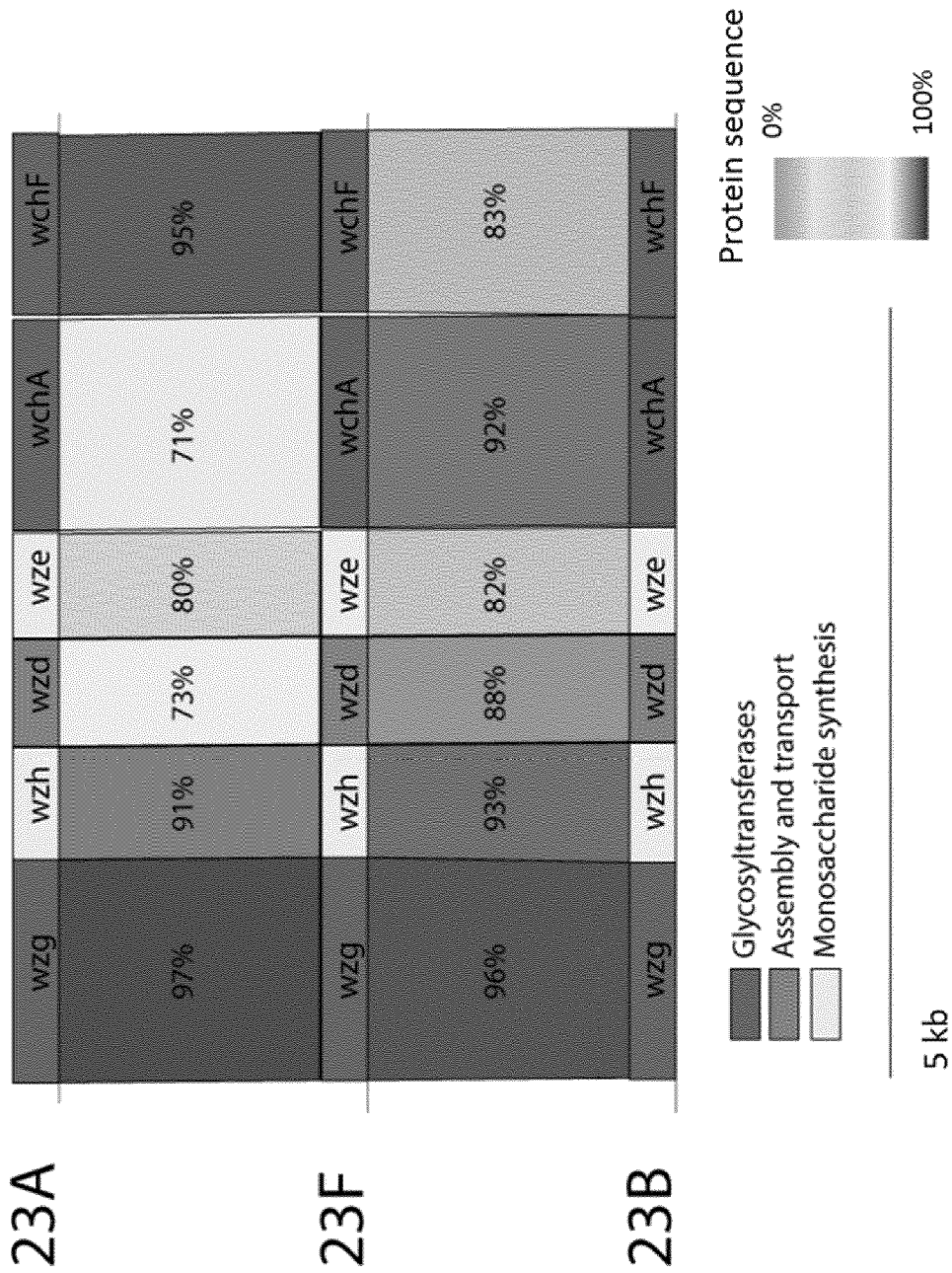
FIG. 1: Comparison of serogroup 23 cps loci. The results of a pairwise BLASTp protein sequence comparison are shown.

Carrier protein: a protein covalently attached to an antigen (e.g. saccharide antigen) to create a conjugate (e.g. bioconjugate). A carrier protein activates T-cell mediated immunity in relation to the antigen to which it is conjugated.

Any amino acid apart from proline (pro, P): refers to an amino acid selected from the group consisting of alanine (ala, A), arginine (arg, R), asparagine (asn, N), aspartic acid (asp, D), cysteine (cys, C), glutamine (gln, Q), glutamic acid (glu, E), glycine (gly, G), histidine (his, H), isoleucine (ile, I), leucine (leu, L), lysine (lys, K), methionine (met, M), phenylalanine (phe, F), serine (ser, S), threonine (thr, T), tryptophan (trp, W), tyrosine (tyr, Y), valine (val, V).

PLY or ply: Pneumolysin from *S. pneumoniae*
CP: Capsular polysaccharide
LPS: lipopolysaccharide.
wzy: the polysaccharide polymerase gene encoding an enzyme which catalyzes polysaccharide polymerization. The encoded enzyme transfers the reducing end of the elongating polysaccharide chain onto a single repeat unit forming a glycosidic linkage.
waaL: the O antigen ligase gene encoding a membrane bound enzyme. The encoded enzyme transfers undecaprenyl-pyrophosphate (UndPP)-bound O antigen to the lipid A core oligosaccharide, forming a lipopolysaccharide.
Und-PP: undecaprenyl pyrophosphate.
Und-P: undecaprenyl phosphate
Reducing end: the reducing end of an oligosaccharide or polysaccharide is the monosaccharide with a free anomeric carbon that is not involved in a glycosidic bond and is thus capable of converting to the open-chain form.

As used herein, the term "bioconjugate" refers to conjugate between a protein (e.g. a carrier protein) and an antigen (e.g. a saccharide) prepared in a host cell background, wherein host cell machinery links the antigen to the protein (e.g. N-links).

As used herein, the term "conjugation" is the coupling of carrier protein to saccharide.

As used herein, the term "effective amount," in the context of administering a therapy (e.g. an immunogenic composition or vaccine of the invention) to a subject refers to the amount of a therapy which has a prophylactic and/or therapeutic effect(s). In certain embodiments, an "effective amount" refers to the amount of a therapy which is sufficient to achieve one, two, three, four, or more of the following effects: (i) reduce or ameliorate the severity of a bacterial infection or symptom associated therewith; (ii) reduce the duration of a bacterial infection or symptom associated therewith; (iii) prevent the progression of a bacterial infection or symptom associated therewith; (iv) cause regression of a bacterial infection or symptom associated therewith; (v) prevent the development or onset of a bacterial infection, or symptom associated therewith; (vi) prevent the recurrence of a bacterial infection or symptom associated therewith; (vii) reduce organ failure associated with a bacterial infection; (viii) reduce hospitalization of a subject having a bacterial infection; (ix) reduce hospitalization length of a subject having a bacterial infection; (x) increase the survival of a subject with a bacterial infection; (xi) eliminate a bacterial infection in a subject; (xii) inhibit or reduce a bacterial replication in a subject; and/or (xiii) enhance or improve the prophylactic or therapeutic effect(s) of another therapy.

As used herein, the term "subject" refers to an animal, in particular a mammal such as a primate (e.g. human).

As used herein, the term "hexose monosaccharide derivative" refers to a derivative of a hexose monosaccharide that can be a substrate for oligosaccharyl transferase activity. In general, hexose monosaccharide derivatives comprise a monosaccharide comprising an acetamido group at position 2. Exemplary hexose monosaccharide derivatives include GlcNAc, HexNAc, deoxy HexNAc, or 2,4-diacetamido-2,4,6-trideoxyhexose.

As used herein, the term "hybrid oligosaccharide or polysaccharide" refers to an engineered oligosaccharide or polysaccharide that does not comprise a hexose at the reducing end of the first repeat unit, but instead comprises a hexose monosaccharide derivative at the reducing end of the first repeat unit.

As used herein, the term "immunogenic fragment" is a portion of an antigen smaller than the whole, that is capable of eliciting a humoral and/or cellular immune response in a host animal, e.g. human, specific for that fragment. Fragments of a protein can be produced using techniques known in the art, e.g. recombinantly, by proteolytic digestion, or by chemical synthesis. Internal or terminal fragments of a polypeptide can be generated by removing one or more nucleotides from one end (for a terminal fragment) or both ends (for an internal fragment) of a nucleic acid which encodes the polypeptide. Typically, fragments comprise at least 10, 20, 30, 40 or 50 contiguous amino acids of the full length sequence. Fragments may be readily modified by adding or removing 1, 2, 3, 4, 5, 6, 7, 8, 9, 10, 20, 30, 40 or 50 amino acids from either or both of the N and C termini.

As used herein, the term "conservative amino acid substitution" involves substitution of a native amino acid residue with a non-native residue such that there is little or no effect on the size, polarity, charge, hydrophobicity, or hydrophilicity of the amino acid residue at that position, and without resulting in decreased immunogenicity. For example, these may be substitutions within the following groups: valine, glycine; glycine, alanine; valine, isoleucine, leucine; aspartic acid, glutamic acid; asparagine, glutamine; serine, threonine; lysine, arginine; and phenylalanine, tyrosine. Conservative amino acid modifications to the sequence of a polypeptide (and the corresponding modifications to the encoding nucleotides) may produce polypeptides having functional and chemical characteristics similar to those of a parental polypeptide.

As used herein, the term "deletion" is the removal of one or more amino acid residues from the protein sequence. Typically, no more than about from 1 to 6 residues (e.g. 1 to 4 residues) are deleted at any one site within the protein molecule.

As used herein, the term "insertion" is the addition of one or more non-native amino acid residues in the protein sequence. Typically, no more than about from 1 to 10 residues, (e.g. 1 to 7 residues, 1 to 6 residues, or 1 to 4 residues) are inserted at any one site within the protein molecule.

As used herein, the term "isolated" refers to pneumococcal capsular saccharides substantially free of bacterial cell material or extraction solvent when produced from growing bacterial strains of *Streptococcus pneumoniae*.

As used herein, the term "purified" or "substantially pure" refers to a preparation is at least about 75% pure, preferably at least about 80% pure, and more preferably more than about 80%, 90%, 95% or 99% pure.

As used herein, the term "synthetic" refers to saccharides produced synthetically to have the same or similar structure and/or composition of the *Streptococcus pneumoniae* saccharides disclosed herein, that are not produced in the native host cell (i.e., *S. pneumoniae*). The term "synthetic" includes for example, saccharides produced from techniques such as recombinant DNA technology (i.e., recombinant) and/or chemical synthesis.

As used herein, the term "recombinant" means produced using recombinant DNA technology. In general, the term "recombinant saccharide" refers to a poly- or oligosaccharide produced in a host cell that does not naturally comprise the nucleic acid encoding the glycosyltransferases for producing said poly- or oligosaccharide (i.e., in a host cell other the *Streptococcus pneumoniae*). In the context of the present invention, this term refers to a pnemococcal saccharide produced recombinantly in a prokaryotic host cell, for example, *Escherichia* spp., *Campylobacter* spp., *Salmonella* spp., *Shigella* spp., *Helicobacter* spp., *Pseudomonas* spp., *Bacillus* spp., and in further embodiments *Escherichia coli*, *Campylobacter jejuni*, *Salmonella typhimurium* etc., wherein the nucleic acid encoding the glycosyltransferases to produce said pneumococcal saccharide has been introduced into said host cell.

As used herein the "size" of, for example, a conjugate or pneumococcal saccharide means the Molecular weight (Mw) of the conjugate or pneumococcal saccharide, respectively. The Mw may be provided in kilodaltons (kDa). As used herein "in the range" and "between" are inclusive of the range's upper and lower limits (for example, "in the range 30-300 kDa" includes 30 kDa and 300 kDa).

Pneumococcal Saccharide

The present invention provides a synthetic (e.g. recombinant) pneumococcal saccharide comprising one or more repeat unit(s) →4)-β-D-Glcp-(1→4)-[Gro-(2→P→3)]-β-D-Galp-(1→4)-β-L-Rhap-(1→.

The present invention also provides a synthetic (e.g. recombinant) pneumococcal saccharide comprising one or more repeat unit(s):

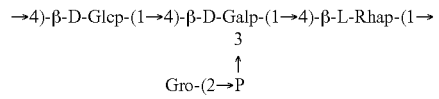

A synthetic (e.g. recombinant) pneumococcal saccharide of the invention may differ from a wild-type (WT) pneumococcal saccharide, e.g. having one or more of the following features: (a) a different number of repeat units (for example, the synthetic (e.g. recombinant pneumococcal saccharide may have fewer repeat units that a WT pneumococcal saccharide), (b) comprising one of more repeat units having a different saccharide structure (for example, the synthetic (e.g. recombinant) pneumococcal saccharide may have a hexose monosaccharide derivative at the reducing end of one or more of the repeat units).

In an embodiment, the pneumococcal saccharide of the present invention, comprises less than 500 repeat units, for example 1 to 200 repeat units (suitably 2 to 200, 1 to 100, 2 to 100, 2 to 50, 2 to 30, 2 to 20 repeat units).

The size (Mw) of the pneumococcal saccharide of the invention is less than 500 kDa, for example in the range 1-500 kDa, 10-450-kDa, 30-400 kDa. In an embodiment, the present invention provides pneumococcal saccharide(s) wherein the size (Mw) of the pneumococcal saccharide is less than 300 kDa, or less than 200 kDa, for example between 1-150 kDa (e.g. between 20-150 kDa).

In an embodiment, the pneumococcal saccharide of the present invention is a hybrid oligosaccharide or polysaccharide having a structure:

(B)$_n$-A→ wherein A is an oligosaccharide containing at least 2, 3, 4, 5, 6, 7 or 8 monosaccharides (e.g. 2 to 10, 2 to 8, 3 to 6, 4 to 5 monosaccharides), with a hexose monosaccharide derivative at the reducing end (indicated by the arrow in the diagram), e.g. wherein the hexose monosaccharide derivative is N-acetylglucosamine (GlcNAc), N-acetylgalactoseamine (GalNAc), 2,4-Diacetamido-2,4,6-trideoxyhexose (DATDH). N-acetylfucoseamine (FucNAc), or N-acetylquinovosamine (QuiNAc) (e.g. N-acetylglucosamine (GlcNAc));

wherein B is an oligosaccharide repeat unit →4)-β-D-Glcp-(1→4)-[Gro-(2→P→3)]-β-D-Galp-(1→4)-β-L-Rhap-(1→; and wherein n is at least 2, 3, 4, 5, 6, 7, 8, 9, 10, 11, 12, 13, 14, 15, 16, 17, 18, 19, or at least 20 (e.g. n is 1 to 100, 2 to 100, 10 to 100, 20 to 100, or 25 to 100).

In an embodiment, A is an oligosaccharide containing no more than 20, 15, 12, 10, 9, 8, 7, 6, or 5 monosaccharides. In an embodiment n is no more than 500, 400, 300, 200, 100, 90, 80, 70, 60, 50, 40, 30, 20, 10 or 5. For example, n may be 1 to 100, 2 to 100, 10 to 100, 20 to 100, or 25 to 100.

In an embodiment, A is an oligosaccharide containing at least 3 monosaccharides. In an embodiment, A is an oligosaccharide containing at least 3 monosaccharides and n is at least 5. In an embodiment, A is an oligosaccharide containing at least 3 monosaccharides and n is at least 20.

In an embodiment, A is an oligosaccharide containing 4 monosaccharides. In an embodiment, A is an oligosaccharide containing 4 monosaccharides and n is at least 5. In an embodiment, A is an oligosaccharide containing 4 monosaccharides and n is at least 20.

In an embodiment, A is an oligosaccharide containing 2-8 monosaccharides. In an embodiment, A is an oligosaccharide containing 2-8 monosaccharides and n is at least 5 and no more than 500. In an embodiment, A is an oligosaccharide containing 2-8 monosaccharides and n is at least 20 and no more than 100.

In an embodiment, A is an oligosaccharide containing 2-10 monosaccharides. In an embodiment, A is an oligosaccharide containing 2-10 monosaccharides and n is at least 5 and no more than 500. In an embodiment, A is an oligosaccharide containing 2-10 monosaccharides and and n is at least 20 and no more than 100.

In an embodiment, A is an oligosaccharide identical to the repeat unit B with the exception that A comprises a hexose monosaccharide derivative at the reducing end of the oligosaccharide in place of the hexose monosaccharide at the reducing end of B (e.g. A is →4)-β-D-GlcNAcp-(1→4)-[Gro-(2→P→3)]-β-D-Galp-(1→4)-β-L-Rhap-(1→.

In an embodiment, A is an oligosaccharide comprising →4)-β-D-Glcp-(1→4)-[Gro-(2→P→3)]-β-D-Galp-(1→4)-β-L-Rhap-(1→ and in addition a hexose monosaccharide derivative at the reducing end of the oligosaccharide (e.g. GlcNAc).

In an embodiment, the hexose monosaccharide derivative is any monosaccharide in which C-2 position is modified with an acetamido group. In one aspect, the hexose monosaccharide is selected from the group consisting of glucose, galactose, rhamnose, arabinotol, fucose and mannose (e.g. galactose). Suitable hexose monosaccharide derivatives include N-acetylglucosamine (GlcNAc), N-acetylgalactoseamine (GalNAc), HexNAc, deoxy HexNAc, 2,4-Diacetamido-2,4,6-trideoxyhexose (DATDH), N-acetylfucoseamine (FucNAc), or N-acetylquinovosamine (QuiNAc). A suitable hexose monosaccharide derivative is N-acetylglucosamine (GlcNAc).

Chemical synthesis of the repeat unit →4)-β-D-Glcp-(1→4)-[Gro-(2→P→3)]-β-D-Galp-(1→4)-β-L-Rhap-(1→ can be performed using synthetic protocols known to the man skilled in the art. For example see the methods for chemical synthesis of pneumococcal polysaccharides disclosed in WO15/004041, WO16/04640, WO16/091399, WO16/198170.

In an embodiment, pneumococcal saccharides of the invention are purified by extracting the pneumococcal saccharides from the bacterial cells by mild acid treatment (e.g. 0.1% to 5%, suitably 2% acetic acid) under conditions to cleave the polysaccharides from the cell surface material, and purifying the extracted cell surface polysaccharides by centrifugation, size exclusion chromatography and/or anion exchange chromatography.

The present invention also provides a method of identifying a *Streptococcus pneumoniae* bacterium designated *S. pneumoniae* 23B comprising elucidating the chemical structure of the capsular polysaccharide characterized as having the repeat unit →4)-β-D-Glcp-(1→4)-[Gro-(2→P→3)]-β-D-Galp-(1→4)-β-L-Rhap-(1→, e.g. using NMR.

Conjugates

The present invention provides a pneumococcal saccharide comprising one or more repeat unit(s) →4)-β-D-Glcp-(1→4)-[Gro-(2→P→3)]-β-D-Galp-(1→4)-β-L-Rhap-(1→ conjugated to a carrier protein. Suitably, the pneumococcal saccharide comprises less than 500 repeat units, for example 1 to 200 repeat units (suitably 2 to 200, 1 to 100, 2 to 100, 2 to 50, 2 to 30, 2 to 20 repeat units) conjugated to a carrier protein.

The present invention also provides a pneumococcal saccharide of the present invention conjugated to a carrier protein (e.g. detoxified exotoxin A from *P. aeruginosa*, CRM197, Diphtheria toxoid, tetanus toxoid, detoxified hemolysin A of *S. aureus*, clumping factor A, clumping factor B, *E. coli* FimH, *E. coli* FimHC, *E. coli* heat labile enterotoxin, detoxified variants of *E. coli* heat labile enterotoxin, Cholera toxin B subunit (CTB), cholera toxin, detoxified variants of cholera toxin, *E. coli* sat protein, the passenger domain of *E. coli* sat protein, *C. jejuni* AcrA, *C. jejuni* natural glycoproteins, *S. pneumoniae* pneumolysin, *S. pneumoniae* NOX, *S. pneumoniae* PspA, *S. pneumoniae* PcpA, *S. pneumoniae* PhtD, *S. pneumoniae* PhtE, *S. pneumoniae* ply (e.g. detoxified ply), or *S. pneumoniae* LytB). Thus, an aspect of the invention is a conjugate (e.g. bioconjugate) comprising (or consisting of) a pneumococcal saccharide of the invention linked (e.g. covalently linked) to a carrier protein. In an embodiment, the pneumococcal saccharide of the present invention is conjugated to a carrier protein selected from detoxified exotoxin A from *P. aeruginosa* (EPA), TT, DT, CRM197, PhtD, detoxified pneumolysin and protein D. In a further embodiment of the invention, the carrier protein is not an *S. pneumoniae* protein. In a further embodiment, the pneumococcal saccharide of the present invention is conjugated to a carrier protein selected from detoxified exotoxin A from *P. aeruginosa* (EPA), TT, DT, or CRM197. In a further embodiment, the pneumococcal saccharide of the present invention is conjugated to exotoxin A from *P. aeruginosa* (EPA).

In an embodiment, the carrier proteins which may be used in the present invention are TT, DT, CRM197, PhtD, detoxified pneumolysin and protein D. In a further embodiment, each *Streptococcus pneumoniae* capsular saccharide serotype in an immunogenic composition of the invention is conjugated to a carrier protein independently selected from the group consisting of detoxified exotoxin A from *P. aeruginosa* (EPA), TT, DT, CRM197 and protein D. In a further embodiment, each *Streptococcus pneumoniae* capsular saccharide serotype in an immunogenic composition of the invention is conjugated to a carrier protein independently selected from the group consisting of TT, DT, CRM197, PhtD and protein D. In a further embodiment, each *Streptococcus pneumoniae* capsular saccharide serotype is conjugated to a carrier protein independently selected from the group consisting of TT, DT, CRM197 and protein D. In another embodiment, the immunogenic composition of the invention comprises two or more different carrier proteins. In another embodiment, the immunogenic composition of the invention comprises 2, 3, 4, 5 or 6 different carrier proteins.

Figure 9A:
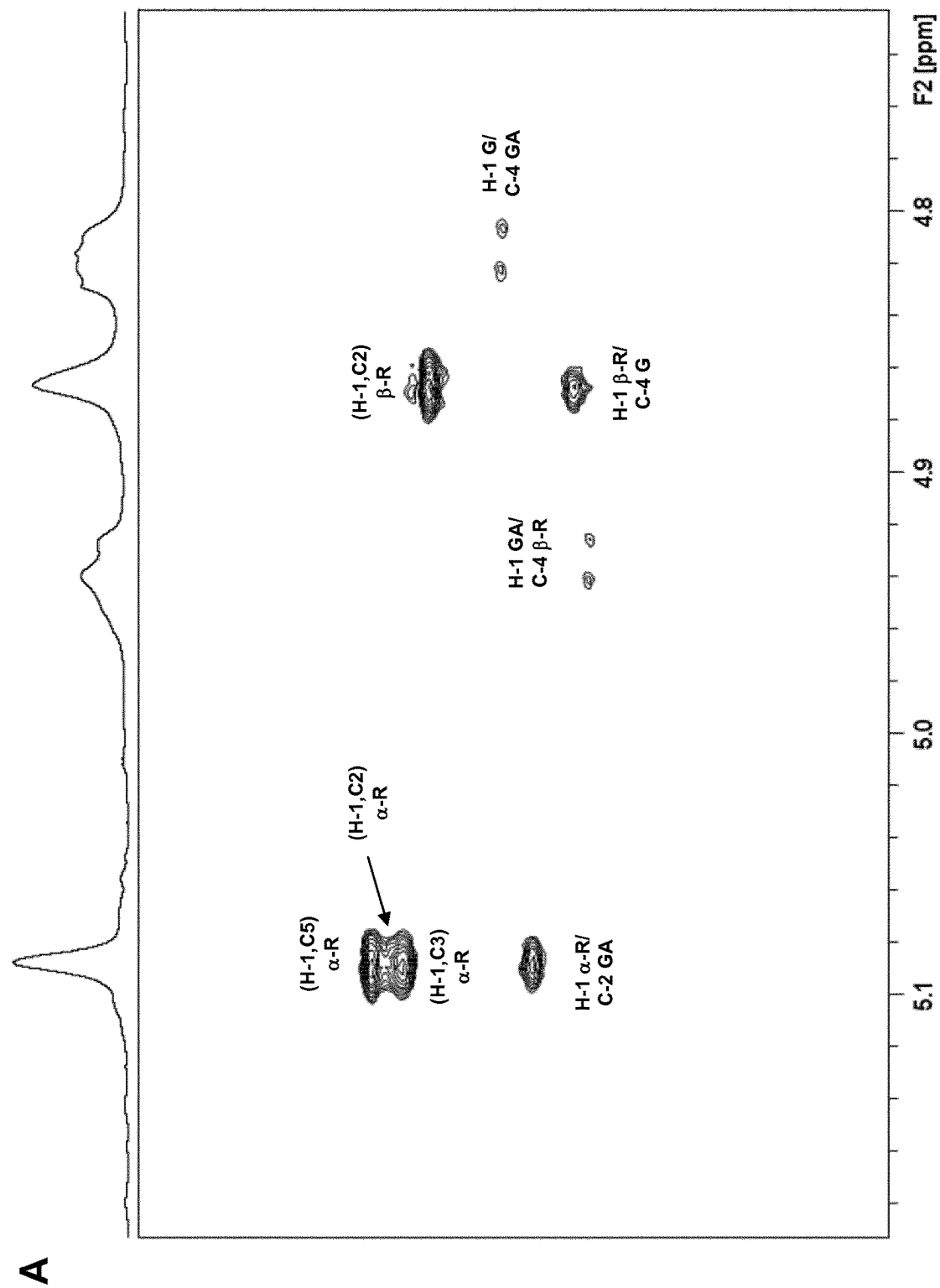
FIG. 9: Expansion of the HMBC spectra of pneumococcal serotype (A) 23F, (B) 23A and (C) 23B capsular polysaccharides showing the anomeric H-1 correlations. Proton/carbon crosspeaks have been labeled according to the corresponding residue (a- and b-R=a- and b-Rha, G=Glc, GA=Gal and Gro=glycerol).
Figure 9B:
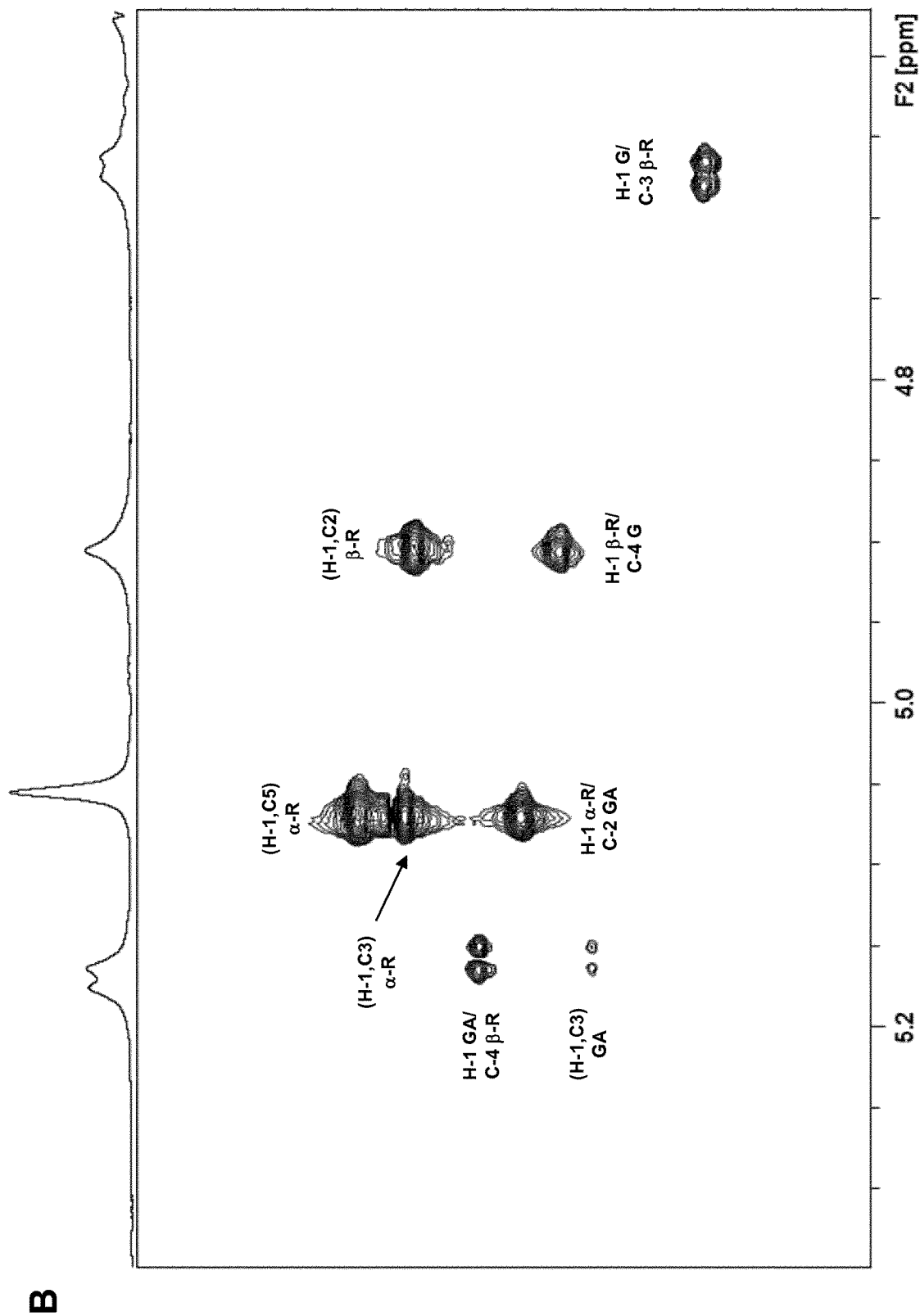
Figure 9C:
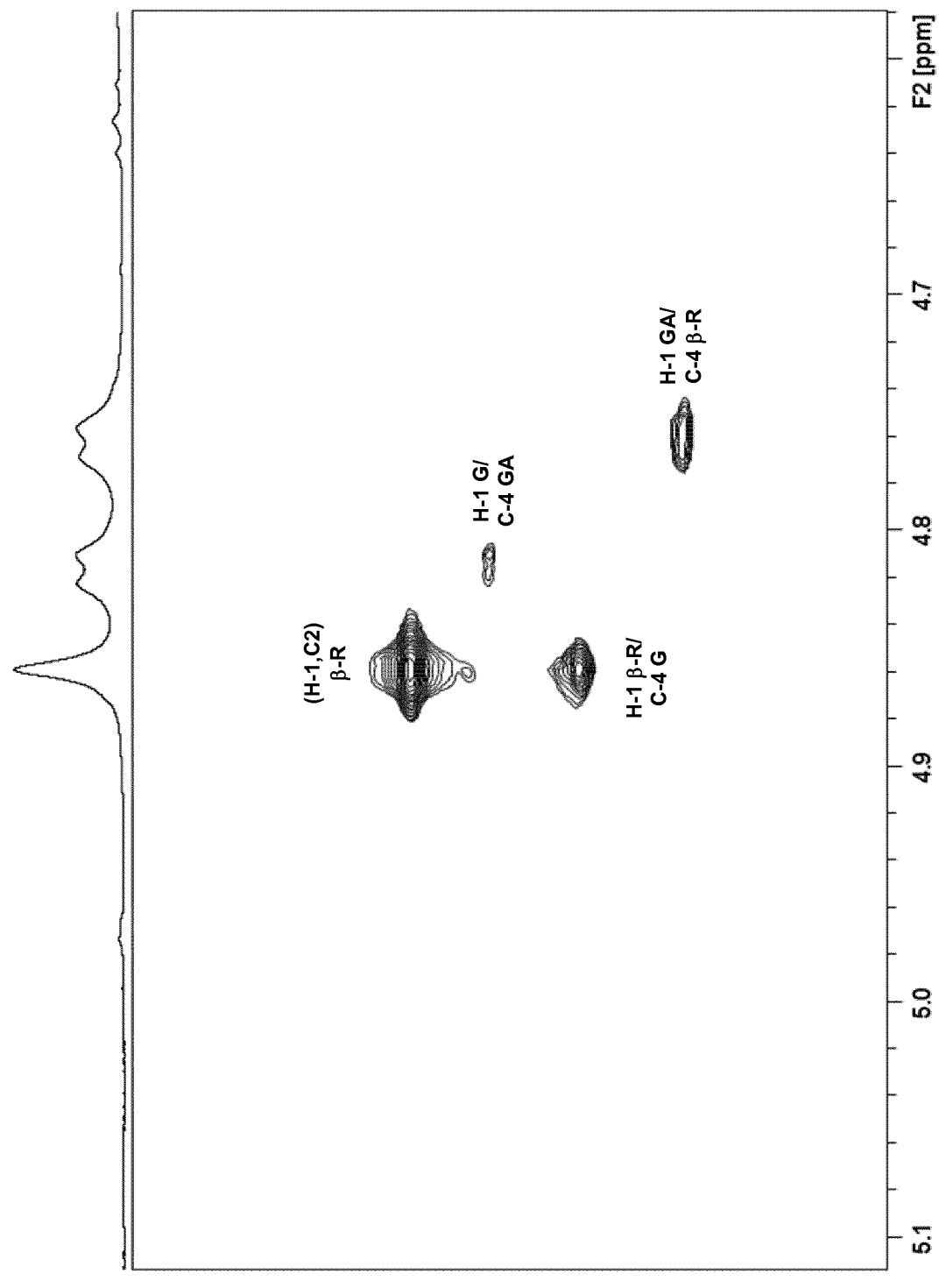

In an embodiment, the carrier protein is protein D from *Haemophilus influenzae* (PD), for example, protein D sequence from FIG. 9 of EP 0594610 (FIGS. 9a and 9b together, 364 amino acids). Inclusion of this protein in the immunogenic composition may provide a level of protection against *Haemophilus influenzae* related otitis media (Pyrmula et. al. Lancet 367; 740-748 (2006)). The Protein D may be used as a full length protein or as a fragment (for example, Protein D may be as described in WO0056360). For example, a protein D sequence may comprise (or consist) a the protein D fragment as described in EP0594610 lacking the 19 N-terminal amino acids from FIG. 9 of EP0594610, optionally with the tripeptide MDP from NS1 fused to the N-terminal of said protein D fragment (348 amino acids). In one aspect, the protein D or fragment of protein D is unlipidated. The protein D could be present in the immunogenic composition as a free protein or as a carrier protein. In one aspect, protein D is present in the immunogenic composition as free protein. In another aspect, protein D is present both as a carrier protein and as free protein. In a further aspect, protein D is present as a carrier protein for one or more of the polysaccharides. In a further aspect, 2-9 of the capsular polysaccharides selected from different serotypes are conjugated to protein D. In a further aspect, protein D is present as a carrier protein for the majority of the polysaccharides, for example 6, 7, 8, 9 or more of the polysaccharides may be conjugated to protein D.

In an embodiment, the carrier protein is CRM197. CRM197 is a non-toxic form of the diphtheria toxin but is immunologically indistinguishable from the diphtheria toxin (DT). Genetically detoxified analogues of diphtheria toxin include CRM197 and other mutants described in U.S. Pat. Nos. 4,709,017, 5,843,711, 5,601,827, and 5,917,017. CRM197 is produced by *C. diphtheriae* infected by the nontoxigenic phase β197tox-created by nitrosoguanidine mutagenesis of the toxigenic carynephage b (Uchida et al Nature New Biology (1971) 233; 8-11). The CRM197 protein has the same molecular weight as the diphtheria toxin but differs from it by a single base change in the structural gene. This leads to a glycine to glutamine change of amino acid at position 52 which makes fragment A unable to bind NAD and therefore non-toxic (Pappenheimer 1977, Ann Rev, Biochem. 46; 69-94, Rappuoli Applied and Environmental Microbiology September 1983 p 560-564).

In an embodiment, the carrier protein is Tetanus Toxoid (TT). Tetanus toxin is a single peptide of approximately 150 kDa, which consists of 1315 amino-acid residues. Tetanus-toxin may be cleaved by papain to yield two fragments; one of them, fragment C, is approximately 50 kDa. Fragment C of TT is described in Neubauer et al. Biochim. Biophys. Acta 1981, 27, 141-148.

In an embodiment, the carrier protein is dPly (detoxified pneumolysin). Pneumolysin (Ply) is a multifunctional toxin with a distinct cytolytic (hemolytic) and complement activation activities (Rubins et al., Am. Respi. Cit Care Med, 153:1339-1346 (1996)). The toxin is not secreted by pneumococci, but it is released upon lysis of pneumococci under the influence of autolysin. Its effects include e.g., the stimulation of the production of inflammatory cytokines by human monocytes, the inhibition of the beating of cilia on human respiratory epithelial, the decrease of bactericidal activity and migration of neutrophils, and in the lysis of red blood cells, which involves binding to cholesterol. Because it is a toxin, it needs to be detoxified (i.e., non-toxic to a human when provided at a dosage suitable for protection) before it can be administered in vivo. Expression and cloning of wild-type or native pneumolysin is known in the art. See, for example, Walker et al. (Infect Immun, 55:1184-1189 (1987)), Mitchell et al. (Biochim Biophys Acta, 1007: 67-72 (1989) and Mitchell et al (NAR, 18:4010 (1990)). Detoxification of Ply can be conducted by chemical means, e.g., subject to formalin or glutaraldehyde treatment or a combination of both (WO 04081515, PCT/EP2005/010258). Such methods are known in the art for various toxins. Alternatively, Ply can be genetically detoxified. Thus, the invention encompasses derivatives of pneumococcal proteins which may be, for example, mutated proteins. The term "mutated" is used herein to mean a molecule which has undergone deletion, addition or substitution of one or more amino acids using known techniques for site directed mutagenesis or any other conventional method. For example, as described above, a mutant Ply protein may be altered so that it is biologically inactive whilst still maintaining its immunogenic epitopes, see, for example, WO90/06951, Berry et al. (Infect Immun, 67:981-985 (1999)) and WO99/03884. As used herein, it is understood that the term "Ply" encompasses mutated pneumolysin and detoxified pneumolysin (dPly) suitable for medical use (i.e., non toxic).

In an embodiment, the carrier protein is detoxified exotoxin A from *P. aeruginosa* (EPA). In an embodiment, the carrier protein is genetically detoxified Exotoxin A of *Pseudomonas aeruginosa* (US2011/0274720 A1; Ihssen, et al., (2010) Microbial cell factories 9, 61). For producing a version of EPA that may be glycosylated, the nucleic acids encoding for EPA need to be modified by insertion of glycosylation sites (consensus sequence(s)) as discussed below.

The size (Mw) of the conjugate is greater than 30 kDa, for example, a MW in the range 30-300 kDa, 30-220 kDa, 50-200 kDa. In an embodiment, the size (Mw) of the conjugate is less than 300 kDa, e.g. between 30-220 kDa.

In an embodiment, the pneumococcal saccharide of the present invention is conjugated to a carrier protein wherein the carrier protein is attached to a glucose or hexose monosaccharide derivative (e.g. N-acetylglucosamine) of the pneumococcal saccharide (e.g. the glucose or hexose monosaccharide derivative (e.g. GlcNAc) at the reducing end of the first repeat unit of the pneumococcal saccharide).

In an embodiment, the pneumococcal saccharide of the present invention is covalently coupled to a carrier protein, either directly (e.g. via an N-linked glycosidic bond or via an O-linked glycosidic bond) or via a linker. In an embodiment, the pneumococcal saccharide of the present invention is directly coupled to a carrier protein (e.g. via an N-linked glycosidic bond or via an O-linked glycosidic bond).

In an embodiment, the pneumococcal saccharide of the present invention is coupled to a carrier protein via an O-linked glycosidic bond. O-linked glycosylation is a form of glycosylation that occurs in eukaryotes, archaea, and bacteria. It consists of the attachment of a sugar molecule to a side-chain hydroxyl group of an amino acid residue in the protein target (Faridmoayer et al. JOURNAL OF BACTERIOLOGY, November 2007, Vol. 189, No. 22, p. 8088-8098).

In an embodiment, the pneumococcal saccharide of the present invention is coupled to a carrier protein via an N-linked glycosidic bond. For example, the pneumococcal saccharide of the present invention may be N-linked to a carrier protein. X can be any amino acid except proline. In a conjugate (e.g. bioconjugate) comprising a carrier protein containing a Asn-X-Ser/Thr consensus sequence (e.g. within D/E-X-N-Z-S/T (SEQ ID NO: 1) or K-D/E-X-N-Z-S/T-K (SEQ ID NO: 3)), the asparagine residue may be linked to the pneumococcal saccharide. X can be any amino acid except proline. In an embodiment, the consensus sequence is D/E-X-N-Z-S/T (SEQ ID NO: 1), wherein X is Q (glutamine) and Z is A (alanine), e.g. D-Q-N-A-T (SEQ ID NO: 2) also referred to as "DQNAT". In an embodiment, the consensus sequence is K-D/E-X-N-Z-S/T-K (SEQ ID NO: 3), wherein X is Q (glutamine) and Z is A (alanine), e.g. K-D-Q-N-A-T-K (SEQ ID NO: 4) also referred to as "KDQNATK". A further aspect of the invention is a conjugate (e.g. bioconjugate) comprising a carrier protein N-linked to a hybrid oligosaccharide or polysaccharide of the invention, wherein said hydrid oligosaccharide or polysaccharide is identical to a 23B oligosaccharide or polysaccharide, with the exception of the fact that the hybrid oligosaccharide or polysaccharide comprises a hexose monosaccharide derivative at the reducing end of the first repeat unit in addition to comprising all of the monosaccharides of the 23B oligosaccharide or polysaccharide. In an embodiment, a conjugate (e.g. bioconjugate) is provided comprising a carrier protein containing a Asn-X-Ser/Thr consensus sequence (e.g. within D/E-X-N-Z-S/T (SEQ ID NO: 1) or K-D/E-X-N-Z-S/T-K (SEQ ID NO: 3)), the asparagine residue of which is linked to a hybrid oligosaccharide or polysaccharide of the invention, wherein said hybrid oligosaccharide or polysaccharide contains at least 2, 3, 4, 5, 6, 7, 8, 9, 10, 20, 30, 40 or 50 saccharide repeat units of a 23B oligosaccharide or polysaccharide and a further repeat unit N-linked to the carrier protein in which a hexose monosaccharide derivative is at the reducing end of said further repeat unit.

In an embodiment of the invention, one or more amino acids (e.g. 1-7 amino acids, e.g. one amino acid) of the carrier protein sequence have been substituted by a five amino acid D/E-X-N-Z-S/T (SEQ ID NO: 1) or by a seven amino acid K-D/E-X-N-Z-S/T-K (SEQ ID NO: 3) (e.g. K-D-Q-N-A-T-K (SEQ ID NO: 4) also referred to as "KDQNATK") consensus sequence. For example, a single amino acid in the carrier protein amino acid sequence may be replaced with a D/E-X-N-Z-S/T (SEQ ID NO: 1) or K-D/E-X-N-Z-S/T-K (SEQ ID NO: 3) (e.g. K-D-Q-N-A-T-K (SEQ ID NO: 4)) consensus sequence. Alternatively, 2, 3, 4, 5, 6 or 7 amino acids in the carrier protein amino acid sequence may be replaced with a D/E-X-N-Z-S/T (SEQ ID NO: 1) or K-D/E-X-N-Z-S/T-K (SEQ ID NO: 3) (e.g. K-D-Q-N-A-T-K (SEQ ID NO: 4)) consensus sequence.

In an embodiment, the pneumococcal saccharide of the invention is linked to an amino acid on the carrier protein selected from asparagine, aspartic acid, glutamic acid, lysine, cysteine, tyrosine, histidine, arginine or tryptophan (e.g. asparagine). In another embodiment, the amino acid residue on the carrier protein to which the a pneumococcal saccharide of the invention is linked is an asparagine residue. In another embodiment, the amino acid residue on the carrier protein to which the a pneumococcal saccharide of the invention is linked is part of the D/E-X-N-Z-S/T (SEQ ID NO: 1) and K-D/E-X-N-Z-S/T-K (SEQ ID NO: 3) consensus sequence (e.g. the asparagine in the D/E-X-N-Z-S/T (SEQ ID NO: 1) and K-D/E-X-N-Z-S/T-K (SEQ ID NO: 3) consensus sequence).

In an embodiment, the amino acid residue on the carrier protein to which the pneumococcal saccharide of the invention is linked is not an asparagine residue and in this case, the conjugate is typically produced by chemical conjugation. In an embodiment, the amino acid residue on the carrier protein to which the pneumococcal saccharide of the invention is linked is selected from the group consisting of: Ala, Arg, Asp, Cys, Gly, Glu, Gln, His, Ile, Leu, Lys, Met, Phe, Pro, Ser, Thr, Trp, Tyr, and Val. Optionally, the amino acid is: an amino acid containing a terminal amine group, a lysine, an arginine, a glutaminic acid, an aspartic acid, a cysteine, a tyrosine, a histidine or a tryptophan. Optionally, the pneumococcal saccharide of the invention is covalently linked to amino acid on the carrier protein selected from: aspartic acid, glutamic acid, lysine, cysteine, tyrosine, histidine, arginine or tryptophan.

In an embodiment, the amino acid residue on the carrier protein to which the pneumococcal saccharide of the invention is linked is not part of the D/E-X-N-Z-S/T (SEQ ID NO: 1) and K-D/E-X-N-Z-S/T-K (SEQ ID NO: 3) consensus sequence pneumococcal saccharide of the invention is linked is not the asparagine residue in the D/E-X-N-Z-S/T (SEQ ID NO: 1) and K-D/E-X-N-Z-S/T-K (SEQ ID NO: 3) consensus sequence.

In an embodiment, the pneumococcal saccharide of the present invention is covalently linked (either directly or through a linker) to an amino acid residue of a carrier protein. In an embodiment, the pneumococcal saccharide is covalently linked to a carrier protein through a chemical linkage obtainable using a chemical conjugation method, optionally selected from the group consisting of carbodiimide chemistry, reductive animation, cyanylation chemistry (for example CDAP chemistry), maleimide chemistry, hydrazide chemistry, ester chemistry, and N-hydroxysuccinimide chemistry either directly or via a linker. As used herein, the term "directly linked" means that the two entities are connected via a chemical bond, preferably a covalent bond. As used herein, the term "indirectly linked" means that the two entities are connected via a linking moiety (as opposed to a direct covalent bond). In certain embodiments the linker is adipic acid dihydrazide.

In an embodiment, the chemical conjugation method is selected from the group consisting of carbodiimide chemistry, reductive animation, cyanylation chemistry (for example CDAP chemistry), maleimide chemistry, hydrazide chemistry, ester chemistry, and N-hydroysuccinimide chemistry. Conjugates can be prepared by direct reductive amination methods as described in, US200710184072 (Hausdorff) U.S. Pat. No. 4,365,170 (Jennings) and U.S. Pat. No. 4,673,574 (Anderson). Other methods are described in EP-0-161-188, EP-208375 and EP-0-477508. The conjugation method may alternatively rely on activation of the pneumococcal saccharide with 1-cyano-4-dimethylamino pyridinium tetrafluoroborate (CDAP) to form a cyanate ester. Such conjugates are described in PCT published application WO 93/15760 Uniformed Services University and WO 95/08348 and WO 96/29094. See also Chu C. et al. Infect. Immunity, 1983, pages 245-256.

In general the following types of chemical groups on a carrier protein can be used for conjugation:

A) Carboxyl (for instance via aspartic acid or glutamic acid). In one embodiment this group is linked to amino groups on saccharides directly or to an amino group on a linker with carbodiimide chemistry e.g. with EDAC.

B) Amino group (for instance via lysine). In one embodiment this group is linked to carboxyl groups on saccharides directly or to a carboxyl group on a linker with carbodiimide chemistry e.g. with EDAC. In another embodiment this group is linked to hydroxyl groups activated with CDAP or CNBr on saccharides directly or to such groups on a linker; to saccharides or linkers having an aldehyde group; to saccharides or linkers having a succinimide ester group.

C) Sulphydryl (for instance via cysteine). In one embodiment this group is linked to a bromo or chloro acetylated saccharide or linker with maleimide chemistry. In one embodiment this group is activated/modified with bis diazobenzidine.

D) Hydroxyl group (for instance via tyrosine). In one embodiment this group is activated/modified with bis diazobenzidine.

E) Imidazolyl group (for instance via histidine). In one embodiment this group is activated/modified with bis diazobenzidine.

F) Guanidyl group (for instance via arginine).

G) Indolyl group (for instance via tryptophan).

On a saccharide, in general the following groups can be used for a coupling: OH, COOH or $NH_2$. Aldehyde groups can be generated after different treatments such as: periodate, acid hydrolysis, hydrogen peroxide, etc.

Direct Coupling Approaches:

Saccharide-OH+CNBr or CDAP→cyanate ester+
  $NH_2$-Protein→conjugate

Saccharide-aldehyde+$NH_2$-Protein→Schiff base+
  NaCNBH3→conjugate

Saccharide-COOH+$NH_2$-Protein+EDAC→conjugate

Saccharide-$NH_2$+COOH-Protein+EDAC→conjugate

Indirect Coupling Via Spacer (Linker) Approaches:

Saccharide-OH+CNBr or CDAP→cyanate ester+
  $NH_2$—$NH_2$→saccharide-$NH_2$+COOH-Protein+
  EDAC→conjugate Saccharide-OH+CNBr or CDAP→cyanate ester+
  $NH_2$—SH→saccharide-SH+SH-Protein (native
  Protein with an exposed cysteine or obtained
  after modification of amino groups of the pro-
  tein by SPDP for instance)→saccharide-S—S-
  Protein Saccharide-OH+CNBr or CDAP→cyanate ester+
  $NH_2$—SH→saccharide-SH+maleimide-Protein
  (modification of amino groups)→conjugate Saccharide-OH+CNBr or CDAP→cyanate ester+
  $NH_2$—SH→Saccharide-SH+haloacetylated-Pro-
  tein→Conjugate Saccharide-COOH+EDAC+$NH_2$—$NH_2$→saccharide-
  $NH_2$+EDAC+COOH-Protein→conjugate Saccharide-COOH+EDAC+$NH_2$—SH→saccharide-
  SH+SH-Protein (native Protein with an exposed
  cysteine or obtained after modification of
  amino groups of the protein by SPDP for
  instance)→saccharide-S—S-Protein Saccharide-COOH+EDAC+$NH_2$—SH→saccharide-
  SH+maleimide-Protein (modification of amino
  groups)→conjugate Saccharide-COOH+EDAC+$NH_2$—SH→Saccharide-
  SH+haloacetylated-Protein→Conjugate Saccharide-Aldehyde+$NH_2$—$NH_2$→saccharide-
  NH2+EDAC+COOH-Protein→conjugate Note: instead of EDAC above, any suitable carbodiimide may be used.

In an embodiment, the pneumococcal saccharide of the invention is attached to the carrier protein via a linker. Optionally, the linker is selected from the group consisting of linkers with 4-12 carbon atoms, bifunctional linkers, linkers containing 1 or 2 reactive amino groups at the end, B-propionamido, nitrophenyl-ethylamine, haloacyl halides, 6-aminocaproic acid and ADH. The activated saccharide may thus be coupled directly or via a spacer (linker) group to an amino group on the carrier protein. For example, the spacer could be cystamine or cysteamine to give a thiolated polysaccharide which could be coupled to the carrier protein via a thioether linkage obtained after reaction with a maleimide-activated carrier protein (for example using GMBS (4-Maleimidobutyric acid N-hydroxysuccinimide ester)) or a haloacetylated carrier protein (for example using SIAB (succinimidyl (4-iodoacetyl)aminobenzoate), or SIA (succinimidyl iodoacetate), or SBAP (succinimidyl-3-(bromoacetamide)propionate)). In an embodiment, the cyanate ester (optionally made by CDAP chemistry) is coupled with hexane diamine or ADH (adipic acid dihydrazide) and the amino-derivatised saccharide is conjugated to the carrier protein using carbodiimide (e.g. 1-Ethyl-3-(3-dimethylaminopropyl)carbodiimide (EDAC or EDC)) chemistry via a carboxyl group on the protein modified pneumolysin. Such conjugates are described in PCT published application WO 93/15760 Uniformed Services University and WO 95/08348 and WO 96/29094.

Host Cell

The present invention provides a host cell comprising:
(i) one or more nucleic acids that encode glycosyltransferase(s) sufficient for synthesis of the repeat unit →4)-β-D-Glcp-(1→4)-[Gro-(2→P→3)]-β-D-Galp-(1→4)-β-L-Rhap-(1→;
(ii) nucleic acid that encodes an oligosaccharyl transferase (optionally a heterologous oligosaccharyltransferase); and optionally
(iii) nucleic acid that encodes a carrier protein comprising an N-glycosylation consensus sequence (e.g. detoxified exotoxin A from *P. aeruginosa*, CRM197, Diphtheria toxoid, tetanus toxoid, detoxified hemolysin A of *S. aureus*, clumping factor A, clumping factor B, *E. coli* FimH, *E. coli* FimHC, *E. coli* heat labile enterotoxin, detoxified variants of *E. coli* heat labile enterotoxin, Cholera toxin B subunit (CTB), cholera toxin, detoxified variants of cholera toxin, *E. coli* sat protein, the passenger domain of *E. coli* sat protein, *C. jejuni* AcrA, *C. jejuni* natural glycoproteins, *S. pneumoniae* pneumolysin, *S. pneumoniae* NOX, *S. pneumoniae* PspA, *S. pneumoniae* PcpA, *S. pneumoniae* PhtD, *S. pneumoniae* PhtE, *S. pneumoniae* ply (e.g. detoxified ply), or *S. pneumoniae* LytB); and optionally (iv) nucleic acid that encodes a polymerase (e.g. wzy).

Host cells that can be used to produce the bioconjugates of the invention, include archea, prokaryotic host cells, and eukaryotic host cells. Exemplary prokaryotic host cells for use in production of the bioconjugates of the invention, without limitation, *Escherichia* species, *Shigella* species, *Klebsiella* species, *Xhantomonas* species, *Salmonella* species, *Yersinia* species, *Lactococcus* species, *Lactobacillus* species, *Pseudomonas* species, *Corynebacterium* species, *Streptomyces* species, *Streptococcus* species, *Staphylococcus* species, *Bacillus* species, and *Clostridium* species. In an embodiment, the host cell is a gram-negative bacterium, optionally selected from the group consisting of *Escherichia* species, *Shigella* species, *Klebsiella* species, *Salmonella* species, *Yersinia* species, *Neisseria* species, *Vibrio* species and *Pseudomonas* species. In an embodiment, the host cell is *E. coli* (e.g. *E. coli* W3110).

In an embodiment, the host cells used to produce the bioconjugates of the invention are engineered to comprise heterologous nucleic acids, e.g. heterologous nucleic acids that encode one or more carrier proteins and/or heterologous nucleic acids that encode one or more proteins, e.g. genes encoding one or more proteins. Thus, a host cell of the invention is not a wild-type (WT) *Streptococcus pneumoniae* host cell. In an embodiment, heterologous nucleic acids that encode proteins involved in glycosylation pathways (e.g. prokaryotic and/or eukaryotic glycosylation pathways) may be introduced into the host cells of the invention. Such nucleic acids may encode proteins including, without limitation, oligosaccharyl transferases, epimerases, flippases, polymerases, and/or glycosyltransferases. Heterologous nucleic acids (e.g. nucleic acids that encode carrier proteins and/or nucleic acids that encode other proteins, e.g. proteins involved in glycosylation) can be introduced into the host cells of the invention using methods such as electroporation, chemical transformation by heat shock, natural transformation, phage transduction, and conjugation. In an embodiment, heterologous nucleic acids are introduced into the host cells of the invention using a plasmid, e.g. the heterologous nucleic acids are expressed in the host cells by a plasmid (e.g. an expression vector). In an embodiment, heterologous nucleic acids are introduced into the host cells of the invention using the method of insertion described in International Patent application NO: PCT/EP2013/068737 (published as WO 14/037585).

In an embodiment, additional modifications may be introduced (e.g. using recombinant techniques) into the host cells of the invention. For example, host cell nucleic acids (e.g. genes) that encode proteins that form part of a possibly competing or interfering glycosylation pathway (e.g. compete or interfere with one or more heterologous genes involved in glycosylation that are recombinantly introduced into the host cell) can be deleted or modified in the host cell background (genome) in a manner that makes them inactive/dysfunctional (i.e., the host cell nucleic acids that are deleted/modified do not encode a functional protein or do not encode a protein whatsoever). In an embodiment, when nucleic acids are deleted from the genome of the host cells of the invention, they are replaced by a desirable sequence, e.g. a sequence that is useful for glycoprotein production.

Exemplary genes that can be deleted in host cells (and, in some cases, replaced with other desired nucleic acid sequences) include genes of host cells involved in glycolipid biosynthesis, such as waaL (see, e.g. Feldman et al. 2005, PNAS USA 102:3016-3021), the lipid A core biosynthesis cluster (waa), galactose cluster (gal), arabinose cluster (ara), colanic acid cluster (wca), capsular polysaccharide cluster, undecaprenyl-pyrophosphate biosynthesis genes (e.g. uppS (Undecaprenyl pyrophosphate synthase), uppP (Undecaprenyl diphosphatase)), Und-P recycling genes, metabolic enzymes involved in nucleotide activated sugar biosynthesis, enterobacterial common antigen cluster, and prophage O antigen modification clusters like the gtrABS cluster. In an embodiment, the waaL gene is deleted. In another embodiment, colanic acid cluster (wca) genes (e.g. the complete colanic acid cluster from wza to wcaM) are replaced by the glycosyltransferase(s) sufficient for synthesis of the repeat unit →4)-β-D-Glcp-(1→4)-[Gro-(2→P→3)]-β-D-Galp-(1→4)-β-L-Rhap-(1→. In another embodiment, the yeaS gene of *E. coli* W3110 is replaced with a gene encoding a glycosyltransferase which transfers a 13-L-rhamnose on position 4 of UndPP-D-GlcpNAc, e.g. wegR from the O-antigen cluster of *E. coli* O2 (e.g. SEQ ID NO: 59). WegR can be added to a strain as a plasmid-encoded gene, but in order to obtain a more stable production strain, wegR may be integrated into the host cell genome replacing the gene yeaS.

Such a modified prokaryotic host cell comprises nucleic acids encoding enzymes capable of producing a bioconjugate comprising a pneumococcal saccharide of the invention attached to a carrier protein. Such host cells may naturally express nucleic acids specific for production of a saccharide antigen, or the host cells may be made to express such nucleic acids, i.e., in certain embodiments said nucleic acids are heterologous to the host cells. In certain embodiments, one or more of said nucleic acids specific for production of a saccharide antigen are heterologous to the host cell and intergrated into the genome of the host cell. In certain embodiments, the host cells of the invention comprise nucleic acids encoding additional enzymes active in the N-glycosylation of proteins, e.g. the host cells of the invention further comprise nucleic acid encoding an oligosaccharyl transferase and/or one or more nucleic acids encoding other glycosyltransferases.

Nucleic acid sequences comprising capsular polysaccharide gene clusters can be inserted into the host cells of the invention. In an embodiment, the capsular polysaccharide gene cluster inserted into a host cell of the invention is a capsular polysaccharide gene cluster from an *E. coli* strain, a *Streptococcus* strain (e.g. *S. pneumoniae*, *S. pyrogenes*, *S. agalacticae*), a *Staphylococcus* strain (e.g. *S. aureus*), or a *Burkholderia* strain (e.g. *B mallei*, *B. pseudomallei*, *B. thailandensis*). Disclosures of methods for making such host cells which are capable of producing bioconjugates are found in WO 06/119987, WO 09/104074, WO 11/62615, WO 11/138361, WO 14/57109, WO14/72405 and WO16/20499.

In an embodiment, the host cell is capable of producing a hybrid oligosaccharide or polysaccharide, wherein said hybrid oligosaccharide or polysaccharide is identical to *S. pneumoniae* CP23B, with the exception of the fact that said hybrid oligosaccharide or polysaccharide comprises a hexose monosaccharide derivative at the reducing end of the first repeat unit in place of the hexose monosaccharide normally present at the reducing end of the first repeat unit of *S. pneumoniae* CP23B, e.g. wherein said hexose monosaccharide derivative is N-acetylglucosamine (GlcNAc), N-acetylgalactoseamine (GalNAc), 2,4-Diacetamido-2,4,6-trideoxyhexose (DATDH), N-acetylfucoseamine (FucNAc), N-acetylquinovosamine (QuiNAc) (e.g. N-acetylglucosamine (GlcNAc)).

Glycosylation Machinery

The host cells of the invention comprise, and/or can be modified to comprise, nucleic acids that encode genetic machinery (e.g. glycosyltransferases, flippases, polymerases, and/or oligosaccharyltransferases) capable of producing hybrid oligosaccharides and/or polysaccharides, as well as genetic machinery capable of linking a pneumococcal saccharide of the invention to a carrier protein.

The capsular polysaccharide gene cluster maps between dexB and aliA in the pneumococcal chromosome (Llull et al., 1999, J. Exp. Med. 190, 241-251). There are typically four relatively conserved genes: (wzg), (wzh), (wzd), (wze) at the 5' end of the capsular polysaccharide gene cluster (Jiang et al., 2001, Infect. Immun. 69, 1244-1255). Also included in the capsular polysaccharide gene cluster of *S. pneumoniae* are wzx (polysaccharide flippase gene) and wzy (polysaccharide polymerase gene). The CP gene clusters of all 90 *S. pneumoniae* serotypes have been sequenced by Sanger Institute (WorldWideWeb(www).sanger.ac.uk/Projects/S_pneumoniae/CPS/), and wzx and wzy of 89 serotypes have been annotated and analyzed (Kong et al., 2005, J. Med. Microbiol. 54, 351-356). The capsular biosynthetic genes of *S. pneumoniae* are further described in Bentley et al. (PLoS Genet. 2006 March; 2(3): e31 and the sequences are provided in GenBank (Genbank CR931632-CR931722). Serotype 23A from *Streptococcus pneumoniae* strain 1196/45 (serotype 23A) is accession number: CR931683.1. Serotype 23B from *Streptococcus pneumoniae* strain 1039/41 is accession number: CR931684.1. Serotype 23F from *Streptococcus pneumoniae* strain Dr. Melchior is accession number: CR931685.1.

Phosphotransferases and Glycosyltransferases

The host cells of the invention comprise nucleic acids that encode phosphotransferases and glycosyltransferases that produce an oligosaccharide or polysaccharide repeat unit. In an embodiment, said repeat unit does not comprise a hexose at the reducing end, and said oligosaccharide or polysaccharide repeat unit is derived from a →4)-β-D-Glcp-(1→4)-[Gro-(2→P→3)]-β-D-Galp-(1→4)-β-L-Rhap-(1→ repeat unit that comprises a hexose (i.e., Glc; glucose) at the reducing end.

In an embodiment, the host cells of the invention may comprise nucleic acid that encodes an enzyme, e.g. a phosphotransferase that assembles a hexose monosaccharide derivative onto undecaprenyl monophopshpate (Und-P) to form a hexose monosaccharide derivative assembled on Und-PP (Und-PP precursor). In one aspect, the phosphotransferase that assembles a hexose monosaccharide derivative onto Und-PP is heterologous to the host cell and/or heterologous to one or more of the genes that encode the glycosyltransferase(s). Said phosphotransferase can be derived from, e.g. *Escherichia* species, *Shigella* species, *Klebsiella* species, *Xhantomonas* species, *Salmonella* species, *Yersinia* species, *Aeromonas* species, *Francisella* species, *Helicobacter* species, *Proteus* species, *Lactococcus* species, *Lactobacillus* species, *Pseudomonas* species, *Corynebacterium* species, *Streptomyces* species, *Streptococcus* species, *Enterococcus* species, *Staphylococcus* species, *Bacillus* species, *Clostridium* species, *Listeria* species, or *Campylobacter* species. For example, GlcNAc may be assembled on UndP from UDP-GlcNAc by a phosphotransferase, e.g. wecA (which exists in all Gram-negative bacteria that synthesize ECA and Gram-positive bacteria that makes Teichoic acid) (Annu Rev Microbiol. 2013; 67:313-36; Glycobiology. 2011 February; 21(2):138-51) to make a β (1,3) linkage and form Und-PP-GlcNAc. In an embodiment, the phosphotransferase that assembles a hexose monosaccharide derivative onto Und-PP is wecA, optionally from *E. coli* (Genbank Accession AAA82970 (nucleotide sequence) AAA24526 (amino acid sequence) SEQ ID NO:63).

In an embodiment, the host cell comprises nucleic acids that encode (a) an enzyme, e.g. a phosphotransferase that assembles a hexose monosaccharide derivative onto undecaprenyl monophosphate (Und-P), optionally wherein said phosphotransferase is wecA, optionally from *E. coli*, and (b) one or more glycosyltransferases capable of adding a monosaccharide to the hexose monosaccharide derivative assembled on Und-PP.

In an embodiment, the host cells of the invention may comprise nucleic acids that encode one or more glycosyltransferases capable of adding a monosaccharide to the Und-PP precursor, (the hexose monosaccharide derivative assembled on Und-PP), for example a rhamnosyltransferase (e.g. 4-linked β-L-rhamnose), for example the rhamnosyltransferase (wegR) from *E. coli* O2 (e.g. SEQ ID NO: 59) or the rhamnosyltransferase (wbuV) from *E. coli* O149 (e.g. SEQ ID NO: 60) or the rhamnosyltransferase (wepI) from *Cronobacter sakazakii* O5 (e.g. SEQ ID NO: 61). In an embodiment, said one or more glycosyltransferases capable of adding a monosaccharide to the hexose monosaccharide derivative comprise the rhamnosyltransferase (wegR) from *E. coli* O2 having an amino acid sequence of SEQ ID NO: 59 (GenBank: EU549863.1) or an amino acid sequence at least 80%, 85%, 90%, 92%, 95%, 96%, 97%, 98% or 99% identical to SEQ ID NO: 59, for example comprising at least 100, 150 or 200 contiguous amino acids of the full length sequence. In an embodiment, said one or more glycosyltransferases capable of adding a monosaccharide to the hexose monosaccharide derivative comprise the rhamnosyltransferase (wbuV) from *E. coli* O149 having an amino acid sequence of SEQ ID NO: 60 (GenBank: DQ868764.1) or an amino acid sequence at least 80%, 85%, 90%, 92%, 95%, 96%, 97%, 98% or 99% identical to SEQ ID NO: 60, for example comprising at least 100, 150 or 200 contiguous amino acids of the full length sequence. In an embodiment, said one or more glycosyltransferases capable of adding a monosaccharide to the hexose monosaccharide derivative comprise the rhamnosyltransferase (wepI) from *Cronobacter sakazakii* O5 having an amino acid sequence of SEQ ID NO: 61 (GenBank: JQ674748.1) or an amino acid sequence at least 80%, 85%, 90%, 92%, 95%, 96%, 97%, 98% or 99% identical to SEQ ID NO: 61, for example comprising at least 100, 150 or 200 contiguous amino acids of the full length sequence.

In an embodiment, a host cell of the invention comprises nucleic acids encoding glycosyltransferases for synthesis of the repeat unit from the capsular polysaccharide gene clusters of *S. pneumoniae* CP23A, CP23B, and/or CP23F. In an embodiment, a host cell of the invention comprises nucleic acids encoding glycosyltransferases for synthesis of the →4)-β-D-Glcp-(1→4)-[Gro-(2→P→3)]-β-D-Galp-(1→4)-β-L-Rhap-(1→ repeat unit from the capsular polysaccharide gene clusters of *S. pneumoniae* CP23B. In an embodiment, said glycosyltransferases for synthesis of the repeat units comprise WchA (glucosyltransferase) (e.g. from *S. pneumoniae* CP23A, CP23B or CP23F, in particular from CP23A), WchF (rhamnosyltransferase) (e.g. from *S. pneumoniae* CP23A, CP23B or CP23F, in particular from CP23B), WchV (galactosyltransferase) (e.g. from *S. pneumoniae* CP23A, CP23B or CP23F, in particular from CP23B), and WchX (e.g. from *S. pneumoniae* CP23A, CP23B or CP23F, in particular from CP23B). In an embodiment, said glycosyltransferases for synthesis of the repeat units comprise WchA (glucosyltransferase) (e.g. from *S. pneumoniae* CP23A, CP23B or CP23F, in particular from CP23B), e.g. having an amino acid sequence of SEQ ID NO: 27 (GenBank: CR931684.1) or an amino acid sequence at least 80%, 85%, 90%, 92%, 95%, 96%, 97%, 98% or 99% identical to SEQ ID NO: 27, for example comprising at least 100, 150 or 200 contiguous amino acids of the full length sequence. In an embodiment, said glycosyltransferases for synthesis of the repeat units comprise WchF (rhamnosyltransferase) (e.g. from *S. pneumoniae* CP23A, CP23B or CP23F, in particular from CP23B), e.g. from *S. pneumoniae* CP23B having an amino acid sequence of SEQ ID NO: 28 (GenBank: CR931684.1) or an amino acid sequence at least 80%, 85%, 90%, 92%, 95%, 96%, 97%, 98% or 99% identical to SEQ ID NO: 28, for example comprising at least 100, 150 or 200 contiguous amino acids of the full length sequence. In an embodiment, said glycosyltransferases for synthesis of the repeat units comprise WchV (galactosyltransferase), (e.g. from *S. pneumoniae* CP23A, CP23B or CP23F, in particular from CP23B), e.g. from *S. pneumoniae*

CP23B having an amino acid sequence of SEQ ID NO: 30 (GenBank: CR931684.1) or an amino acid sequence at least 80%, 85%, 90%, 92%, 95%, 96%, 97%, 98% or 99% identical to SEQ ID NO: 30, for example comprising at least 100, 150 or 200 contiguous amino acids of the full length sequence. In an embodiment, said glycosyltransferases for synthesis of the repeat units comprise WchW (rhamnosyltransferase), (e.g. from *S. pneumoniae* CP23A, CP23B or CP23F, in particular from CP23B), e.g. from *S. pneumoniae* CP23B having an amino acid sequence of SEQ ID NO: 31 (GenBank: CR931684.1) or an amino acid sequence at least 80%, 85%, 90%, 92%, 95%, 96%, 97%, 98% or 99% identical to SEQ ID NO: 31, for example comprising at least 100, 150 or 200 contiguous amino acids of the full length sequence. In an embodiment, said glycosyltransferases for synthesis of the repeat units do not comprise WchW (rhamnosyltransferase), (e.g. from *S. pneumoniae* CP23A, CP23B or CP23F, in particular from CP23B), e.g. from *S. pneumoniae* CP23B having an amino acid sequence of SEQ ID NO: 31 (GenBank: CR931684.1) or an amino acid sequence at least 80%, 85%, 90%, 92%, 95%, 96%, 97%, 98% or 99% identical to SEQ ID NO: 31, for example comprising at least 100, 150 or 200 contiguous amino acids of the full length sequence. In an embodiment, said glycosyltransferases for synthesis of the repeat units comprise WchX, (e.g. from *S. pneumoniae* CP23A, CP23B or CP23F, in particular from CP23B), e.g. from *S. pneumoniae* CP23B having an amino acid sequence of SEQ ID NO: 33 (GenBank: CR931684.1) or an amino acid sequence at least 80%, 85%, 90%, 92%, 95%, 96%, 97%, 98% or 99% identical to SEQ ID NO: 33, for example comprising at least 100, 150 or 200 contiguous amino acids of the full length sequence.

In one embodiment, the glycosyltransferases that assemble the →4)-β-D-Glcp-(1→4)-[Gro-(2→P→3-β-D-Galp-(1→4)]-β-L-Rhap-(1→ repeat unit onto the hexose monosaccharide derivative comprise a glycosyltransferase that is capable of adding the monosaccharide that is adjacent to the hexose monosaccharide present at the reducing end of the first repeat unit of the donor oligosaccharide or polysaccharide to the hexose monosaccharide present at the reducing end of the first repeat unit of the pneumococcal saccharide.

In an embodiment, a host cell of the invention also comprises nucleic acids encoding wzg, wzh, wzd and/or wze from *S. pneumoniae* CP23A, CP23B or CP23F, in particular from CP23B, e.g. having amino acid sequences of SEQ ID NOs. 23, 24, 25 and 26 respectively (GenBank: CR931684.1) or amino acid sequences at least 80%, 85%, 90%, 92%, 95%, 96%, 97%, 98% or 99% identical to SEQ ID NOs. 23, 24, 25 and 26, for example comprising at least 100, 150 or 200 contiguous amino acids of the full length sequence. The genes wzg, wzh, wzd and wze from *S. pneumoniae* are regulatory genes.

In another embodiment, the host cells of the invention lack one or more of the regulatory genes from *Streptococcus pnuemoniae* that are involved in biosynthesis of capsular polysaccharide 23B. Thus, in an embodiment, the host cells of the invention do not comprise nucleic acid that encodes one or more of these regulatory gene from a *Streptococcus pneumoniae* that are involved in polysaccharide biosynthesis of capsular polysaccharide 23B. The present inventors have found that sufficient yield of capsular polysaccharide 23B may be produced without these regulatory genes.

In an embodiment, a host cell of the invention does not comprise nucleic acids encoding wzg, wzh, wzd or wze from *S. pneumoniae* CP23A, CP23B or CP23F, in particular from CP23B, e.g. amino acid sequences of SEQ ID NOs. 23, 24, 25 and 26 respectively (GenBank: CR931684.1). In an embodiment, a host cell of the invention does not comprise nucleic acid encoding wzg from *S. pneumoniae* CP23A, CP23B or CP23F, in particular from CP23B, e.g. amino acid sequence of SEQ ID NO. 23 (GenBank: CR931684.1). In an embodiment, a host cell of the invention does not comprise nucleic acid encoding wzh from *S. pneumoniae* CP23A, CP23B or CP23F, in particular from CP23B, e.g. amino acid sequence of SEQ ID NO. 24 respectively (GenBank: CR931684.1). In an embodiment, a host cell of the invention does not comprise nucleic acid encoding wzd from *S. pneumoniae* CP23A, CP23B or CP23F, in particular from CP23B, e.g. amino acid sequence of SEQ ID NO. 25 respectively (GenBank: CR931684.1). In an embodiment, a host cell of the invention does not comprise nucleic acids encoding wze from *S. pneumoniae* CP23A, CP23B or CP23F, in particular from CP23B, e.g. amino acid sequence of SEQ ID NO. 26 respectively (GenBank: CR931684.1).

In an embodiment, the host cell of the invention may comprise nucleic acid sequence encoding genes from the CDP-glycerol pathway for biosynthesis of capsular polysaccharide 23B: gtp1, gtp2 and gtp3. In an embodiment, the host cell of the invention may comprise nucleic acid sequence encoding a gtp1 (e.g. from *S. pneumoniae* CP23B) having an amino acid sequence of SEQ ID NO: 34 (GenBank: CR931684.1) or an amino acid sequence at least 80%, 85%, 90%, 92%, 95%, 96%, 97%, 98% or 99% identical to SEQ ID NO: 34, for example comprising at least 100, 150 or 200 contiguous amino acids of the full length sequence. In an embodiment, the host cell of the invention may comprise nucleic acid sequence encoding a gtp2 (e.g. from *S. pneumoniae* CP23B) having an amino acid sequence of SEQ ID NO: 35 (GenBank: CR931684.1) or an amino acid sequence at least 80%, 85%, 90%, 92%, 95%, 96%, 97%, 98% or 99% identical to SEQ ID NO: 35, for example comprising at least 100, 150 or 200 contiguous amino acids of the full length sequence. In an embodiment, the host cell of the invention may comprise nucleic acid sequence encoding a gtp3 (e.g. from *S. pneumoniae* CP23B) having an amino acid sequence of SEQ ID NO: 36 (GenBank: CR931684.1) or an amino acid sequence at least 80%, 85%, 90%, 92%, 95%, 96%, 97%, 98% or 99% identical to SEQ ID NO: 36, for example comprising at least 100, 150 or 200 contiguous amino acids of the full length sequence. In an embodiment, the host cell of the invention may comprise nucleic acid sequence encoding genes from the dTDP-L-rhamnose pathway for biosynthesis of capsular polysaccharide 23B: rmlA, rmlB, rmlC and rmlD. In an embodiment, the host cell of the invention may comprise nucleic acid sequence encoding a rmlA (e.g. from *S. pneumoniae* CP23B) having an amino acid sequence of SEQ ID NO: 37 (GenBank: CR931684.1) or an amino acid sequence at least 80%, 85%, 90%, 92%, 95%, 96%, 97%, 98% or 99% identical to SEQ ID NO: 37, for example comprising at least 100, 150 or 200 contiguous amino acids of the full length sequence. In an embodiment, the host cell of the invention may comprise nucleic acid sequence encoding a rmlC (e.g. from *S. pneumoniae* CP23B) having an amino acid sequence of SEQ ID NO: 38 (GenBank: CR931684.1) or an amino acid sequence at least 80%, 85%, 90%, 92%, 95%, 96%, 97%, 98% or 99% identical to SEQ ID NO: 38, for example comprising at least 100, 150 or 200 contiguous amino acids of the full length sequence. In an embodiment, the host cell of the invention may comprise nucleic acid sequence encoding a rmlB (e.g. from *S. pneumoniae* CP23B) having an amino acid sequence of SEQ ID NO: 39 (GenBank: CR931684.1) or an amino acid sequence at least 80%, 85%, 90%, 92%, 95%, 96%, 97%, 98% or 99% identical to SEQ ID NO: 39, for example comprising at least 100, 150 or 200 contiguous amino acids of the full length sequence. In an embodiment, the host cell of the invention may comprise nucleic acid sequence encoding a rmlD (e.g. from *S. pneumoniae* CP23B) having an amino acid sequence of SEQ ID NO: 40 (GenBank: CR931684.1) or an amino acid sequence at least 80%, 85%, 90%, 92%, 95%, 96%, 97%, 98% or 99% identical to SEQ ID NO: 40, for example comprising at least 100, 150 or 200 contiguous amino acids of the full length sequence.

In a embodiment, the host cell of the present invention comprises *S. pneumoniae* 23B capsular polysaccharide genes from wchA to rmlD (see GenBank: CR931683). The *S. pneumoniae* 23B capsular polysaccharide genes from wchA to rmlD (GenBank: CR931683) may be cloned into a plasmid, e.g. pDOC, which acts as a donor for the replacement of the complete colanic acid cluster (from wza to wcaM) with the 23B cluster. For the replacement a helper plasmid may be used, e.g. pTKRED (GenBank: GU327533.1), which has been mutagenized so that nucleotides A9477 and G9478 have been replaced by C and A, respectively, translating in a V to A mutation in the RepA protein to ensure better temperature sensitivity of the replicon.

In an embodiment, the host cell of the present invention is engineered so that it produces a repeat unit with a trisaccharide backbone (Glc-Gal-βRha) without a terminal α-Rha. In an embodiment, wchA attaches a D-glucose-P onto UndP, followed by WchF attaching a L-rhamnose onto UndPP-Glucose, followed by WchV attaching a D-galactose, followed by WchX attaching a glycerol-2-phosphate to the galactose. In an embodiment Wzx (e.g. wzx flippase from *S. pneumoniae* CP23B) flips a single repeat unit into the periplasm, followed by the Wzy polymerase attaching the D-glucose at reducing end of the growing chain to the D-galactose of the single repeating unit, to produce a polysaccharide.

In an embodiment, a plasmid may be used to produce the CP23B engineered subunit in the cytoplasm, from which it may be translocated into the periplasm by the flippase of CP23B wherein wild type oligosaccharide or polysaccharide can be assembled on it by action of CP23B polymerase (wzy).

Further details on the synthesis of capsular polysaccharides can be found in WO2014/072405A1 and further details on glycoengineering can be found in WO2016/020499A2.

Oligosaccharyltransferases

Oligosaccharyltransferases (OSTs) are membrane-embedded enzymes that transfer oligosaccharides from a lipid carrier to a nascent polypeptide (a type of glycosyltransferase).

N-linked protein glycosylation, the addition of carbohydrate molecules to an asparagine residue in the polypeptide chain of the target protein, is the most common type of post-translational modification occurring in the endoplasmic reticulum of eukaryotic organisms. The process is accomplished by the enzymatic oligosaccharyltransferase complex (OST) responsible for the transfer of a preassembled oligosaccharide from a lipid carrier (e.g. undecaprenyl pyrophosphate or dolichyl pyrophosphate) to an asparagine residue of a nascent protein within the conserved sequence Asn-X-Ser/Thr (where X is any amino acid except proline) in the Endoplasmic reticulum.

In N-linked protein glycosylation, oligosaccharyl transferases transfer lipid-linked oligosaccharides to asparagine residues of nascent polypeptide chains that comprise a N-glycosylation consensus motif, e.g. Asn-X-Ser(Thr), wherein X can be any amino acid except Pro; or Asp(Glu)-X-Asn-Z-Ser(Thr) (SEQ ID NO: 1), wherein X and Z are independently selected from any natural amino acid except Pro (see WO 2006/119987). See, e.g. WO 2003/074687 and WO 2006/119987, the disclosures of which are herein incorporated by reference in their entirety. It has been shown that a bacterium, the food-borne pathogen *Campylobacter jejuni*, can also N-glycosylate its proteins (Wacker et al. Science. 2002; 298(5599):1790-3) due to the fact that it possesses its own glycosylation machinery. The machinery responsible of this reaction is encoded by a cluster called "pgl" (for protein glycosylation).

The *C. jejuni* glycosylation machinery can be transferred to *E. coli* to allow for the glycosylation of recombinant proteins expressed by the *E. coli* cells. Previous studies have demonstrated how to generate *E. coli* strains that can perform N-glycosylation (see, e.g. Wacker et al. Science. 2002; 298 (5599):1790-3; Nita-Lazar et al. Glycobiology. 2005; 15(4):361-7; Feldman et al. Proc Natl Acad Sci USA. 2005; 102(8):3016-21; Kowarik et al. EMBO J. 2006; 25(9):1957-66; Wacker et al. Proc Natl Acad Sci USA. 2006; 103(18): 7088-93; International Patent Application Publication Nos. WO2003/074687, WO2006/119987, WO 2009/104074, and WO/2011/06261, and WO2011/138361).

In an embodiment, the host cells of the invention comprise nucleic acid that encodes an oligosaccharyl transferase. The nucleic acid that encodes an oligosaccharyl transferase can be native to the host cell, or can be introduced into the host cell using genetic approaches, as described above. In an embodiment, the oligosaccharyl transferase is heterologous to the host cell. In an embodiment, the oligosaccharyl transferase is an oligosaccharyl transferase from *Campylobacter*, e.g. *Campylobacter jejuni* (i.e., pglB; see, e.g. Wacker et al. 2002, Science 298:1790-1793; see also, e.g. NCBI Gene ID: 3231775, UniProt Accession NO: O86154). In an embodiment, the oligosaccharyl transferase is an oligosaccharyl transferase from *Campylobacter lari* (see, e.g. NCBI Gene ID: 7410986). In an embodiment, the host cell of the present invention comprises nucleic acid encoding pglB, for example from from *C. jejuni*, in particular from pglB having amino acid sequence of SEQ ID NOs. 62 (GenBank: AF108897.1) or amino acid sequences at least 80%, 85%, 90%, 92%, 95%, 96%, 97%, 98% or 99% identical to SEQ ID NO: 62, for example comprising at least 100, 150 or 200 contiguous amino acids of the full length sequence. In another embodiment, the host cell of the present invention comprises nucleic acid encoding pglB, for example from from *C. jejuni*, in particular from pglB having amino acid sequence of SEQ ID NOs. 65 (GenBank: WP_087705088.1) or amino acid sequences at least 80%, 85%, 90%, 92%, 95%, 96%, 97%, 98% or 99% identical to SEQ ID NO: 65, for example comprising at least 100, 150 or 200 contiguous amino acids of the full length sequence. In another embodiment, the host cell of the present invention comprises nucleic acid encoding pglB, for example a homolog of pglB from *C. jejuni*, in particular a pglB homolog having amino acid sequence of SEQ ID NOs. 65 (GenBank: WP_087705088.1) or amino acid sequences at least 30% identical to SEQ ID NO: 65.

Optionally, the nucleic acid encoding the oligosaccharyl transferase is integrated into the host cell genome and optionally at least one gene of the host cell has been functionally inactivated or deleted, optionally the waaL gene of the host cell has been functionally inactivated or deleted, optionally the waaL gene of the host cell has been replaced by nucleic acid encoding an oligosaccharyltransferase.

In an embodiment, the host cells of the invention comprise nucleic acid sequence encoding an oligosaccharyl transferase, wherein said nucleic acid sequence encoding an oligosaccharyl transferase (e.g. pglB) is integrated into the genome of the host cell.

In an embodiment, provided herein is a modified prokaryotic host cell comprising (i) a glycosyltransferase derived from an capsular polysaccharide cluster from S. pneumoniae, wherein said glycosyltransferase is integrated into the genome of said host cell; (ii) nucleic acid encoding an oligosaccharyl transferase (e.g. pglB), wherein said nucleic acid encoding an oligosaccharyl transferase is integrated into the genome of the host cell; and (iii) a carrier protein, wherein said carrier protein is either plasmid-borne or integrated into the genome of the host cell. There is also provided a method of making a modified prokaryotic host cell comprising (i) integrating a glycosyltransferase derived from an capsular polysaccharide cluster from S. pneumoniae into the genome of said host cell; (ii) integrating nucleic acid encoding an oligosaccharyl transferase (e.g. pglB from Campylobacter jejuni) into the genome of the host cell; and (iii) integrating into a host cell a carrier protein either plasmid-borne or integrated into the genome of the host cell.

Polymerases

In an embodiment, a polymerase (e.g. wzy) is introduced into a host cell of the invention (i.e., the polymerase is heterologous to the host cell). Thus a host cell of the invention may comprise nucleic acid encoding a heterologous polymerase. In an embodiment, the polymerase is a bacterial polymerase. In an embodiment, the polymerase is a capsular polysaccharide polymerase (e.g. wzy) or an O antigen polymerase (e.g. wzy). In an embodiment, the polymerase is a capsular polysaccharide polymerase e.g. from S. pneumoniae.

In an embodiment, the polymerase introduced into the host cells of the invention is the wzy gene from a capsular polysaccharide gene cluster of S. pneumoniae CP1, CP2, CP4, CP5, CP6(A,B,C,D), CP7 (A,B, C), CP8, CP9(A,L,N,V), CP10(A,B,C,F), CP11(A, B,C,D,F), CP12(A,B,F), CP13, CP14 CP15(A,B,C,F), CP16(A,F), CP17(A,F), CP18 (A,B,C,F), CP19(A,B,C,F), CP20, CP21, CP22(A,F), CP23 (A,B,F), CP24(A,B,F), CP25(A,F), CP26, CP27, CP28(A,F), CP29, CP31, CP32(A,F), CP33(A,B,C,D,F), CP34, CP35(A,B,C,D,F), CP36, CP38, CP39, CP40, CP41(A,F), CP42, CP43, CP44, CP45, CP46, CP47(A,F) or CP48. For example, a host cell of the invention may comprise nucleic acid encoding a wzy polymerase from S. pneumoniae CP23A, CP23B or CP23F, in particular from CP23B having an amino acid sequence of SEQ ID NO: 29 (GenBank: CR931684.1) or an amino acid sequence at least 80%, 85%, 90%, 92%, 95%, 96%, 97%, 98% or 99% identical to SEQ ID NO: 29, for example comprising at least 100, 150 or 200 contiguous amino acids of the full length sequence.

Other polymerases that can introduced into the host cells of the invention are from S. pneumoniae described in Bentley S D, Aanensen D M, Mavroidi A, Saunders D, Rabbinowitsch E, Collins M, Donohoe K, Harris D, Murphy L, Quail M A et al: Genetic analysis of the capsular biosynthetic locus from all 90 pneumococcal serotypes. PLoS genetics 2006, 2(3):e31) (Genbank CR931632-CR931722).

In an embodiment, said wzy polymerase is incorporated (e.g. inserted into the genome of or plasmid expressed by) in said host cell as part of a S. pneumoniae capsular polysaccharide cluster, wherein said S. pneumoniae capsular polysaccharide cluster has been modified to comprise the wzy polymerase. In an embodiment, nucleic acid encoding the S. pneumoniae wzy polymerase is inserted into and expressed by the host cells of the invention.

Flippases

In an embodiment, a flippase (wzx) is introduced into a host cell of the invention (i.e., the flippase is heterologous to the host cell). Thus, a host cell of the invention may comprise nucleic acid encoding a heterologous flippase. In an embodiment, the flippase is a bacterial flippase. Flippases translocate lipid-linked wild type repeat units and/or their corresponding engineered (hybrid) repeat units from the cytoplasm into the periplam of host cells (e.g. E. coli). Thus, a host cell of the invention may comprise nucleic acid that encodes a flippase (wzx).

In an embodiment, a flippase of a capsular polysaccharide biosynthetic pathway of S. pneumoniae is introduced into a host cell of the invention. In certain embodiments, the flippase introduced into the host cells of the invention is the wzx gene from a capsular polysaccharide gene cluster of S. pneumoniae CP1, CP2, CP4, CP5, CP6(A,B,C,D), CP7(A,B,C), CP8, CP9(A,L,N,V), CP10(A,B,C,F), CP11(A,B,C,D,F), CP12(A,B,F), CP13, CP14 CP15(A,B,C,F), CP16(A,F), CP17(A,F), CP18(A,B,C,F), CP19(A,B,C,F), CP20, CP21, CP22(A,F), CP23(A,B,F), CP24(A,B,F), CP25(A,F), CP26, CP27, CP28(A,F), CP29, CP31, CP32(A,F), CP33(A,B,C,D,F), CP34, CP35(A,B,C,D,F), CP36, CP38, CP39, CP40, CP41(A,F), CP42, CP43, CP44, CP45, CP46, CP47(A,F), or CP48. In an embodiment, the flippase introduced into the host cells of the invention is the wzx gene from S. pneumoniae CP23A, CP23B or CP23F, in particular from CP23B having an amino acid sequence of SEQ ID NO: 32 or an amino acid sequence at least 80%, 85%, 90%, 92%, 95%, 96%, 97%, 98% or 99% identical to SEQ ID NO: 32, for example comprising at least 100, 150 or 200 contiguous amino acids of the full length sequence.

In an embodiment, the flippase (e.g. Wzx flippase from S. pneumoniae CP23B) flips a single repeat unit into the periplasm, followed by the polymerase attaching the D-glucose at reducing end of the growing chain to the β-L-rhamnose of the single repeat unit, to produce an oligosaccharide or polysaccharide.

Other flippases that can be introduced into the host cells of the invention are for example from Campylobacter jejuni (e.g. pglK). Other flippases that can introduced into the host cells of the invention are from S. pneumoniae described in Bentley S D, Aanensen D M, Mavroidi A, Saunders D, Rabbinowitsch E, Collins M, Donohoe K, Harris D, Murphy L, Quail M A et al. "Genetic analysis of the capsular biosynthetic locus from all 90 pneumococcal serotypes" PLoS genetics 2006, 2(3):e31) (Genbank CR931632-CR931722).

Enzymes that Modify Monosaccharides

Accessory Enzymes

In an embodiment, nucleic acids encoding one or more accessory enzymes are introduced into the host cells of the invention. Thus, a host cell of the invention may further comprise one or more of these accessory enzymes. Such nucleic acids encoding one or more accessory enzymes can be either plasmid-borne or integrated into the genome of the host cells of the invention. Exemplary accessory enzymes include, without limitation, epimerases, branching, modifying (e.g. to add cholins, glycerolphosphates, pyruvates), amidating, chain length regulating, acetylating, formylating, polymerizing enzymes. For example, in one embodiment the the host cell of the present invention comprises nucleic acid encoding a chain length regulator, for example fepE (ferric enterobactin (Enterochelin) transporter) from Salmonella typhimurium having amino acid sequence of SEQ ID NO. 66

(WP_001139584.1) or amino acid sequences at least 80%, 85%, 90%, 92%, 95%, 96%, 97%, 98% or 99% identical to SEQ ID NO: 66, for example comprising at least 100, 150 or 200 contiguous amino acids of the full length sequence.

In certain embodiments, enzymes that are capable of modifying monosaccharides are introduced into a host cell of the invention (i.e., the enzymes that are capable of modifying monosaccharides are heterologous to the host cell). Such enzymes include, e.g. epimerases and racemases. Thus, a host cell of the invention may further comprise nucleic acid encoding an epimerase and/or racemase.

In an embodiment, the epimerases and racemases are from bacteria. In certain embodiments, the epimerases and/or racemases introduced into the host cells of the invention are from *Escherichia* species, *Shigella* species, *Klebsiella* species, *Xhantomonas* species, *Salmonella* species, *Yersinia* species, *Aeromonas* species, *Francisella* species, *Helicobacter* species, *Proteus* species, *Lactococcus* species, *Lactobacillus* species, *Pseudomonas* species, *Corynebacterium* species, *Streptomyces* species, *Streptococcus* species, *Enterococcus* species, *Staphylococcus* species, *Bacillus* species, *Clostridium* species, *Listeria* species, or *Campylobacter* species. In certain embodiments, the epimerase inserted into a host cell of the invention is an epimerase described in International Patent Application Publication No. WO2011/062615.

In an embodiment, a host cell of the invention further comprises RcsA (an activator of CP synthesis). RcsA is an unstable positive regulator required for the synthesis of colanic acid capsular polysaccharide in *Escherichia coli*. (GenBank Accession M58003 (nucleotide sequence), AAA82970 (amino acid sequence) SEQ ID NO:64)

Genetic Background

Exemplary host cells that can be used to generate the host cells of the invention include, without limitation, *Escherichia* species, *Shigella* species, *Klebsiella* species, *Xhantomonas* species, *Salmonella* species, *Yersinia* species, *Lactococcus* species, *Lactobacillus* species, *Pseudomonas* species, *Corynebacterium* species, *Streptomyces* species, *Streptococcus* species, *Staphylococcus* species, *Bacillus* species, and *Clostridium* species. In an embodiment, the host cell used herein is *E. coli*.

In an embodiment, the host cell genetic background is modified by, e.g. deletion of one or more genes. Exemplary genes that can be deleted in host cells (and, in some cases, replaced with other desired nucleic acid sequences) include genes of host cells involved in glycolipid biosynthesis, such as waaL (see, e.g. Feldman et al. 2005, PNAS USA 102: 3016-3021), the O antigen cluster (rfb or wb), enterobacterial common antigen cluster (wec), the lipid A core biosynthesis cluster (waa), and prophage O antigen modification clusters like the gtrABS cluster. In an embodiment, one or more of the waaL gene, gtrA gene, gtrB gene, gtrS gene, or a gene or genes from the wec cluster or a gene or genes from the rfb gene cluster are deleted or functionally inactivated from the genome of a prokaryotic host cell of the invention. In one embodiment, a host cell used herein is *E. coli*, wherein the waaL gene, gtrA gene, gtrB gene, gtrS gene are deleted or functionally inactivated from the genome of the host cell. In another embodiment, a host cell used herein is *E. coli*, wherein the waaL gene and gtrS gene are deleted or functionally inactivated from the genome of the host cell. In another embodiment, a host cell used herein is *E. coli*, wherein the waaL gene and genes from the wec cluster are deleted or functionally inactivated from the genome of the host cell.

Benefits

The host cells of the invention are of particular commercial importance and relevance, as they allow for large scale fermentation of bioconjugates comprising saccharide, for example, *Streptococcus* antigens that can be used as therapeutics (e.g. in immunogenic compositions, vaccines), at a lower risk due to the increased stability of the chromosomally inserted DNA and thus expression of the DNA of interest during fermentation. The host cells of the invention are advantageous over host cells that rely on plasmid borne expression of nucleic acids required for generation of the bioconjugates of the invention because, inter alia, antibiotic selection during fermentation is not required once the heterologous DNA is inserted into the host cell genome. That is, when the insert DNA is inserted in the chromosome, it doesn't need to be selected for, because it is propagated along with replication of the host genome. Further, it is a disadvantage in plasmid borne systems that with every generation (i.e., cycle of host cell replication) the risk for losing the plasmid increases. This loss of plasmid is due to the sometimes inappropriate distribution of plasmids to daughter cells at the stage of cell separation during cell division. At large scale, bacterial cell cultures duplicate more often than in smaller fermentation scales to reach high cell densities. Thus, higher cell stability and insert DNA expression leads to higher product yields, providing a distinct advantage. Cell stability is furthermore a process acceptance criteria for approval by regulatory authorities, while antibiotic selection is generally not desired during fermentation for various reasons, e.g. antibiotics present as impurities in the final medicial products and bear the risk of causing allergic reactions, and antibiotics may promote antibiotic resistance (e.g. by gene transfer or selection of resistant pathogens).

The present application provides host cells for use in making bioconjugates comprising saccharide antigens that can be used as therapeutics (e.g. in immunogenic compositions, vaccines), wherein certain genetic elements required to drive the production of bioconjugates are integrated stably into the host cell genome. Consequently the host cell can contain a reduced number of plasmids, just a single plasmid or no plasmids at all. In some embodiments, the presence of a single plasmid can result in greater flexibility of the production strain and the ability to change the nature of the conjugation (in terms of its saccharide or carrier protein content) easily leading to greater flexibility of the production strain.

In general, a reduction in the use of plasmids leads to a production strain which is more suited for use in the production of medicinal products. A drawback of essential genetic material being present on plasmids is the requirement for selection pressure to maintain the episomal elements in the host cell. The selection pressure requires the use of antibiotics, which is undesirable for the production of medicinal products due to, e.g. the danger of allergic reactions against the antibiotics and the additional costs of manufacturing. Furthermore, selection pressure is often not complete, resulting in inhomogeneous bacterial cultures in which some clones have lost the plasmid and thus are not producing the bioconjugate. The host cells of the invention therefore are able to produce a safer product that can be obtained in high yields.

Bioconjugates

The host cells of the invention can be used to produce bioconjugates comprising a pneumococcal saccharide of the invention, for example a pneumococcal saccharide of the invention linked to a carrier protein. Methods of producing bioconjugates using host cells are described for example in WO 2003/074687 and WO 2006/119987. Bioconjugates, as described herein, have advantageous properties over chemical conjugates of antigen-carrier protein, in that they require less chemicals in manufacture and are more consistent in terms of the final product generated.

In an embodiment, provided herein is a bioconjugate comprising a recombinant pneumococcal saccharide of the invention linked to a carrier protein.

The bioconjugates of the invention can be purified (to remove host cell impurities and unglycosylated carrier protein) e.g. by chromatography (e.g. ion exchange, anionic exchange, affinity, and sizing column chromatography), centrifugation, differential solubility, or by any other standard technique for the purification of proteins. See, e.g. Saraswat et al. 2013, Biomed. Res. Int. ID #312709 (p. 1-18); see also the methods described in WO 2009/104074. For example, affinity column IMAC (Immobilized metal ion affinity chromatography) may be used to bind the poly-histidine tag of the carrier protein, followed by two anion exchange chromatography and a size exclusion chromatography (SEC). Further, the bioconjugates may be fused to heterologous polypeptide sequences described herein or otherwise known in the art to facilitate purification. The actual conditions used to purify a particular bioconjugate will depend, in part, on the synthesis strategy and on factors such as net charge, hydrophobicity, and/or hydrophilicity of the bioconjugate, and will be apparent to those having skill in the art.

A further aspect of the invention is a process for producing a bioconjugate that comprises (or consists of) a recombinant pneumococcal saccharide of the invention linked to a carrier protein, said process comprising (i) culturing the host cell of the invention under conditions suitable for the production of proteins (and optionally under conditions suitable for the production of saccharides) and (ii) isolating the bioconjugate produced by said host cell.

A further aspect of the invention is a bioconjugate produced by the process of the invention, wherein said bioconjugate comprises a recombinant pneumococcal saccharide of the invention linked to a carrier protein.

Analytical Methods

Various methods can be used to analyze the structural compositions and sugar chain lengths of the bioconjugates of the invention.

In one embodiment, hydrazinolysis can be used to analyze glycans. First, polysaccharides are released from their protein carriers by incubation with hydrazine according to the manufacturer's instructions (Ludger Liberate Hydrazinolysis Glycan Release Kit, Oxfordshire, UK). The nucleophile hydrazine attacks the glycosidic bond between the polysaccharide and the carrier protein and allows release of the attached glycans. N-acetyl groups are lost during this treatment and have to be reconstituted by re-N-acetylation. The free glycans are purified on carbon columns and subsequently labeled at the reducing end with the fluorophor 2-amino benzamide. See Bigge J C, Patel T P, Bruce J A, Goulding P N, Charles S M, Parekh R B: Nonselective and efficient fluorescent labeling of glycans using 2-amino benzamide and anthranilic acid. Anal Biochem 1995, 230(2): 229-238. The labeled polysaccharides are separated on a GlycoSep-N column (GL Sciences) according to the HPLC protocol of Royle et al. See Royle L, Mattu T S, Hart E, Langridge J I, Merry A H, Murphy N, Harvey D J, Dwek R A, Rudd P M: An analytical and structural database provides a strategy for sequencing O-glycans from microgram quantities of glycoproteins. Anal Biochem 2002, 304(1):70-90. The resulting fluorescence chromatogram indicates the polysaccharide length and number of repeat units. Structural information can be gathered by collecting individual peaks and subsequently performing MS/MS analysis. Thereby the monosaccharide composition and sequence of the repeat unit could be confirmed and additionally in homogeneity of the polysaccharide composition could be identified.

In another embodiment, SDS-PAGE or capillary gel electrophoresis can be used to assess glycans and bioconjugates. Polymer length for the O antigen glycans is defined by the number of repeat units that are linearly assembled. This means that the typical ladder like pattern is a consequence of different repeat unit numbers that compose the glycan. Thus, two bands next to each other in SDS PAGE or other techniques that separate by size differ by only a single repeat unit. These discrete differences are exploited when analyzing glycoproteins for glycan size. The unglycosylated carrier protein and the bioconjugate with different polymer chain lengths separate according to their electrophoretic mobilities. The first detectable repeat unit number ($n_1$) and the average repeat unit number ($n_{average}$) present on a bioconjugate are measured. These parameters can be used to demonstrate batch to batch consistency or polysaccharide stability.

In another embodiment, high mass MS and size exclusion HPLC could be applied to measure the size of the complete bioconjugates.

In another embodiment, an anthrone-sulfuric acid assay can be used to measure polysaccharide yields. See Leyva A, Quintana A, Sanchez M, Rodriguez E N, Cremata J, Sanchez J C: Rapid and sensitive anthrone-sulfuric acid assay in microplate format to quantify carbohydrate in biopharmaceutical products: method development and validation. Biologicals: journal of the International Association of Biological Standardization 2008, 36(2):134-141. In another embodiment, a Methylpentose assay can be used to measure polysaccharide yields. See, e.g. Dische et al. J Biol Chem. 1948 September; 175(2):595-603.

Change in Glycosylation Site Usage

To show that the site usage in a specific protein is changed in a multiple plasmid system as opposed to an inserted system, the glycosylation site usage must be quantified. Methods to do so are listed below.

Glycopeptide LC-MS/MS: bioconjugates are digested with protease(s), and the peptides are separated by a suitable chromatographic method (C18, Hydrophilic interaction HPLC HILIC, GlycoSepN columns, SE HPLC, AE HPLC), and the different peptides are identified using MS/MS. This method can be used with our without previous sugar chain shortening by chemical (smith degradation) or enzymatic methods. Quantification of glycopeptide peaks using UV detection at 215 to 280 nm allow relative determination of glycosylation site usage.

Size exclusion HPLC: Higher glycosylation site usage is reflected by a earlier elution time from a SE HPLC column.

Homogeneity

Bioconjugate homogeneity (i.e., the homogeneity of the attached sugar residues) can be assessed using methods that measure glycan length and hydrodynamic radius.

Analytical Methods for Testing Benefit

Yield.

Yield is measured as carbohydrate amount derived from a liter of bacterial production culture grown in a bioreactor under controlled and optimized conditions. After purification of bioconjugate, the carbohydrate yields can be directly measured by either the anthrone assay or ELISA using carbohydrate specific antisera. Indirect measurements are possible by using the protein amount (measured by BCA, Lowry, or bardford assays) and the glycan length and structure to calculate a theoretical carbohydrate amount per gram of protein. In addition, yield can also be measured by drying the glycoprotein preparation from a volatile buffer and using a balance to measure the weight.

Homogeneity.

Homogeneity means the variability of glycan length and possibly the number of glycosylation sites. Methods listed above can be used for this purpose. SE-HPLC allows the measurement of the hydrodynamic radius. Higher numbers of glycosylation sites in the carrier lead to higher variation in hydrodynamic radius compared to a carrier with less glycosylation sites. However, when single glycan chains are analyzed, they may be more homogenous due to the more controlled length. Glycan length is measured by hydrazinolysis, SDS PAGE, and CGE. In addition, homogeneity can also mean that certain glycosylation site usage patterns change to a broader/narrower range. These factors can be measured by Glycopeptide LC-MS/MS.

Strain Stability and Reproducibility.

Strain stability during bacterial fermentation in absence of selective pressure is measured by direct and indirect methods that confirm presence or absence of the recombinant DNA in production culture cells. Culture volume influence can be simulated by elongated culturing times meaning increased generation times. The more generations in fermentation, the more it is likely that a recombinant element is lost. Loss of a recombinant element is considered instability. Indirect methods rely on the association of selection cassettes with recombinant DNA, e.g. the antibiotic resistance cassettes in a plasmid. Production culture cells are plated on selective media, e.g. LB plates supplemented with antibiotics or other chemicals related to a selection system, and resistant colonies are considered as positive for the recombinant DNA associated to the respective selection chemical. In the case of a multiple plasmid system, resistant colonies to multiple antibiotics are counted and the proportion of cells containing all three resistances is considered the stable population. Alternatively, quantitative PCR can be used to measure the amount of recombinant DNA of the three recombinant elements in the presence, absence of selection, and at different time points of fermentation. Thus, the relative and absolute amount of recombinant DNA is measured and compared. Reproducibility of the production process is measured by the complete analysis of consistency batches by the methods stated in this application.

Immunogenic Compositions

The pneumococcal saccharides and conjugates (e.g. bioconjugate), of the invention are particularly suited for inclusion in immunogenic compositions and vaccines. The present invention provides an immunogenic composition comprising the pneumococcal saccharide of the invention, or the conjugate of the invention, or the bioconjugate of the invention.

Immunogenic compositions comprise an immunologically effective amount of the pneumococcal saccharide or conjugate (e.g. bioconjugate) of the invention, as well as any other components. By "immunologically effective amount", it is meant that the administration of that amount to an individual, either as a single dose or as part of a series is effective for treatment or prevention. This amount varies depending on the health and physical condition of the individual to be treated, age, the degree of protection desired, the formulation of the vaccine and other relevant factors. It is expected that the amount will fall in a relatively broad range that can be determined through routine trials.

In an embodiment, the immunogenic composition of the invention further comprises a pharmaceutically acceptable excipient, carrier or diluent. Also provided is a method of making the immunogenic composition of the invention comprising the step of mixing the pneumococcal saccharide or the conjugate (e.g. bioconjugate) of the invention with a pharmaceutically acceptable excipient, carrier or diluent.

Pharmaceutically acceptable excipients and carriers can be selected by those of skill in the art. For example, the pharmaceutically acceptable excipient or carrier can include a buffer, such as Tris (trimethamine), phosphate (e.g. sodium phosphate), acetate, borate (e.g. sodium borate), citrate, glycine, histidine and succinate (e.g. sodium succinate), suitably sodium chloride, histidine, sodium phosphate or sodium succinate. The pharmaceutically acceptable excipient may include a salt, for example sodium chloride, potassium chloride or magnesium chloride. Optionally, the pharmaceutically acceptable excipient contains at least one component that stabilizes solubility and/or stability. Examples of solubilizing/stabilizing agents include detergents, for example laurel sarcosine and/or polysorbate (e.g. TWEEN 80 (Polysorbate-80)). Examples of stabilizing agents also include poloxamer (e.g. poloxamer 124, poloxamer 188, poloxamer 237, poloxamer 338 and poloxamer 407). The pharmaceutically acceptable excipient may include a non-ionic surfactant, for example polyoxyethylene sorbitan fatty acid esters, TWEEN 80 (Polysorbate-80), TWEEN 60 (Polysorbate-60), TWEEN 40 (Polysorbate-40) and TWEEN 20 (Polysorbate-20), or polyoxyethylene alkyl ethers (suitably polysorbate-80). Alternative solubilizing/stabilizing agents include arginine, and glass forming polyols (such as sucrose, trehalose and the like). The pharmaceutically excipient may be a preservative, for example phenol, 2-phenoxyethanol, or thiomersal. Other pharmaceutically acceptable excipients include sugars (e.g. lactose, sucrose), and proteins (e.g. gelatine and albumin). Pharmaceutically acceptable carriers include water, saline solutions, aqueous dextrose and glycerol solutions. Numerous pharmaceutically acceptable excipients and carriers are described, for example, in Remington's Pharmaceutical Sciences, by E. W. Martin, Mack Publishing Co. Easton, Pa., 5th Edition (1975).

Immunogenic compositions if the invention may also contain diluents such as water, saline, glycerol etc. Additionally, auxiliary substances, such as wetting or emulsifying agents, pH buffering substances, polyols and the like may be present.

In an embodiment, the immunogenic composition of the invention additionally comprises one or more buffers, e.g. phosphate buffer and/or sucrose phosphate glutamate buffer. In other embodiments, the immunogenic composition of the invention does not comprise a buffer.

In an embodiment, the immunogenic composition of the invention additionally comprises one or more salts, e.g. sodium chloride, calcium chloride, sodium phosphate, monosodium glutamate, and aluminum salts (e.g. aluminum hydroxide, aluminum phosphate, alum (potassium aluminum sulfate), or a mixture of such aluminum salts). In other embodiments, the immunogenic composition of the invention does not comprise a salt.

In an embodiment, the immunogenic composition of the invention additionally comprises a preservative, e.g. a mercury derivative thimerosal or 2-phenoxyethanol. In an embodiment, the immunogenic composition of the invention comprises 0.001% to 0.01% thimerosal. In an embodiment, the immunogenic composition of the invention comprises 0.001% to 0.01% 2-phenoxyethanol. In other embodiments, the immunogenic composition or vaccine of the invention do not comprise a preservative.

In an embodiment, the immunogenic composition of the invention additionally comprises a detergent e.g. polysorbate, such as TWEEN 80 (Polysorbate-80). Detergents may be present at low levels e.g. <0.01%, but higher levels have been suggested for stabilising antigen formulations e.g. up to 10%.

The immunogenic compositions comprising the pneumococcal saccharide of the invention or conjugates (or bioconjugates) may comprise any additional components suitable for use in pharmaceutical administration. In an embodiment, the immunogenic compositions of the invention are monovalent formulations. In other embodiments, the immunogenic compositions of the invention are multivalent formulations, e.g. bivalent, trivalent, and tetravalent formulations. For example, a multivalent formulation comprises more than one antigen for example more than one conjugate.

In an embodiment, the immunogenic composition of the invention comprises 10 or more, 11 or more, 12 or more, 13 or more, 14 or more, 15 or more, 16 or more, 17 or more, 18 or more, 19 or more, 20 or more capsular saccharide conjugates from different *S. pneumoniae* serotypes. The immunogenic composition of the invention may comprise 10, 11, 12, 13, 14, 15, 16, 17, 18, 19, 20, 21, 22, 23, 24, or 25 capsular saccharide conjugates from different *S. pneumoniae* serotypes.

The immunogenic compositions of the invention may also comprise *S. pneumoniae* capsular saccharides (suitably conjugated to a carrier protein), for example as described in WO2007/071707A2. The *S. pneumoniae* capsular saccharides (suitably conjugated to a carrier protein) may be selected from a *Streptococcus pneumoniae* serotypes 1, 2, 3, 4, 5, 6A, 6B, 7A, 7B, 7C, 8, 9A, 9L, 9N, 9V, 10A, 10B, 10C, 10F, 11A, 11B, 11C, 11D, 11F, 12A, 12B, 12F, 13, 14, 15A, 15B, 15C, 15F, 16A, 16F, 17A, 17F, 18A, 18B, 18C, 18F, 19A, 19B, 19C, 19F, 20, 21, 22A, 22F, 23A, 23B, 23F, 24A, 24B, 24F, 25A, 25F, 26, 27, 28A, 28F, 29, 31, 32A, 32F, 33A, 33B, 33C, 33D, 33F, 34, 35A, 35B, 35C, 35D, 35F, 36, 37, 38, 39, 40, 41A, 41F, 42, 43, 44, 45, 46, 47A, 47F or 48 capsular saccharide. For example, the *S. pneumoniae* capsular saccharides (suitably conjugated to a carrier protein) may be selected from a *Streptococcus pneumoniae* serotypes 1, 2, 3, 4, 5, 6A, 6B, 7F, 8, 9N, 9V, 10A, 11A, 12F, 14, 15B, 17F, 18C, 19A, 19F, 20, 22F, 23F and 33F. In an embodiment, at least four serotypes are included in the composition, e.g. 6B, 14, 19F and 23F (suitably conjugated to a carrier protein). In another embodiment, at least 7 serotypes are included in the composition, e.g. 4, 6B, 9V, 14, 18C, 19F and 23F (suitably conjugated to a carrier protein). In another embodiment the immunogenic composition comprises 10 or more, 11 or more, 12 or more, 13 or more, 14 or more, 15 or more, 16 or more, 17 or more, 19 or more, or 20 capsular saccharides from different *S. pneumoniae* serotypes (suitably conjugated to a carrier protein). In an embodiment the immunogenic composition comprises 10 to 23 capsular saccharides from different *S. pneumoniae* serotypes (suitably conjugated to a carrier protein). In an embodiment, the vaccine may be an 11-valent vaccine. For example, a 11-valent vaccine may comprise saccharides from serotypes 1, 4, 5, 6A, 6B, 7F, 9V, 14, 18C, 19F and 23F. In an embodiment, the vaccine may be an 12-valent or 13-valent vaccine. A 12 or 13-valent paediatric (infant) vaccine may also include the 11 valent formulation supplemented with serotypes 19A, or 22F, whereas a 13-valent elderly vaccine may include the 11 valent formulation supplemented with serotypes 19A and 22F, 8 and 12F, or 8 and 15, or 8 and 19A, or 8 and 22F, or 12F and 15, or 12F and 19A, or 12F and 22F, or 15 and 19A, or 15 and 22F. In an embodiment, the vaccine may be a 14-valent or 15-valent vaccine. A 14 or 15-valent paediatric vaccine may include the 11 valent formulation described above supplemented with serotypes 3, 19A and 22F; serotypes 8, 19A and 22F; serotypes 12F, 19A and 22F; serotypes 15, 19A and 22F; serotypes 3, 8, 19A and 22F; serotypes 3, 12F, 19A and 22F; serotypes 3, 15, 19A and 22F. In an embodiment, the vaccine may be a 16-valent vaccine. A 16 valent vaccine may include the 11 valent formulation described above supplemented with serotypes 3, 15B, 19A, 22F and 23F. A 16 valent vaccine may include the 11 valent formulation described above supplemented with serotypes 3, 15B, 19A, 22F and 33F. In an embodiment, the vaccine may be a 19-valent vaccine. A 19 valent vaccine may include the 11 valent formulation described above supplemented with serotypes 8, 10A, 11A, 12F, 15B, 19A, 22F and 23F. A 19 valent vaccine may include the 11 valent formulation described above supplemented with serotypes 8, 10A, 11A, 12F, 15B, 19A, 22F and 33F. In an embodiment, the vaccine may be a 20-valent vaccine. A 20 valent vaccine may include the 11 valent formulation described above supplemented with serotypes 3, 8, 10A, 11A, 12F, 15B, 19A, 22F and 23F. A 20 valent vaccine may include the 11 valent formulation described above supplemented with serotypes 3, 8, 10A, 11A, 12F, 15B, 19A, 22F and 33F. In an embodiment, the vaccine may be a 21-valent vaccine. In an embodiment, the vaccine may be a 22-valent vaccine. In an embodiment, the vaccine may be a 23-valent vaccine. In an embodiment, the vaccine may be a 24-valent vaccine. In an embodiment, the vaccine may be a 25-valent vaccine.

The immunogenic composition of the invention may optionally further comprise additional antigens. Examples of such additional antigens are *S. pneumoniae* antigens selected from the following categories, such as proteins having a Type II Signal sequence motif of LXXC (where X is any amino acid, e.g. the polyhistidine triad family (PhtX)), choline binding proteins (e.g. CbpX (choline binding protein family), PcpA (pneumococcal choline-binding protein A)), proteins having a Type I Signal sequence motif (e.g. Sp101), and proteins having a LPXTG motif (where X is any amino acid, e.g. Sp128, Sp130). Thus, the immunogenic composition of the invention may comprise one or more *S. pneumoniae* proteins selected from polyhistidine triad family (PhtX), Choline Binding Protein family (CbpX), CbpX truncates, pneumococcal autolysin family (LytX) (e.g. LytA (N-acetylmuramoyl-l-alanine amidase), LytB, LytC), LytX truncates, CbpX truncate-LytX truncate chimeric proteins, PspA (pneumococcal surface protein A), PsaA (pneumococcal surface adhesion A), Sp128, Sp101, Sp130, Sp125 and Sp133. In a further embodiment, the immunogenic composition of the invention comprises 2 or more proteins selected from the group consisting of the polyhistidine triad family (PhtX), Choline Binding Protein family (CbpX), CbpX truncates, LytX family, LytX truncates, CbpXtruncate-LytXtruncate chimeric proteins (or fusions), PspA (pneumococcal surface protein A), PsaA (pneumococcal surface adhesion A), and Sp128. In a further embodiment, the immunogenic composition comprises 2 or more proteins selected from the group consisting of the polyhistidine triad family (PhtX) e.g. PhtD, Choline Binding Protein family (CbpX), CbpX truncates, LytX family, LytX truncates, CbpX truncate-LytX truncate chimeric proteins (or fusions), and Sp128.

In an embodiment, the *S. pneumoniae* antigen selected from member(s) of the polyhistidine triad family is PhtD.

The term "PhtD" as used herein includes the full length protein with the signal sequence attached or the mature full length protein with the signal peptide (for example 20 amino acids at N-terminus) removed, and immunogenic fragments, variants and/or fusion proteins thereof, e.g. SEQ ID NO: 4 of WO00/37105. In one aspect, PhtD is the full length protein with the signal sequence attached e.g. SEQ ID NO: 4 of WO00/37105. In another aspect, PhtD is a sequence comprising the mature full length protein with the signal peptide (for example 20 amino acids at N-terminus) removed, e.g. amino acids 21-838 of SEQ ID NO: 4 of WO00/37105. Suitably, the PhtD sequence comprises an N-terminal methionine. The present invention also includes PhtD polypeptides which are immunogenic fragments of PhtD, variants of PhtD and/or fusion proteins of PhtD. For example, as described in WO00/37105, WO00/39299, U.S. Pat. No. 6,699,703 and WO09/12588.

Immunogenic compositions of the present invention may comprise additional antigens capable of eliciting an immune response against a human or animal pathogen. These additional antigens include, for example, additional *S. pneumoniae* antigens, e.g. *S. pneumoniae* protein antigens. Such proteins may be used as carrier proteins, or may be present as a free protein (unconjugated), or may be present both as a carrier protein and a free protein. Where the additional antigen is a pneumococcal protein, the protein may be conjugated for example to a saccharide. In an embodiment, the immunogenic composition of the invention further comprises one or more unconjugated *S. pneumoniae* proteins, for example, unconjugated pneumococcal polyhistidine triad protein D (PhtD). In another embodiment, the immunogenic composition of the invention further comprises one or more conjugated *S. pneumoniae* proteins, for example, conjugated pneumococcal polyhistidine triad protein D (PhtD).

The additional *Streptococcus pneumoniae* antigens are either surface exposed, at least during part of the life cycle of the pneumococcus, or are proteins which are secreted or released by the pneumococcus. In an embodiment, the *S. pneumoniae* antigens are selected from the following categories, such as proteins having a Type II Signal sequence motif of LXXC (where X is any amino acid, e.g. the polyhistidine triad family (PhtX)), choline binding proteins (e.g. CbpX (choline binding protein family), PcpA (pneumococcal choline-binding protein A)), proteins having a Type I Signal sequence motif (e.g. Sp101), and proteins having a LPXTG motif (where X is any amino acid, e.g., Sp128, Sp130). Preferred examples within these categories (or motifs) are the following proteins, or immunologically functional equivalents thereof. Thus, the immunogenic composition of the invention may comprise one or more *S. pneumoniae* proteins selected from polyhistidine triad family (PhtX), Choline Binding Protein family (CbpX), CbpX truncates, pneumococcal autolysin family (LytX) (e.g. LytA (N-acetylmuramoyl-l-alanine amidase), LytB, LytC), LytX truncates, CbpX truncate-LytX truncate chimeric proteins, PspA (pneumococcal surface protein A), PsaA (pneumococcal surface adhesion A), Sp128, Sp101, Sp130, Sp125 and Sp133. In a further embodiment, the immunogenic composition of the invention comprises 2 or more proteins selected from the group consisting of the polyhistidine triad family (PhtX), Choline Binding Protein family (CbpX), CbpX truncates, LytX family, LytX truncates, CbpXtruncate-LytXtruncate chimeric proteins (or fusions), PspA (pneumococcal surface protein A), PsaA (pneumococcal surface adhesion A), and Sp128. In a further embodiment, the immunogenic composition comprises 2 or more proteins selected from the group consisting of the polyhistidine triad family (PhtX), Choline Binding Protein family (CbpX), CbpX truncates, LytX family, LytX truncates, CbpX truncate-LytX truncate chimeric proteins (or fusions), and Sp128.

The Pht (polyhistidine triad) family comprises proteins PhtA, PhtB, PhtD, and PhtE. The family is characterized by a lipidation sequence, two domains separated by a proline-rich region and several histidine triads, possibly involved in metal or nucleoside binding or enzymatic activity, (3-5) coiled-coil regions, a conserved N-terminus and a heterogeneous C terminus. It is present in all strains of pneumococci tested. Homologous proteins have also been found in other Streptococci and *Neisseria*. In one embodiment of the invention, the immunogenic composition comprises PhtD. It is understood, however, that the terms Pht A, B, D, and E refer to proteins having sequences disclosed in the citations below as well as variants thereof that have a sequence homology that is at least 90% identical to the proteins described below, e.g. amino acids 21-838 of SEQ ID NO: 4 of WO00/37105. In an embodiment it is at least 95% identical and in another embodiment it is 97% identical to the proteins described below, e.g. amino acids 21-838 of SEQ ID NO: 4 of WO00/37105.

With regards to the PhtX proteins, PhtA is disclosed in WO 98/18930, and is also referred to Sp36. As noted herein, it is a protein from the polyhistidine triad family and has the type II signal motif of LXXC. PhtD is disclosed in WO 00/37105, and is also referred to Sp036D. As noted herein, it also is a protein from the polyhistidine triad family and has the type II LXXC signal motif. PhtB is disclosed in WO 00/37105, and is also referred to Sp036B. Another member of the PhtB family is the C3-Degrading Polypeptide, as disclosed in WO 00/17370. This protein also is from the polyhistidine triad family and has the type II LXXC signal motif. A preferred immunologically functional equivalent is the protein Sp42 disclosed in WO 98/18930. A PhtB truncate (a "truncate" being part of a protein having an N-terminal and/or C-terminal deletion) (approximately 79 kD) is disclosed in WO99/15675 which is also considered a member of the PhtX family. PhtE is disclosed in WO00/30299 and is referred to as BVH-3. Where any Pht protein is referred to herein, it is meant that immunogenic fragments or fusions thereof of the Pht protein can be used.

In one embodiment, the *S. pneumoniae* antigen selected from member(s) of the polyhistidine triad family is PhtD. The term "PhtD" as used herein includes the full length protein with the signal sequence attached or the mature full length protein with the signal peptide (for example 20 amino acids at N-terminus) removed, and immunogenic fragments, variants and/or fusion proteins thereof, e.g. SEQ ID NO: 4 of WO00/37105. In one aspect, PhtD is the full length protein with the signal sequence attached e.g. SEQ ID NO: 4 of WO00/37105. In another aspect, PhtD is a sequence comprising the mature full length protein with the signal peptide (for example 20 amino acids at N-terminus) removed, e.g. amino acids 21-838 of SEQ ID NO: 4 of WO00/37105. Suitably, the PhtD sequence comprises an N-terminal methionine. The present invention also includes PhtD polypeptides which are immunogenic fragments of PhtD, variants of PhtD and/or fusion proteins of PhtD. For example, as described in WO00/37105, WO00/39299, U.S. Pat. No. 6,699,703 and WO09/12588.

Where immunogenic fragments of PhtD proteins are used (separately or as part of a fusion protein), these immunogenic fragments will be at least about 15, at least about 20, at least about 40, or at least about 60 contiguous amino acid residues in length, e.g. from a PhtD amino acid sequence in WO00/37105 or WO00/39299, such as SEQ ID NO: 4 of WO00/37105. In an embodiment of the invention, immunogenic fragments of PhtD protein comprise at least about 15, at least about 20, at least about 40, or at least about 60 contiguous amino acid residues of the sequence shown in SEQ ID NO: 4 of WO00/37105, wherein said polypeptide is capable of eliciting an immune response specific for said amino acid sequence. In an embodiment, the immunogenic composition of the invention comprises an immunogenic fragment of PhtD, for example described in WO09/12601, WO01/98334 and WO09/12588. Where immunogenic fragments of PhtD proteins are used (separately or as part of a fusion protein), each immunogenic fragment optionally contains one or more histidine triad motif(s) of such polypeptides. A histidine triad motif is the portion of polypeptide that has the sequence HxxHxH where H is histidine and x is an amino acid other than histidine. In an embodiment of the present invention, the or each immunogenic fragment contains exactly or at least 2, 3, 4 or 5 histidine triad motifs (optionally, with native PhtD sequence between the 2 or more triads, or intra-triad sequence) where the immunogenic fragment is more than 50, 60, 70, 80, 90 or 100% identical to a native pneumococcal intra-triad PhtD sequence (e.g. the intra-triad sequence shown in SEQ ID NO: 4 of WO00/37105). Immunogenic fragments of PhtD proteins optionally contain one or more coiled coil regions of such polypeptides. A coiled coil region is a region predicted by "Coils" algorithm Lupus, A et al (1991) Science 252; 1162-1164. In an embodiment of the present invention, each immunogenic fragment contains exactly or at least 2, 3 or 4 coiled coil regions. In an embodiment of the present invention, the or each immunogenic fragment contains exactly or at least 2, 3 or 4 coiled coil regions where the immunogenic fragment is more than 50, 60, 70, 80, 90, 95, 96 or 100% identical to a native pneumococcal PhtD sequence (e.g. the sequence shown in SEQ ID NO: 4 of WO00/37105). In another embodiment of the present invention, the immunogenic fragment includes one or more histidine triad motif as well as at least 1, 2, 3 or 4 coiled coil regions.

In the case where the PhtD polypeptide is a variant, the variation is generally in a portion thereof other than the histidine triad residues and the coiled-coil region, although variations in one or more of these regions may be made. In accordance with the present invention, a variant is a protein in which the native pneumolysin is mutated. Amino acid substitution may be conservative or non-conservative. In one aspect, amino acid substitution is conservative. Substitutions, deletions, insertions or any combination thereof may be combined in a single variant so long as the variant is an immunogenic polypeptide. Variants typically include polypeptides which share at least 80, 90, 94, 95, 98, or 99% amino acid sequence identity with a wild-type sequence. Variants of PhtD typically include any immunogenic fragment or variation of PhtD which shares at least 80, 90, 95, 96, 98, or 99% amino acid sequence identity with a wild-type PhtD sequence, e.g. SEQ ID NO: 4 of WO00/37105. In an embodiment, the present invention includes immunogenic fragments and/or variants in which several, 5 to 10, 1 to 5, 1 to 3, 1 to 2 or 1 amino acid(s) are substituted, deleted, or added in any combination. In another embodiment, the present invention includes immunogenic fragments and/or variants which comprise a B-cell or T-cell epitope. Such epitopes may be predicted using a combination of 2D-structure prediction, e.g. using the PSIPRED program (from David Jones, Brunel Bioinformatics Group, Dept. Biological Sciences, Brunel University, Uxbridge UB8 3PH, UK) and antigenic index calculated on the basis of the method described by Jameson and Wolf (CABIOS 4:181-186 [1988]).

In an embodiment of the invention, PhtD and its immunogenic fragments, variants and/or fusion proteins thereof comprise an amino acid sequence sharing at least 80, 85, 90, 95, 96, 97, 98, 99 or 100% identity with amino acid sequence 21 to 838 of SEQ ID NO:4 of WO00/37105. In another embodiment of the invention, PhtD and its immunogenic fragments, variants and/or fusion proteins thereof have an amino acid sequence sharing at least 80, 85, 90, 95, 96, 97, 98, 99 or 100% identity with amino acid sequence 21 to 838 of SEQ ID NO:4 of WO00/37105. Suitably, PhtD and its immunogenic fragments, variants and/or fusion proteins thereof comprise an amino acid sequence having an N-terminal methionine. In another embodiment of the invention, PhtD and its immunogenic fragments, variants and/or fusion proteins thereof comprise at least about 15, at least about 20, at least about 40, or at least about 60 or at least about 100, or at least about 200, or at least about 400 or at least about 800 contiguous amino acid residues of the sequence shown in SEQ ID NO: 4 of WO00/37105.

In one aspect the PhtD is conjugated to a saccharide, e.g. a capsular saccharide of S. pneumoniae. For example, PhtD may be conjugated to a capsular saccharide of S. pneumoniae selected from serotypes 1, 2, 3, 4, 5, 6A, 6B, 7F, 8, 9N, 9V, 10A, 11A, 12F, 14, 15, 17F, 18C, 19A, 19F, 20, 22F, 23F and 33F. In particular, PhtD may be conjugated to a capsular saccharide of S. pneumoniae serotype 22F. In another aspect, PhtD is unconjugated or present in the immunogenic composition as a free protein. In an aspect of the invention, more than 80% (e.g. more than 82%, 85%, 90%, 91%, 92%, 93%, 94%, 95%, 96%, 97%, 98% or 99%) of the PhtD is adsorbed onto aluminium phosphate. In another aspect of the invention, greater than 80% (e.g. more than 81%, 82%, 83%, 84%, 85%, 86%, 87%, 88%, 89% or 90%) of the particles of PhtD (e.g. unconjugated PhtD) adsorbed onto aluminium phosphate have a size less than 10 µm.

The present invention also provides an immunogenic composition comprising PhtD adsorbed onto aluminium phosphate, wherein more than 85% (e.g. more than 90%, 91%, 92%, 93%, 94%, 95%, 96%, 97%, 98% or 99%) of the PhtD is adsorbed onto aluminium phosphate. The present invention also provides an immunogenic composition wherein greater than 80% (e.g. more than 81%, 82%, 83%, 84%, 85%, 86%, 87%, 88%, 89% or 90%) of the particles of PhtD adsorbed onto aluminium phosphate have has a particle a size less than 10 µm.

Concerning the Choline Binding Protein family (CbpX), members of that family were originally identified as pneumococcal proteins that could be purified by choline-affinity chromatography. All of the choline-binding proteins are non-covalently bound to phosphorylcholine moieties of cell wall teichoic acid and membrane-associated lipoteichoic acid. Structurally, they have several regions in common over the entire family, although the exact nature of the proteins (amino acid sequence, length, etc.) can vary. In general, choline binding proteins comprise an N terminal region (N), conserved repeat regions, a proline rich region (P) and a conserved choline binding region (C), made up of multiple repeats, that comprises approximately one half of the protein. As used in this application, the term "Choline Binding Protein family (CbpX)" is selected from the group consisting of Choline Binding Proteins as identified in WO97/41151, Choline binding protein A, CbpA (also referred to as PbcA (C3-binding protein A), SpsA (*Streptococcus pneumoniae* secretory IgA binding protein), PspC (pneumococcal surface protein C)), Choline binding protein D (CbpD), and Choline binding protein G (CbpG). CbpA is disclosed in WO97/41151. CbpD and CbpG are disclosed in WO00/29434. PspC is disclosed in WO97/09994. PbcA is disclosed in WO98/21337. SpsA is a Choline binding protein disclosed in WO 98/39450. In an embodiment, the Choline Binding Proteins is CbpA. Another Choline Binding Protein is pneumococcal choline-binding protein A (PcpA) (Sanchez-Beato et al FEMS Microbiology Letters 164 (1998) 207-214).

Another preferred embodiment is CbpX truncates wherein "CbpX" is CbpA, CbpD or CbpG and "CbpX truncates" refers to CbpX proteins lacking 50% or more of the Choline binding region (C). Another preferred embodiment is PcpA truncates wherein "PcpA truncates" refers to PcpA proteins lacking 50% or more of the Choline binding region (C). In an embodiment, CbpX truncates or PcpA truncates lack the entire choline binding region. In another embodiment, the CbpX truncates or PcpA truncates lack (i) the choline binding region and (ii) a portion of the N-terminal half of the protein as well, yet retain at least one repeat region. In another embodiment, the truncate has at least 2 repeat regions. Examples of such preferred embodiments are illustrated in WO99/51266 or WO99/51188, however, other choline binding proteins lacking a similar choline binding region are also contemplated within the scope of this invention.

The LytX family is membrane associated proteins associated with cell lysis. The N-terminal domain comprises choline binding domain(s), however the LytX family does not have all the features found in the CbpA family noted herein and thus for the present invention, the LytX family is considered distinct from the CbpX family. In contrast with the CbpX family, the C-terminal domain contains the catalytic domain of the LytX protein family. The family comprises LytA, LytB and LytC. With regards to the LytX family, LytA is disclosed in Ronda et al., Eur J Biochem, 164:621-624 (1987). LytB is disclosed in WO 98/18930, and is also referred to as Sp46. LytC is also disclosed in WO 98/18930, and is also referred to as Sp91. A preferred member of that family is LytC.

Another preferred embodiment are LytX truncates wherein "LytX" is LytA, LytB or LytC and "LytX truncates" refers to LytX proteins lacking 50% or more of the Choline binding region. Suitably such proteins lack the entire choline binding region. Yet another preferred embodiment of this invention are CbpX truncate-LytX truncate chimeric proteins (or fusions). In an embodiment, the CbpX truncate-LytX truncate chimeric protein comprises the repeat regions of CbpX and the C-terminal portion (Cterm, i.e., lacking the choline binding domains) of LytX (e.g., LytCCterm or Sp91Cterm). In another embodiment, CbpX is selected from the group consisting of CbpA, PbcA, SpsA and PspC. In another embodiment, it is CbpA. In an embodiment, LytX is LytC (also referred to as Sp91). Another embodiment of the present invention is a PspA (pneumococcal surface protein A) or PsaA (pneumococcal surface adhesion A) truncates lacking the choline binding domain (C) and expressed as a fusion protein with LytX. In an embodiment, LytX is LytC.

PsaA (pneumococcal surface adhesion A) and transmembrane deletion variants thereof have been described by Berry & Paton, Infect Immun 1996 December; 64(12):5255-62. PspA (pneumococcal surface protein A) and transmembrane deletion variants thereof have been disclosed in, for example, U.S. Pat. No. 5,804,193, WO 92/14488, and WO 99/53940.

Sp128 and Sp130 are disclosed in WO00/76540. Sp125 is an example of a pneumococcal surface protein with the Cell Wall Anchored motif of LPXTG (i.e., leucine-proline-X-threonine-glycine where X is any amino acid). Any protein within this class of pneumococcal surface protein with this motif has been found to be useful within the context of this invention, and is therefore considered a further protein of the invention. Sp125 itself is disclosed in WO 98/18930, and is also known as ZmpB—a zinc metalloproteinase. Sp101 is disclosed in WO 98/06734 (where it has the reference #y85993). It is characterized by a Type I signal sequence. Sp133 is disclosed in WO 98/06734 (where it has the reference #y85992). It is also characterized by a Type I signal sequence.

The S. pneumoniae antigens may also be beneficially combined. By combined is meant that the immunogenic composition comprises all of the proteins from within the combination, either as carrier proteins or as free proteins or a mixture of the two. For example, in a combination of two proteins as set out hereinafter, both proteins may be used as carrier proteins, or both proteins may be present as free proteins, or both may be present as carrier and as free protein, or one may be present as a carrier protein and a free protein whilst the other is present only as a carrier protein or only as a free protein, or one may be present as a carrier protein and the other as a free protein. Where a combination of three proteins is given, similar possibilities exist. Preferred combinations include, but are not limited to PhtD+CbpX repeat regions, PhtD+dPly, PhtD+Sp128, PhtD+PsaA, PhtD+PspA, PhtA+CbpX repeat regions, PhtA+CbpX repeat regions-Sp91 Cterm chimeric or fusion proteins, PhtA+dPly, PhtA+Sp128, PhtA+PsaA, PhtA+PspA, CbpX repeat regions+LytC, CbpX repeat regions+PspA, CbpX repeat regions+PsaA, CbpX repeat regions+Sp128, CbpX repeat regions+LytC, CbpX repeat regions+PspA, CbpX repeat regions+PsaA, CbpX repeat regions+Sp128, CbpX repeat regions+PhtD, CbpX repeat regions+PhtA. In an embodiment, CbpX repeat regions is from CbpA. In another embodiment, it is from CbpA. Other combinations include 3 protein combinations such as PhtD+CbpX repeat regions+dPly, and PhtA+CbpX repeat regions+PhtD. In one embodiment, the immunogenic composition comprises detoxified pneumolysin and PhtD as carrier proteins. In a further embodiment, the immunogenic composition comprises detoxified pneumolysin and PhtD as free proteins.

Adjuvants

In an embodiment, the immunogenic composition of the invention further comprises an adjuvant (suitably a pharmaceutically acceptable adjuvant). Also provided is a method of making the immunogenic composition of the invention comprising the step of mixing the pneumococcal saccharide or the conjugate (e.g. bioconjugate) of the invention with an adjuvant.

In an embodiment, the immunogenic composition of the invention comprises, or is administered in combination with, an adjuvant. The adjuvant for administration in combination with an immunogenic composition of the invention may be administered before, concomitantly with, or after administration of said immunogenic composition or vaccine. In some embodiments, the term "adjuvant" refers to a compound that when administered in conjunction with or as part of an immunogenic composition of the invention augments, enhances and/or boosts the immune response to a bioconjugate, but when the compound is administered alone does not generate an immune response to the pneumococcal saccharide/conjugate/bioconjugate. In some embodiments, the adjuvant generates an immune response to the pneumococcal saccharide, conjugate or bioconjugate and does not produce an allergy or other adverse reaction.

Adjuvants can enhance an immune response by several mechanisms including, e.g. lymphocyte recruitment, stimulation of B and/or T cells, and stimulation of macrophages. Specific examples of adjuvants include, but are not limited to, aluminum salts (alum) (such as aluminum hydroxide, aluminum phosphate, and aluminum sulfate), 3 De-O-acylated monophosphoryl lipid A (MPL) (see United Kingdom Patent GB2220211), MF59 (Novartis), AS03 (GlaxoSmithKline), AS04 (GlaxoSmithKline), polysorbate 80 (TWEEN 80; ICL Americas, Inc.), imidazopyridine compounds (see International Application NO: PCT/US2007/064857, published as International Publication NO: WO2007/109812), imidazoquinoxaline compounds (see International Application NO: PCT/US2007/064858, published as International Publication NO: WO2007/109813) and saponins, such as QS21 (see Kensil et al. in Vaccine Design: The Subunit and Adjuvant Approach (eds. Powell & Newman, Plenum Press, N Y, 1995); U.S. Pat. No. 5,057, 540). In some embodiments, the adjuvant is Freund's adjuvant (complete or incomplete). Other adjuvants are oil in water emulsions (such as squalene or peanut oil), optionally in combination with immune stimulants, such as monophosphoryl lipid A (see Stoute et al. N. Engl. J. Med. 336, 86-91 (1997)). Another adjuvant is CpG (Bioworld Today, Nov. 15, 1998).

In one aspect of the invention, the adjuvant is an aluminum salt such as aluminum hydroxide gel (alum) or aluminium phosphate.

In another aspect of the invention, the adjuvant is selected to be a preferential inducer of either a TH1 or a TH2 type of response. High levels of Th1-type cytokines tend to favor the induction of cell mediated immune responses to a given antigen, whilst high levels of Th2-type cytokines tend to favour the induction of humoral immune responses to the antigen. It is important to remember that the distinction of Th1 and Th2-type immune response is not absolute. In reality an individual will support an immune response which is described as being predominantly Th1 or predominantly Th2. However, it is often convenient to consider the families of cytokines in terms of that described in murine CD4 +ve T cell clones by Mosmann and Coffman (Mosmann, T. R. and Coffman, R. L. (1989) TH1 and TH2 cells: different patterns of lymphokine secretion lead to different functional properties. Annual Review of Immunology, 7, p 145-173). Traditionally, Th1-type responses are associated with the production of the INF-γ and IL-2 cytokines by T-lymphocytes. Other cytokines often directly associated with the induction of Th1-type immune responses are not produced by T-cells, such as IL-12. In contrast, Th2-type responses are associated with the secretion of Il-4, IL-5, IL-6, IL-10. Suitable adjuvant systems which promote a predominantly Th1 response include: Monophosphoryl lipid A or a derivative thereof, particularly 3-de-O-acylated monophosphoryl lipid A (3D-MPL) (for its preparation see GB 2220211 A); and a combination of monophosphoryl lipid A, for example 3-de-O-acylated monophosphoryl lipid A, together with either an aluminium salt (for instance aluminium phosphate or aluminium hydroxide) or an oil-in-water emulsion. In such combinations, antigen and 3D-MPL are contained in the same particulate structures, allowing for more efficient delivery of antigenic and immunostimulatory signals. Studies have shown that 3D-MPL is able to further enhance the immunogenicity of an alum-adsorbed antigen [Thoelen et al. Vaccine (1998) 16:708-14; EP 689454-B1]. Unmethylated CpG containing oligonucleotides (WO 96/02555) are also preferential inducers of a TH1 response and are suitable for use in the present invention.

The immunogenic composition of the invention may contain an oil in water emulsion, since these have been suggested to be useful as adjuvant compositions (EP 399843; WO 95/17210). Oil in water emulsions such as those described in WO95/17210 (which discloses oil in water emulsions comprising from 2 to 10% squalene, from 2 to 10% alpha tocopherol and from 0.3 to 3% Tween 80 (Polysorbate 80) and their use alone or in combination with QS21 and/or 3D-MPL), WO99/12565 (which discloses oil in water emulsion compositions comprising a metabolisable oil, a saponin and a sterol and MPL) or WO99/11241 may be used. Further oil in water emulsions such as those disclosed in WO 09/127676 and WO 09/127677 are also suitable. A particularly potent adjuvant formulation involving QS21, 3D-MPL and tocopherol in an oil in water emulsion is described in WO 95/17210. In an embodiment, the immunogenic composition or vaccine additionally comprises a saponin, for example QS21. The immunogenic composition may also comprise an oil in water emulsion and tocopherol (WO 95/17210).

Vaccines

The present invention also provides a vaccine comprising an immunogenic composition of the invention.

The immunogenic compositions or vaccines of the invention can be included in a container, pack, or dispenser together with instructions for administration.

The immunogenic compositions or vaccines of the invention can be stored before use, e.g. the compositions can be stored frozen (e.g. at about −20° C. or at about −70° C.); stored in refrigerated conditions (e.g. at about 4° C.); or stored at room temperature.

The immunogenic compositions or vaccines of the invention may be stored in solution or lyophilized. In an embodiment, the solution is lyophilized in the presence of a sugar such as sucrose, trehalose or lactose. In another embodiment, the vaccines of the invention are lyophilized and extemporaneously reconstituted prior to use.

Vaccine preparation is generally described in Vaccine Design ("The subunit and adjuvant approach" (eds Powell M. F. & Newman M. J.) (1995) Plenum Press New York). Encapsulation within liposomes is described by Fullerton, U.S. Pat. No. 4,235,877.

The present invention also provides a kit comprising a pneumococcal saccharide of the invention, a bioconjugate of the invention, an immunogenic composition of the invention or a vaccine of the invention and instructions for the use thereof.

Method of Administration

Immunogenic compositions or vaccines of the invention may be used to protect or treat a mammal susceptible to infection, by means of administering said immunogenic composition or vaccine via systemic or mucosal route. These administrations may include injection via the intramuscular (IM), intraperitoneal, intradermal (ID) or subcutaneous routes; or via mucosal administration to the oral/alimentary, respiratory, genitourinary tracts. For example, intranasal (IN) administration may be used for the treatment of pneumonia or otitis media (as nasopharyngeal carriage of pneumococci can be more effectively prevented, thus attenuating infection at its earliest stage). Although the immunogenic composition or vaccine of the invention may be administered as a single dose, components thereof may also be co-administered together at the same time or at different times (for instance pneumococcal saccharides could be administered separately, at the same time or 1-2 weeks after the administration of any bacterial protein component of the vaccine for optimal coordination of the immune responses with respect to each other). For co-administration, the optional Th1 adjuvant may be present in any or all of the different administrations, however in one particular aspect of the invention it is present in combination with the pneumococcal saccharide component of the immunogenic composition or vaccine. In addition to a single route of administration, 2 different routes of administration may be used. For example, saccharides may be administered IM (or ID) and bacterial proteins may be administered IN (or ID). In addition, the vaccines of the invention may be administered IM for priming doses and IN for booster doses.

In one aspect, the immunogenic composition or vaccine of the invention is administered by the intramuscular delivery route. Intramuscular administration may be to the thigh or the upper arm. Injection is typically via a needle (e.g. a hypodermic needle), but needle-free injection may alternatively be used. A typical intramuscular dose is 0.5 ml.

In another aspect, the immunogenic composition or vaccine of the invention is administered by the intradermal administration. Human skin comprises an outer "horny" cuticle, called the stratum corneum, which overlays the epidermis. Underneath this epidermis is a layer called the dermis, which in turn overlays the subcutaneous tissue. The conventional technique of intradermal injection, the "mantoux procedure", comprises steps of cleaning the skin, and then stretching with one hand, and with the bevel of a narrow gauge needle (26 to 31 gauge) facing upwards the needle is inserted at an angle of between 10 to 15°. Once the bevel of the needle is inserted, the barrel of the needle is lowered and further advanced whilst providing a slight pressure to elevate it under the skin. The liquid is then injected very slowly thereby forming a bleb or bump on the skin surface, followed by slow withdrawal of the needle.

More recently, devices that are specifically designed to administer liquid agents into or across the skin have been described, for example the devices described in WO 99/34850 and EP 1092444, also the jet injection devices described for example in WO 01/13977; U.S. Pat. Nos. 5,480,381, 5,599,302, 5,334,144, 5,993,412, 5,649,912, 5,569,189, 5,704,911, 5,383,851, 5,893,397, 5,466,220, 5,339,163, 5,312,335, 5,503,627, 5,064,413, 5,520,639, 4,596,556, 4,790,824, 4,941,880, 4,940,460, WO 97/37705 and WO 97/13537. Alternative methods of intradermal administration of the vaccine preparations may include conventional syringes and needles, or devices designed for ballistic delivery of solid vaccines (WO 99/27961), or transdermal patches (WO 97/48440; WO 98/28037); or applied to the surface of the skin (transdermal or transcutaneous delivery WO 98/20734; WO 98/28037).

In another aspect, the immunogenic composition or vaccine of the invention is administered by the intranasal administration. Typically, the immunogenic composition or vaccine is administered locally to the nasopharyngeal area, e.g. without being inhaled into the lungs. It is desirable to use an intranasal delivery device which delivers the immunogenic composition or vaccine formulation to the nasopharyngeal area, without or substantially without it entering the lungs. Suitable devices for intranasal administration of the vaccines according to the invention are spray devices.

In an embodiment, spray devices for intranasal use are devices for which the performance of the device is not dependent upon the pressure applied by the user. These devices are known as pressure threshold devices. Liquid is released from the nozzle only when a threshold pressure is applied. These devices make it easier to achieve a spray with a regular droplet size. Pressure threshold devices suitable for use with the present invention are known in the art and are described for example in WO91/13281 and EP311863 and EP516636, incorporated herein by reference. Such devices are commercially available from Pfeiffer GmbH and are also described in Bommer, R. Pharmaceutical Technology Europe, September 1999.

In another embodiment, intranasal devices produce droplets (measured using water as the liquid) in the range 1 to 200 µm, e.g. 10 to 120 µm. Below 10 µm there is a risk of inhalation, therefore it is desirable to have no more than about 5% of droplets below 10 µm. Droplets above 120 µm do not spread as well as smaller droplets, so it is desirable to have no more than about 5% of droplets exceeding 120 µm.

Following an initial vaccination, subjects may receive one or several booster immunizations adequately spaced.

The immunogenic composition or vaccine of the present invention may be used to protect or treat a mammal, e.g. human, susceptible to infection, by means of administering said immunogenic composition or vaccine via a systemic or mucosal route. These administrations may include injection via the intramuscular (IM), intraperitoneal (IP), intradermal (ID) or subcutaneous (SC) routes; or via mucosal administration to the oral/alimentary, respiratory, genitourinary tracts. Although the vaccine of the invention may be administered as a single dose, components thereof may also be co-administered together at the same time or at different times (for instance pneumococcal saccharide conjugates could be administered separately, at the same time or 1-2 weeks after the administration of the any pneumococcal saccharide, conjugate or bioconjugate of the invention for optimal coordination of the immune responses with respect to each other). For co-administration, the optional adjuvant may be present in any or all of the different administrations. In addition to a single route of administration, 2 different routes of administration may be used. For example, the pneumococcal saccharide, conjugate or bioconjugate of the invention may be administered IN (or ID). In addition, the immunogenic compositions or vaccines of the invention may be administered IM for priming doses and IN for booster doses.

Dosage

The amount of conjugate antigen in each immunogenic composition or vaccine dose is selected as an amount which induces an immunoprotective response without significant, adverse side effects in typical vaccines. Such amount will vary depending upon which specific immunogen is employed and how it is presented. The content of penumococcal saccharide will typically be in the range 1-100 µg, suitably 5-50 µg. The content of saccharide will typically be in the range 0.1-10 µg, suitably 1-5 µg.

A dose which is in a volume suitable for human use is generally between 0.25 and 1.5 ml, although, for administration to the skin a lower volume of between 0.05 ml and 0.2 ml may be used. In one embodiment, a human dose is 0.5 ml. In a further embodiment, a human dose is higher than 0.5 ml, for example 0.6, 0.7, 0.8, 0.9 or 1 ml. In a further embodiment, a human dose is between 1 ml and 1.5 ml. In another embodiment, in particular when the immunogenic composition is for the paediatric population, a human dose may be less than 0.5 ml such as between 0.25 and 0.5 ml.

Prophylactic and Therapeutic Uses

The present invention also provides methods of treating and/or preventing bacterial infections of a subject comprising administering to the subject a pneumococcal saccharide, conjugate or bioconjugate of the invention. The pneumococcal saccharide, conjugate or bioconjugate may be in the form of an immunogenic composition or vaccine. In an embodiment, the immunogenic composition or vaccine of the invention is used in the prevention of infection of a subject (e.g. human subjects) by *Streptococcus* species (e.g. *Streptococcus pneumoniae*). In an embodiment, the immunogenic composition or vaccine of the invention is used to treat or prevent an infection by *Streptococcus* species (e.g. *Streptococcus pneumoniae*).

Also provided herein are methods of inducing an immune response in a subject against a bacterium, comprising administering to the subject a pneumococcal saccharide, or conjugate or bioconjugate of the invention (or immunogenic composition or vaccine). In one embodiment, said subject has bacterial infection at the time of administration. In another embodiment, said subject does not have a bacterial infection at the time of administration. The pneumococcal saccharide, conjugate or bioconjugate of the invention can be used to induce an immune response against *Escherichia* species, *Shigella* species, *Klebsiella* species, *Xhantomonas* species, *Salmonella* species, *Yersinia* species, *Aeromonas* species, *Francisella* species, *Helicobacter* species, *Proteus* species, *Lactococcus* species, *Lactobacillus* species, *Pseudomonas* species, *Corynebacterium* species, *Streptomyces* species, *Streptococcus* species, *Enterococcus* species, *Staphylococcus* species, *Bacillus* species, *Clostridium* species, *Listeria* species, or *Campylobacter* species. In an embodiment, pneumococcal saccharide, or conjugate or bioconjugate of the invention is used to induce an immune response against *Streptococcus* species (e.g. *Streptococcus pneumoniae*).

Also provided herein are methods of inducing the production of opsonophagocytic antibodies in a subject against a bacterium, comprising administering to the subject a pneumococcal saccharide, or conjugate or bioconjugate of the invention (or immunogenic composition or vaccine). In one embodiment, said subject has bacterial infection at the time of administration. In another embodiment, said subject does not have a bacterial infection at the time of administration. The pneumococcal saccharide, or conjugate or bioconjugate of the invention (or immunogenic composition or vaccine) provided herein can be used to induce the production of opsonophagocytic antibodies against *Streptococcus pneumoniae*.

In an embodiment, the present invention is an improved method to elicit an immune response in infants (defined as 0-2 years old in the context of the present invention) by administering a therapeutically effective amount of an immunogenic composition or vaccine of the invention (a paediatric vaccine). In an embodiment, the vaccine is a paediatric vaccine.

In an embodiment, the present invention is an improved method to elicit an immune response in the elderly population (in the context of the present invention a patient is considered elderly if they are 50 years or over in age, typically over 55 years and more generally over 60 years) by administering a therapeutically effective amount of the immunogenic composition or vaccine of the invention. In an embodiment, the vaccine is a vaccine for the elderly.

The disease caused by *Streptococcus pneumoniae* infection may be selected from pneumonia, invasive pneumococcal disease (IPD), exacerbations of chronic obstructive pulmonary disease (eCOPD), otitis media, meningitis, bacteraemia, pneumonia and/or conjunctivitis. Where the human host is an infant (defined as 0-2 years old in the context of the present invention), the disease may be selected from otitis media, meningitis, bacteraemia, pneumonia and/or conjunctivitis. In one aspect, where the human host is an infant (defined as 0-2 years old in the context of the present invention), the disease is selected from otitis media and/or pneumonia. Where the human host is elderly (i.e., 50 years or over in age, typically over 55 years and more generally over 60 years), the disease may be selected from pneumonia, invasive pneumococcal disease (IPD), and/or exacerbations of chronic obstructive pulmonary disease (eCOPD). In one aspect, where the human host is elderly, the disease is invasive pneumococcal disease (IPD). In another aspect, where the human host is elderly, the disease is exacerbations of chronic obstructive pulmonary disease (eCOPD).

The present invention provides a pneumococcal saccharide of the invention, or the conjugate of the invention, or the bioconjugate of the invention, or the immunogenic composition or vaccine of the invention for use in the treatment or prevention of a disease caused by *S. pneumoniae* infection. In an embodiment, the disease is pneumonia, invasive pneumococcal disease (IPD), exacerbations of chronic obstructive pulmonary disease (COPD), otitis media, meningitis, bacteraemia, pneumonia and/or conjunctivitis.

The present invention provides provides a pneumococcal saccharide of the invention, or the conjugate of the invention, or the bioconjugate of the invention, or the immunogenic composition or vaccine of the invention, for use in immunizing against infection by *Streptococcus pneumoniae*.

The present invention provides a pneumococcal saccharide of the invention, or the conjugate of the invention, or the bioconjugate of the invention, or the immunogenic composition or vaccine of the invention for inducing an immune response against *Streptococcus pneumoniae*.

The present invention provides use of the pneumococcal saccharide of the invention, or the conjugate of the invention, or the bioconjugate of the invention, or the immunogenic composition or vaccine of the invention in the manufacture of a medicament for the treatment or prevention of a disease caused by *Streptococcus pneumoniae* infection. In an embodiment, the disease is pneumonia, invasive pneumococcal disease (IPD), exacerbations of chronic obstructive pulmonary disease (COPD), otitis media, meningitis, bacteraemia, pneumonia and/or conjunctivitis.

The present invention provides use of a pneumococcal saccharide of the invention, or a conjugate of the invention, or a bioconjugate of the invention, or a immunogenic composition or a vaccine of the invention, in the manufacture of a medicament for immunizing against infection by *Streptococcus pneumoniae*.

The present invention provides use of a pneumococcal saccharide of the invention, or a conjugate of the invention, or a bioconjugate of the invention, or a immunogenic composition or a vaccine of the invention, in the manufacture of a medicament for inducing an immune response against *Streptococcus pneumoniae*.

The present invention provides a method for the treatment or prevention of *Streptococcus pneumoniae* infection in a subject (e.g. human) in need thereof comprising administering to said subject a therapeutically effective amount of the pneumococcal saccharide of the invention, or the conjugate of the invention, or the bioconjugate of the invention, or the immunogenic composition or vaccine of the invention. In an embodiment, the disease is pneumonia, invasive pneumococcal disease (IPD), exacerbations of chronic obstructive pulmonary disease (COPD), otitis media, meningitis, bacteraemia, pneumonia and/or conjunctivitis.

The present invention provides a method of immunizing a subject (e.g. human) against infection by *Streptococcus pneumoniae* comprising administering to the host an immunoprotective amount of the pneumococcal saccharide of the invention, or the conjugate of the invention, or the bioconjugate of the invention, or the immunogenic composition or vaccine of the invention.

The present invention provides a method of inducing an immune response to *Streptococcus pneumoniae* in a subject (e.g. human), comprising administering a therapeutically or prophylactically effective amount of the pneumococcal saccharide of the invention, or the conjugate of the invention, or the bioconjugate of the invention, or the immunogenic composition or vaccine of the invention.

All references or patent applications cited within this patent specification are incorporated by reference herein.

In order that this invention may be better understood, the following examples are set forth. These examples are for purposes of illustration only, and are not to be construed as limiting the scope of the invention in any manner.

```
Sequences of proteins and nucleic acids
consensus sequence
                                        SEQ ID NO: 1
D/E-X-N-Z-S/T consensus sequence
                                        SEQ ID NO: 2
D-Q-N-A-T consensus sequence
                                        SEQ ID NO: 3
K-D/E-X-N-Z-S/T-K consensus sequence
                                        SEQ ID NO: 4
K-D-Q-N-A-T-K Streptococcus pneumoniae 23A wzg
                                        SEQ ID NO: 5
MSRRFKKSGSQKVKRSVNIVLLTIYLLLVCFLLFLIFKYNILAFRYLNLVV

TALVLLVALVGLLLIIYKKAEKFTIFLLVFSILVSSVSLFAVQQFVGLTNR

LNATSNYSEYSISVAVLADSDIENVTQLTSVTAPTGTDNENIQKLLADIKS

SQNTDLTVNQSSSYLAAYKSLIAGETKAIVLNSVFENIIESEYPDYASKIK

KIYTKGFTKKVEAPKTSKNQSFNIYVSGIDTYGPISSVSRSDVNILMTVNR

DTKKILLTTTPRDAYVPIADGGNNQKDKLTHAGIYGVDSSIHTLENLYGVD

INYYVRLNFTSFLKLIDLLGGIDVYNDQEFTAHTNGKYYPAGNVHLDSEQA

LGFVRERYSLADGDRDRGRNQQKVIVAILQKLTSTEALKNYSTIINSLQDS

IQTNMPLETMINLVNAQLESGGNYKVNSQDLKGTGRTDLPSYAMPDSNLYV

MEIDDSSLAVVKAAIQDVMEGR

Streptococcus pneumoniae 23A wzh
                                        SEQ ID NO: 6
MIDIHSHIVFDVDDGPKSREESKALLTESYRQGVRTIVSTSHRRKGMFETP

EEKIAENFLQVREIAKEVADDLVIAYGAEIYYTLDALEKLEKKEIPTLNDS

RYALIEFSMNTPYRDIHSALSKILMLGITPVIAHIERYDALENNGKRVREL

IDMGCYTQINSYHVSKPKFFGEKYKFMKKRARYFLERDLVHVVASDMHNLD

SRPPYMQQAYDIIAKKYGAKKAKELFVDNPRKIIMDQLI

Streptococcus pneumoniae 23A wzd
                                        SEQ ID NO: 7
MKEQNTLEIDVLQLFRALWKRKLVILLVAIITSSVAFTYSTFVIKPEFTST

TRIYVVNRNQGEKSGLTNQDLQAGTYLVKDYREIILSQDVLEEVVSDLKLD

LTPKGLANKIKVTVPVDTRIVSVSVNDRVPEEASRIANSLREVAAQKIISI

TRVSDVTTLEEARPAISPSSPNIKRNILIGFLAGVIGTSVIVLLLELLDTR

VKRPEDIEDTLQMTLLGVVPNLNKLK

Streptococcus pneumoniae 23A wze
                                        SEQ ID NO: 8
MPTLEIAQKKLEFIKKAEEYYNALCTNIQLSGDKLKVISVTSVSPGEGKTT

TSVNIAWSFARAGYKTLLIDGDTRNSVISGFFKSREKITGLTEFLSGTADL

SHGLCDTNIENLFVVQSGSVSPNPTALLQSKNFNDMIETLRKYFDYIIVDT

APIGIVIDAAIITQKCDASILVTATGEANKRDVQKAKQQLKQTGKLFLGVV

LNKLDISVDKYGVYGFYGNYGKK

Streptococcus pneumoniae 23A wchA
                                        SEQ ID NO: 9
MDEKGLKIFMAVLQSIIVILLVYFLSFVRETELERSSMVILYLLHFFVFYV

SSYGNNFFKRGYLVEFNSTIRYIFFFAIAISVLNFFIAERFSISRRGMVYF

LTLEGISLYLLNFLVKKYWKHVFFNLKNSKKILLLTVTKNMEKVLDKLLES

DELSWKLVAVSVLNKSDFQHDKIPVIEKEKIIEFATHEVVDEVFVNLPGES

YDIGEIISRFETMGIDVTVNLKAFDKNLGRNKQIHEMVGLNVVTFSTNFYK

TSHVISKRILDICGATIGLILFAIASLVLVPLIRKDGGPAIFAQTRIGKNG

RHFTFYKFRSMRIDAEAIKEQLMDQNTMQGGMFKIDNDPRVTKIGRFIRKT

SLDELPQFWNVFIGDMSLVGTRPPTVDEYDQYTPEQKRRLSFKPGITGLWQ

VSGRSKITDFDDVVKLDVSYIDNWTIWKDIEILLKTVKVVFMRDGAK

Streptococcus pneumoniae 23A wchF
                                        SEQ ID NO: 10
MKKSVYIIGSKGIPAKYGGFETFVEKLTAFQQDKAIQYYVACMRENSAKSG

TTEDVFEHNGAICYNVDVPNIGPARAIVYDIAAINRAIEIAKENKDEDPIF

YILACRIGPFIHGIKKKIQAIGGTLLVNPDGHEWLRAKWSTPVRRYWKISE

GLMVKHADLLVCDSKNIEQYIQEDYKQFQPKTTYIAYGTDTTRSILKSSDE

KVRSWFKEKNVSENEYYLVVGRFVPENNYESMILGFLASNSKKDFVLITNV

EQNKFYNQLLAKTGFDKDPRVKFVGTVYNQELLKYIRENAFAYFHGHEVGG

TNPSLLEALASTKLNLLLDVGFNREVAEDGADYWEKDNLHKVIEASEQKTQ

EEINEKNILSTKQVTERFSWDLIVNEYEKLFTRKN

Streptococcus pneumoniae 23A wzy
                                        SEQ ID NO: 11
MRYGIMRISFSKKTMLCGLLYIGLILSVVTIPTIVTFLYSLLFIGIVTVLN

YNSILASDEDANSFFVALPIILSSFQNVYLGFGADRLNSVTLQVLLSISIA

IITITVFLGIILNRFKSKEFSWLVLSILVIIIQSVILLIFFPTTLPAYLSS

MRNILAPLLIFYFSIYGFKNINLQKFYKYMFIIILVVLIFGFIEYIYGNSL

WTRLNIKKLWALKGLAIENRVVPGNWHSSELIGGKQLRRMVSTFADPVNLG

SYLFAAFMLAWYKNKKLLQVLLLASFVLSVSKAAFLSMLVYIIIYTWVVDK

NKILSIFGIIISTVLGLYFYNFSQVSSYGSINAHIDGFFSALSTPLHYPFG

MGVGSVGVLASKLGSQTALSSEVLETGIGMIIAQLGFVGVIIYLIFFVKLS

VIGKNINNKRDKILWFTLIYSFLANAFFNEVALSPNSCTLYFLILGLLYNK

NKIRSTEFS

Streptococcus pneumoniae 23A wchV
                                        SEQ ID NO: 12
MEKLVSIILPVYNVEQYIKNCLESIQQQTYPNLEVIIVNDGSTDKSVEYCE

QICKIDSRFSITHKENGGLSDARNVGIDKAKGDYLIFVDSDDFVSQDMVSY
```

LVSCMENNEADIAICDPVHYYSDRQNNDLNIFSPASSVKVYETTEALCEMF

YQKSFLVSAWAKIFKRELFDDIRFPVGKLFEDSAIMYLLLEKCETIAYSDA

KLYAYVHRDNSITTKKFSDRDLDILEITNTIINHYGDNLRVYTAAVSYKVS

ACFRILLNSPSEEKYKKVQKECLSYILQNWRNILFNNNVRLKNKLALISIT

IFNPFVKLIYSKVNRWE"

*Streptococcus pneumoniae* 23A wchW

SEQ ID NO: 13

MNKYEERYQENLSKNDFYKLINKSYLSDKELQVQQVKAGIVLPPKAFETKL

SNKLGLQKSLHGKGGVVDSNGNYIELSAQKAVGMRNRVYGPYKINYDNLPI

RNEKVIYLNYFIKQWGHFLLDVVGRLWYPLLQDNDTKLVYTCYAGTETKIE

GNYLEFLKLLGIDQSRLIMINCPTQFSEVIIPESSILPGGYYTKEYKQLFS

SVVENIKLDKYDVNAKMIYCSRSKLGIAKSKEFGEDGIEGIFKQNGYTSVY

METMSLEEQIKTLLSAKTIVLTSGSLAHNLLFVNKDIDVFILNKTYRVNLH

QFLINEISDATVRFVDIYRSPLPILYGYGPFLMDLTKPLANFLDDNEFVYE

KGTVLSKKDYFKYYLKWLWSYRFFLFRLNGIKEGNSEFEKSFKIIRRYYKT

GR

*Streptococcus pneumoniae* 23A wzx

SEQ ID NO: 14

MSKYKELAKNTGIFALANFSSKILIFLLVPIYTRVLTTTEYGFYDLVYTTI

QLFVPILTLNISEAVMRFLMKDGVSKKSVFSIAVLDIFIGSIAFALLLLVN

NLFSLSDLISQYSIYIFVIFVFYTLNNFLIQFSKGIDKIGVTAISGVISTA

VMLAMNVILLVVFDWGLLGFFIANVCGYVIPCIYIVSRLRLWELFEIKIDK

KLQWEMVYYALPLVLNILSWWVNNTSDRYIVTAIVGIQASAIISVAYKIPQ

ILSTISAIFIQSWQISAIKIQEDKSGTTFVSNMLLYYNALLLIIASGIILF

VKPISNILFGISFYSAWELVPFLIISSLFNAISGCIGAIMGAKMDTHNIAK

SALVGMIANIILNIVLTFLMGPQGITISTLIASFLIFYMRKDSVKEINSET

YRAIYLSWILLVVEACLLIYMDFIIGALIAMVINLFLLKDVIKPLYLKIFK

RN

*Streptococcus pneumoniae* 23A wchX

SEQ ID NO: 15

MIVLQYFKILARFVFMFLISAVLLPFKIKPNKIVFINFNGKGYGDNPKSIC

EYLRTTYPDLDLVWLARDNEGFPDGVRVVKYGTFQAFYEQASSKVWVYNVR

AFARILKKRGQIYIQTWHGASSFKLIEKQADLPINYVLEAKYDARVTDIMI

SDSRKQTEEFQKYFWYSGEIFEVGMPRNDALFHYKEDYDKLNNIRKELSIH

SDDYVILYAPTFRDDGDASYLDINFERLLQCVEHGIKKKCKFLIRLHPNHS

HLCNNISFNKNIINATFYSDMQELTLLADVLVTDYSSSIFDFMLLNKPYVR

YVNDLEKYAELRGVSDTYYELPDSIIKTAEELYDLLPKKIENFDYDSIKKY

RNEILCPIFNGTASENVGRRIIQEL

*Streptococcus pneumoniae* 23A gtp1

SEQ ID NO: 16

MKNNDLKIGSGAIHQISATLSQNSISGKILYCADPVVDDLYGSIVRSQIEE

IGRVKEESCNYNTIAYAMNIAERAIATDIDCIVGMGGGRVLDVCKYASFIS

KRPYLSIPTTAANDGIASPVAVLKRQDDRPKSLGAAIPSMTLIDIDVIASG

PIQNIKAGIGDTISNYTALKDWELAVERGKDEMHGFAYLMSQNSLDALMKT

KYNSITPDFIEVLVNSLVLSGIAMDFAGSSRPVSGSEHLFSHALDYYGSTR

NLHGIQVALGTVAVLKLIENSVDTVVDYLQRFEVHINPKLLGIDEELFIYC

MQHATKMRSNRYTYLHEVDLSTDRLKQIYKELISEL

*Streptococcus pneumoniae* 23A gtp2

SEQ ID NO: 17

MKALILAAGLGTRLAPITNEVPKSLVPVNGKPILMKQIENLYQNNITDITI

IAGYKSSVLTDAVTEKYPEINIIDNVDFKTTNNMYSAYLGKAAMGDSDFLM

MNADVFYDASVIKSLLLHKAPNAIVTDLGIYIEESMKVVEKNGRLVEISKQ

ISPEETLGASIDVYKFSYEAGARFFEKCKEFIEDKRELQMWSEVALNAILS

EVEFVACPLEGRWLEIDNHEDLVAAEKLFA

*Streptococcus pneumoniae* 23A gtp3

SEQ ID NO: 18

MKLTNRVDYFGADISELQNKKLFLFDMDGTIYEEDRLFEGTLELLDYIHNI

GGEYIFITNNSSKSVVDYVEKVNRLGIKAERDNFFTSAQATIVYIKENYPK

SKVYCQGTKSLIKELSDAGIDVTEQVSADIDVVLVGFDTELTSDKIRNTCE

ILSTKDVPFIATNPDIRCPVSFGFIPDCGSICDMISKSVDRKPVYIGKPEP

TMVDIVRKKLNYSLFETVVIGDRLYTDIMTGINAGVTSVCVLTGEATVNDI

QQDSIKPTYTFKNVKEMWKGIV

*Streptococcus pneumoniae* 23A rmlA

SEQ ID NO: 19

MKGIILAGGSGTRLYPLTRAASKQLMPVYDKPMIYYPLSTLMLAGIRDILI

ISTPQDLPRFKELLQDGSEFGIKLSYAEQPSPDGLAQAFIIGEEFIGDDSV

ALILGDNIYHGPGLSTMLQKAAKKEKGATVFGYHVKDPERFGVVEFDENMN

AISIEEKPEYPRSNYAVTGLYFYDNDVVEIAKSIKPSPRGELEITDVNKAY

LDRGDLSVELMGRGFAWLDTGTHESLLEASQYIETVQRMQNVQVANLEEIA

YRRGYISREDVLALAQSLKKNEYGQYLLRLIGEA

*Streptococcus pneumoniae* 23A rmlC

SEQ ID NO: 20

MTDNFFGKTLAARKVEAIPGMLEFDIPVHGDNRGWFKENFQKEKMLPLGFP

ESFFAEGKLQNNVSFSRKNVLRGLHAEPWDKYISVADGGKVLGSWVDLREG

ETFGNTYQTVIDASKGIFVPRGVANGFQVLSDTVSYSYLVNDYWALELKPK

YAFVNYADPSLGIEWENIAEAEVSEADKNHPLLKDVKPLKKEDL

*Streptococcus pneumoniae* 23A rmlB

SEQ ID NO: 21

MTEYKNIIVTGGAGFIGSNFVHYVYENFPDVHVTVLDKLTYAGNRANIEEI

LGNRVELVVGDIADAELVDKLAAQADAIVHYAAESHNDNSLNDPSPFIHTN

FIGTYTLLEAARKYDIRFHHVSTDEVYGDLPLREDLPGHGEGPGEKFTAET

KYNPSSPYSSTKAASDLIVKAWVRSFGVKATISNCSNNYGPYQHIEKFIPR

QITNILSGIKPKLYGEGKNVRDWIHTNDHSSGVWTILTKGQIGETYLIGAD

GEKNNKEVLELILKEMGQAVDAYDHVTDRAGHDLRYAIDASKLRDELGWKP

EFTNFEAGLKATIKWYTDNQEWWKAEKEAVEANYAKTQEIITV

*Streptococcus pneumoniae* 23A rmlD

SEQ ID NO: 22

MILITGANGQLGTELRYLLDERNEEYVAVDVAEMDITDAEMVEKVFEEVKP

TLVYHCAAYTAVDAAEDEGRELDFAINVTGTKNVAKASEKHGATLVYISTD

YVFDGKKPVGQEWEVDDRRPDPQTEYGRTKRMGEELVEKHVSNFYIIRTAW

FGNYGKNFVFTMQNLAKTHKTLTVVNDQYGRPTWTRTLAEFMTYLAENRKE

FGYYHLSNDATEDTTWYDFAVEILKGTDVEVKPVDSSQFPAKAKRPLNSTM

SLAKAKATGFVIPTWQDALQEFYKQEVR

Streptococcus pneumoniae 23B wzg

SEQ ID NO: 23

MLIMSRRFKKSGSQKVKRSVNIVLLTIYLLLVCFLLFLIFKYNILAFRYFN

LVVTALVLLVALVGLLLIIYKKAEKFTIFLLVFSILVSSVSLFAVQQFVGL

TNRLNATSNYSEYSISVAVLADSDIENVTQLTSVTAPTGTDNENIQKLLAD

IKSSQNIDLTVNQSSSYLAAYKSLIAGETKAIVLNSVFENIIESEYPDYAS

KIKKIYTKGFTKKVEAPKTSKNQSFNIYVSGIDTYGPISSVSRSDVNILMT

VNRDTKKILLTTTPRDAYVPIADGGNNQKDKLTHAGIYGVDSSIHTLENLY

GVDIHYYVRLNFTSFLKLIDLLGGVDVYNDQDFTSLHGKFHFPVGNVHLDS

EQALGFVRERYSLADGDHDRGRNQQKVIAAILQKLTSSEALKNYSMIIDSL

QDSIQTNMPLETMINLVNAQLESGGTYKVNSQDLKGRGRTDLPSYAMPDSN

LYMMEINDSSLASVKTAIQDVLEGR"

Streptococcus pneumoniae 23B wzh

SEQ ID NO: 24

MHLSKLLFRMCWRADEMIDIHSHIVFDVDDGPKSREESKALLTEAYRQGVR

TIVSTSHRRKGMFETPEEKIAENFLQVREIAKEVASDLVIAYGAEIYYTPD

VLGKLEKNRIPTLNNSRYALIEFSMNTPYRDIHSALIKILMLGITPVIAHI

ERYDALENNEKRVRELINMGCYTQVNSSHVLKSKLFGEPYKFMKKRAQYFL

ERDLVHVIASDMHNVDSRPPHMAEAYDLVSQKYGETKAQDLFIDNPRKIVM

DQLI"

Streptococcus pneumoniae 23B wzd

SEQ ID NO: 25

MKEQNTIEIDVFQLLKTLWKHKLIILLVALVTGAGAFAYSIFIVKPEYTST

TRIYVVNRNQENKPGLTNQDLQAGTYLVKDYHEIILSQDVLEKVATNLKLD

IPVKTLTSKVQVTVPADTRIVSISVKDKQPEEASRIANSIREVAAEKIIAV

TRVSDVTTLEEARPATTPSSPNVRRNTLVGFLGAAAVTVITVLLIELFDTR

VKRPEEVEDVLQMPLLGVVPDFNKMK

Streptococcus pneumoniae 23B wze

SEQ ID NO: 26

MPTLEISQAKLELAKKTEEYYNALCTNPQLSGDDLKVFSISSVKAGEGKTT

TSTNIAWAFAHAGYKTLLIDADMRNSVMSGVFKSRERITGLTEFLSGTTDL

SQGLCDTNVENLFVIQAGSVSPNPIALLQSKNFSTMLGTLRKYFDYIVVDT

APIGIVIDAAIIMQKCDASILVTKAGETKRRELQKAKEQLEQTGKSCLGVV

LNKFDTSVDKYGFYGSYGSYRKQKK

Streptococcus pneumoniae 23B wchA

SEQ ID NO: 27

MNEKLAKSSVAIVQSFLVILLTYLLSAVRETEIVSTTAIVLYILHYFVFYI

SDYGRNFFKRRYLIELVQTLKYILFFALAISISNFFLEDRFSISRRGMIYF

LLLHVFLVYMLNLFIKWYWKRAYPNFKGSKKVFLLTATSHVEKVLDRLIES

DDVVGELVAVSVLDKPDFQHDDLKVVAEGEIVNFATREVVDEVFINLPSEK

YNIGELVSQFETMGIDVTVNLNAFDWARNKQICEMAGLNVVTFSTTFYKTS

HVIAKRVIDIIGSLVGLILCGLVSIVLVPLIRKDGGSAIFAQTRIGKNGRH

FTFYKFRSMCVDAEDKKRELMEQNTMQGGMFKVDDDPRITKIGHFIRKTSL

DELPQFYNVLKGDMSLVGTRPPTVDEYEHYTPEQKRRLSFKPGITGLWQVS

GRSEIKNFDEVVKLDVVYIDGWTIWKDIEILLKTVKVVLMKDGAK

Streptococcus pneumoniae 23B wchF

SEQ ID NO: 28

MERNSLLLFQTIRRKMKKSVYIIGSKGIPAKYGGFETFVEKLTEYQKDGNI

QYYVACMRENSAKSGFTADTFEYNDAICYNIDVPNIGPARAIAYDIAAVNK

AIEIAKKNKDEAPIFYILACRIGPFIARLKKKIQAIGGTLFVNPDGHEWLR

AKWSLPVRKYWKFSEQLMVKYADLLVCDSKNIEKYIQNDYKQYQPKTTYIA

YGTDTSPSILKSEDLKIRSWYQEKGLSENGYYLVVGRFVPENNYETMIREF

IKSKSKKDFVLITNVEQNKFYDQLLQETGFDKDPRVKFVGTVYDQELLKYI

RENAFAYFHGHEVGGTNPSLLEALASTKLNLLLDVGFNREVGEDGAIYWRK

DNLHKVIEESEQKTIEEIKEIDILSTEQVEKRFTWDFIVNEYENLFLLGK

Streptococcus pneumoniae 23B wzy

SEQ ID NO: 29

MTIKINYMFFVCLSFFGIVLSSSQVIVNLGLSSIVQYIAYFLLLLCIFFTL

IKNSPDVIANRIAYFSIISFLFIIGINLQNLPFSTKIYLSFSMLIISSLST

LPIKLINNINDFRRISYFLLNGILLSTFLGWLFNISLVTVAVEGIGFAYGF

NGGLTHKNFYAITILVSYILLFISRKHGTKYQVDSLVLWFDLFLLLVSNTR

TIYIILVVFWIVVHSGFIKYIKKNHRPVIITTWLVISLLSIIFFFKHIINN

SESYTHRVLGIVNFFKYYESSKFHLFFGDAELAFGDMTKGYTHNIRSVLGW

DGTVEMPLLSVMIKNGYVGLIGYGVVLFKFISSVLSMEDRRVKNIGLSILI

PLLLSAMVENYIVNISFVFMPVCFCILCSIKNIEFKNN

Streptococcus pneumoniae 23B wchV

SEQ ID NO: 30

MKKVSIILPVYNVEQYIKKCLESIQQQTYPNLEVIIVNDGATDKSVEYCEQ

ICKIDSRFSVTHKENGGLSDARNVGIDKAKGDYLIFVDSDDFVSQDMVSYL

VSSMENNEADIAICDPAHYYSDRQNNDLNIFYPASSVKVYEKTEALCEMFY

QKSFLVSAWAKIYKKELFDDIRFPVGKLFEDSAVMYLLFEKCEKIVYSNAK

LYAYVHRDNSITTKKFSDKDLDILDISNTILDHYSGNFRVYKAAVSYKVSA

CFRILLNSSSEKKYNQIQKDCMTYILRNWRNMLFDKNVRLKNKLALISITL

FNPFVKFIYSKVNRWE

Streptococcus pneumoniae 23B wchW

SEQ ID NO: 31

MNKYEERYQEDLSKNDFEKLINRRYLSDKELQVEYVKKGTVLPPKVFEMKL

SNKLGLQKALHGKGGVVDSKGNYVELSEQKAVGMRNRVYGSYKFNHKNLAI

RNEKVIYLNYFINQWGHFLLDVVGRLWYPLLKDTDTKLDYTCYAGTETKLE

GNYLEFLELLGIDKSRLILINRPTQFSEIIIPESSILPGEYYTKEYKMLFN

SLVANVKLDNNLESKKIYCSRARLDLAKGKEFGENGIEKVFLKNGYTPVYM

ETMSLKEQIRTLLSATTIVLTSGSLAHNLLFINNKINVFILNKTYRVNLHQ

FLINKISEASVSFVDIYRSPLPILYGYGPFLMDITKPLVNFFEDSGFTYDS

GTILDKTDYFKFYLKWLWSYKFFLFRLNHIKEGNSEFEKSFKIIRRYYKMG

RQYE

Streptococcus pneumoniae 23B wzx

SEQ ID NO: 32

MSKYKELAKNTGTFALANFSSKILIFLLVPIYTKVLTTTEYGFYDLVYTTI

QLLVPILTLNISEAVMRFLMKEDVSKKSVFSIAILDIFLGSIIFCLLLLVN

-continued
QIFSLSELISQYSIYIMAIFAFYTLNNFLIQYSKGIDKIGVTAISGVISAA

VMLSMNILLLVVLNWGLLGFFIANICGYVIPCVYIIVKLKLWDLFELKIDR

SLQWEMIYYTLPLILNTLSWWVNNTSDRYIITVIIGIQASAIISVAYKIPQ

IFSTISAIFIQSWQISAIKIQEEKEGNTFISKMLLYYNALLLIIASGIILF

VKPISNILFGASFYSAWTLVPFLIISSLFNAISGYIGAIMGAKMDTKNIAK

SALVGMIANVFLNIVLTFLMGLQGITISTMIASFLIFYMRKDSVEEIAPET

YRAIYLSWFLLVVEASLLVYIDFIIGATLVTLINLFLLKDTLKPLCLKLLK

GFK

*Streptococcus pneumoniae* 23B wchX
SEQ ID NO: 33
MKMNILQYIKILARTIFMLLISTVLLPVRLKNNKILFINFNGKGYGDNPKS

ICEYLRTTYPDLDLVWLARDNEGFPDGVRVVKYGTFQAFYEQASSKVWVYN

VRAFARILKKRGQIYIQTWHGASSFKLIEKQADLPINYVLEAKYDARVTDI

MISDSRKQTEEFQKYFWYSGEIFEVGMPRNDALFHYKEDYDKLNNIRKELS

IHSDDYVILYAPTFRDDGDASYLDINFERLLQCVEHGIKKKCKFLIRLHPN

HSHLCNNISFNKNIINATFYSDMQELTLLADVLVTDYSSSIFDFMLLNKPY

VRYVNDLEKYAELRGVSDTYYELPDSIIKTAEELYDLLPKKIENFDYDSIK

KYRNEILCPIFNGTASENVGRRIIQEL

*Streptococcus pneumoniae* 23B gtp1
SEQ ID NO: 34
MKNNDLKIGSGAIHQISATLSQNSISGKILYCADPVVDDLYGSIVRSQIEE

IGRVKEESCNYNTIAYAMNIAERAIATDIDCIVGMGGGRVLDVCKYASFIS

KRPYLSIPTTAANDGIASPVAVLKRQDDRPKSLGAAIPSMTLIDIDVIASG

PIQNIKAGIGDTISNYTALKDWELAVERGKDEMHGFAYLMSQNSLDALMKT

KYNSITPDFIEVLVNSLVLSGIAMDFAGSSRPVSGSEHLFSHALDYYGSTR

NLHGIQVALGTVAVLKLIENSVDTVVDYLQRFEVHINPKLLGIDEELFIYC

MQHATKMRSNRYTYLHEVDLSTDRLKQIYKELISEL

*Streptococcus pneumoniae* 23B gtp2
SEQ ID NO: 35
MKALILAAGLGTRLAPITNEVPKSLVPVNGKPILMKQIENLYQNNITDITI

IAGYKSSVLTDAVTEKYPEINIIDNVDFKTTNNMYSAYLGKAAMGDSDFLM

MNADVFYDASVIKSLLLHKAPNAIVTDLGIYIEESMKVVEKNGRLVEISKQ

ISPEETLGASIDVYKFSYEAGARFFEKCKEFIEDKRELQMWSEVALNAILS

EVEFVACPLEGRWLEIDNHEDLVAAEKLFA

*Streptococcus pneumoniae* 23B gtp3
SEQ ID NO: 36
MNRIRRMKLTNRVDYFGADISELQNKKLFLFDMDGTIYEEDRLFEGTLELL

DYIHNIGGEYIFITNNSSKSVVDYVEKVNRLGIKAERDNFFTSAQATIVYI

KENYPKSKVYCQGTKSLIKELSDAGIDVTEQVSADIDVVLVGFDTELTSDK

IRNTCEILSTKDVPFIATNPDIRCPVSFGFIPDCGSICDMISKSVDRKPVY

IGKPEPTMVDIVRKKLNYSLFETVVIGDRLYTDIMTGINAGVTSVCVLTGE

ATVNDIQQDSIKPTYTFKNVKEMWKGIV

*Streptococcus pneumoniae* 23B rmlA
SEQ ID NO: 37
MKGIILAGGSGTRLYPLTRAASKQLMPVYDKPMIYYPLSTLMLAGIRDILI

ISTPQDLPRFKELLQDGSEFGIKLSYAEQPSPDGLAQAFIIGEEFIGDDSV

-continued
ALILGDNIYHGPGLSTMLQKAAKKEKGATVFGYHVKDPERFGVVEFDENMN

AISIEEKPEYPRSNYAVTGLYFYDNDVVEIAKSIKPSPRGELEITDVNKAY

LDRGDLSVELMGRGFAWLDTGTHESLLEASQYIETVQRMQNVQVANLEEIA

YRMGYISREDVLALAQPLKKNEYGQYLLRLIGEA

*Streptococcus pneumoniae* 23B rmlC
SEQ ID NO: 38
MTDNFFGKTLAARKVEAIPGMLEFDIPVHGDNRGWFKENFQKEKMLPLGFP

ESFFAEGKLQNNVSFSRKNVLRGLHAEPWDKYISVADGGKVLGSWVDLREG

ETFGNTYQTVIDASKGIFVPRGVANGFQVLSDTVSYSYLVNDYWALELKPK

YAFVNYADPSLGIEWENIAEAEVSEADKNHPLLKDVKPLKKEDL

*Streptococcus pneumoniae* 23B rmlB
SEQ ID NO: 39
MTEYKNIIVTGGAGFIGSNFVHYVYENFPGVHVTVLDKLTYAGNRANIEEI

LGNRVELVVGDIADAELVDKLAAQADAIVHYAAESHNDNSLNDPSPFIHTN

FIGTYTLLEAARKYDIRFHHVSTDEVYGDLPLREDLPGHGEGPGEKFTAET

KYNPSSPYSSTKAASDLIVKAWVRSFGVKATISNCSNNYGPYQHIEKFIPR

QITNILSGIKPKLYGEGKNVRDWIHTNDHSSGVWTILTKGQIGETYLIGAD

GEKNNKEVLELILKEMGQATDAYDHVTDRAGHDLRYAIDASKLRDELGWKP

EFTNFEAGLKATIKWYTDNQEWWKAEKEAVEANYAKTQEIITV

*Streptococcus pneumoniae* 23B rmlD
SEQ ID NO: 40
MILITGANGQLGTELRYLLDERNEEYVAVDVAEMDITNEEMVEKVFEEVKP

TLVYHCAAYTAVDAAEDEGKELNFAINVTGTKNVAKASEKHGATLVYISTD

YVFDGKKPVGQEWEVDDRPDPQTEYGRTKRMGEELVEKHVSNFYIIRTAWV

FGNYGKNFVFTMQNLAKTHKTLTVVNDQYGRPTWTRTLAEFMTYLAENRKE

FGYYHLSNDATEDTTWYDFAVEILKDTDVEVKPVDSSQFPAKAKRPLNSTM

SLAKAKATGFVIPTWQDALQEFYKQEVR

*Streptococcus pneumoniae* 23F wzg
SEQ ID NO: 41
MSRRFKKSRSQKVKRSVNIVLLTIYLLLVCFLLFLIFKYNILAFRYLNLVV

TALVLLVALVGLLLIIYKKAEKFTIFLLVFSILVSSVSLFAVQQFVGLTNR

LNATSNYSEYSISVAVLADSDIENVTQLTSVTAPTGTDNENIQKLLADIKS

SQNTDLTVDQSSSYLAAYKSLIAGETKAIVLNSVFENIIESEYPDYASKIK

KIYTKGFTKKVEAPKTSKNQSFNIYVSGIDTYGPISSVSRSDVNILMTVNR

DTKKILLTTTPRDAYVPIADGGNNQKDKLTHAGIYGVDSSIHTLENLYGVD

INYYVRLNFTSFLKMIDLLGGVDVHNDQEFSALHGKFHFPVGNVHLDSEQA

LGFVRERYSLADGDRDRGRNQQKVIVAILQKLTSTEALKNYSTIIDSLQDS

IQTNMPLETMINLVNAQLESGGNYKVNSQDLKGTGRTDLPSYAMPDSNLYV

MEIDDSSLAVVKAAIQDVMEGR

*Streptococcus pneumoniae* 23F wzh
SEQ ID NO: 42
MIDIHSHIVFDVDDGPKSREEESKALLTESYRQGVRTIVSTSHRRKGMFETP

EEKIAENFLQVREIAKEVADDLVIAYGAEIYYTLDALEKLEKKEIPTLNDS

RYALIEFSMNTPYRDIHSALSKILMLGITPVIAHIERYDALENNEKRVREL

IDMGCYTQVNSSHVLKPKLFGERYKFMKKRAQYFLEQDLVHVIASDMHNLD

GRPPHMAEAYDLVTQKYGEAKAQELFIDNPRKIVMDQLI

Streptococcus pneumoniae 23F wzd
SEQ ID NO: 43
MMKEQNTIEIDVFQLFKTLWKRKLMILIVALVTGTGAFAYSTFIVKPEYTS
TTRIYVVNRNQGDKPGLTNQDLQAGTYLVKDYREIILSQDALEKVATNLKL
DMPAKTLASKVQVAVPADTRIVSISVKDKQPEEASRIANSLREVAAEKIVA
VTRVSDVTTLEEARPATTPSSPNVRRNSLFGFLGGAVVTVIAVLLIELLDT
RVKRPEDVEDVLKIPLLGLVPDFDKIK Streptococcus pneumoniae 23F wze
SEQ ID NO: 44
MPTLEISQAKLDSVKKAEEYYNALCTNLQLSGDGLKVFSITSVKIGEGKST
TSANIAWAFARAGYKTLLIDGDIRNSVMLGVFKARNKITGLTEFLSGTTDL
SQGLCDTNIENLFVIQAGSVSPNPTALLQSKNFTTMLETLRKYFDYIIVDT
APVGVVIDAAIITRNCDASILVTEAGEINRRDIQKAKEQLEHTGKPFLGIV
LNKFDTSVDKYGSYGNYGNYGKNKK Streptococcus pneumoniae 23F wchA
SEQ ID NO: 45
MNEKILRSSLAIIQSFLVILLTYLLSAVRETEIVSTTAIALCILHYFVFYI
SDYGQDFFKRRYLIELVQTLKYILFFALAIGISNFFLEDRFSISRRGMIYF
LTLHALLVYVLNLFIKWYWKRAYPNFKGSKKILLLTATSRVEKVLDRLIES
NEVVGKLVAVSVLDKPDFQHDCLKVVAEGGIVNFATHEVVDEVFINLPSEK
YNIGELVSQFETMGIDVIVNLNAFDRSLARNKQIREMAGLNVVTFSTTFYK
TSHVIAKRIIDIVGALVGLILCGLVSIVLVPLIRKDGGSAIFAQTRIGKNG
RQFTFYKFRSMCVDAEAKKRELMEQNTMQGGMFKVDDDPRITKIGCFIRKT
SLDELPQFYNVLKGDMSLVGTRPPTVDEYEHYTPEQKRRLSFKPGITGLWQ
VSGRSEIKNFDEVVKLDVAYIDGWTIWKDIEILLKTVKVVFMRDGAK Streptococcus pneumoniae 23F wchF
SEQ ID NO: 46
MKKSVYIIGSKGIPAKYGGFETFVEKLTAFQQDKAIQYYVACMRENSAKSG
TTEDVFEHNGAICYNVDVPNFGPARAIAYDIAAINRAIEIAKENKDEDPIF
YILACRIGPFIHGIKKKIQEIGGTLLVNPDGHEWLRAKWSAPVRRYWKISE
GLMVKHADLLVCDSKNIEKYIQEDYKQYQPKTTYIAYGTDTTRSVLKSSDE
KVRSWFKEKNVSENEYYLVVGRFVPENNYESMIRGFLASNSKKDFVLITNV
EQNKFYNQLLAKTGFDKDPRVKFVGTVYEQELLKYIRENAFAYFHGHEVGG
TNPSLLEALASTKLNLLLDVGFNREVAEDGAIYWKKDNLHEIIETSEQKTQ
KEIDEKDILSIKQVTERFSWELIVNEYEKLFLCEK Streptococcus pneumoniae 23F wzy
SEQ ID NO: 47
MTIKINNLFFVCLSFFGIVLSSSQVIVNLGLSSIIQYISYFMLMLCVFLTL
IKNTLNVFANRIIYFLIISFLFIIGINLQNLPLSRKIYLSFSMLIISSLST
LPIKLINNLSDLRRISYYLLHSIFLSVFLGLVFKISLVTVAVEGIGFSYGF
NGGLTHKNFYAITILVSYILLYVSRKYDAKHQIDSFVLWLDLFLLLISNTR
TVYIILVVFWIIINRNFINNIKKEHRLVVTATTIVISLLALTFFFKHIINN
SESYSHRVLGVVNFFKYYESDRFHLFFGDAELAFGNTTKGYGHNIRSVLGW
DGTVEMPLLSVMIKNGYVGLVGYIIVLFKFISSIISVKNSTKKNIGLSIFI
PLLLSATVENYIVNISFVFMPVCFCILCSIKNIKLVNNRK Streptococcus pneumoniae 23F wchV
SEQ ID NO: 48
MEKLVSIILPVYNVEQYIKNCLESIQQQTYSNLEVIIVNDGSTDKSVEYCE
QICKIDSRFSITHKENGGLSDARNVGIDKSKGDYLIFVDSDDFVSQDMVSY
LVSCMENNEADIAICDPVHYYSDRQNNDLNIFSPASNVKVYETTEALCEMF
YQKSFLVSAWAKIFKRELFDDIRFPVGKLFEDSAIMYLLFEKCETIAYSDA
ELYAYVHRDNSITTKKFSDRDLDILEITNTIINHYGDNLRVYTAAVSYKVS
ACFRILLNSPSGEKYKKVQKECLSYILQNWRNILFNNNVRLKNKLALISIT
IFNPFVKFIYSKVNRWE Streptococcus pneumoniae 23F wchW
SEQ ID NO: 49
MNKYEERYQENLSKNDFYKLINKSYLSDKELQVQQVKAGIVLPPKAFETKL
SNKLGLQKSLHGKGGVVDSNGNYIELSAQKAVGMRNRVYGPYKINYDNLPI
RNEKVIYLNYFIKQWGHFLLDVVGRLWYPLLQDNDTKLVYTCYAGTETKIE
GNYLEFLKLLGIDQSRLIMINCPTQFSEVIIPESSILPGGYYTKEYKQLFS
SVVENIKLDKYDVNAKMIYCSRSKLGIAKSKEFGEDGIEGIFKQNGYTSVY
METMSLEEQIKTLLSAKTIVLTSGSLAHNLLFVNKDIDVFILNKTYRVNLH
QFLINEISDATVRFVDIYRSPLPILYGYGPFLMDLTKPLANFLDDNEFVYE
KGTVLSKKDYFKYYLKWLWSYRFFLFRLNGIKEGNSEFEKSFKIIRRYYKT
GR Streptococcus pneumoniae 23F wzx
SEQ ID NO: 50
MSKYKELAKNTGIFALANFSSKILIFLLVPIYTRVLTTTEYGFYDLVYTTI
QLFVPILTLNISEAVMRFLMKDGVSKKSVFSIAVLDIFIGSIAFALLLLVN
NLFSLSDLISQYSIYIFVIFVFYTLNNFLIQFSKGIDKIGVTAISGVISTA
VMLAMNVILLVVFDWGLLGFFIANVCGYVIPCIYIVSRLRLWELFEIKIDK
KLQWEMVYYALPLVLNILSWWVNNTSDRYIVTAIVGIQASAIISVAYKIPQ
ILSTISAIFIQSWQISAIKIQEDKSDTTFVSNMLLYYNALLLIIASGIILF
VKPISNILFGISFYSAWELVPFLIISSLFNAISGCIGAIMGAKMDTHNIAK
SALVGMIANIILNIVLTFLMGPQGITISTLIASFLIFYMRKDSVKEINSET
YRAIYLSWILLVVEACLLIYMDFIIGALIAMVINLFLLKDVIKPLYLKIFK
RN Streptococcus pneumoniae 23F wchX
SEQ ID NO: 51
MIVLQYFKILARFVFMFLISAVLLPFKIKPNKIVFINFNGKGYGDNPKSIC
EYLRTTYPDLDLVWLARDNEGFPDGVRVVKYGTFQAFYEQASSKVWVYNVR
AFARILKKRGQIYIQTWHGASSFKLIEKQADLPINYVLEAKYDARVTDIMI
SDSRKQTEEFQKYFWYSGEIFEVGMPRNDALFHYKEDYDKLNNIRKELSIH
SDDYVILYAPTFRDDGDASYLDINFERLLQCVEHGIKKKCKFLIRLHPNHS
HLCNNISFNKNIIINATFYSDMQELTLLADVLVTDYSSSIFDFMLLNKPYVR
YVNDLEKYAELRGVSDTYYELPDSIIKTAEELYDLLPKKIENFDYDSIKKY
RNEILCPIFNGTASENVGRRIIQEL Streptococcus pneumoniae 23F gtp1
SEQ ID NO: 52
MKNNDLKIGSGAIHQISATLSQNSISGKILYCADPVVDDLYGSIVRSQIEE
IGRVKEESCNYNTIAYAMNIAERAIATDIDCIVGMGGGRVLDVCKYASFIS KRPYLSIPTTAANDGIASPVAVLKRQDDRPKSLGAAIPSMTLIDIDVIASG
PIQNIKAGIGDTISNYTALKDWELAVERGKDEMHGFAYLMSQNSLDALMKT
KYNSITPDFIEVLVNSLVLSGIAMDFAGSSRPVSGSEHLFSHALDYYGSTR
NLHGIQVALGTVAVLKLIENSVDTVVDYLQRFEVHINPKLLGIDEELFIYC
MQHATKMRSNRYTYLHEVDLSTDRLKQIYKELISEL

*Streptococcus pneumoniae* 23F gtp2
SEQ ID NO: 53
MKALILAAGLGTRLAPITNEVPKSLVPVNGKPILMKQIENLYQNNITDITI
IAGYKSSVLTDAVTEKYPEINIIDNVDFKTTNNMYSAYLGKAAMGDSDFLM
MNADVFYDASVIKSLLLHKAPNAIVTDLGIYIEESMKVVEKNGRLVEISKQ
ISPEETLGASIDVYKFSYEAGARFFEKCKEFIEDKRELQMWSEVALNAILS
EVEFVACPLEGRWLEIDNHEDLVAAEKLFA

*Streptococcus pneumoniae* 23F gtp3
SEQ ID NO: 54
MKLTNRVDYFGADISELQNKKLFLFDMDGTIYEEDRLFEGTLELLDYIHNI
GGEYIFITNNSSKSVVDYVEKVNRLGIKAERDNFFTSAQATIVYIKENYPK
SKVYCQGTKSLIKELSDAGIDVTEQVSADIDVVLVGFDTELTSDKIRNTCE
ILSTKDVPFIATNPDIRCPVSFGFIPDCGSICDMISKSVDRKPVYIGKPEP
TMVDIVRKKLNYSLFETVVIGDRLYTDIMTGINAGVTSVCVLTGEATVNDI
QQDSIKPTYTFKNVKEMWKGIV

*Streptococcus pneumoniae* 23F rmlA
SEQ ID NO: 55
MKGIILAGGSGTRLYPLTRAASKQLMPVYDKPMIYYPLSTLMLAGIRDILI
ISTPQDLPRFKELLQDGSEFGIKLSYAEQPSPDGLAQAFIIGEEFIGDDSV
ALILGDNIYHGPGLSTMLQKAAKKEKGATVFGYHVKDPERFGVVEFDENMN
AISIEEKPEYPRSNYAVTGLYFYDNDVVEIAKSIKPSPRGELEITDVNKAY
LDRGDLSVELMGRGFAWLDTGTHESLLEASQYIETVQRMQNVQVANLEEIA
YRRGYISREDVLALAQSLKKNEYGQYLLRLIGEA

*Streptococcus pneumoniae* 23F rmlC
SEQ ID NO: 56
MTDNFFGKTLAARKVEAIPGMLEFDIPVHGDNRGWFKENFQKEKMLPLGFP
ESFFAEGKLQNNVSFSRKNVLRGLHAEPWDKYISVADGGKVLGSWVDLREG
ETFGNTYQTVIDASKGIFVPRGVANGFQVLSDTVSYSYLVNDYWALELKPK
YAFVNYADPSLGIEWENIAEAEVSEADKNHPLLKDVKPLKKEDL

*Streptococcus pneumoniae* 23F rmlB
SEQ ID NO: 57
MTEYKNIIVTGGAGFIGSNFVHYVYENFPDVHVTVLDKLTYAGNRANIEEI
LGNRVELVVGDIADAELVDKLAAQADAIVHYAAESHNDNSLNDPSPFIHTN
FIGTYTLLEAARKYDIRFHHVSTDEVYGDLPLREDLPGHGEGPGEKFTAET
KYNPSSPYSSTKAASDLIVKAWVRSFGVKATISNCSNNYGPYQHIEKFIPR
QITNILSGIKPKLYGEGKNVRDWIHTNDHSSGVWTILTKGQIGETYLIGAD
GEKNNKEVLELILKEMGQAVDAYDHVTDRAGHDLRYAIDASKLRDELGWKP
EFTNFEAGLKATIKWYTDNQEWWKAEKEAVEANYAKTQEIITV

*Streptococcus pneumoniae* 23F rmlD
SEQ ID NO: 58
MILITGANGQLGTELRYLLDERNEEYVAVDVAEMDITDAEMVEKVFEEVKP
TLVYHCAAYTAVDAAEDEGRELDFAINVTGTKNVAKASEKHGATLVYISTD YVFDGKKPVGQEWEVDDRPDPQTEYGRTKRMGEELVEKHVSNFYIIRTAWV
FGNYGKNFVFTMQNLAKTHKTLTVVNDQYGRPTWTRTLAEFMTYLAENRKE
FGYYHLSNDATEDTTWYDFAVEILKGTDVEVKPVDSSQFPAKAKRPLNSTM
SLAKAKATGFVIPTWQDALQEFYKQEVR

*E. coli* O2 WegR
SEQ ID NO: 59
MEENNMKTVAVVGTVGVPACYGGFESLVQNLIDYQSDGIQYQIFCSSKKYD
KKFKNYKNAELIYLPINANGVSSIIYDIMCLIICLFKRPDVVLILGVSGCL
FLPIYKLFSKSKIIVNIDGLEWRRNKWGTFAKKFLKISEAISIRIADIIIS
DNQAIADYVENKYKKKSVVIAYGGDHATNLSTPIDNDQKKEGYYLGLCRIE
PENNIEMILNAFINTDKKIKFMGNWDNSEYGRQLKKYYSNYPNITLLEPNY
NIEELYKLRKNCLAYIHGHSAGGTNPSLVEAMHFNIPIFAFDCDFNRYTTN
NLAHYFNDSEQLSLLAESLSFGNLKCRVLDLKNYAEDMYNWRHIAAMYESI
Y

*E. coli* O149 WbuV
SEQ ID NO: 60
MTEQFSEKKIDVVGIVGLPACYGGFESLVQNLVDYQSQNIKYNVYCSRKKY
KNTPKKYKRADLKYIPFDANGSSSILYDIYSLFLSLFNKVDVVLILGVSGC
VFLPIYRFFSSSKVIVNIDGLEWKRAKWKGIAKWYLKISEKIAVKYSDVVV
ADNEAIAKYVLKKYGLEAKIIAYGGDHSLVKKPISVIKEDYFFTVCRIEPE
NNIRMILEAFKNTTHSLKIVGNWDSSLYGRRLKEEFGNYNNIEIIDPIYDS
DILFNFRSLCRGYIHGHSAGGTNPSLVEAMHFQIPIIAFDCDFNRFTTDNY
AFYFKNKNELSFIVNDILNGNQNEQAEICAKKMKEIATKKYTWDTIAKMYE
ELY

*Cronobacter sakazakii* WepI
SEQ ID NO: 61
MKRIAVVGTVGIPACYGGFESLVENLTKYKGAGYQYYIFCSSKNYPEKSDS
HNDAQLIYVPLKANGIQSILYDIVSLWKCLFLKVDTILILGVSGCIFLPVF
RLLSNAKIITNIDGLEWKREKWNYPIKKFLKFSELLAVKYSHAIVTDNRAI
TDYVKKEYNVSSFTIAYGGDHAVRPSNNNNNIKSSYALGLCRIEPENNVEL
ILKAFTLSEDKLKFVGNWNASSYGRMLKKNYSNYSNIELIEPIYDIDKLYI
LRSGCDKYIHGHSAGGTNPSLVEMMHFGVPIFAFDCEFNRHSTDNKAFYFK
DAQHLADLVKMKDNTELEKNSCNMKVLAQENYTWQKITASYESLY pglB from *Campylobacter jejuni*
SEQ ID NO: 62
IISNDGYAFAEGARDMIAGFHQPNDLSYYGSSLSTLTYWLYKITPFSFESI
ILYMSTFLSSLVVIPIILLANEYKRPLMGFVAALLASIANSYYNRTMSGYY
DTDMLVIVLPMFILFFMVRMILKKDFFSLIALPLFIGIYLWWYPSSYTLNV
ALIGLFLIYTLIFHRKEKIFYIAVILSSLTLSNIAWFYQSTIIVILFALFA
LEQKRLNFVIIGILASVTLIFLILSGGVDPILYQLKFYIFRSDESANLTQG
FMYFNVNQTIQEVENVDLSEFMRRISGSEIVFLFSLFGFVWLLRKHKSMIM
ALPILVLGFLALKGGLRFTIYSVPVMALGFGFLLSEFKAILVKKYSQLTSN
VCIVFATILTLAPVFIHIYNYKAPTVFSQNEASLLNQLKNIANREDYVVTW
WDYGYPVRYYSDVKTLVDGGKHLGKDNFFPSFALSKDEQAAANMARLSVEY
TEKSFYAPQNDILKTDILQAMMKDYNQSNVDLFLASLSKPDFKIDTPKTRD

```
-continued
IYLYMPARMSLIFSTVASFSFINLDTGVLDKPFTFSTAYPLDVKNGEIYLS

NGVVLSDDFRSFKIGDNVVSVNSIVEINSIKQGEYKITPIDDKAQFYIFYL

KDSAIPYAQFILMDKTMFNSAYVQMFFLGNYDKNLFDLVINSRDAKVFKLK
I

E. coli wecA
                                    SEQ ID NO: 63
MMVFGKLYLS SLGYIFGSWE MVLGPFGYFL TLFAVWAAIN

AFNMVDGIDG LLGGLSCVSF AAIGMILWFD GQTSLAIWCF

AMIAAILPYI MLNLGILGRR YKVFMGDAGS TLIGFTVIWI

LLETTQGKTH PISPVTALWI IAIPLMDMVA IMYRRLRKGM

SPFSPDRQHI HHLIMRAGFT SRQAFVLITL AAALLASIGV

LAEYSHFVPE WVMLVLFLLA FFLYGYCIKR AWKVARFIKR

VKRRLRRNRG GSPNLTK

E. coli RcsA
                                    SEQ ID NO: 64
MSTIIMDLCS YTRLGLTGYL LSRGVKKREI NDIETVDDLA

IACDSQRPSV VFINEDCFIH DASNSQRIKL IINQHPNTLF

IVFMAIANVH FDEYLLVRKN LLISSKSIKP ESLDDILGDI

LKKETTITSF LNMPTLSLSR TESSMLRMWM AGQGTIQISD

QMNIKAKTVS SHKGNIKRKI KTHNKQVIYH VVRLTDNVTN

GIFVNMR pglB from Campylobacter jejuni
                                    SEQ ID NO: 65
MLKKEYLKNPYLVLFAMIILAYVFSVFCRFYWVWWASEFNEYFFNNQLMII

SNDGYAFAEGARDMIAGFHQPNDLSYYGSSLSALTYWLYKITPFSFESIIL

YMSTFLSSLVVIPTILLANEYKRPLMGFAAALLASIANSYYNRTMSGYYDT

DMLVIVLPMFILFFMVRMILKKDFFSLIALPLFIGIYLWWYPSSYTLNVAL

IGLFLIYTLIFHRKEKIFYIAVILSSLTLSNIAWFYQSAIIVILFALFALE

QKRLNFMIIGILGSATLIFLILSGGVDPILYQLKFYIFRSDESANLTQGFM

YFNVNQTIQEVENVDLSEFMRRISGSEIVFLFSLFGFVWLLRKHKSMIMAL

PILVLGFLALKGGLRFTIYSVPVMALGFGFLLSEFKAIMVKKYSQLTSNVC

IVFATILTLAPVFIHIYNYKAPTVFSQNEASLLNQLKNIANREDYVVTWWD

YGYPVRYYSDVKTLVDGGKHLGKDNFFPSFALSKDEQAAANMARLSVEYTE

KSFYAPQNDILKTDILQAMMKDYNQSNVDLFLASLSKPDFKIDTPKTRDIY

LYMPARMSLIFSTVASFSFINLDTGVLDKPFTFSTAYPLDVKNGEIYLSNG

VVLSDDFRSFKIGDNVVSVNSIVEINSIKQGEYKITPIDDKAQFYIFYLKD

SAIPYAQFILMDKTMFNSAYVQMFFLGNYDKNLFDLVINSRDAKVFKLKI fepE from Salmonella typhimurium
                                    SEQ ID NO: 66
MPSLNVKQEKNQSFAGYSLPPANSHEIDLFSLIEVLWQAKRRILATVFAFA

CVGLLLSFLLPQKWTSQAIVTPAESVQWQGLERTLTALRVLDMEVSVDRGS

VFNLFIKKFSSPSLLEEYLRSSPYVMDQLKGAQIDEQDLHRAIVLLSEKMK

AVDSNVGKKNETSLFTSWTLSFTAPTREEAQKVLAGYIQYISDIVVKETLE

NIRNQLEIKTRYEQEKLAMDRVRLKNQLDANIQRLHYSLEIANAAGIKRPV

YSNGQAVKDDPDFSISLGADGISRKLEIEKGVTDVAEIDGDLRNRQYHVEQ

-continued
LAAMNVSDVKFTPFKYQLSPSLPVKKDGPGKAIIIILAALIGGMMACGGVL

LRHAMVSRKMENALAIDERLV
```

EXAMPLES

Example 1

Genetic Analysis and Predicted Structures for Serotype 23B Capsular Polysaccharide Repeating Units The presence of the same glycosyltransferase (GT) genes (wchA, wchF, wchV, wchW and wchX) that are present in the cps locus of serotype 23F, indicates the possibility that serotype 23A and 23B contain the same monosaccharide composition as serotype 23F (FIG. 1).

In the cps cluster of serotype 23B, the highest sequence diversity among GT genes are observed for WchA and WchW. The function of WchA is biochemically demonstrated as undecaprenyl-phosphate glucosyl-1-phosphate transferase [Pelosi, L.; Boumedienne, M.; Saksouk, N.; Geiselmann, J.; Geremia, R. A. Biochem. Biophys. Res. Commun. 2005, 327(3), 857-865] which is a highly conserved function irrelevant to sequence diversity within S. pneumoniae [Bentley, S. D.; Aanensen, D. M.; Mavroidi, A.; Saunders, D.; Rabbinowitsch, E.; Collins, M.; Donohoe, K.; Harris, D.; Murphy, L.; Quail, M. A.; Samuel, G. PLoS Genet. 2006, 2(3), e31]. WchW is a putative α-1,2-L-rhamnosyltransferase [Morona, J. K.; Miller, D. C.; Coffey, T. J.; Vindurampulle, C. J.; Spratt, B. G.; Morona, R.; Paton, J. C. Microbiology. 1999, 145(4), 781-789]. A search for WchW homologues revealed no hits outside of serogroup 23 cps loci within S. pneumoniae; however a homologue to WchW was found in the cps locus of Klebsiella pneumoniae serotype K56, designated as WcpL (accession CZQ24634 [Follador, R.; Heinz, E.; Wyres, K. L.; Ellington, M. J.; Kowarik, M.; Holt, K. E.; Thomson, N. R. Microb. Genom. 2016, 2(8)]). The K. pneumoniae K56 CPS repeating unit also contains a rhamnose which is α-1,2-linked to galactose [Choy, Y. M.; Dutton, G. G. Can. J. Biochem. 1973, 51(18), 3021-3026]. The fact that WchW of 23B has the lowest sequence identity to WchW of 23A/F suggests that there may be a different bond between the L-rhamnose and the D-galactose, possibly explaining the serotyping differences. Due to the homology of the 23B and 23F repeat unit polymerase (Wzy), the polymerization is most likely to be similar for both serotypes.

NMR Assignments for Serotype 23F Capsular Polysaccharide Repeating Unit

Figure 2:
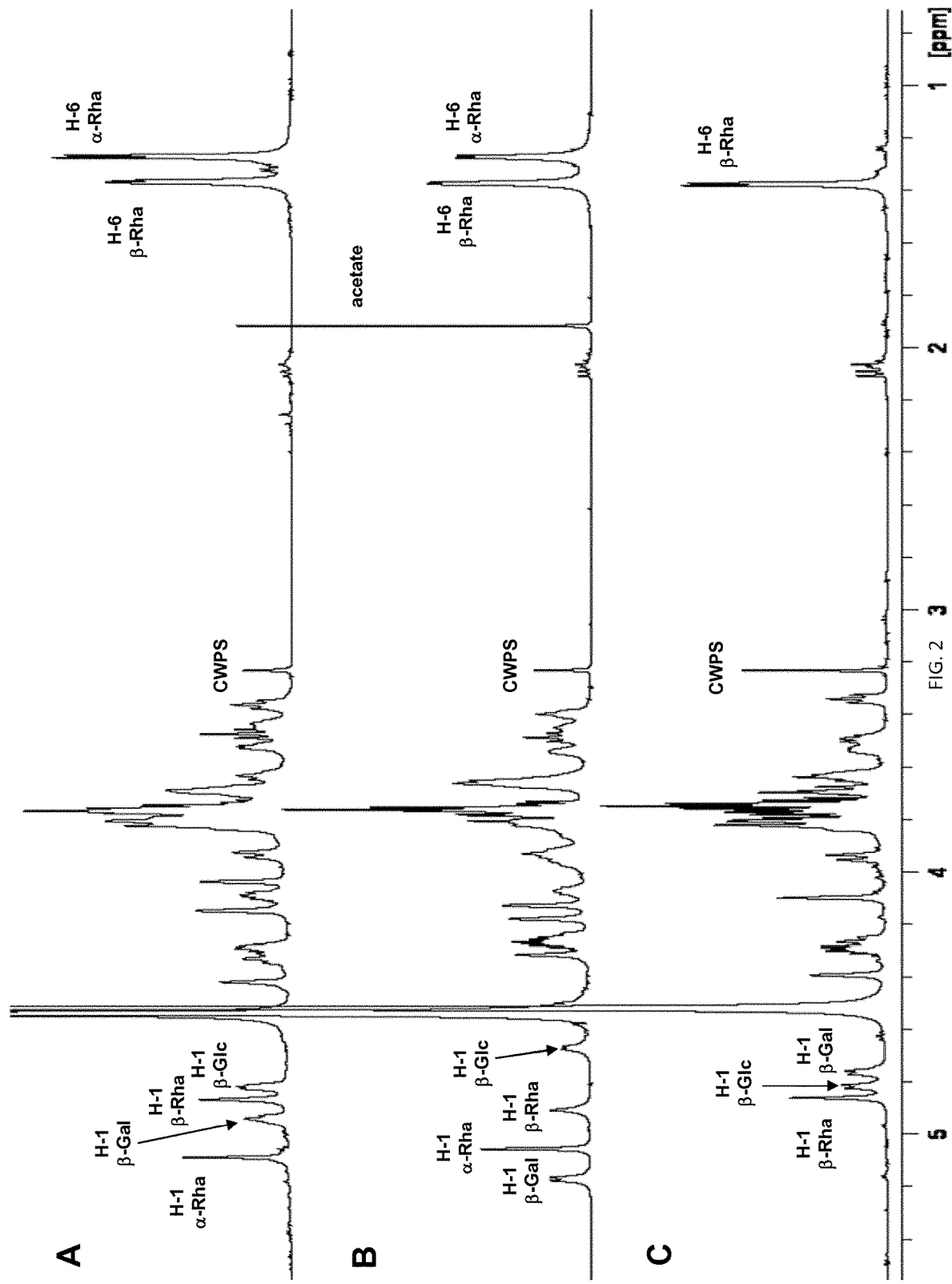
FIG. 2: 1D $^1$H NMR spectra of pneumococcal serotype (A) 23F, (B) 23A and (C) 23B capsular polysaccharides. Some signals including the diagnostic anomeric and methyl protons are labeled.

The $^1$H NMR spectrum (FIG. 2A) shows the expected signals for the 23F tetrasaccharide RU: four H-1, ring signals (including sharp peaks from glycerol) and two methyl signals from α- and β-Rha, together with small signals from residual CWPS (Genetic and structural elucidation of capsular polysaccharides from Streptococcus pneumoniae serotype 23A and 23B, and comparison to serotype 23F., "/pubmed/28837839", "Ravenscroft N, Omar A, Hlozek J, Edmonds-Smith C, Follador R, Serventi F, Lipowsky G, Kuttel M M, Cescutti P, Faridmoayer A.", "Carbohydr Res. 2017 Oct. 10).

Figure 3:
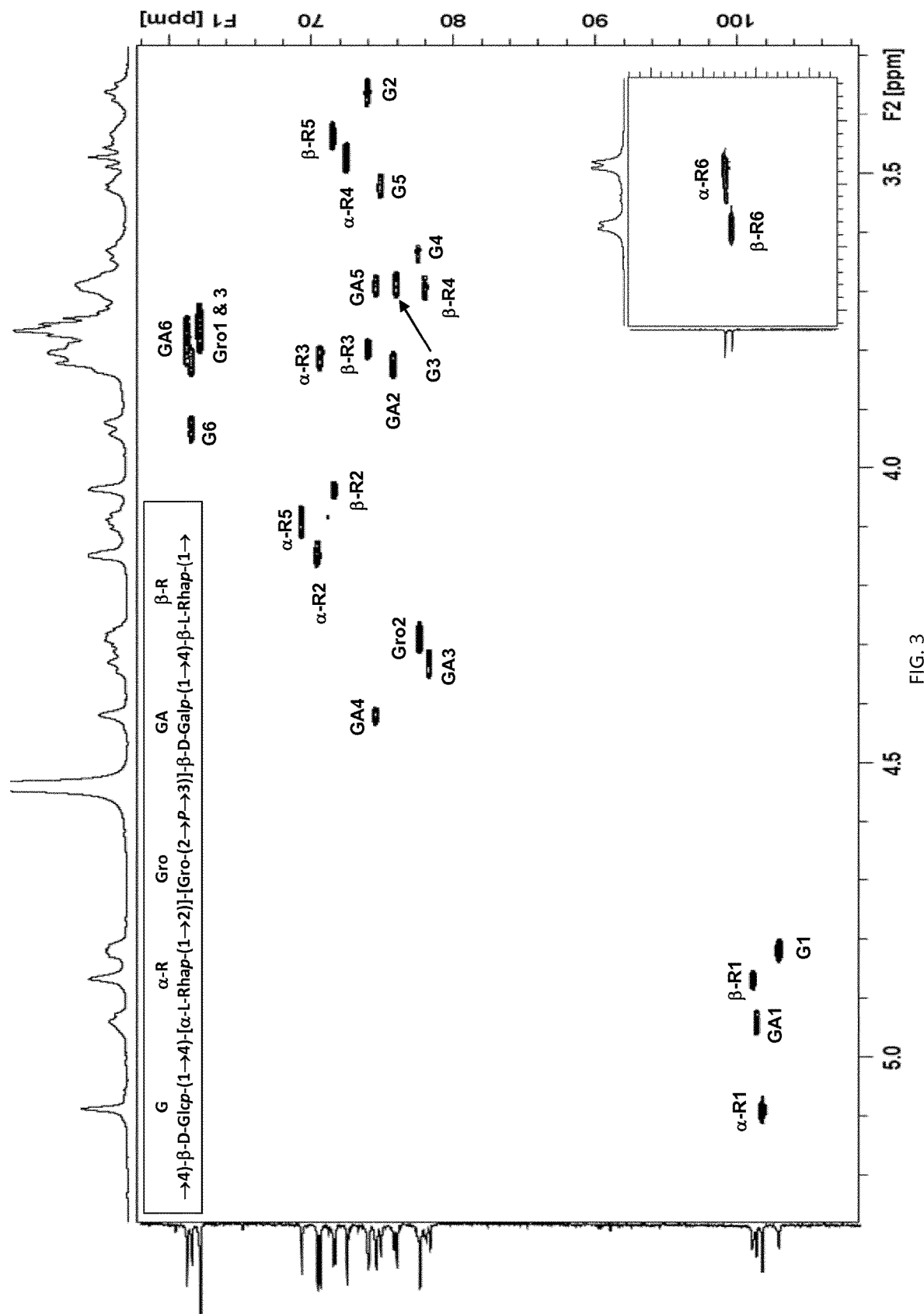
FIG. 3: Expansion of the HSQC spectrum of polysaccharide 23F recorded at 600 MHz, the crosspeaks from the methyl region of the spectrum are shown in the insert. Key tetrasaccharide repeating unit proton/carbon crosspeaks have been labeled according to the carbon atom of the corresponding residue (α- and β-R=α- and β-Rha, G=Glc, GA=Gal and Gro=glycerol).
Figure 4:
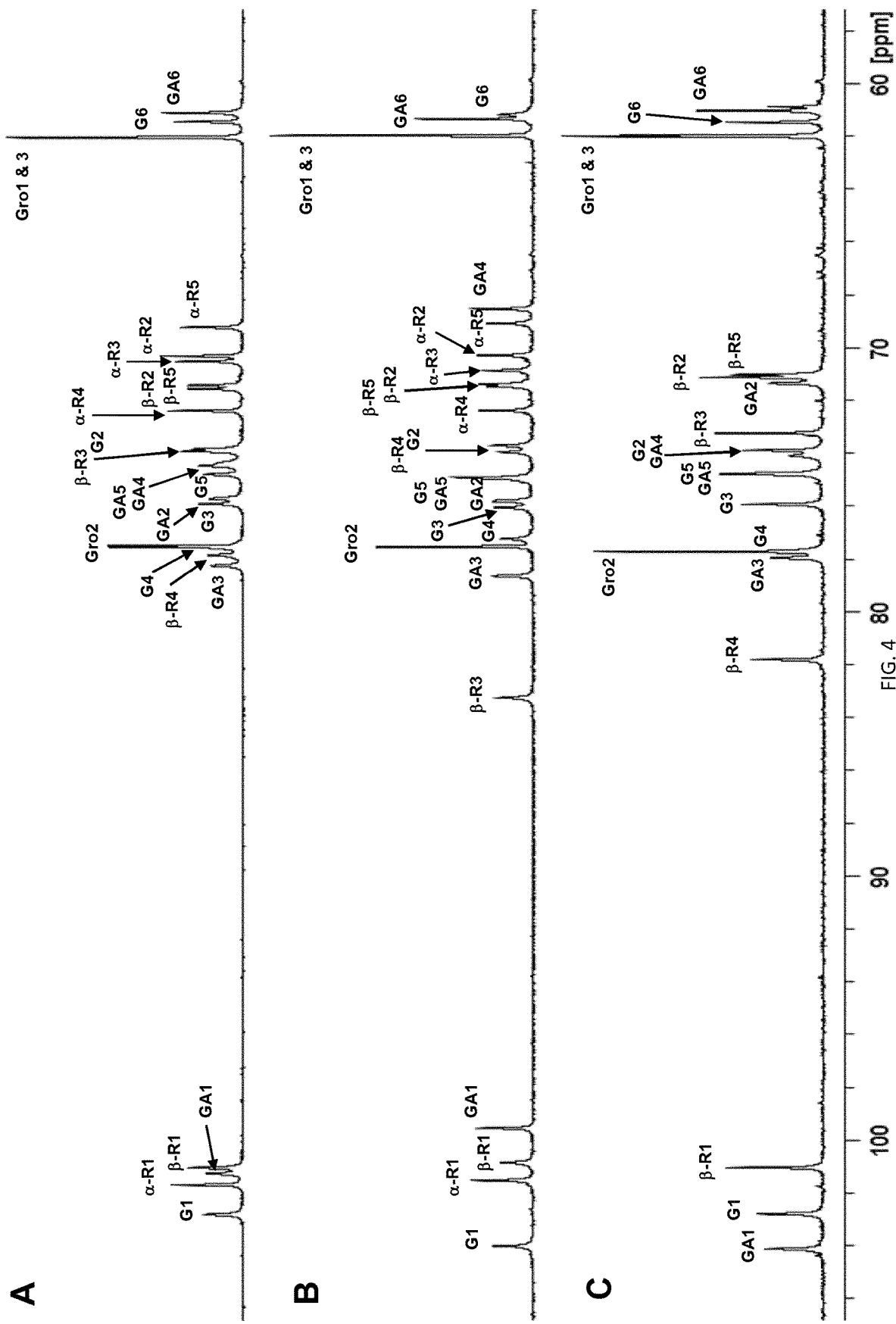
FIG. 4: Expansion of the 1D 13C NMR spectra of pneumococcal serotype (A) 23F, (B) 23A and (C) 23B capsular polysaccharides showing the anomeric and ring regions. Carbon peaks have been labeled according to the corresponding residue (α- and β-R=α- and β-Rha, G=Glc, GA=Gal and Gro=glycerol).

The diagnostic anomeric and methyl proton signals were used as starting points for the $^1$H-$^1$H correlation experiments (COSY and TOCSY) which elucidated H-1 to H-6 for β-Glc, α- and β-Rha and H-1 to H-4 for β-Gal. H-5 of β-Gal was assigned from the H-1/H-5 crosspeak in the NOESY experiment and H-6 from the H-4/C-6 crosspeak in the HSQC-NOESY experiment. All of the HSQC crosspeaks (FIG. 3)

could be assigned from the proton assignments already established aided by overlays with 1D TOCSY (200 ms), HSQC-TOCSY, HSQC-NOESY and HMBC experiments. The $^1$H and $^{13}$C NMR data are collected in Table 1. The deshielded carbons and glycosylation shifts compared to the corresponding monosaccharide [Jansson, P. E.; Kenne, L.; Widmalm, G. Carbohydr. Res. 1989, 188, 169-191] confirmed the linkage positions: C-2 (+2.73 ppm), C-3 (+4.45 ppm) and C-4 (+4.65 ppm) of β-Gal, C-4 (+4.96 ppm) of β-Rha and C-4 (+6.90 ppm) of β-Glc. The relatively small glycosylation shift for C-2 of Gal has been observed for other 2,3-β-Gal residues in serotypes 15B and 33F and was attributed to the strong steric hindrance imposed by vicinal 2,3-disubstitution [Jansson, P. E.; Kenne, L.; Wehler, T. Carbohydr. Res. 1988, 179, 359-368]. The sequence of sugar residues indicated by glycosylation shifts followed from the HMBC interresidue correlations (FIG. 9A) and transglycosidic correlations in the NOESY experiment. The $^1$H-$^{31}$P HMBC experiment showed major crosspeaks from the phosphodiester signal at −0.09 ppm to H-3 of β-Gal at 4.33 ppm and H-2 (and H-1/H-3) of Gro confirming the presence of the Gro-(2→P→3)-β-D-Galp-linkage. An expansion of the fully assigned $^{13}$C NMR spectrum is shown in FIG. 4A; the splitting of C-2 of glycerol (6 Hz) is from $^{31}$P coupling. Lastly the proton-coupled $^{13}$C spectrum gave $J_{H1,C1}$ for the anomeric carbons confirming the β-configuration of the terminal Rha (174 Hz) and β- for the remaining residues (162-168 Hz). Thus NMR analysis confirmed the structure of the tetrasaccharide repeating unit of serotype 23F polysaccharide as →4)-β-D-Glcp-(1→4)-[α-L-Rhap-(1→2)]-[Gro-(2→P→3)]-β-D-Galp-(1→4)-β-L-Rhap-(1→.

TABLE 1

$^1$H and $^{13}$C NMR chemical shifts (δ, ppm) for the serotype 23F polysaccharide repeating unit

| Residue | H-1<br>C-1 | H-2<br>C-2 | H-3<br>C-3 | H-4<br>C-4 | H-5<br>C-5 | H-6<br>C-6 |
|---|---|---|---|---|---|---|
| α-L-Rhap-(1→ | 5.10 | 4.15 | 3.82 | 3.47 | 4.10 | 1.27 |
| α-R | 101.66 | 70.30 | 70.51 | 72.37 | 69.20 | 16.94 |
| →2,3,4)-β-D-Galp-(1→ | 4.95 | 3.82 | 4.33 | 4.42 | 3.81 | 3.94 |
| GA | 101.22 | 75.69 | 78.23 | 74.34 | 74.45 | 61.08 |
| →4)-β-L-Rhap-(→ | 4.86 | 4.04 | 3.80 | 3.70 | 3.44 | 1.36 |
| β-R | 101.05 | 71.55 | 73.91 | 77.79 | 71.41 | 17.59 |
| →4)-β-D-Glcp-(1→ | 4.83 | 3.36 | 3.68 | 3.64 | 3.53 | 3.94, 3.83 |
| G | 102.76 | 73.81 | 75.88 | 77.61 | 74.78 | 61.42 |

Phosphoglycerol at C-3 of Gal: $^1$H, $^{13}$C and $^{31}$P assignments; δ CH: (4.29, 77.49); δ CH$_2$: (3.77, 62.03) and $^{31}$P at −0.09 ppm.

Structure of Serotype 23B Capsular Polysaccharide Repeating Unit

Figure 5:
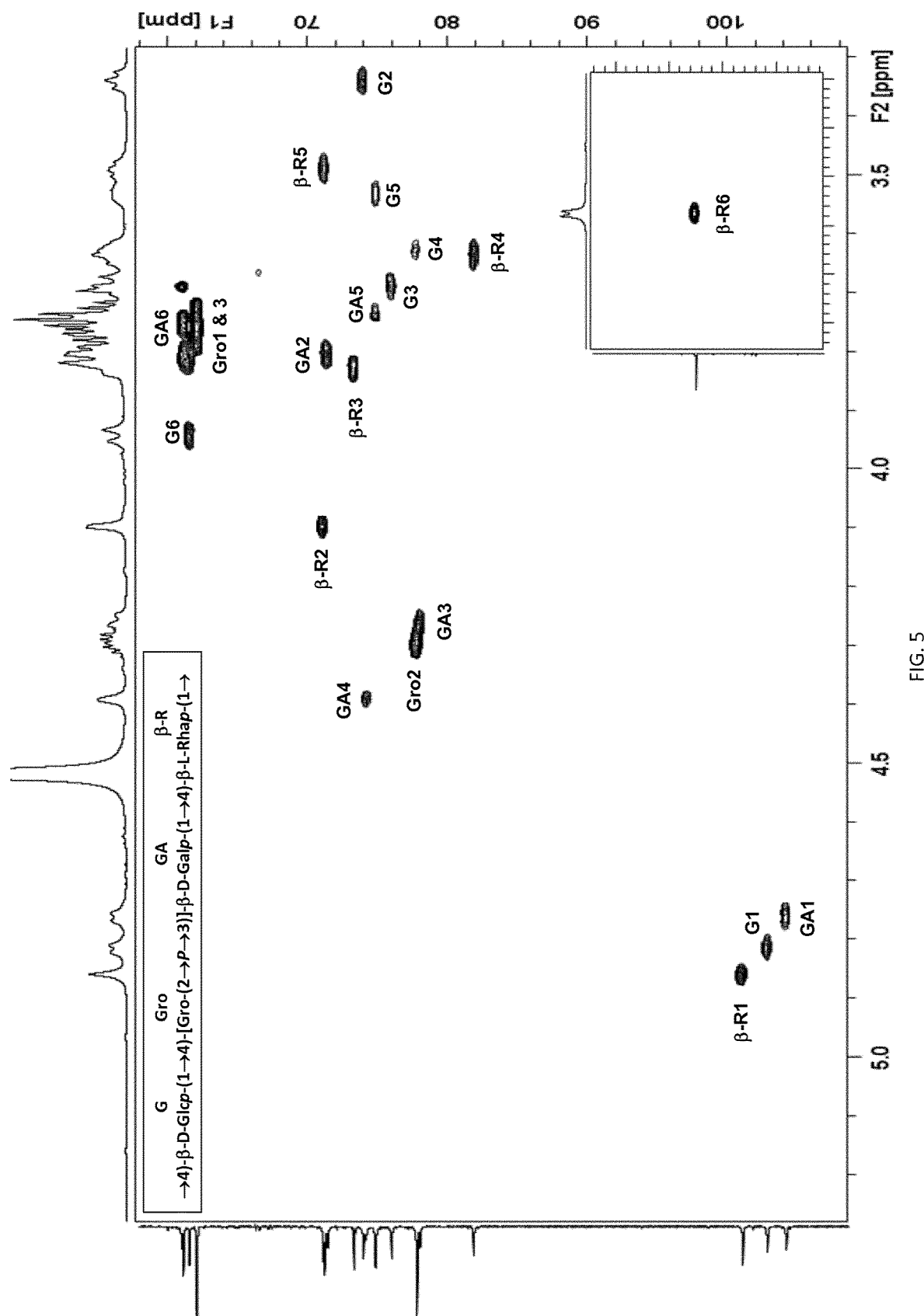
FIG. 5: Expansion of the HSQC spectrum of polysaccharide 23B recorded at 600 MHz, the crosspeaks from the methyl region of the spectrum are shown in the insert. Key trisaccharide repeating unit proton/carbon crosspeaks have been labeled according to the carbon atom of the corresponding residue β-R=β-Rha, G=Glc, GA=Gal and Gro=glycerol).
Figure 10:
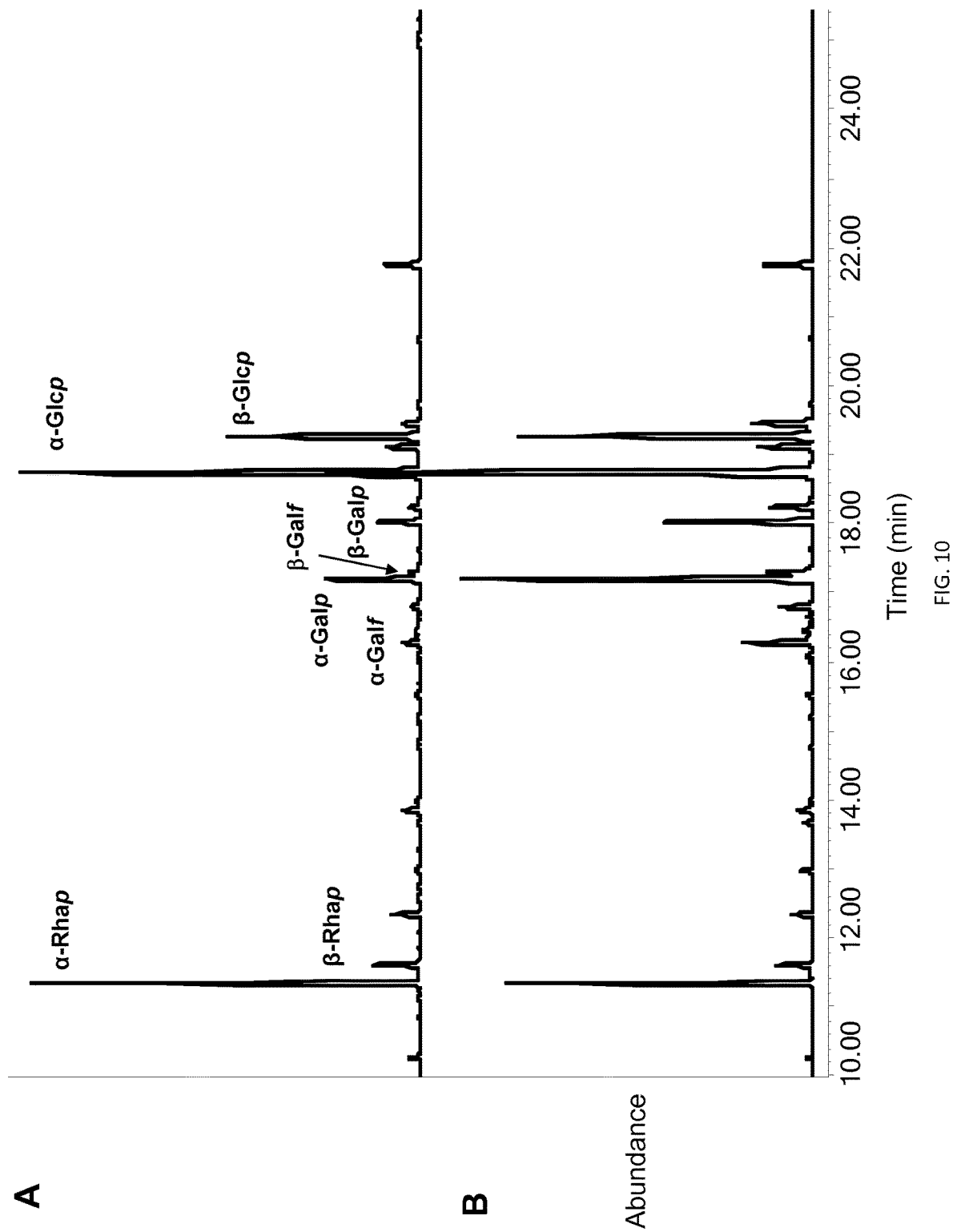
FIG. 10: GC-MS chromatograms of the TMS methyl glycosides of polysaccharide (A) 23A and (B) 23B. Peak identity shown confirmed by retention time and MS.

Composition analysis of the 23B polysaccharide gave similar results to those obtained for 23F and 23A. GC-MS analysis of the TMS methyl glycosides (FIG. 10B) showed the presence of Rha, Gal and Glc (relative peak areas of 0.22:0.53:1.00) together with trace amounts of glycerol. The $^1$H NMR spectrum (FIG. 2C) shows signals for the 23B trisaccharide RU: three H-1, ring signals (including sharp signals from glycerol) and one methyl signal from β-Rha, together with signals from residual CWPS. The 1D spectrum indicated that 23B has the same structure as 23F, but without the terminal α-Rha. This was confirmed by the full set of $^1$H, $^{13}$C and $^{31}$P 1D and 2D NMR experiments performed. All of the HSQC crosspeaks (FIG. 5) could be assigned from the proton assignments aided by appropriate overlays with hybrid and HMBC experiments. The $^1$H and $^{13}$C NMR data are collected in Table 2. The deshielded carbons and glycosylation shifts established the linkage positions: C-3 (+4.15 ppm) and C-4 (+4.38 ppm) of β-Gal, C-4 (+8.96 ppm) of β-Rha and C-4 (+7.10 ppm) of β-Glc. The similarity of the glycosylation shifts to those obtained for 23F provide proof that the bonds have the same configuration factors i.e., that the hexoses have the D absolute configuration and Rha the L absolute configuration. The sequence of sugar residues indicated by glycosylation shifts followed from the HMBC interresidue correlations (FIG. 9C) and transglycosidic correlations in the NOESY experiment. The $^1$H-$^{31}$P HMBC experiment showed major crosspeaks from the phosphodiester signal at −0.26 ppm to H-3 of β-Gal at 4.26 ppm and H-2 (and H-1/H-3) of Gro confirming the presence of the Gro-(2→P→3)-β-D-Galp-linkage. An expansion of the fully assigned $^{13}$C NMR spectrum is shown in FIG. 4C; the splitting of C-2 of glycerol (5.8 Hz) is from $^{31}$P coupling. Lastly the proton-coupled $^{13}$C spectrum gave $J_{H1,C1}$ for the anomeric carbons confirming the β-configuration for all the residues (162-165 Hz). Thus NMR analysis established the tetrasaccharide repeating unit of serotype 23B polysaccharide as →4)-β-D-Glcp-(1→4)-[Gro-(2→P→3)]-β-D-Galp-(1→4)-β-L-Rhap-(1→.

TABLE 2

$^1$H and $^{13}$C NMR chemical shifts (δ, ppm) for the serotype 23B polysaccharide repeating unit

| Residue | H-1<br>C-1 | H-2<br>C-2 | H-3<br>C-3 | H-4<br>C-4 | H-5<br>C-5 | H-6<br>C-6 |
|---|---|---|---|---|---|---|
| →3,4)-β-D-Galp-(1→ | 4.77 | 3.80 | 4.26 | 4.39 | 3.73 | 3.82, 3.76 |
| GA | 104.10 | 71.34 | 77.93 | 74.07 | 74.77 | 60.92 |
| →4)-β-L-Rhap-(1→ | 4.86 | 4.09 | 3.82 | 3.63 | 3.49 | 1.37 |
| β-R | 101.02 | 71.02 | 73.27 | 81.79 | 71.12 | 17.35 |
| →4)-β-D-Glcp-(1→ | 4.81 | 3.34 | 3.68 | 3.64 | 3.53 | 3.94, 3.82 |
| G | 102.76 | 73.87 | 75.91 | 77.69 | 74.79 | 61.43 |

Phosphoglycerol at C-3 of Gal: $^1$H, $^{13}$C and $^{31}$P assignments; δ CH: (4.29, 77.69); δ CH$_2$: (3.76, 61.9); $^{31}$P at −0.26 ppm.

Molecular Models

Figure 6:
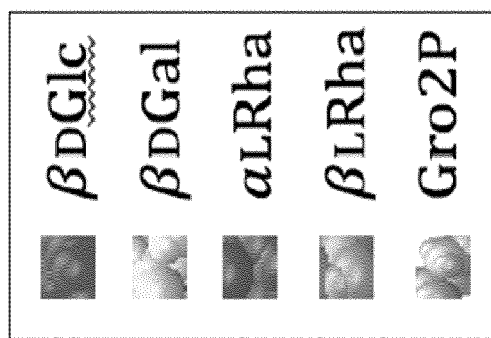
FIG. 6: Minimized molecular models for 10RU of 23F (left) 23A (middle) and 23B (right), shown in space-filling representation and colored according to residue type. The models for 23F and 23B show a very similar loose helical conformation, the model for 23A is a slightly twisted ribbon, with clear steric crowding at the β-L-Rha branch point.
Figure 6:
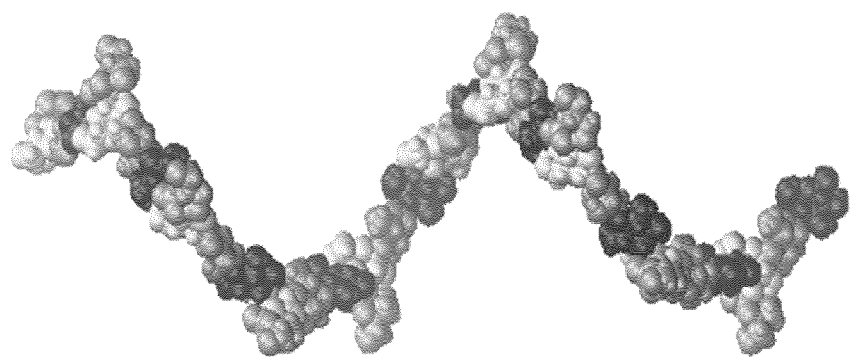
Figure 6:
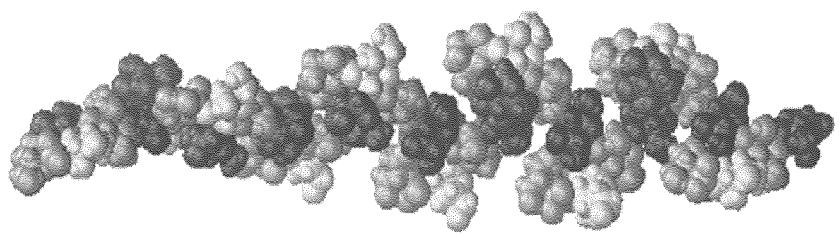
Figure 6:
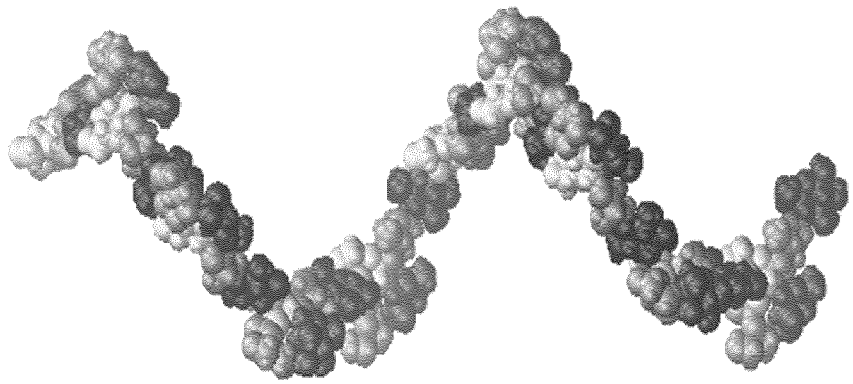

Molecular models of 10RU of the three polysaccharides were built with CarbBuilder [Kuttel, M. M.; Ståhle, J.; Widmalm, G. J. Comput. Chem. 2016, 37(22), 2098-2105] and subsequently minimized. The models for 23F and 23B show a very similar loose helical conformation (FIG. 6). However, the immunodominant terminal α-Rha in 23F (absent in 23B) is clearly exposed on the edge of the helix (purple residues in FIG. 6), and would present a markedly different surface for antibody binding. In contrast to the conformations of 23F and 23B, the model for 23A is a slightly twisted ribbon, with clear steric crowding at the β-L-Rha branch point: the β-Glc is in close proximity to β-Gal (<3 Å). This model thus explains the strong deshielding of H-1 of 2,3-β-Gal observed in the NMR spectrum of polysaccharide 23A. Further, the presentation of the terminal α-Rha in 23A is quite different to 23F: the α-Rha forms a long, almost straight line along the chain in 23A, as opposed to its orientation in the 23F helix. These very different conformations depicted in these preliminary models suggest little likelihood of cross-protection between either 23F or 23B with 23A.

3. Conclusions

Figure 7:
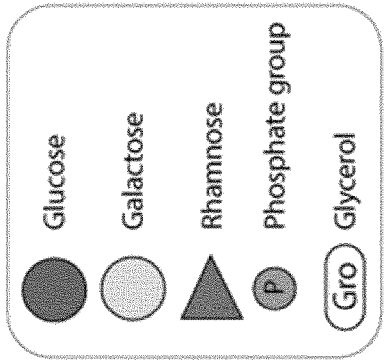
FIG. 7: Proposed glycosyltransferase and polymerase activity in serogroup 23 polysaccharides. Glycosyltransferases responsible for each elongation step are listed above the respective glycosidic linkage in italics. The polymerization site is marked by an arrow.
Figure 7:
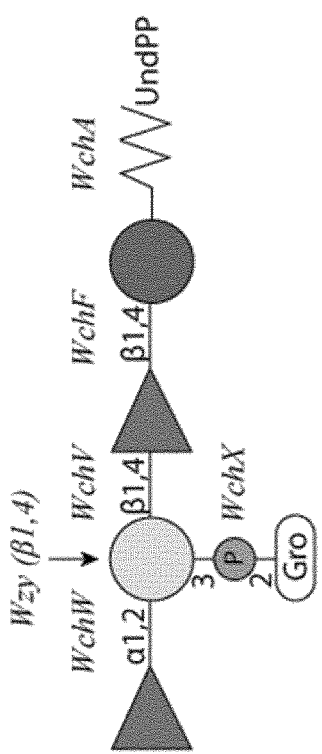
Figure 7:
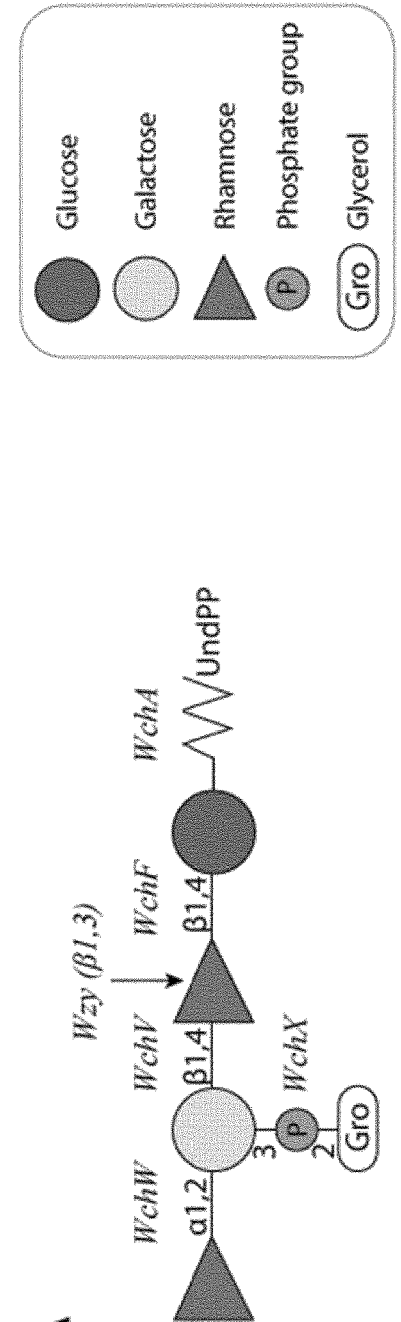
Figure 7:
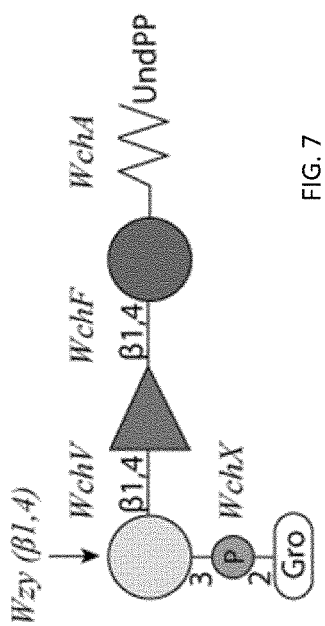
Figure 8:
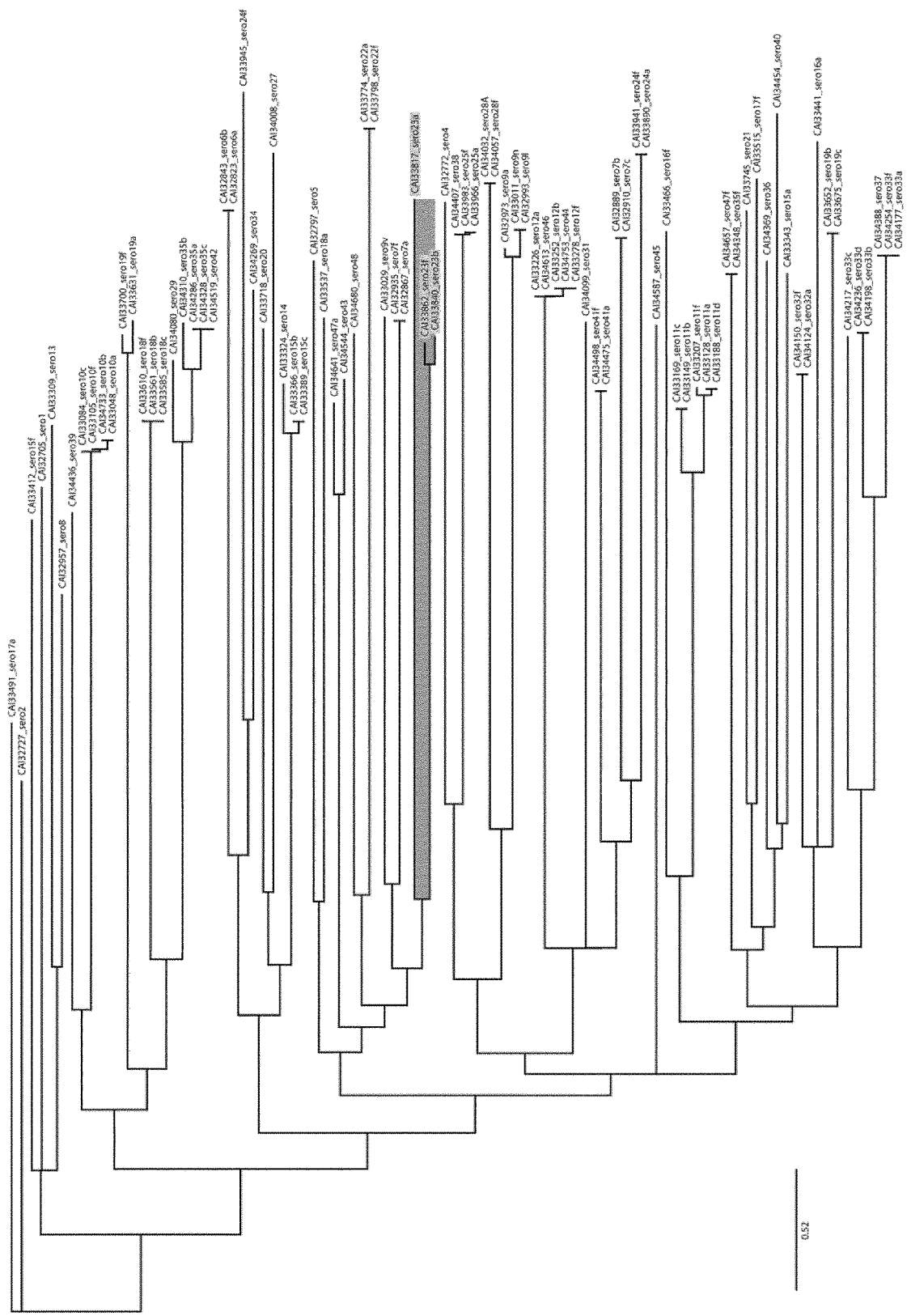
FIG. 8: Unrooted phylogenetic tree of *S. pneumoniae* polymerase Wzy illustrating sequence diversity. Serogroup 23 clade marked in blue. Leaves are labelled with the protein accession number and serogroup.

Structural predictions of the 23B polysaccharide based on the genetic analyses is in agreement with the experimentally-obtained structures. The biological repeat units of the polysaccharide can be identified with confidence, and the glycosyltransferases responsible for each elongation step can be assigned by comparison with the 23F cps locus (FIG. 7).

WchW activity in 23B is not only different to its 23F counterpart as predicted, but it is even absent. The lack of the α-1-2-linked-rhamnose constitutes the only difference between 23F and 23B capsular polysaccharides. The reasons for WchW's missing activity are not clearly deducible from a comparison of the known homologues; it could be due to either several inactivating mutations in the protein, comparing to 23F, or a halt at the transcriptional level. As Geno at al. [Geno, K. A.; Saad, J. S.; Nahm, M. H. *J. Clin. Microbiol.* 2017, JCM-00054] have recently shown, a subtle difference of only two amino acid substitutions can be responsible for the inactivation of the acetyltransferase in an isolate of serotype 35B, resulting in a novel, non-acetylated serotype.

Molecular modelling shows similar helical structures for 23F and 23B, but a markedly different sterically-crowded ribbon-like structure for 23A. The repeating unit structures for 23A and 23B may explain why the typing antiserum prepared in rabbits with type 23F bacteria reacts only slightly with serotype 23A and hardly at all with serotype 23B [Robbins, J. B.; Austrian. R.; Lee, C. J.; Rastogi, S. C.; Schiffman, G.; Henrichsen, J.; Mäkelä, P. H.; Broome, C. V.; Facklam, R. R; Tiesjema, R. H.; Parke, J. C. *J. Infect. Dis.* 1983, 148(6), 1136-1159]. In 23A, the immunodominant terminal α-Rha [Park, S.; Nahm, M. H. *PLoS One.* 2013, 8(12), e83810] is no longer a pendant group at C-2 of the main backbone 2,3,4-Gal as in 23F, but on C-2 of the sterically constrained 2,3-Gal, now present as a side chain (FIG. 6). This means that the terminal α-Rha of 23A will be less accessible to 23F antibody directed against this dominant epitope. The terminal α-Rha is absent in 23B, which means little or no cross reaction with 23F antisera as reported.

Experimental

Purified pneumococcal polysaccharide serotypes 23B were purchased from Statens Serum Institut (SSI). The comparator polysaccharide 23F were obtained from GSK.

Genetic Analysis of Serogroup 23 Cps Locus Sequence

The published cps locus sequences (serotype 23a: accession CR931683; 23b: CR931684; 23f: CR931685) and Wzy sequences [Bentley, S. D.; Aanensen, D. M.; Mavroidi, A.; Saunders, D.; Rabbinowitsch, E.; Collins, M.; Donohoe, K.; Harris, D.; Murphy, L.; Quail, M. A.; Samuel, G. *PLoS Genet.* 2006, 2(3), e31.] have been downloaded from GenBank (WorldWideWeb(www).ncbi.nlm.nih.gov/nuccore). Pairwise protein sequence identity has been assessed using BLASTp [Camacho, C.; Coulouris, G.; Avagyan, V.; Ma, N.; Papadopoulos, J.; Bealer, K.; Madden, T. L. *BMC Bioinf.* 2009, 10(1), 421]. Multiple sequence alignments have been performed using T-Coffee and standard parameters (v11.00) [Notredame, C.; Higgins, D. G.; Heringa, J. *J. Mol. Biol.* 2000, 302(1), 205-217]. Wzy phylogeny was inferred from multiple sequence alignments by running RAxML using a gamma distribution to model site-specific rate variation and 100 bootstrap replicates [Stamatakis, A. *Bioinformatics.* 2006, 22(21), 2688-2690].

Monosaccharide Composition Analysis by GC-MS

Methanolysis (3 M HCl) of polysaccharide 23F, 23A and 23B samples (0.5-1 mg) was performed in a CEM Discover SP-d Microwave reactor at 120 W and 121° C. for 5 minutes and the tri-methyl silyl ethers (TMS) derivatives prepared as described by Kim et al. [Kim, J. S.; Laskowich, E. R.; Arumugham, R. G.; Kaiser, R. E.; MacMichael, G. J. *Anal. Biochem.* 2005, 347(2), 262-274]. GC-MS analysis was performed on an Agilent 8720A Gas Chromatograph equipped with a Agilent 5975 mass spectrometer and a DB-1MS column (30 m); temperature program: 50° C. for 2 min, 50-150° C. at 30° C./min, 150-220° C. at 3° C./min, 220-300° C. at 30° C./min and 300° C. for 10 min. The inlet temperature was set at 250° C. and the MS transfer line at 300° C. The MS acquisition parameters were set to scan at m/z 50-550 in electron impact (EI) mode. GC-MS data was processed using Agilent Chemstation software. A mixture of standard monosaccharides was used to determine the retention times and corresponding mass spectra for each sugar derivative.

NMR Spectroscopy

Polysaccharide samples (~10 mg) were lyophilized and exchanged twice with 99.9% deuterium oxide (Sigma Aldrich), then dissolved in 600 μL of $D_2O$ and introduced into a 5 mm NMR tube for data acquisition. Preliminary NMR studies yielded broad lines and poor 2D crosspeaks for polysaccharide 23A and 23F, the spectral resolution was improved by placing the NMR sample in a Branson 1200 Sonicator water bath for 1-2 days. 1D $^1H$, $^{13}C$ and $^{31}P$ and 2D, COSY, TOCSY, NOESY, HSQC, HMBC and hybrid H2BC, HSQC-TOCSY and HSQC-NOESY NMR spectra were obtained using a Bruker Advance III 600 MHz NMR spectrometer equipped with a BBO Prodigy cryoprobe and processed using standard Bruker software (Topspin 3.2). The probe temperature was set at 313 or 323 K. 2D TOCSY experiments were performed using mixing times of 120 or 180 ms and the 1D variants using mixing times up to 200 ms. The HSQC experiment was optimized for J=145 Hz (for directly attached $^1H$-$^{13}C$ correlations), and the HMBC experiment optimized for a coupling constant of 6 Hz (for long-range $^1H$-$^{13}C$ correlations). HSQC-TOCSY and HSQC-NOESY NMR spectra were recorded using mixing times of 120 and 250 ms respectively. Polysaccharide spectra were referenced to residual cell wall polysaccharide signals (phosphocholine $^1H$ signal at 3.23 ppm and $^{13}C$ signal at 54.5 ppm and the shielded $^{31}P$ signal at 1.30 ppm) [Vialle, S.; Sepulcri, P.; Dubayle, J.; Talaga, P. *Carbohydr. Res.* 2005, 340, 91-96].

Molecular Modeling

Optimal dihedral angle conformations for the glycosidic linkages were taken from the corresponding disaccharide potential of mean force free energy surfaces calculated with the metadynamics routine incorporated into NAMD [Laio, A.; Parrinello, M. *Proc. Natl. Acad. Sci. U.S.A.* 2002, 99, 12562-12565], with the φ, ψ glycosidic linkage torsion angles used as collective variables. The optimal conformations are listed in Table 3.

TABLE 3

Optimal values for the φ, ψ glycosidic linkage torsion angles determined from vacuum metadyamics.

| Disaccharide | φ, ψ |
| --- | --- |
| α-L-Rhap-(1→2)-β-D-Galp | 39, 21 |
| β-D-Glcp-(1→3)-β-L-Rhap | 46, 11; 59 −13[a] |
| β-D-Galp-(1→4)-β-L-Rhap | 26, 26 |
| β-D-Glcp-(1→4)-β-D-Galp | 44, 16 |
| β-L-Rhap-(1→4)-β-D-Glcp | −51, −8 |

[a]Value used for 23A, to avoid atomic collisions. This value is still within the vacuum global minimum energy well.

Molecular models of 10 repeat units of 23F, 23A and 23B were built with CarbBuilder version 2.1.17 [Kuttel, M. M.; Ståhle, J.; Widmalm, G. *J. Comput. Chem.* 2016, 37(22), 2098-2105] using the dihedral angles listed in Table 3. We added bond, angle and dihedral parameters to the CHARMM36 additive force field for carbohydrates [Guvench, O.; Hatcher, E.; Venable, R. M.; Pastor, R. W.; MacKerell, Jr A. D. *J Chem Theory Comput,* 2009, 5(9), 2353-2370; Mallajosyula, S. S.; Guvench, O.; Hatcher, E.; MacKerell, Jr A D. *J Chem, Theory Comput,* 2012, 8, 759-776] to represent the 2-phosphate substitution on glycerol, as well as the glycosidic phosphodiester (2→3) linkage. These parameters were adapted from the ribitol phosphodiester parameters previously added to the force field [Kuttel, M. M.; Jackson, G. E.; Mfata, M.; Ravenscroft, N. *Carbohydr. Res,* 2015, 406, 27-33]. These initial oligosaccharide structures were optimized through 20000 steps of standard NAMD (version 2.9) minimization in vacuum [Phillips, J. C.; Braun, R; Wang, W; Gumbart, J.; Tajkhorshid, E; Villa, E; et al. *J Comput Chem* 2005, 26, 1781-1802].

The present disclosure is not to be limited in scope by the specific embodiments described herein. Indeed, various modifications of the subject matter provided herein, in addition to those described, will become apparent to those skilled in the art from the foregoing description and accompanying figures. Such modifications are intended to fall within the scope of the appended claims.

Various publications, patents and patent applications are cited herein, the disclosures of which are incorporated by reference in their entireties.

Example 2

Obtainment of 23B Bioconjugate Using the Glycoengineering Strategy.

A protein glycosylation experiment was carried out in order to assess whether the engineered Sp23B polysaccharide could be transferred onto EPA.

At this scope, strain stLMTB13743 (W3110; ΔwaaL; wca::23B cluster) was transformed with different plasmid combinations (see below).

5-mL TB-dev 10 mM $MgCl_2$+antibiotics precultures were grown o/n at 30° C. The following day, 50-mL TB-dev 10 mM $MgCl_2$+antibiotics+0.1% arabinose main cultures were inoculated with 0.1 $OD_{600}$ from the precultures. At $OD_{600}$=0.9, main cultures have been induced with 0.1 mM IPTG for the induction and grown o/n at 30° C.

From each culture 2 OD600 were harvested, resuspended in 100 uL Lämmli buffer, incubated 10 min @95° C., 2 uL Proteinase K were added and incubated 1 h at 55° C., transferred to 70° C. for 10 min, vortexed (LLO sample).

From each culture a periplasmic extraction (PPE) was carried out: 100 ODs were harvested and resuspended completely in 1000 ul lysis buffer (30 mM Tris-HCl pH 8.5.1 mM EDTA, 20% Sucrose) at 4° C. 1 mg/ml of lysozyme was added to the cells (20 mg/ml stock solution in $ddH_2O$; Sigma-Aldrich ref. #L6876-10G), incubated at 4° C. on a rotating wheel during 20 minutes in 2 ml tubes. The cells were then centrifuged at 16'000 rcf 30 minutes, and the supernatant was transferred to a new tube.

Figure 11:
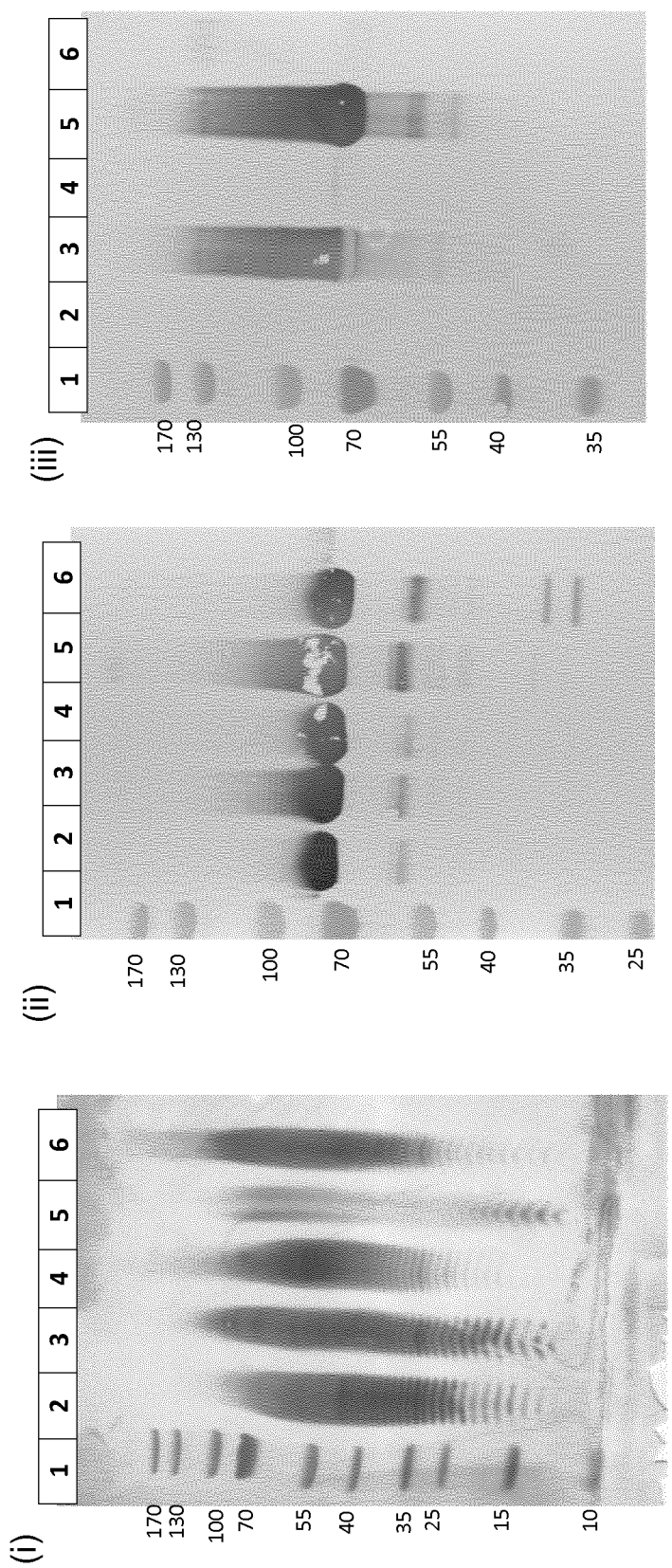
FIG. 11: The LLO samples were analyzed via SDS-PAGE (4-12% NuPAGE Gel, MES Running Buffer, 55 min at 200V) followed by transfer onto membrane and anti-23B Western Blot (i). The enriched samples were analyzed via SDS PAGE SDS-PAGE (4-12% NuPAGE Gel, MOPS Running Buffer, 55 min at 200V) followed by transfer onto membrane and anti-His (ii) or anti-23A (ii) Western Blot. The volumes corresponding to 0.2 OD600 (i), 0.6 OD600 (ii) and (iii) of culture volume were mixed to loading buffer and loaded. Lane 1: Marker PageRuler from Thermo-Fischer Scientific; lane 2-6 stLMTB13743 transformed with pLMTB3130 (pLAFR$^{tet}$_Sp15Agtp123) and pLMTB6015 (pEXT22$^{Kan}$_EPA_rcsA_fepE). Lane 2: additional co-transformed plasmids pGVXN72 (empty pEXT21$^{sp}$), pLMTB4640 (pDISC$^{tmp}$_engineering cluster (23AwchX_23AwchV_*E. coli* O2 wegR_23Awzx)). Lane 3: additional plasmids pLMTB4640 and pLMTB4623 (pEXT21$^{sp}$_pglB_homolog). Lane 4: additional plasmids pLMTB4623 and pGVXN1387 (empt pDISC). Lane 5: additional plasmids pLMTB4640 and pLMTB4620 (pEXT21$^{sp}$ pglB homolog). Lane 6 additional plasmids pGVYN1387 and pLMTB4620. 23B LLO's are produced in every combination (FIG. 11 (i)).

The PPE were enriched exploiting the poly-His tag of EPA: 500 ul of PPE were mixed with 125 ul of 4 mM $MgCl_2$, 150 mM Tris pH8.0, 50 mM Imidazole, 2.5M NaCl, 150 ul of 50% slurry (=75 ul resin) of pre-equilibrated IMAC resin (for equlibration the resin was washed 3× with and resuspended in final equal volume of 1× binding buffer: 30 mM Tris pH8.0, 10 mM Imidazole, 500 mM NaCl). The samples were incubated 90 min on a rotating wheel at RT; the resin was centrifuged at 8000 rcf 1 min and supernatant was discarded; the Ni-NTA agarose was resuspended in 500 ul 1× binding buffer supplemented with 0.025% n-Dodecyl-B-maltoside (DDM; Glycon ref. #D97002-C; stock solution: 10%) by pipetting and transferred to Corning Costar Spin-X centrifuge tube filters (Sigma-aldrich CLS8163) and centrifuged 1 min at 4000 rcf. Flowthrough was discarded, the resin was then washed 3 more times with 500 ul of 1× Binding buffer. The flowthrough was completely removed using vacuum pump, 80 ul of elution buffer (30 mM Tris pH8.0, 500 mM imidazole, 200 mM NaCl) was added to the resin, mixed by vortexing, incubated at RT 2 h. The eluate was recovered. FIG. 11. The LLO samples were analyzed via SDS-PAGE (4-12% NuPAGE Gel, MES Running Buffer, 55 min at 200V) followed by transfer onto membrane and anti-23B Western Blot (i). The enriched samples were analyzed via SDS PAGE SDS-PAGE (4-12% NuPAGE Gel, MOPS Running Buffer, 55 min at 200V) followed by transfer onto membrane and anti-His (ii) or anti-23A (ii) Western Blot. The volumes corresponding to 0.2 OD600 (i), 0.6 OD600 (ii) and (iii) of culture volume were mixed to loading buffer and loaded. Lane 1: Marker PageRuler from Thermo-Fischer Scientific; lane 2-6 stLMTB13743 transformed with pLMTB3130 (pLAFR$^{tet}$_Sp15Agtp123) and pLMTB6015 (pEXT22$^{Kan}$_EPA_rcsA_fepE). Lane 2: additional co-transformed plasmids pGVXN72 (empty pEXT21$^{SP}$), pLMTB4640 (pDISC$^{tmp}$_engineering cluster (23AwchX_23AwchV_*E. coli* O2 wegR_23Awzx)). Lane 3: additional plasmids pLMTB4640 and pLMTB4623 (pEXT21$^{SP}$_pglB_homolog). Lane 4: additional plasmids pLMTB4623 and pGVXN1387 (empt pDISC). Lane 5: additional plasmids pLMTB4640 and pLMTB4620 (pEXT21$^{SP}$_pglB homolog). Lane 6 additional plasmids pGVYN1387 and pLMTB4620.

23B LLO's are produced in every combination (FIG. 11 (*i*)). Conjugate is produced in lanes 3 and 5 only. This indicates that both homologs of *C. jejuni* pglB are able to transfer the engineered polysaccharide but not the not-engineered, as combinations with empty pDISC's don't result in conjugates.

What is claimed is:

1. A synthetic pneumococcal saccharide comprising one or more repeat unit(s) →4)-β-D-Glcp-(1→4)-[Gro-(2→P→3)]-β-D-Galp-(1→4)-β-L-Rhap-(1→; wherein the pneumococcal saccharide is conjugated to a carrier protein; wherein the carrier protein is selected from a group consisting of CRM1 97, Diphtheria toxoid, tetanus toxoid, detoxified exotoxin A from *P. aeruginosa*, detoxified hemolysin A of *S. aureus*, clumping factor A, clumping factor B, *E. coli* FimH, *E. coli* FimHC, *E. coli* heat labile enterotoxin, detoxified variants of *E. coli* heat labile enterotoxin, Cholera toxin B subunit (CTB), cholera toxin, detoxified variants of cholera toxin, *E. coli* sat protein, the passenger domain of *E. coli* sat protein, *C. jejuni* AcrA, *C. jejuni* natural glycoproteins, *S. pneumoniae* pneumolysin, *S. pneumoniae* NOX, *S. pneumoniae* PspA, *S. pneumoniae* PcpA, *S. pneumoniae* PhtD, *S. pneumoniae* PhtE, *S. pneumoniae* ply, and *S. pneumoniae* LytB; wherein the pneumococcal saccharide is a hybrid oligosaccharide or polysaccharide having a structure: (B)n-A→ wherein A is an oligosaccharide containing at least 2, 3, 4, 5, 6, 7 or 8 monosaccharides, with a hexose monosaccharide derivative at the reducing end (indicated by the arrow in the diagram): wherein B is an oligosaccharide repeat unit →4)-β-D-Glcp-(1→4)-[Gro-(2→P→3)]-β-D-Galp-(1→4)-β-L-Rhap-(1→; and wherein n is at least 2, 3, 4, 5, 6, 7, 8, 9, 10, 11, 12, 13, 14, 15, 16, 17, 18, 19, or at least 20.

2. The pneumococcal saccharide according to claim 1, comprising less than 500 repeat units.

3. The pneumococcal saccharide according to claim 2, comprising 1 to 200 repeat units.

4. The pneumococcal saccharide according to claim 2, comprising 2 to 50 repeat units.

5. The pneumococcal saccharide according to claim 2, comprising 2 to 20 repeat units.

6. The pneumococcal saccharide according to claim 1 wherein A is an oligosaccharide identical to the repeat unit B with the exception that A comprises a hexose monosaccharide derivative at the reducing end of the oligosaccharide in place of the hexose monosaccharide at the reducing end of B.

7. The pneumococcal saccharide according to claim 6, wherein A is →4)-β-D-GlcNAcp-(1→4)-[Gro-(2→P→3)]-β-D-Galp-(1→4)-β-L-Rhap-(1→).

8. A pneumococcal saccharide according to claim 1, for use in the treatment or prevention of a disease caused by *Streptococcus pneumoniae* infection.

9. The pneumococcal saccharide according to claim 1 is a recombinant pneumococcal saccharide.

10. The pneumococcal saccharide according to claim 1, wherein the hexose monosaccharide' derivative is N-acetylglucosamine (GlcNAc), N-acetylgalactoseamine (GalNAc), 2,4-Diacetamido-2,4,6-trideoxyhexose (DATDH), N-acetylfucoseamine (FucNAc), or N-acetylquinovosamine (QuiNAc).

11. The pneumococcal saccharide according to claim 10, wherein the monosaccharide derivative is N-acetylglucosamine.

12. An immunogenic composition comprising a pneumococcal saccharide comprising one or more repeat unit(s) →4)-β-D-Glcp-(1→4)-[Gro-(2→P→3)]-β-D-Galp-(1→4)-β-L-Rhap-(1→ conjugated to a carrier protein wherein the carrier protein is selected from a group comprising consisting of detoxified exotoxin A from *P. aeruginosa* (EPA), TT, DT, CRM197, PhtD, detoxified pneumolysin and protein D; wherein the pneumococcal saccharide is a hybrid oligosaccharide or polysaccharide having a structure: (B)n-A→ wherein A is an oligosaccharide containing at least 2, 3, 4, 5, 6, 7 or 8 monosaccharides, with a hexose monosaccharide derivative at the reducing end (indicated by the arrow in the diagram): wherein B is an oligosaccharide repeat unit →4)-β-D-Glcp-(1→4)-[Gro-(2→P→3)]-β-D-Galp-(1→4)-β-L-Rhap-(1→; and wherein n is at least 2, 3, 4, 5, 6, 7, 8, 9, 10, 11, 12, 13, 14, 15, 16, 17, 18, 19, or at least 20.

13. An immunogenic composition according to claim 12, for use in the treatment or prevention of a disease caused by *Streptococcus pneumoniae* infection.

14. The immunogenic composition according to claim 12, wherein the carrier protein is exotoxin A from *P. aeruginosa* (EPA).

15. The immunogenic composition according to claim 12, further comprising an adjuvant.

16. A pneumococcal saccharide comprising one or more repeat unit(s) →4)-β-D-Glcp-(1→4)-[Gro-(2→P→3)]-β-D-Galp-(1→4)-β-L-Rhap-(1→ conjugated to a carrier protein, wherein the pneumococcal saccharide is a hybrid oligosaccharide or polysaccharide having a structure: (B)n-A→ wherein A is an oligosaccharide containing at least 2, 3, 4, 5, 6, 7 or 8 monosaccharides, with a hexose monosaccharide derivative at the reducing end (indicated by the arrow in the diagram): wherein B is an oligosaccharide repeat unit →4)-β-D-Glcp-(1→4)-[Gro-(2→P→3)]-β-D-Galp-(1→4)-β-L-Rhap-(1→; and wherein n is at least 2, 3, 4, 5, 6, 7, 8, 9, 10, 11, 12, 13, 14, 15, 16, 17, 18, 19, or at least 20, wherein the carrier protein is attached to a glucose or the hexose monosaccharide derivative of the pneumococcal saccharide.

\* \* \* \* \*

SEQUENCE LISTING

<160> NUMBER OF SEQ ID NOS: 66

<210> SEQ ID NO 1
<211> LENGTH: 5
<212> TYPE: PRT
<213> ORGANISM: Artificial
<220> FEATURE:
<223> OTHER INFORMATION: consensus sequence

```
<220> FEATURE:
<221> NAME/KEY: MISC_FEATURE
<222> LOCATION: (1)..(1)
<223> OTHER INFORMATION: Xaa="Asp" or "Glu"
<220> FEATURE:
<221> NAME/KEY: MISC_FEATURE
<222> LOCATION: (2)..(2)
<223> OTHER INFORMATION: Xaa="Ala" or "Arg" or "Asn" or "Asp" or "Cys"
     or "Gln" or "Glu" or "Gly" or "His" or "Ile" or "Leu" or "Lys" or
     "Met" or "Phe" or "Ser" or "Thr" or "Trp" or "Tyr" or "Val"
<220> FEATURE:
<221> NAME/KEY: MISC_FEATURE
<222> LOCATION: (4)..(4)
<223> OTHER INFORMATION: Xaa="Ala" or "Arg" or "Asn" or "Asp" or "Cys"
     or "Gln" or "Glu" or "Gly" or "His" or "Ile" or "Leu" or "Lys" or
     "Met" or "Phe" or "Ser" or "Thr" or "Trp" or "Tyr" or "Val"
<220> FEATURE:
<221> NAME/KEY: MISC_FEATURE
<222> LOCATION: (5)..(5)
<223> OTHER INFORMATION: Xaa="Ser" or "Thr"

<400> SEQUENCE: 1

Xaa Xaa Asn Xaa Xaa
1               5

<210> SEQ ID NO 2
<211> LENGTH: 5
<212> TYPE: PRT
<213> ORGANISM: Artificial
<220> FEATURE:
<223> OTHER INFORMATION: consensus sequence

<400> SEQUENCE: 2

Asp Gln Asn Ala Thr
1               5

<210> SEQ ID NO 3
<211> LENGTH: 7
<212> TYPE: PRT
<213> ORGANISM: Artificial
<220> FEATURE:
<223> OTHER INFORMATION: consensus sequence
<220> FEATURE:
<221> NAME/KEY: MISC_FEATURE
<222> LOCATION: (2)..(2)
<223> OTHER INFORMATION: Xaa="Asp" or "Glu"
<220> FEATURE:
<221> NAME/KEY: MISC_FEATURE
<222> LOCATION: (3)..(3)
<223> OTHER INFORMATION: Xaa="Ala" or "Arg" or "Asn" or "Asp" or "Cys"
     or "Gln" or "Glu" or "Gly" or "His" or "Ile" or "Leu" or "Lys" or
     "Met" or "Phe" or "Ser" or "Thr" or "Trp" or "Tyr" or "Val"
<220> FEATURE:
<221> NAME/KEY: MISC_FEATURE
<222> LOCATION: (5)..(5)
<223> OTHER INFORMATION: Xaa="Ala" or "Arg" or "Asn" or "Asp" or "Cys"
     or "Gln" or "Glu" or "Gly" or "His" or "Ile" or "Leu" or "Lys" or
     "Met" or "Phe" or "Ser" or "Thr" or "Trp" or "Tyr" or "Val"
<220> FEATURE:
<221> NAME/KEY: MISC_FEATURE
<222> LOCATION: (6)..(6)
<223> OTHER INFORMATION: Xaa="Ser" or "Thr"

<400> SEQUENCE: 3

Lys Xaa Xaa Asn Xaa Xaa Lys
1               5

<210> SEQ ID NO 4
<211> LENGTH: 7
<212> TYPE: PRT
<213> ORGANISM: Artificial
<220> FEATURE:
<223> OTHER INFORMATION: consensus sequence
```

<400> SEQUENCE: 4

```
Lys Asp Gln Asn Ala Thr Lys
1               5
```

<210> SEQ ID NO 5
<211> LENGTH: 481
<212> TYPE: PRT
<213> ORGANISM: Streptococcus pneumoniae

<400> SEQUENCE: 5

```
Met Ser Arg Arg Phe Lys Lys Ser Gly Ser Gln Lys Val Lys Arg Ser
1               5                   10                  15

Val Asn Ile Val Leu Leu Thr Ile Tyr Leu Leu Val Cys Phe Leu
                20                  25                  30

Leu Phe Leu Ile Phe Lys Tyr Asn Ile Leu Ala Phe Arg Tyr Leu Asn
            35                  40                  45

Leu Val Val Thr Ala Leu Val Leu Leu Val Ala Leu Val Gly Leu Leu
        50                  55                  60

Leu Ile Ile Tyr Lys Lys Ala Glu Lys Phe Thr Ile Phe Leu Leu Val
65                  70                  75                  80

Phe Ser Ile Leu Val Ser Ser Val Ser Leu Phe Ala Val Gln Gln Phe
                85                  90                  95

Val Gly Leu Thr Asn Arg Leu Asn Ala Thr Ser Asn Tyr Ser Glu Tyr
            100                 105                 110

Ser Ile Ser Val Ala Val Leu Ala Asp Ser Asp Ile Glu Asn Val Thr
        115                 120                 125

Gln Leu Thr Ser Val Thr Ala Pro Thr Gly Thr Asp Asn Glu Asn Ile
130                 135                 140

Gln Lys Leu Leu Ala Asp Ile Lys Ser Ser Gln Asn Thr Asp Leu Thr
145                 150                 155                 160

Val Asn Gln Ser Ser Tyr Leu Ala Ala Tyr Lys Ser Leu Ile Ala
                165                 170                 175

Gly Glu Thr Lys Ala Ile Val Leu Asn Ser Val Phe Glu Asn Ile Ile
            180                 185                 190

Glu Ser Glu Tyr Pro Asp Tyr Ala Ser Lys Ile Lys Lys Ile Tyr Thr
        195                 200                 205

Lys Gly Phe Thr Lys Lys Val Glu Ala Pro Lys Thr Ser Lys Asn Gln
    210                 215                 220

Ser Phe Asn Ile Tyr Val Ser Gly Ile Asp Thr Tyr Gly Pro Ile Ser
225                 230                 235                 240

Ser Val Ser Arg Ser Asp Val Asn Ile Leu Met Thr Val Asn Arg Asp
                245                 250                 255

Thr Lys Lys Ile Leu Leu Thr Thr Thr Pro Arg Asp Ala Tyr Val Pro
            260                 265                 270

Ile Ala Asp Gly Gly Asn Asn Gln Lys Asp Lys Leu Thr His Ala Gly
        275                 280                 285

Ile Tyr Gly Val Asp Ser Ser Ile His Thr Leu Glu Asn Leu Tyr Gly
    290                 295                 300

Val Asp Ile Asn Tyr Tyr Val Arg Leu Asn Phe Thr Ser Phe Leu Lys
305                 310                 315                 320

Leu Ile Asp Leu Leu Gly Gly Ile Asp Val Tyr Asn Asp Gln Glu Phe
                325                 330                 335

Thr Ala His Thr Asn Gly Lys Tyr Tyr Pro Ala Gly Asn Val His Leu
            340                 345                 350
```

-continued

```
Asp Ser Glu Gln Ala Leu Gly Phe Val Arg Glu Arg Tyr Ser Leu Ala
        355                 360                 365
Asp Gly Asp Arg Asp Arg Gly Arg Asn Gln Gln Lys Val Ile Val Ala
    370                 375                 380
Ile Leu Gln Lys Leu Thr Ser Thr Glu Ala Leu Lys Asn Tyr Ser Thr
385                 390                 395                 400
Ile Ile Asn Ser Leu Gln Asp Ser Ile Gln Thr Asn Met Pro Leu Glu
                405                 410                 415
Thr Met Ile Asn Leu Val Asn Ala Gln Leu Glu Ser Gly Gly Asn Tyr
            420                 425                 430
Lys Val Asn Ser Gln Asp Leu Lys Gly Thr Gly Arg Thr Asp Leu Pro
        435                 440                 445
Ser Tyr Ala Met Pro Asp Ser Asn Leu Tyr Val Met Glu Ile Asp Asp
    450                 455                 460
Ser Ser Leu Ala Val Val Lys Ala Ala Ile Gln Asp Val Met Glu Gly
465                 470                 475                 480
Arg

<210> SEQ ID NO 6
<211> LENGTH: 243
<212> TYPE: PRT
<213> ORGANISM: Streptococcus pneumoniae

<400> SEQUENCE: 6

Met Ile Asp Ile His Ser His Ile Val Phe Asp Val Asp Asp Gly Pro
1               5                   10                  15
Lys Ser Arg Glu Glu Ser Lys Ala Leu Leu Thr Glu Ser Tyr Arg Gln
            20                  25                  30
Gly Val Arg Thr Ile Val Ser Thr Ser His Arg Arg Lys Gly Met Phe
        35                  40                  45
Glu Thr Pro Glu Glu Lys Ile Ala Glu Asn Phe Leu Gln Val Arg Glu
    50                  55                  60
Ile Ala Lys Glu Val Ala Asp Asp Leu Val Ile Ala Tyr Gly Ala Glu
65                  70                  75                  80
Ile Tyr Tyr Thr Leu Asp Ala Leu Glu Lys Leu Glu Lys Lys Glu Ile
                85                  90                  95
Pro Thr Leu Asn Asp Ser Arg Tyr Ala Leu Ile Glu Phe Ser Met Asn
            100                 105                 110
Thr Pro Tyr Arg Asp Ile His Ser Ala Leu Ser Lys Ile Leu Met Leu
        115                 120                 125
Gly Ile Thr Pro Val Ile Ala His Ile Glu Arg Tyr Asp Ala Leu Glu
    130                 135                 140
Asn Asn Gly Lys Arg Val Arg Glu Leu Ile Asp Met Gly Cys Tyr Thr
145                 150                 155                 160
Gln Ile Asn Ser Tyr His Val Ser Lys Pro Lys Phe Phe Gly Glu Lys
                165                 170                 175
Tyr Lys Phe Met Lys Lys Arg Ala Arg Tyr Phe Leu Glu Arg Asp Leu
            180                 185                 190
Val His Val Ala Ser Asp Met His Asn Leu Asp Ser Arg Pro Pro
        195                 200                 205
Tyr Met Gln Gln Ala Tyr Asp Ile Ile Ala Lys Lys Tyr Gly Ala Lys
    210                 215                 220
```

```
Lys Ala Lys Glu Leu Phe Val Asp Asn Pro Arg Lys Ile Ile Met Asp
225                 230                 235                 240

Gln Leu Ile

<210> SEQ ID NO 7
<211> LENGTH: 230
<212> TYPE: PRT
<213> ORGANISM: Streptococcus pneumoniae

<400> SEQUENCE: 7

Met Lys Glu Gln Asn Thr Leu Glu Ile Asp Val Leu Gln Leu Phe Arg
1               5                   10                  15

Ala Leu Trp Lys Arg Lys Leu Val Ile Leu Leu Val Ala Ile Ile Thr
                20                  25                  30

Ser Ser Val Ala Phe Thr Tyr Ser Thr Phe Val Ile Lys Pro Glu Phe
            35                  40                  45

Thr Ser Thr Thr Arg Ile Tyr Val Val Asn Arg Asn Gln Gly Glu Lys
        50                  55                  60

Ser Gly Leu Thr Asn Gln Asp Leu Gln Ala Gly Thr Tyr Leu Val Lys
65                  70                  75                  80

Asp Tyr Arg Glu Ile Ile Leu Ser Gln Asp Val Leu Glu Glu Val Val
                85                  90                  95

Ser Asp Leu Lys Leu Asp Leu Thr Pro Lys Gly Leu Ala Asn Lys Ile
            100                 105                 110

Lys Val Thr Val Pro Val Asp Thr Arg Ile Val Ser Val Ser Val Asn
        115                 120                 125

Asp Arg Val Pro Glu Glu Ala Ser Arg Ile Ala Asn Ser Leu Arg Glu
130                 135                 140

Val Ala Ala Gln Lys Ile Ile Ser Ile Thr Arg Val Ser Asp Val Thr
145                 150                 155                 160

Thr Leu Glu Glu Ala Arg Pro Ala Ile Ser Pro Ser Ser Pro Asn Ile
                165                 170                 175

Lys Arg Asn Ile Leu Ile Gly Phe Leu Ala Gly Val Ile Gly Thr Ser
            180                 185                 190

Val Ile Val Leu Leu Leu Glu Leu Leu Asp Thr Arg Val Lys Arg Pro
        195                 200                 205

Glu Asp Ile Glu Asp Thr Leu Gln Met Thr Leu Leu Gly Val Val Pro
210                 215                 220

Asn Leu Asn Lys Leu Lys
225                 230

<210> SEQ ID NO 8
<211> LENGTH: 227
<212> TYPE: PRT
<213> ORGANISM: Streptococcus pneumoniae

<400> SEQUENCE: 8

Met Pro Thr Leu Glu Ile Ala Gln Lys Lys Leu Glu Phe Ile Lys Lys
1               5                   10                  15

Ala Glu Glu Tyr Tyr Asn Ala Leu Cys Thr Asn Ile Gln Leu Ser Gly
                20                  25                  30

Asp Lys Leu Lys Val Ile Ser Val Thr Ser Val Ser Pro Gly Glu Gly
            35                  40                  45

Lys Thr Thr Thr Ser Val Asn Ile Ala Trp Ser Phe Ala Arg Ala Gly
        50                  55                  60
```

```
Tyr Lys Thr Leu Leu Ile Asp Gly Asp Thr Arg Asn Ser Val Ile Ser
 65                  70                  75                  80

Gly Phe Phe Lys Ser Arg Glu Lys Ile Thr Gly Leu Thr Glu Phe Leu
                 85                  90                  95

Ser Gly Thr Ala Asp Leu Ser His Gly Leu Cys Asp Thr Asn Ile Glu
            100                 105                 110

Asn Leu Phe Val Val Gln Ser Gly Ser Val Ser Pro Asn Pro Thr Ala
        115                 120                 125

Leu Leu Gln Ser Lys Asn Phe Asn Asp Met Ile Glu Thr Leu Arg Lys
    130                 135                 140

Tyr Phe Asp Tyr Ile Ile Val Asp Thr Ala Pro Ile Gly Ile Val Ile
145                 150                 155                 160

Asp Ala Ala Ile Ile Thr Gln Lys Cys Asp Ala Ser Ile Leu Val Thr
                165                 170                 175

Ala Thr Gly Glu Ala Asn Lys Arg Asp Val Gln Lys Ala Lys Gln Gln
            180                 185                 190

Leu Lys Gln Thr Gly Lys Leu Phe Leu Gly Val Val Leu Asn Lys Leu
        195                 200                 205

Asp Ile Ser Val Asp Lys Tyr Gly Val Tyr Gly Phe Tyr Gly Asn Tyr
    210                 215                 220

Gly Lys Lys
225

<210> SEQ ID NO 9
<211> LENGTH: 455
<212> TYPE: PRT
<213> ORGANISM: Streptococcus pneumoniae

<400> SEQUENCE: 9

Met Asp Glu Lys Gly Leu Lys Ile Phe Met Ala Val Leu Gln Ser Ile
  1               5                  10                  15

Ile Val Ile Leu Leu Val Tyr Phe Leu Ser Phe Val Arg Glu Thr Glu
                 20                  25                  30

Leu Glu Arg Ser Ser Met Val Ile Leu Tyr Leu Leu His Phe Phe Val
            35                  40                  45

Phe Tyr Val Ser Ser Tyr Gly Asn Asn Phe Phe Lys Arg Gly Tyr Leu
        50                  55                  60

Val Glu Phe Asn Ser Thr Ile Arg Tyr Ile Phe Phe Ala Ile Ala
 65                  70                  75                  80

Ile Ser Val Leu Asn Phe Phe Ile Ala Glu Arg Phe Ser Ile Ser Arg
                 85                  90                  95

Arg Gly Met Val Tyr Phe Leu Thr Leu Glu Gly Ile Ser Leu Tyr Leu
            100                 105                 110

Leu Asn Phe Leu Val Lys Lys Tyr Trp Lys His Val Phe Phe Asn Leu
        115                 120                 125

Lys Asn Ser Lys Lys Ile Leu Leu Leu Thr Val Thr Lys Asn Met Glu
    130                 135                 140

Lys Val Leu Asp Lys Leu Leu Glu Ser Asp Glu Leu Ser Trp Lys Leu
145                 150                 155                 160

Val Ala Val Ser Val Leu Asn Lys Ser Asp Phe Gln His Asp Lys Ile
                165                 170                 175

Pro Val Ile Glu Lys Glu Lys Ile Ile Glu Phe Ala Thr His Glu Val
            180                 185                 190

Val Asp Glu Val Phe Val Asn Leu Pro Gly Glu Ser Tyr Asp Ile Gly
        195                 200                 205
```

Glu Ile Ile Ser Arg Phe Glu Thr Met Gly Ile Asp Val Thr Val Asn
210                 215                 220

Leu Lys Ala Phe Asp Lys Asn Leu Gly Arg Asn Lys Gln Ile His Glu
225                 230                 235                 240

Met Val Gly Leu Asn Val Val Thr Phe Ser Thr Asn Phe Tyr Lys Thr
            245                 250                 255

Ser His Val Ile Ser Lys Arg Ile Leu Asp Ile Cys Gly Ala Thr Ile
            260                 265                 270

Gly Leu Ile Leu Phe Ala Ile Ala Ser Leu Val Leu Val Pro Leu Ile
            275                 280                 285

Arg Lys Asp Gly Gly Pro Ala Ile Phe Ala Gln Thr Arg Ile Gly Lys
290                 295                 300

Asn Gly Arg His Phe Thr Phe Tyr Lys Phe Arg Ser Met Arg Ile Asp
305                 310                 315                 320

Ala Glu Ala Ile Lys Glu Gln Leu Met Asp Gln Asn Thr Met Gln Gly
                325                 330                 335

Gly Met Phe Lys Ile Asp Asn Asp Pro Arg Val Thr Lys Ile Gly Arg
            340                 345                 350

Phe Ile Arg Lys Thr Ser Leu Asp Glu Leu Pro Gln Phe Trp Asn Val
            355                 360                 365

Phe Ile Gly Asp Met Ser Leu Val Gly Thr Arg Pro Pro Thr Val Asp
370                 375                 380

Glu Tyr Asp Gln Tyr Thr Pro Glu Gln Lys Arg Arg Leu Ser Phe Lys
385                 390                 395                 400

Pro Gly Ile Thr Gly Leu Trp Gln Val Ser Gly Arg Ser Lys Ile Thr
                405                 410                 415

Asp Phe Asp Asp Val Val Lys Leu Asp Val Ser Tyr Ile Asp Asn Trp
            420                 425                 430

Thr Ile Trp Lys Asp Ile Glu Ile Leu Leu Lys Thr Val Lys Val Val
            435                 440                 445

Phe Met Arg Asp Gly Ala Lys
            450                 455

<210> SEQ ID NO 10
<211> LENGTH: 392
<212> TYPE: PRT
<213> ORGANISM: Streptococcus pneumoniae

<400> SEQUENCE: 10

Met Lys Lys Ser Val Tyr Ile Ile Gly Ser Lys Gly Ile Pro Ala Lys
1               5                   10                  15

Tyr Gly Gly Phe Glu Thr Phe Val Glu Lys Leu Thr Ala Phe Gln Gln
            20                  25                  30

Asp Lys Ala Ile Gln Tyr Tyr Val Ala Cys Met Arg Glu Asn Ser Ala
        35                  40                  45

Lys Ser Gly Thr Thr Glu Asp Val Phe Glu His Asn Gly Ala Ile Cys
    50                  55                  60

Tyr Asn Val Asp Val Pro Asn Ile Gly Pro Ala Arg Ala Ile Val Tyr
65                  70                  75                  80

Asp Ile Ala Ala Ile Asn Arg Ala Ile Glu Ile Ala Lys Glu Asn Lys
                85                  90                  95

Asp Glu Asp Pro Ile Phe Tyr Ile Leu Ala Cys Arg Ile Gly Pro Phe
            100                 105                 110

Ile His Gly Ile Lys Lys Lys Ile Gln Ala Ile Gly Gly Thr Leu Leu
        115                 120                 125

```
Val Asn Pro Asp Gly His Glu Trp Leu Arg Ala Lys Trp Ser Thr Pro
    130                 135                 140

Val Arg Arg Tyr Trp Lys Ile Ser Glu Gly Leu Met Val Lys His Ala
145                 150                 155                 160

Asp Leu Leu Val Cys Asp Ser Lys Asn Ile Glu Gln Tyr Ile Gln Glu
                165                 170                 175

Asp Tyr Lys Gln Phe Gln Pro Lys Thr Thr Tyr Ile Ala Tyr Gly Thr
            180                 185                 190

Asp Thr Thr Arg Ser Ile Leu Lys Ser Ser Asp Glu Lys Val Arg Ser
        195                 200                 205

Trp Phe Lys Glu Lys Asn Val Ser Glu Asn Tyr Tyr Leu Val Val
210                 215                 220

Gly Arg Phe Val Pro Glu Asn Asn Tyr Glu Ser Met Ile Leu Gly Phe
225                 230                 235                 240

Leu Ala Ser Asn Ser Lys Lys Asp Phe Val Leu Ile Thr Asn Val Glu
                245                 250                 255

Gln Asn Lys Phe Tyr Asn Gln Leu Leu Ala Lys Thr Gly Phe Asp Lys
            260                 265                 270

Asp Pro Arg Val Lys Phe Val Gly Thr Val Tyr Asn Gln Glu Leu Leu
        275                 280                 285

Lys Tyr Ile Arg Glu Asn Ala Phe Ala Tyr Phe His Gly His Glu Val
    290                 295                 300

Gly Gly Thr Asn Pro Ser Leu Leu Glu Ala Leu Ala Ser Thr Lys Leu
305                 310                 315                 320

Asn Leu Leu Leu Asp Val Gly Phe Asn Arg Glu Val Ala Glu Asp Gly
                325                 330                 335

Ala Asp Tyr Trp Glu Lys Asp Asn Leu His Lys Val Ile Glu Ala Ser
            340                 345                 350

Glu Gln Lys Thr Gln Glu Glu Ile Asn Glu Lys Asn Ile Leu Ser Thr
        355                 360                 365

Lys Gln Val Thr Glu Arg Phe Ser Trp Asp Leu Ile Val Asn Glu Tyr
    370                 375                 380

Glu Lys Leu Phe Thr Arg Lys Asn
385                 390

<210> SEQ ID NO 11
<211> LENGTH: 468
<212> TYPE: PRT
<213> ORGANISM: Streptococcus pneumoniae

<400> SEQUENCE: 11

Met Arg Tyr Gly Ile Met Arg Ile Ser Phe Ser Lys Lys Thr Met Leu
1               5                   10                  15

Cys Gly Leu Leu Tyr Ile Gly Leu Ile Leu Ser Val Val Thr Ile Pro
            20                  25                  30

Thr Ile Val Thr Phe Leu Tyr Ser Leu Leu Phe Ile Gly Ile Val Thr
        35                  40                  45

Val Leu Asn Tyr Asn Ser Ile Leu Ala Ser Asp Glu Asp Ala Asn Ser
    50                  55                  60

Phe Phe Val Ala Leu Pro Ile Ile Leu Ser Ser Phe Gln Asn Val Tyr
65                  70                  75                  80

Leu Gly Phe Gly Ala Asp Arg Leu Asn Ser Val Thr Leu Gln Val Leu
                85                  90                  95

Leu Ser Ile Ser Ile Ala Ile Ile Thr Ile Thr Val Phe Leu Gly Ile
            100                 105                 110
```

```
Ile Leu Asn Arg Phe Lys Ser Lys Glu Phe Ser Trp Leu Val Leu Ser
            115                 120                 125

Ile Leu Val Ile Ile Ile Gln Ser Val Ile Leu Leu Ile Phe Phe Pro
        130                 135                 140

Thr Thr Leu Pro Ala Tyr Leu Ser Ser Met Arg Asn Ile Leu Ala Pro
145                 150                 155                 160

Leu Leu Ile Phe Tyr Phe Ser Ile Tyr Gly Phe Lys Asn Ile Asn Leu
                165                 170                 175

Gln Lys Phe Tyr Lys Tyr Met Phe Ile Ile Leu Val Val Leu Ile
            180                 185                 190

Phe Gly Phe Ile Glu Tyr Ile Tyr Gly Asn Ser Leu Trp Thr Arg Leu
        195                 200                 205

Asn Ile Lys Lys Leu Trp Ala Leu Lys Gly Leu Ala Ile Glu Asn Arg
210                 215                 220

Val Val Pro Gly Asn Trp His Ser Ser Glu Leu Ile Gly Gly Lys Gln
225                 230                 235                 240

Leu Arg Arg Met Val Ser Thr Phe Ala Asp Pro Val Asn Leu Gly Ser
                245                 250                 255

Tyr Leu Phe Ala Ala Phe Met Leu Ala Trp Tyr Lys Asn Lys Lys Leu
            260                 265                 270

Leu Gln Val Leu Leu Ala Ser Phe Val Leu Ser Val Ser Lys Ala
        275                 280                 285

Ala Phe Leu Ser Met Leu Val Tyr Ile Ile Ile Tyr Thr Trp Val Val
290                 295                 300

Asp Lys Asn Lys Ile Leu Ser Ile Phe Gly Ile Ile Ile Ser Thr Val
305                 310                 315                 320

Leu Gly Leu Tyr Phe Tyr Asn Phe Ser Gln Val Ser Ser Tyr Gly Ser
                325                 330                 335

Ile Asn Ala His Ile Asp Gly Phe Phe Ser Ala Leu Ser Thr Pro Leu
            340                 345                 350

His Tyr Pro Phe Gly Met Gly Val Gly Ser Val Gly Val Leu Ala Ser
        355                 360                 365

Lys Leu Gly Ser Gln Thr Ala Leu Ser Ser Glu Val Leu Glu Thr Gly
370                 375                 380

Ile Gly Met Ile Ile Ala Gln Leu Gly Phe Val Gly Val Ile Ile Tyr
385                 390                 395                 400

Leu Ile Phe Phe Val Lys Leu Ser Val Ile Gly Lys Asn Ile Asn Asn
                405                 410                 415

Lys Arg Asp Lys Ile Leu Trp Phe Thr Leu Ile Tyr Ser Phe Leu Ala
            420                 425                 430

Asn Ala Phe Phe Asn Glu Val Ala Leu Ser Pro Asn Ser Cys Thr Leu
        435                 440                 445

Tyr Phe Leu Ile Leu Gly Leu Leu Tyr Asn Lys Asn Lys Ile Arg Ser
450                 455                 460

Thr Glu Phe Ser
465

<210> SEQ ID NO 12
<211> LENGTH: 323
<212> TYPE: PRT
<213> ORGANISM: Streptococcus pneumoniae
```

<400> SEQUENCE: 12

```
Met Glu Lys Leu Val Ser Ile Ile Leu Pro Val Tyr Asn Val Glu Gln
1               5                   10                  15

Tyr Ile Lys Asn Cys Leu Glu Ser Ile Gln Gln Gln Thr Tyr Pro Asn
            20                  25                  30

Leu Glu Val Ile Ile Val Asn Asp Gly Ser Thr Asp Lys Ser Val Glu
        35                  40                  45

Tyr Cys Glu Gln Ile Cys Lys Ile Asp Ser Arg Phe Ser Ile Thr His
    50                  55                  60

Lys Glu Asn Gly Gly Leu Ser Asp Ala Arg Asn Val Gly Ile Asp Lys
65                  70                  75                  80

Ala Lys Gly Asp Tyr Leu Ile Phe Val Asp Ser Asp Phe Val Ser
                85                  90                  95

Gln Asp Met Val Ser Tyr Leu Val Ser Cys Met Glu Asn Glu Ala
            100                 105                 110

Asp Ile Ala Ile Cys Asp Pro Val His Tyr Ser Asp Arg Gln Asn
            115                 120                 125

Asn Asp Leu Asn Ile Phe Ser Pro Ala Ser Val Lys Val Tyr Glu
    130                 135                 140

Thr Thr Glu Ala Leu Cys Glu Met Phe Tyr Gln Lys Ser Phe Leu Val
145                 150                 155                 160

Ser Ala Trp Ala Lys Ile Phe Lys Arg Glu Leu Phe Asp Asp Ile Arg
                165                 170                 175

Phe Pro Val Gly Lys Leu Phe Glu Asp Ser Ala Ile Met Tyr Leu Leu
            180                 185                 190

Leu Glu Lys Cys Glu Thr Ile Ala Tyr Ser Asp Ala Lys Leu Tyr Ala
        195                 200                 205

Tyr Val His Arg Asp Asn Ser Ile Thr Thr Lys Lys Phe Ser Asp Arg
    210                 215                 220

Asp Leu Asp Ile Leu Glu Ile Thr Asn Thr Ile Ile Asn His Tyr Gly
225                 230                 235                 240

Asp Asn Leu Arg Val Tyr Thr Ala Ala Val Ser Tyr Lys Val Ser Ala
                245                 250                 255

Cys Phe Arg Ile Leu Leu Asn Ser Pro Ser Glu Glu Lys Tyr Lys Lys
            260                 265                 270

Val Gln Lys Glu Cys Leu Ser Tyr Ile Leu Gln Asn Trp Arg Asn Ile
        275                 280                 285

Leu Phe Asn Asn Asn Val Arg Leu Lys Asn Lys Leu Ala Leu Ile Ser
    290                 295                 300

Ile Thr Ile Phe Asn Pro Phe Lys Leu Ile Tyr Ser Lys Val Asn
305                 310                 315                 320

Arg Trp Glu
```

<210> SEQ ID NO 13
<211> LENGTH: 410
<212> TYPE: PRT
<213> ORGANISM: Streptococcus pneumoniae

<400> SEQUENCE: 13

```
Met Asn Lys Tyr Glu Glu Arg Tyr Gln Glu Asn Leu Ser Lys Asn Asp
1               5                   10                  15

Phe Tyr Lys Leu Ile Asn Lys Ser Tyr Leu Ser Asp Lys Glu Leu Gln
            20                  25                  30
```

Val Gln Gln Val Lys Ala Gly Ile Val Leu Pro Pro Lys Ala Phe Glu
            35                  40                  45

Thr Lys Leu Ser Asn Lys Leu Gly Leu Gln Lys Ser Leu His Gly Lys
 50                  55                  60

Gly Gly Val Val Asp Ser Asn Gly Asn Tyr Ile Glu Leu Ser Ala Gln
 65                  70                  75                  80

Lys Ala Val Gly Met Arg Asn Arg Val Tyr Gly Pro Tyr Lys Ile Asn
                 85                  90                  95

Tyr Asp Asn Leu Pro Ile Arg Asn Glu Lys Val Ile Tyr Leu Asn Tyr
                100                 105                 110

Phe Ile Lys Gln Trp Gly His Phe Leu Leu Asp Val Val Gly Arg Leu
            115                 120                 125

Trp Tyr Pro Leu Leu Gln Asp Asn Asp Thr Lys Leu Val Tyr Thr Cys
130                 135                 140

Tyr Ala Gly Thr Glu Thr Lys Ile Glu Gly Asn Tyr Leu Glu Phe Leu
145                 150                 155                 160

Lys Leu Leu Gly Ile Asp Gln Ser Arg Leu Ile Met Ile Asn Cys Pro
                165                 170                 175

Thr Gln Phe Ser Glu Val Ile Ile Pro Glu Ser Ser Ile Leu Pro Gly
            180                 185                 190

Gly Tyr Tyr Thr Lys Glu Tyr Lys Gln Leu Phe Ser Ser Val Val Glu
            195                 200                 205

Asn Ile Lys Leu Asp Lys Tyr Asp Val Asn Ala Lys Met Ile Tyr Cys
210                 215                 220

Ser Arg Ser Lys Leu Gly Ile Ala Lys Ser Lys Glu Phe Gly Glu Asp
225                 230                 235                 240

Gly Ile Glu Gly Ile Phe Lys Gln Asn Gly Tyr Thr Ser Val Tyr Met
                245                 250                 255

Glu Thr Met Ser Leu Glu Glu Gln Ile Lys Thr Leu Leu Ser Ala Lys
            260                 265                 270

Thr Ile Val Leu Thr Ser Gly Ser Leu Ala His Asn Leu Leu Phe Val
            275                 280                 285

Asn Lys Asp Ile Asp Val Phe Ile Leu Asn Lys Thr Tyr Arg Val Asn
290                 295                 300

Leu His Gln Phe Leu Ile Asn Glu Ile Ser Asp Ala Thr Val Arg Phe
305                 310                 315                 320

Val Asp Ile Tyr Arg Ser Pro Leu Pro Ile Leu Tyr Gly Tyr Gly Pro
                325                 330                 335

Phe Leu Met Asp Leu Thr Lys Pro Leu Ala Asn Phe Leu Asp Asp Asn
            340                 345                 350

Glu Phe Val Tyr Glu Lys Gly Thr Val Leu Ser Lys Lys Asp Tyr Phe
            355                 360                 365

Lys Tyr Tyr Leu Lys Trp Leu Trp Ser Tyr Arg Phe Phe Leu Phe Arg
370                 375                 380

Leu Asn Gly Ile Lys Glu Gly Asn Ser Glu Phe Glu Lys Ser Phe Lys
385                 390                 395                 400

Ile Ile Arg Arg Tyr Tyr Lys Thr Gly Arg
                405                 410

<210> SEQ ID NO 14
<211> LENGTH: 461
<212> TYPE: PRT
<213> ORGANISM: Streptococcus pneumoniae

```
<400> SEQUENCE: 14

Met Ser Lys Tyr Lys Glu Leu Ala Lys Asn Thr Gly Ile Phe Ala Leu
1               5                   10                  15

Ala Asn Phe Ser Ser Lys Ile Leu Ile Phe Leu Leu Val Pro Ile Tyr
            20                  25                  30

Thr Arg Val Leu Thr Thr Thr Glu Tyr Gly Phe Tyr Asp Leu Val Tyr
        35                  40                  45

Thr Thr Ile Gln Leu Phe Val Pro Ile Leu Thr Leu Asn Ile Ser Glu
    50                  55                  60

Ala Val Met Arg Phe Leu Met Lys Asp Gly Val Ser Lys Lys Ser Val
65                  70                  75                  80

Phe Ser Ile Ala Val Leu Asp Ile Phe Ile Gly Ser Ile Ala Phe Ala
                85                  90                  95

Leu Leu Leu Leu Val Asn Asn Leu Phe Ser Leu Ser Asp Leu Ile Ser
            100                 105                 110

Gln Tyr Ser Ile Tyr Ile Phe Val Phe Val Phe Tyr Thr Leu Asn
        115                 120                 125

Asn Phe Leu Ile Gln Phe Ser Lys Gly Ile Asp Lys Ile Gly Val Thr
130                 135                 140

Ala Ile Ser Gly Val Ile Ser Thr Ala Val Met Leu Ala Met Asn Val
145                 150                 155                 160

Ile Leu Leu Val Val Phe Asp Trp Gly Leu Leu Gly Phe Phe Ile Ala
                165                 170                 175

Asn Val Cys Gly Tyr Val Ile Pro Cys Ile Tyr Ile Val Ser Arg Leu
            180                 185                 190

Arg Leu Trp Glu Leu Phe Glu Ile Lys Ile Asp Lys Lys Leu Gln Trp
        195                 200                 205

Glu Met Val Tyr Tyr Ala Leu Pro Leu Val Leu Asn Ile Leu Ser Trp
    210                 215                 220

Trp Val Asn Asn Thr Ser Asp Arg Tyr Ile Val Thr Ala Ile Val Gly
225                 230                 235                 240

Ile Gln Ala Ser Ala Ile Ile Ser Val Ala Tyr Lys Ile Pro Gln Ile
                245                 250                 255

Leu Ser Thr Ile Ser Ala Ile Phe Ile Gln Ser Trp Gln Ile Ser Ala
            260                 265                 270

Ile Lys Ile Gln Glu Asp Lys Ser Gly Thr Thr Phe Val Ser Asn Met
        275                 280                 285

Leu Leu Tyr Tyr Asn Ala Leu Leu Ile Ile Ala Ser Gly Ile Ile
    290                 295                 300

Leu Phe Val Lys Pro Ile Ser Asn Ile Leu Phe Gly Ile Ser Phe Tyr
305                 310                 315                 320

Ser Ala Trp Glu Leu Val Pro Phe Leu Ile Ser Ser Leu Phe Asn
                325                 330                 335

Ala Ile Ser Gly Cys Ile Gly Ala Ile Met Gly Ala Lys Met Asp Thr
            340                 345                 350

His Asn Ile Ala Lys Ser Ala Leu Val Gly Met Ile Ala Asn Ile Ile
        355                 360                 365

Leu Asn Ile Val Leu Thr Phe Leu Met Gly Pro Gln Gly Ile Thr Ile
    370                 375                 380

Ser Thr Leu Ile Ala Ser Phe Leu Ile Phe Tyr Met Arg Lys Asp Ser
385                 390                 395                 400

Val Lys Glu Ile Asn Ser Glu Thr Tyr Arg Ala Ile Tyr Leu Ser Trp
                405                 410                 415
```

```
Ile Leu Leu Val Val Glu Ala Cys Leu Ile Tyr Met Asp Phe Ile
            420                 425                 430

Ile Gly Ala Leu Ile Ala Met Val Ile Asn Leu Phe Leu Leu Lys Asp
            435                 440                 445

Val Ile Lys Pro Leu Tyr Leu Lys Ile Phe Lys Arg Asn
450                 455                 460

<210> SEQ ID NO 15
<211> LENGTH: 382
<212> TYPE: PRT
<213> ORGANISM: Streptococcus pneumoniae

<400> SEQUENCE: 15

Met Ile Val Leu Gln Tyr Phe Lys Ile Leu Ala Arg Phe Val Phe Met
1               5                   10                  15

Phe Leu Ile Ser Ala Val Leu Leu Pro Phe Lys Ile Lys Pro Asn Lys
                20                  25                  30

Ile Val Phe Ile Asn Phe Asn Gly Lys Gly Tyr Gly Asp Asn Pro Lys
            35                  40                  45

Ser Ile Cys Glu Tyr Leu Arg Thr Thr Tyr Pro Asp Leu Asp Leu Val
        50                  55                  60

Trp Leu Ala Arg Asp Asn Glu Gly Phe Pro Asp Gly Val Arg Val Val
65                  70                  75                  80

Lys Tyr Gly Thr Phe Gln Ala Phe Tyr Glu Gln Ala Ser Ser Lys Val
                85                  90                  95

Trp Val Tyr Asn Val Arg Ala Phe Ala Arg Ile Leu Lys Lys Arg Gly
                100                 105                 110

Gln Ile Tyr Ile Gln Thr Trp His Gly Ala Ser Ser Phe Lys Leu Ile
            115                 120                 125

Glu Lys Gln Ala Asp Leu Pro Ile Asn Tyr Val Leu Glu Ala Lys Tyr
        130                 135                 140

Asp Ala Arg Val Thr Asp Ile Met Ile Ser Asp Ser Arg Lys Gln Thr
145                 150                 155                 160

Glu Glu Phe Gln Lys Tyr Phe Trp Tyr Ser Gly Glu Ile Phe Glu Val
                165                 170                 175

Gly Met Pro Arg Asn Asp Ala Leu Phe His Tyr Lys Glu Asp Tyr Asp
                180                 185                 190

Lys Leu Asn Asn Ile Arg Lys Glu Leu Ser Ile His Ser Asp Asp Tyr
            195                 200                 205

Val Ile Leu Tyr Ala Pro Thr Phe Arg Asp Asp Gly Asp Ala Ser Tyr
        210                 215                 220

Leu Asp Ile Asn Phe Glu Arg Leu Leu Gln Cys Val Glu His Gly Ile
225                 230                 235                 240

Lys Lys Lys Cys Lys Phe Leu Ile Arg Leu His Pro Asn His Ser His
                245                 250                 255

Leu Cys Asn Asn Ile Ser Phe Asn Lys Asn Ile Asn Ala Thr Phe
                260                 265                 270

Tyr Ser Asp Met Gln Glu Leu Thr Leu Leu Ala Asp Val Leu Val Thr
            275                 280                 285

Asp Tyr Ser Ser Ser Ile Phe Asp Phe Met Leu Leu Asn Lys Pro Tyr
        290                 295                 300

Val Arg Tyr Val Asn Asp Leu Glu Lys Tyr Ala Glu Leu Arg Gly Val
305                 310                 315                 320

Ser Asp Thr Tyr Tyr Glu Leu Pro Asp Ser Ile Ile Lys Thr Ala Glu
                325                 330                 335
```

```
Glu Leu Tyr Asp Leu Leu Pro Lys Lys Ile Glu Asn Phe Asp Tyr Asp
                340                 345                 350

Ser Ile Lys Lys Tyr Arg Asn Glu Ile Leu Cys Pro Ile Phe Asn Gly
        355                 360                 365

Thr Ala Ser Glu Asn Val Gly Arg Arg Ile Ile Gln Glu Leu
370                 375                 380

<210> SEQ ID NO 16
<211> LENGTH: 342
<212> TYPE: PRT
<213> ORGANISM: Streptococcus pneumoniae

<400> SEQUENCE: 16

Met Lys Asn Asn Asp Leu Lys Ile Gly Ser Gly Ala Ile His Gln Ile
1               5                   10                  15

Ser Ala Thr Leu Ser Gln Asn Ser Ile Ser Gly Lys Ile Leu Tyr Cys
                20                  25                  30

Ala Asp Pro Val Val Asp Leu Tyr Gly Ser Ile Val Arg Ser Gln
            35                  40                  45

Ile Glu Glu Ile Gly Arg Val Lys Glu Ser Cys Asn Tyr Asn Thr
50                  55                  60

Ile Ala Tyr Ala Met Asn Ile Ala Glu Arg Ala Ile Ala Thr Asp Ile
65                  70                  75                  80

Asp Cys Ile Val Gly Met Gly Gly Arg Val Leu Asp Val Cys Lys
                85                  90                  95

Tyr Ala Ser Phe Ile Ser Lys Arg Pro Tyr Leu Ser Ile Pro Thr Thr
            100                 105                 110

Ala Ala Asn Asp Gly Ile Ala Ser Pro Val Ala Val Leu Lys Arg Gln
        115                 120                 125

Asp Asp Arg Pro Lys Ser Leu Gly Ala Ala Ile Pro Ser Met Thr Leu
130                 135                 140

Ile Asp Ile Asp Val Ile Ala Ser Gly Pro Ile Gln Asn Ile Lys Ala
145                 150                 155                 160

Gly Ile Gly Asp Thr Ile Ser Asn Tyr Thr Ala Leu Lys Asp Trp Glu
                165                 170                 175

Leu Ala Val Glu Arg Gly Lys Asp Glu Met His Gly Phe Ala Tyr Leu
            180                 185                 190

Met Ser Gln Asn Ser Leu Asp Ala Leu Met Lys Thr Lys Tyr Asn Ser
        195                 200                 205

Ile Thr Pro Asp Phe Ile Glu Val Leu Val Asn Ser Leu Val Leu Ser
210                 215                 220

Gly Ile Ala Met Asp Phe Ala Gly Ser Ser Arg Pro Val Ser Gly Ser
225                 230                 235                 240

Glu His Leu Phe Ser His Ala Leu Asp Tyr Tyr Gly Ser Thr Arg Asn
                245                 250                 255

Leu His Gly Ile Gln Val Ala Leu Gly Thr Val Ala Val Leu Lys Leu
            260                 265                 270

Ile Glu Asn Ser Val Asp Thr Val Asp Tyr Leu Gln Arg Phe Glu
        275                 280                 285

Val His Ile Asn Pro Lys Leu Leu Gly Ile Asp Glu Glu Leu Phe Ile
290                 295                 300

Tyr Cys Met Gln His Ala Thr Lys Met Arg Ser Asn Arg Tyr Thr Tyr
305                 310                 315                 320
```

```
Leu His Glu Val Asp Leu Ser Thr Asp Arg Leu Lys Gln Ile Tyr Lys
                325                 330                 335
Glu Leu Ile Ser Glu Leu
            340

<210> SEQ ID NO 17
<211> LENGTH: 234
<212> TYPE: PRT
<213> ORGANISM: Streptococcus pneumoniae

<400> SEQUENCE: 17

Met Lys Ala Leu Ile Leu Ala Ala Gly Leu Gly Thr Arg Leu Ala Pro
1               5                   10                  15

Ile Thr Asn Glu Val Pro Lys Ser Leu Val Pro Val Asn Gly Lys Pro
            20                  25                  30

Ile Leu Met Lys Gln Ile Glu Asn Leu Tyr Gln Asn Asn Ile Thr Asp
        35                  40                  45

Ile Thr Ile Ile Ala Gly Tyr Lys Ser Ser Val Leu Thr Asp Ala Val
    50                  55                  60

Thr Glu Lys Tyr Pro Glu Ile Asn Ile Asp Asn Val Asp Phe Lys
65                  70                  75                  80

Thr Thr Asn Asn Met Tyr Ser Ala Tyr Leu Gly Lys Ala Ala Met Gly
                85                  90                  95

Asp Ser Asp Phe Leu Met Met Asn Ala Asp Val Phe Tyr Asp Ala Ser
            100                 105                 110

Val Ile Lys Ser Leu Leu Leu His Lys Ala Pro Asn Ala Ile Val Thr
        115                 120                 125

Asp Leu Gly Ile Tyr Ile Glu Glu Ser Met Lys Val Val Glu Lys Asn
    130                 135                 140

Gly Arg Leu Val Glu Ile Ser Lys Gln Ile Ser Pro Glu Glu Thr Leu
145                 150                 155                 160

Gly Ala Ser Ile Asp Val Tyr Lys Phe Ser Tyr Glu Ala Gly Ala Arg
                165                 170                 175

Phe Phe Glu Lys Cys Lys Glu Phe Ile Glu Asp Lys Arg Glu Leu Gln
            180                 185                 190

Met Trp Ser Glu Val Ala Leu Asn Ala Ile Leu Ser Glu Val Glu Phe
        195                 200                 205

Val Ala Cys Pro Leu Glu Gly Arg Trp Leu Gly Ile Asp Asn His Glu
    210                 215                 220

Asp Leu Val Ala Ala Glu Lys Leu Phe Ala
225                 230

<210> SEQ ID NO 18
<211> LENGTH: 277
<212> TYPE: PRT
<213> ORGANISM: Streptococcus pneumoniae

<400> SEQUENCE: 18

Met Lys Leu Thr Asn Arg Val Asp Tyr Phe Gly Ala Asp Ile Ser Glu
1               5                   10                  15

Leu Gln Asn Lys Lys Leu Phe Leu Phe Asp Met Asp Gly Thr Ile Tyr
            20                  25                  30

Glu Glu Asp Arg Leu Phe Glu Gly Thr Leu Glu Leu Leu Asp Tyr Ile
        35                  40                  45

His Asn Ile Gly Gly Glu Tyr Ile Phe Ile Thr Asn Asn Ser Ser Lys
    50                  55                  60
```

```
Ser Val Val Asp Tyr Val Glu Lys Val Asn Arg Leu Gly Ile Lys Ala
 65                  70                  75                  80

Glu Arg Asp Asn Phe Phe Thr Ser Ala Gln Ala Thr Ile Val Tyr Ile
                 85                  90                  95

Lys Glu Asn Tyr Pro Lys Ser Lys Val Tyr Cys Gln Gly Thr Lys Ser
            100                 105                 110

Leu Ile Lys Glu Leu Ser Asp Ala Gly Ile Asp Val Thr Glu Gln Val
        115                 120                 125

Ser Ala Asp Ile Asp Val Leu Val Gly Phe Asp Thr Glu Leu Thr
130                 135                 140

Ser Asp Lys Ile Arg Asn Thr Cys Glu Ile Leu Ser Thr Lys Asp Val
145                 150                 155                 160

Pro Phe Ile Ala Thr Asn Pro Asp Ile Arg Cys Pro Val Ser Phe Gly
                165                 170                 175

Phe Ile Pro Asp Cys Gly Ser Ile Cys Asp Met Ile Ser Lys Ser Val
                180                 185                 190

Asp Arg Lys Pro Val Tyr Ile Gly Lys Pro Glu Pro Thr Met Val Asp
            195                 200                 205

Ile Val Arg Lys Lys Leu Asn Tyr Ser Leu Phe Glu Thr Val Val Ile
        210                 215                 220

Gly Asp Arg Leu Tyr Thr Asp Ile Met Thr Gly Ile Asn Ala Gly Val
225                 230                 235                 240

Thr Ser Val Cys Val Leu Thr Gly Glu Ala Thr Val Asn Asp Ile Gln
                245                 250                 255

Gln Asp Ser Ile Lys Pro Thr Thr Phe Lys Asn Val Lys Glu Met
            260                 265                 270

Trp Lys Gly Ile Val
        275

<210> SEQ ID NO 19
<211> LENGTH: 289
<212> TYPE: PRT
<213> ORGANISM: Streptococcus pneumoniae

<400> SEQUENCE: 19

Met Lys Gly Ile Ile Leu Ala Gly Gly Ser Gly Thr Arg Leu Tyr Pro
  1               5                  10                  15

Leu Thr Arg Ala Ala Ser Lys Gln Leu Met Pro Val Tyr Asp Lys Pro
                 20                  25                  30

Met Ile Tyr Tyr Pro Leu Ser Thr Leu Met Leu Ala Gly Ile Arg Asp
             35                  40                  45

Ile Leu Ile Ile Ser Thr Pro Gln Asp Leu Pro Arg Phe Lys Glu Leu
         50                  55                  60

Leu Gln Asp Gly Ser Glu Phe Gly Ile Lys Leu Ser Tyr Ala Glu Gln
 65                  70                  75                  80

Pro Ser Pro Asp Gly Leu Ala Gln Ala Phe Ile Ile Gly Glu Glu Phe
                 85                  90                  95

Ile Gly Asp Asp Ser Val Ala Leu Ile Leu Gly Asp Asn Ile Tyr His
            100                 105                 110

Gly Pro Gly Leu Ser Thr Met Leu Gln Lys Ala Lys Lys Glu Lys
        115                 120                 125

Gly Ala Thr Val Phe Gly Tyr His Val Lys Asp Pro Glu Arg Phe Gly
130                 135                 140

Val Val Glu Phe Asp Glu Asn Met Asn Ala Ile Ser Ile Glu Glu Lys
145                 150                 155                 160
```

```
Pro Glu Tyr Pro Arg Ser Asn Tyr Ala Val Thr Gly Leu Tyr Phe Tyr
            165                 170                 175

Asp Asn Asp Val Val Glu Ile Ala Lys Ser Ile Lys Pro Ser Pro Arg
        180                 185                 190

Gly Glu Leu Glu Ile Thr Asp Val Asn Lys Ala Tyr Leu Asp Arg Gly
        195                 200                 205

Asp Leu Ser Val Glu Leu Met Gly Arg Gly Phe Ala Trp Leu Asp Thr
        210                 215                 220

Gly Thr His Glu Ser Leu Glu Ala Ser Gln Tyr Ile Glu Thr Val
225                 230                 235                 240

Gln Arg Met Gln Asn Val Gln Val Ala Asn Leu Glu Glu Ile Ala Tyr
            245                 250                 255

Arg Arg Gly Tyr Ile Ser Arg Glu Asp Val Leu Ala Leu Ala Gln Ser
            260                 265                 270

Leu Lys Lys Asn Glu Tyr Gly Gln Tyr Leu Leu Arg Leu Ile Gly Glu
        275                 280                 285

Ala

<210> SEQ ID NO 20
<211> LENGTH: 197
<212> TYPE: PRT
<213> ORGANISM: Streptococcus pneumoniae

<400> SEQUENCE: 20

Met Thr Asp Asn Phe Phe Gly Lys Thr Leu Ala Ala Arg Lys Val Glu
1               5                   10                  15

Ala Ile Pro Gly Met Leu Glu Phe Asp Ile Pro Val His Gly Asp Asn
            20                  25                  30

Arg Gly Trp Phe Lys Glu Asn Phe Gln Lys Glu Lys Met Leu Pro Leu
        35                  40                  45

Gly Phe Pro Glu Ser Phe Phe Ala Glu Gly Lys Leu Gln Asn Asn Val
    50                  55                  60

Ser Phe Ser Arg Lys Asn Val Leu Arg Gly Leu His Ala Glu Pro Trp
65                  70                  75                  80

Asp Lys Tyr Ile Ser Val Ala Asp Gly Gly Lys Val Leu Gly Ser Trp
                85                  90                  95

Val Asp Leu Arg Glu Gly Glu Thr Phe Gly Asn Thr Tyr Gln Thr Val
            100                 105                 110

Ile Asp Ala Ser Lys Gly Ile Phe Val Pro Arg Gly Val Ala Asn Gly
        115                 120                 125

Phe Gln Val Leu Ser Asp Thr Val Ser Tyr Ser Tyr Leu Val Asn Asp
    130                 135                 140

Tyr Trp Ala Leu Glu Leu Lys Pro Lys Tyr Ala Phe Val Asn Tyr Ala
145                 150                 155                 160

Asp Pro Ser Leu Gly Ile Glu Trp Glu Asn Ile Ala Glu Ala Glu Val
                165                 170                 175

Ser Glu Ala Asp Lys Asn His Pro Leu Leu Lys Asp Val Lys Pro Leu
            180                 185                 190

Lys Lys Glu Asp Leu
        195

<210> SEQ ID NO 21
<211> LENGTH: 349
<212> TYPE: PRT
<213> ORGANISM: Streptococcus pneumoniae
```

```
<400> SEQUENCE: 21

Met Thr Glu Tyr Lys Asn Ile Ile Val Thr Gly Gly Ala Gly Phe Ile
1               5                   10                  15

Gly Ser Asn Phe Val His Tyr Val Tyr Glu Asn Phe Pro Asp Val His
            20                  25                  30

Val Thr Val Leu Asp Lys Leu Thr Tyr Ala Gly Asn Arg Ala Asn Ile
            35                  40                  45

Glu Glu Ile Leu Gly Asn Arg Val Glu Leu Val Val Gly Asp Ile Ala
        50                  55                  60

Asp Ala Glu Leu Val Asp Lys Leu Ala Ala Gln Ala Asp Ala Ile Val
65                  70                  75                  80

His Tyr Ala Ala Glu Ser His Asn Asp Asn Ser Leu Asn Asp Pro Ser
                85                  90                  95

Pro Phe Ile His Thr Asn Phe Ile Gly Thr Tyr Thr Leu Leu Glu Ala
            100                 105                 110

Ala Arg Lys Tyr Asp Ile Arg Phe His His Val Ser Thr Asp Glu Val
            115                 120                 125

Tyr Gly Asp Leu Pro Leu Arg Glu Asp Leu Pro Gly His Gly Glu Gly
        130                 135                 140

Pro Gly Glu Lys Phe Thr Ala Glu Thr Lys Tyr Asn Pro Ser Ser Pro
145                 150                 155                 160

Tyr Ser Ser Thr Lys Ala Ala Ser Asp Leu Ile Val Lys Ala Trp Val
                165                 170                 175

Arg Ser Phe Gly Val Lys Ala Thr Ile Ser Asn Cys Ser Asn Asn Tyr
            180                 185                 190

Gly Pro Tyr Gln His Ile Glu Lys Phe Ile Pro Arg Gln Ile Thr Asn
        195                 200                 205

Ile Leu Ser Gly Ile Lys Pro Lys Leu Tyr Gly Glu Gly Lys Asn Val
        210                 215                 220

Arg Asp Trp Ile His Thr Asn Asp His Ser Ser Gly Val Trp Thr Ile
225                 230                 235                 240

Leu Thr Lys Gly Gln Ile Gly Glu Thr Tyr Leu Ile Gly Ala Asp Gly
                245                 250                 255

Glu Lys Asn Asn Lys Glu Val Leu Glu Leu Ile Leu Lys Glu Met Gly
            260                 265                 270

Gln Ala Val Asp Ala Tyr Asp His Val Thr Asp Arg Ala Gly His Asp
        275                 280                 285

Leu Arg Tyr Ala Ile Asp Ala Ser Lys Leu Arg Asp Glu Leu Gly Trp
        290                 295                 300

Lys Pro Glu Phe Thr Asn Phe Glu Ala Gly Leu Lys Ala Thr Ile Lys
305                 310                 315                 320

Trp Tyr Thr Asp Asn Gln Glu Trp Trp Lys Ala Glu Lys Glu Ala Val
                325                 330                 335

Glu Ala Asn Tyr Ala Lys Thr Gln Glu Ile Ile Thr Val
            340                 345

<210> SEQ ID NO 22
<211> LENGTH: 283
<212> TYPE: PRT
<213> ORGANISM: Streptococcus pneumoniae
```

<400> SEQUENCE: 22

```
Met Ile Leu Ile Thr Gly Ala Asn Gly Gln Leu Gly Thr Glu Leu Arg
1               5                   10                  15

Tyr Leu Leu Asp Glu Arg Asn Glu Glu Tyr Val Ala Val Asp Val Ala
            20                  25                  30

Glu Met Asp Ile Thr Asp Ala Glu Met Val Glu Lys Val Phe Glu Glu
        35                  40                  45

Val Lys Pro Thr Leu Val Tyr His Cys Ala Ala Tyr Thr Ala Val Asp
    50                  55                  60

Ala Ala Glu Asp Glu Gly Arg Glu Leu Asp Phe Ala Ile Asn Val Thr
65                  70                  75                  80

Gly Thr Lys Asn Val Ala Lys Ala Ser Glu Lys His Gly Ala Thr Leu
                85                  90                  95

Val Tyr Ile Ser Thr Asp Tyr Val Phe Asp Gly Lys Lys Pro Val Gly
            100                 105                 110

Gln Glu Trp Glu Val Asp Asp Arg Pro Asp Pro Gln Thr Glu Tyr Gly
        115                 120                 125

Arg Thr Lys Arg Met Gly Glu Glu Leu Val Glu Lys His Val Ser Asn
130                 135                 140

Phe Tyr Ile Ile Arg Thr Ala Trp Val Phe Gly Asn Tyr Gly Lys Asn
145                 150                 155                 160

Phe Val Phe Thr Met Gln Asn Leu Ala Lys Thr His Lys Thr Leu Thr
                165                 170                 175

Val Val Asn Asp Gln Tyr Gly Arg Pro Thr Trp Thr Arg Thr Leu Ala
            180                 185                 190

Glu Phe Met Thr Tyr Leu Ala Glu Asn Arg Lys Glu Phe Gly Tyr Tyr
        195                 200                 205

His Leu Ser Asn Asp Ala Thr Glu Asp Thr Thr Trp Tyr Asp Phe Ala
    210                 215                 220

Val Glu Ile Leu Lys Gly Thr Asp Val Glu Val Lys Pro Val Asp Ser
225                 230                 235                 240

Ser Gln Phe Pro Ala Lys Ala Lys Arg Pro Leu Asn Ser Thr Met Ser
                245                 250                 255

Leu Ala Lys Ala Lys Ala Thr Gly Phe Val Ile Pro Thr Trp Gln Asp
            260                 265                 270

Ala Leu Gln Glu Phe Tyr Lys Gln Glu Val Arg
        275                 280
```

<210> SEQ ID NO 23
<211> LENGTH: 484
<212> TYPE: PRT
<213> ORGANISM: Streptococcus pneumoniae

<400> SEQUENCE: 23

```
Met Leu Ile Met Ser Arg Arg Phe Lys Lys Ser Gly Ser Gln Lys Val
1               5                   10                  15

Lys Arg Ser Val Asn Ile Val Leu Leu Thr Ile Tyr Leu Leu Leu Val
            20                  25                  30

Cys Phe Leu Leu Phe Leu Ile Phe Lys Tyr Asn Ile Leu Ala Phe Arg
        35                  40                  45

Tyr Phe Asn Leu Val Val Thr Ala Leu Val Leu Val Ala Leu Val
    50                  55                  60

Gly Leu Leu Leu Ile Ile Tyr Lys Lys Ala Glu Lys Phe Thr Ile Phe
65                  70                  75                  80
```

```
Leu Leu Val Phe Ser Ile Leu Val Ser Ser Val Ser Leu Phe Ala Val
                 85                  90                  95

Gln Gln Phe Val Gly Leu Thr Asn Arg Leu Asn Ala Thr Ser Asn Tyr
            100                 105                 110

Ser Glu Tyr Ser Ile Ser Val Ala Val Leu Ala Asp Ser Asp Ile Glu
        115                 120                 125

Asn Val Thr Gln Leu Thr Ser Val Thr Ala Pro Thr Gly Thr Asp Asn
    130                 135                 140

Glu Asn Ile Gln Lys Leu Leu Ala Asp Ile Lys Ser Ser Gln Asn Ile
145                 150                 155                 160

Asp Leu Thr Val Asn Gln Ser Ser Tyr Leu Ala Ala Tyr Lys Ser
                165                 170                 175

Leu Ile Ala Gly Glu Thr Lys Ala Ile Val Leu Asn Ser Val Phe Glu
                180                 185                 190

Asn Ile Ile Glu Ser Glu Tyr Pro Asp Tyr Ala Ser Lys Ile Lys Lys
                195                 200                 205

Ile Tyr Thr Lys Gly Phe Thr Lys Lys Val Glu Ala Pro Lys Thr Ser
    210                 215                 220

Lys Asn Gln Ser Phe Asn Ile Tyr Val Ser Gly Ile Asp Thr Tyr Gly
225                 230                 235                 240

Pro Ile Ser Ser Val Ser Arg Ser Asp Val Asn Ile Leu Met Thr Val
                245                 250                 255

Asn Arg Asp Thr Lys Lys Ile Leu Leu Thr Thr Thr Pro Arg Asp Ala
                260                 265                 270

Tyr Val Pro Ile Ala Asp Gly Gly Asn Asn Gln Lys Asp Lys Leu Thr
    275                 280                 285

His Ala Gly Ile Tyr Gly Val Asp Ser Ser Ile His Thr Leu Glu Asn
    290                 295                 300

Leu Tyr Gly Val Asp Ile His Tyr Tyr Val Arg Leu Asn Phe Thr Ser
305                 310                 315                 320

Phe Leu Lys Leu Ile Asp Leu Leu Gly Gly Val Asp Val Tyr Asn Asp
                325                 330                 335

Gln Asp Phe Thr Ser Leu His Gly Lys Phe His Phe Pro Val Gly Asn
            340                 345                 350

Val His Leu Asp Ser Glu Gln Ala Leu Gly Phe Val Arg Glu Arg Tyr
        355                 360                 365

Ser Leu Ala Asp Gly Asp His Asp Arg Gly Arg Asn Gln Gln Lys Val
    370                 375                 380

Ile Ala Ala Ile Leu Gln Lys Leu Thr Ser Ser Glu Ala Leu Lys Asn
385                 390                 395                 400

Tyr Ser Met Ile Ile Asp Ser Leu Gln Asp Ser Ile Gln Thr Asn Met
                405                 410                 415

Pro Leu Glu Thr Met Ile Asn Leu Val Asn Ala Gln Leu Glu Ser Gly
            420                 425                 430

Gly Thr Tyr Lys Val Asn Ser Gln Asp Leu Lys Gly Arg Gly Arg Thr
        435                 440                 445

Asp Leu Pro Ser Tyr Ala Met Pro Asp Ser Asn Leu Tyr Met Met Glu
    450                 455                 460

Ile Asn Asp Ser Ser Leu Ala Ser Val Lys Thr Ala Ile Gln Asp Val
465                 470                 475                 480

Leu Glu Gly Arg
```

```
<210> SEQ ID NO 24
<211> LENGTH: 259
<212> TYPE: PRT
<213> ORGANISM: Streptococcus pneumoniae

<400> SEQUENCE: 24

Met His Leu Ser Lys Leu Leu Phe Arg Met Cys Trp Arg Ala Asp Glu
1               5                   10                  15

Met Ile Asp Ile His Ser His Ile Val Phe Asp Val Asp Asp Gly Pro
            20                  25                  30

Lys Ser Arg Glu Glu Ser Lys Ala Leu Leu Thr Glu Ala Tyr Arg Gln
        35                  40                  45

Gly Val Arg Thr Ile Val Ser Thr Ser His Arg Arg Lys Gly Met Phe
    50                  55                  60

Glu Thr Pro Glu Glu Lys Ile Ala Glu Asn Phe Leu Gln Val Arg Glu
65                  70                  75                  80

Ile Ala Lys Glu Val Ala Ser Asp Leu Val Ile Ala Tyr Gly Ala Glu
                85                  90                  95

Ile Tyr Tyr Thr Pro Asp Val Leu Gly Lys Leu Glu Lys Asn Arg Ile
            100                 105                 110

Pro Thr Leu Asn Asn Ser Arg Tyr Ala Leu Ile Glu Phe Ser Met Asn
        115                 120                 125

Thr Pro Tyr Arg Asp Ile His Ser Ala Leu Ile Lys Ile Leu Met Leu
    130                 135                 140

Gly Ile Thr Pro Val Ile Ala His Ile Glu Arg Tyr Asp Ala Leu Glu
145                 150                 155                 160

Asn Asn Glu Lys Arg Val Arg Glu Leu Ile Asn Met Gly Cys Tyr Thr
                165                 170                 175

Gln Val Asn Ser Ser His Val Leu Lys Ser Lys Leu Phe Gly Glu Pro
            180                 185                 190

Tyr Lys Phe Met Lys Lys Arg Ala Gln Tyr Phe Leu Glu Arg Asp Leu
        195                 200                 205

Val His Val Ile Ala Ser Asp Met His Asn Val Asp Ser Arg Pro Pro
    210                 215                 220

His Met Ala Glu Ala Tyr Asp Leu Val Ser Gln Lys Tyr Gly Glu Thr
225                 230                 235                 240

Lys Ala Gln Asp Leu Phe Ile Asp Asn Pro Arg Lys Ile Val Met Asp
                245                 250                 255

Gln Leu Ile

<210> SEQ ID NO 25
<211> LENGTH: 230
<212> TYPE: PRT
<213> ORGANISM: Streptococcus pneumoniae

<400> SEQUENCE: 25

Met Lys Glu Gln Asn Thr Ile Glu Ile Asp Val Phe Gln Leu Leu Lys
1               5                   10                  15

Thr Leu Trp Lys His Lys Leu Ile Ile Leu Leu Val Ala Leu Val Thr
            20                  25                  30

Gly Ala Gly Ala Phe Ala Tyr Ser Ile Phe Ile Val Lys Pro Glu Tyr
        35                  40                  45

Thr Ser Thr Thr Arg Ile Tyr Val Val Asn Arg Asn Gln Glu Asn Lys
    50                  55                  60

Pro Gly Leu Thr Asn Gln Asp Leu Gln Ala Gly Thr Tyr Leu Val Lys
65                  70                  75                  80
```

Asp Tyr His Glu Ile Ile Leu Ser Gln Asp Val Leu Glu Lys Val Ala
                85                  90                  95

Thr Asn Leu Lys Leu Asp Ile Pro Val Lys Thr Leu Thr Ser Lys Val
            100                 105                 110

Gln Val Thr Val Pro Ala Asp Thr Arg Ile Val Ser Ile Ser Val Lys
        115                 120                 125

Asp Lys Gln Pro Glu Glu Ala Ser Arg Ile Ala Asn Ser Ile Arg Glu
    130                 135                 140

Val Ala Ala Glu Lys Ile Ile Ala Val Thr Arg Val Ser Asp Val Thr
145                 150                 155                 160

Thr Leu Glu Glu Ala Arg Pro Ala Thr Thr Pro Ser Ser Pro Asn Val
                165                 170                 175

Arg Arg Asn Thr Leu Val Gly Phe Leu Gly Ala Ala Ala Val Thr Val
            180                 185                 190

Ile Thr Val Leu Leu Ile Glu Leu Phe Asp Thr Arg Val Lys Arg Pro
        195                 200                 205

Glu Glu Val Glu Asp Val Leu Gln Met Pro Leu Leu Gly Val Val Pro
    210                 215                 220

Asp Phe Asn Lys Met Lys
225                 230

<210> SEQ ID NO 26
<211> LENGTH: 229
<212> TYPE: PRT
<213> ORGANISM: Streptococcus pneumoniae

<400> SEQUENCE: 26

Met Pro Thr Leu Glu Ile Ser Gln Ala Lys Leu Glu Leu Ala Lys Lys
1               5                   10                  15

Thr Glu Glu Tyr Tyr Asn Ala Leu Cys Thr Asn Pro Gln Leu Ser Gly
            20                  25                  30

Asp Asp Leu Lys Val Phe Ser Ile Ser Ser Val Lys Ala Gly Glu Gly
        35                  40                  45

Lys Thr Thr Thr Ser Thr Asn Ile Ala Trp Ala Phe Ala His Ala Gly
    50                  55                  60

Tyr Lys Thr Leu Leu Ile Asp Ala Asp Met Arg Asn Ser Val Met Ser
65                  70                  75                  80

Gly Val Phe Lys Ser Arg Glu Arg Ile Thr Gly Leu Thr Glu Phe Leu
                85                  90                  95

Ser Gly Thr Thr Asp Leu Ser Gln Gly Leu Cys Asp Thr Asn Val Glu
            100                 105                 110

Asn Leu Phe Val Ile Gln Ala Gly Ser Val Ser Pro Asn Pro Ile Ala
        115                 120                 125

Leu Leu Gln Ser Lys Asn Phe Ser Thr Met Leu Gly Thr Leu Arg Lys
    130                 135                 140

Tyr Phe Asp Tyr Ile Val Val Asp Thr Ala Pro Ile Gly Ile Val Ile
145                 150                 155                 160

Asp Ala Ala Ile Ile Met Gln Lys Cys Asp Ala Ser Ile Leu Val Thr
                165                 170                 175

Lys Ala Gly Glu Thr Lys Arg Arg Glu Leu Gln Lys Ala Lys Glu Gln
            180                 185                 190

Leu Glu Gln Thr Gly Lys Ser Cys Leu Gly Val Val Leu Asn Lys Phe
        195                 200                 205

Asp Thr Ser Val Asp Lys Tyr Gly Phe Tyr Gly Ser Tyr
210                 215                 220

Arg Lys Gln Lys Lys
225

<210> SEQ ID NO 27
<211> LENGTH: 453
<212> TYPE: PRT
<213> ORGANISM: Streptococcus pneumoniae

<400> SEQUENCE: 27

Met Asn Glu Lys Leu Ala Lys Ser Ser Val Ala Ile Val Gln Ser Phe
1               5                   10                  15

Leu Val Ile Leu Leu Thr Tyr Leu Leu Ser Ala Val Arg Glu Thr Glu
            20                  25                  30

Ile Val Ser Thr Thr Ala Ile Val Leu Tyr Ile Leu His Tyr Phe Val
        35                  40                  45

Phe Tyr Ile Ser Asp Tyr Gly Arg Asn Phe Phe Lys Arg Arg Tyr Leu
    50                  55                  60

Ile Glu Leu Val Gln Thr Leu Lys Tyr Ile Leu Phe Phe Ala Leu Ala
65                  70                  75                  80

Ile Ser Ile Ser Asn Phe Leu Glu Asp Arg Phe Ser Ile Ser Arg
                85                  90                  95

Arg Gly Met Ile Tyr Phe Leu Leu His Val Phe Leu Val Tyr Met
                100                 105                 110

Leu Asn Leu Phe Ile Lys Trp Tyr Trp Lys Arg Ala Tyr Pro Asn Phe
            115                 120                 125

Lys Gly Ser Lys Lys Val Phe Leu Leu Thr Ala Thr Ser His Val Glu
130                 135                 140

Lys Val Leu Asp Arg Leu Ile Glu Ser Asp Val Val Gly Glu Leu
145                 150                 155                 160

Val Ala Val Ser Val Leu Asp Lys Pro Asp Phe Gln His Asp Leu
                165                 170                 175

Lys Val Val Ala Glu Gly Glu Ile Val Asn Phe Ala Thr Arg Glu Val
            180                 185                 190

Val Asp Glu Val Phe Ile Asn Leu Pro Ser Glu Lys Tyr Asn Ile Gly
        195                 200                 205

Glu Leu Val Ser Gln Phe Glu Thr Met Gly Ile Asp Val Thr Val Asn
    210                 215                 220

Leu Asn Ala Phe Asp Trp Ala Arg Asn Lys Gln Ile Cys Glu Met Ala
225                 230                 235                 240

Gly Leu Asn Val Thr Phe Ser Thr Thr Phe Tyr Lys Thr Ser His
                245                 250                 255

Val Ile Ala Lys Arg Val Asp Ile Ile Gly Ser Leu Val Gly Leu
                260                 265                 270

Ile Leu Cys Gly Leu Val Ser Ile Val Leu Val Pro Leu Ile Arg Lys
            275                 280                 285

Asp Gly Gly Ser Ala Ile Phe Ala Gln Thr Arg Ile Gly Lys Asn Gly
        290                 295                 300

Arg His Phe Thr Phe Tyr Lys Phe Arg Ser Met Cys Val Asp Ala Glu
305                 310                 315                 320

Asp Lys Lys Arg Glu Leu Met Glu Gln Asn Thr Met Gln Gly Gly Met
                325                 330                 335

Phe Lys Val Asp Asp Pro Arg Ile Thr Lys Ile Gly His Phe Ile
                340                 345                 350

```
Arg Lys Thr Ser Leu Asp Glu Leu Pro Gln Phe Tyr Asn Val Leu Lys
            355                 360                 365

Gly Asp Met Ser Leu Val Gly Thr Arg Pro Thr Val Asp Glu Tyr
    370                 375                 380

Glu His Tyr Thr Pro Glu Gln Lys Arg Leu Ser Phe Lys Pro Gly
385                 390                 395                 400

Ile Thr Gly Leu Trp Gln Val Ser Gly Arg Ser Glu Ile Lys Asn Phe
                405                 410                 415

Asp Glu Val Val Lys Leu Asp Val Val Tyr Ile Asp Gly Trp Thr Ile
                420                 425                 430

Trp Lys Asp Ile Glu Ile Leu Leu Lys Thr Val Lys Val Val Leu Met
            435                 440                 445

Lys Asp Gly Ala Lys
    450

<210> SEQ ID NO 28
<211> LENGTH: 407
<212> TYPE: PRT
<213> ORGANISM: Streptococcus pneumoniae

<400> SEQUENCE: 28

Met Glu Arg Asn Ser Leu Leu Leu Phe Gln Thr Ile Arg Arg Lys Met
1               5                   10                  15

Lys Lys Ser Val Tyr Ile Ile Gly Ser Lys Gly Ile Pro Ala Lys Tyr
            20                  25                  30

Gly Gly Phe Glu Thr Phe Val Glu Lys Leu Thr Glu Tyr Gln Lys Asp
        35                  40                  45

Gly Asn Ile Gln Tyr Tyr Val Ala Cys Met Arg Glu Asn Ser Ala Lys
    50                  55                  60

Ser Gly Phe Thr Ala Asp Thr Phe Glu Tyr Asn Asp Ala Ile Cys Tyr
65                  70                  75                  80

Asn Ile Asp Val Pro Asn Ile Gly Pro Ala Arg Ala Ile Ala Tyr Asp
                85                  90                  95

Ile Ala Ala Val Asn Lys Ala Ile Glu Ile Ala Lys Lys Asn Lys Asp
            100                 105                 110

Glu Ala Pro Ile Phe Tyr Ile Leu Ala Cys Arg Ile Gly Pro Phe Ile
        115                 120                 125

Ala Arg Leu Lys Lys Lys Ile Gln Ala Ile Gly Gly Thr Leu Phe Val
    130                 135                 140

Asn Pro Asp Gly His Glu Trp Leu Arg Ala Lys Trp Ser Leu Pro Val
145                 150                 155                 160

Arg Lys Tyr Trp Lys Phe Ser Glu Gln Leu Met Val Lys Tyr Ala Asp
                165                 170                 175

Leu Leu Val Cys Asp Ser Lys Asn Ile Glu Lys Tyr Ile Gln Asn Asp
            180                 185                 190

Tyr Lys Gln Tyr Gln Pro Lys Thr Thr Tyr Ile Ala Tyr Gly Thr Asp
        195                 200                 205

Thr Ser Pro Ser Ile Leu Lys Ser Glu Asp Leu Lys Ile Arg Ser Trp
    210                 215                 220

Tyr Gln Glu Lys Gly Leu Ser Glu Asn Gly Tyr Tyr Leu Val Val Gly
225                 230                 235                 240

Arg Phe Val Pro Glu Asn Asn Tyr Glu Thr Met Ile Arg Glu Phe Ile
                245                 250                 255

Lys Ser Lys Ser Lys Lys Asp Phe Val Leu Ile Thr Asn Val Glu Gln
            260                 265                 270
```

```
Asn Lys Phe Tyr Asp Gln Leu Leu Gln Glu Thr Gly Phe Asp Lys Asp
                275                 280                 285

Pro Arg Val Lys Phe Val Gly Thr Val Tyr Asp Gln Glu Leu Leu Lys
            290                 295                 300

Tyr Ile Arg Glu Asn Ala Phe Ala Tyr Phe His Gly His Glu Val Gly
305                 310                 315                 320

Gly Thr Asn Pro Ser Leu Leu Glu Ala Leu Ala Ser Thr Lys Leu Asn
                325                 330                 335

Leu Leu Leu Asp Val Gly Phe Asn Arg Glu Val Gly Glu Asp Gly Ala
                340                 345                 350

Ile Tyr Trp Arg Lys Asp Asn Leu His Lys Val Ile Glu Glu Ser Glu
                355                 360                 365

Gln Lys Thr Ile Glu Glu Ile Lys Glu Ile Asp Ile Leu Ser Thr Glu
            370                 375                 380

Gln Val Glu Lys Arg Phe Thr Trp Asp Phe Ile Val Asn Glu Tyr Glu
385                 390                 395                 400

Asn Leu Phe Leu Leu Gly Lys
                405

<210> SEQ ID NO 29
<211> LENGTH: 395
<212> TYPE: PRT
<213> ORGANISM: Streptococcus pneumoniae

<400> SEQUENCE: 29

Met Thr Ile Lys Ile Asn Tyr Met Phe Phe Val Cys Leu Ser Phe Phe
1               5                   10                  15

Gly Ile Val Leu Ser Ser Ser Gln Val Ile Val Asn Leu Gly Leu Ser
                20                  25                  30

Ser Ile Val Gln Tyr Ile Ala Tyr Phe Leu Leu Leu Cys Ile Phe
            35                  40                  45

Phe Thr Leu Ile Lys Asn Ser Pro Asp Val Ile Ala Asn Arg Ile Ala
    50                  55                  60

Tyr Phe Ser Ile Ile Ser Phe Leu Phe Ile Ile Gly Ile Asn Leu Gln
65                  70                  75                  80

Asn Leu Pro Phe Ser Thr Lys Ile Tyr Leu Ser Phe Ser Met Leu Ile
                85                  90                  95

Ile Ser Ser Leu Ser Thr Leu Pro Ile Lys Leu Ile Asn Asn Ile Asn
                100                 105                 110

Asp Phe Arg Arg Ile Ser Tyr Phe Leu Leu Asn Gly Ile Leu Leu Ser
            115                 120                 125

Thr Phe Leu Gly Trp Leu Phe Asn Ile Ser Leu Val Thr Val Ala Val
    130                 135                 140

Glu Gly Ile Gly Phe Ala Tyr Gly Phe Asn Gly Gly Leu Thr His Lys
145                 150                 155                 160

Asn Phe Tyr Ala Ile Thr Ile Leu Val Ser Tyr Ile Leu Leu Phe Ile
                165                 170                 175

Ser Arg Lys His Gly Thr Lys Tyr Gln Val Asp Ser Leu Val Leu Trp
                180                 185                 190

Phe Asp Leu Phe Leu Leu Val Ser Asn Thr Arg Thr Ile Tyr Ile
            195                 200                 205

Ile Leu Val Val Phe Trp Ile Val Val His Ser Gly Phe Ile Lys Tyr
    210                 215                 220

Ile Lys Lys Asn His Arg Pro Val Ile Ile Thr Thr Trp Leu Val Ile
225                 230                 235                 240
```

Ser Leu Leu Ser Ile Ile Phe Phe Lys His Ile Asn Asn Ser
            245                 250                 255

Glu Ser Tyr Thr His Arg Val Leu Gly Ile Val Asn Phe Phe Lys Tyr
        260                 265                 270

Tyr Glu Ser Ser Lys Phe His Leu Phe Phe Gly Asp Ala Glu Leu Ala
            275                 280                 285

Phe Gly Asp Met Thr Lys Gly Tyr Thr His Asn Ile Arg Ser Val Leu
    290                 295                 300

Gly Trp Asp Gly Thr Val Glu Met Pro Leu Leu Ser Val Met Ile Lys
305                 310                 315                 320

Asn Gly Tyr Val Gly Leu Ile Gly Tyr Gly Val Val Leu Phe Lys Phe
                325                 330                 335

Ile Ser Ser Val Leu Ser Met Glu Asp Arg Arg Val Lys Asn Ile Gly
            340                 345                 350

Leu Ser Ile Leu Ile Pro Leu Leu Leu Ser Ala Met Val Glu Asn Tyr
        355                 360                 365

Ile Val Asn Ile Ser Phe Val Phe Met Pro Val Cys Phe Cys Ile Leu
    370                 375                 380

Cys Ser Ile Lys Asn Ile Glu Phe Lys Asn Asn
385                 390                 395

<210> SEQ ID NO 30
<211> LENGTH: 322
<212> TYPE: PRT
<213> ORGANISM: Streptococcus pneumoniae

<400> SEQUENCE: 30

Met Lys Lys Val Ser Ile Ile Leu Pro Val Tyr Asn Val Glu Gln Tyr
1               5                   10                  15

Ile Lys Lys Cys Leu Glu Ser Ile Gln Gln Thr Tyr Pro Asn Leu
            20                  25                  30

Glu Val Ile Ile Val Asn Asp Gly Ala Thr Asp Lys Ser Val Glu Tyr
        35                  40                  45

Cys Glu Gln Ile Cys Lys Ile Asp Ser Arg Phe Ser Val Thr His Lys
    50                  55                  60

Glu Asn Gly Gly Leu Ser Asp Ala Arg Asn Val Gly Ile Asp Lys Ala
65                  70                  75                  80

Lys Gly Asp Tyr Leu Ile Phe Val Asp Ser Asp Phe Val Ser Gln
            85                  90                  95

Asp Met Val Ser Tyr Leu Val Ser Ser Met Glu Asn Asn Glu Ala Asp
        100                 105                 110

Ile Ala Ile Cys Asp Pro Ala His Tyr Tyr Ser Asp Arg Gln Asn Asn
    115                 120                 125

Asp Leu Asn Ile Phe Tyr Pro Ala Ser Ser Val Lys Val Tyr Glu Lys
        130                 135                 140

Thr Glu Ala Leu Cys Glu Met Phe Tyr Gln Lys Ser Phe Leu Val Ser
145                 150                 155                 160

Ala Trp Ala Lys Ile Tyr Lys Lys Glu Leu Phe Asp Asp Ile Arg Phe
                165                 170                 175

Pro Val Gly Lys Leu Phe Glu Asp Ser Ala Val Met Tyr Leu Leu Phe
            180                 185                 190

Glu Lys Cys Glu Lys Ile Val Tyr Ser Asn Ala Lys Leu Tyr Ala Tyr
        195                 200                 205

Val His Arg Asp Asn Ser Ile Thr Lys Lys Phe Ser Asp Lys Asp
    210                 215                 220

-continued

```
Leu Asp Ile Leu Asp Ile Ser Asn Thr Ile Leu Asp His Tyr Ser Gly
225                 230                 235                 240

Asn Phe Arg Val Tyr Lys Ala Ala Val Ser Tyr Lys Val Ser Ala Cys
                245                 250                 255

Phe Arg Ile Leu Leu Asn Ser Ser Glu Lys Lys Tyr Asn Gln Ile
            260                 265                 270

Gln Lys Asp Cys Met Thr Tyr Ile Leu Arg Asn Trp Arg Asn Met Leu
        275                 280                 285

Phe Asp Lys Asn Val Arg Leu Lys Asn Lys Leu Ala Leu Ile Ser Ile
        290                 295                 300

Thr Leu Phe Asn Pro Phe Val Lys Phe Ile Tyr Ser Lys Val Asn Arg
305                 310                 315                 320

Trp Glu

<210> SEQ ID NO 31
<211> LENGTH: 412
<212> TYPE: PRT
<213> ORGANISM: Streptococcus pneumoniae

<400> SEQUENCE: 31

Met Asn Lys Tyr Glu Glu Arg Tyr Gln Glu Asp Leu Ser Lys Asn Asp
1               5                   10                  15

Phe Glu Lys Leu Ile Asn Arg Arg Tyr Leu Ser Asp Lys Glu Leu Gln
            20                  25                  30

Val Glu Tyr Val Lys Lys Gly Thr Val Leu Pro Pro Lys Val Phe Glu
        35                  40                  45

Met Lys Leu Ser Asn Lys Leu Gly Leu Gln Lys Ala Leu His Gly Lys
50                  55                  60

Gly Gly Val Val Asp Ser Lys Gly Asn Tyr Val Glu Leu Ser Glu Gln
65                  70                  75                  80

Lys Ala Val Gly Met Arg Asn Arg Val Tyr Gly Ser Tyr Lys Phe Asn
                85                  90                  95

His Lys Asn Leu Ala Ile Arg Asn Glu Lys Val Ile Tyr Leu Asn Tyr
            100                 105                 110

Phe Ile Asn Gln Trp Gly His Phe Leu Leu Asp Val Val Gly Arg Leu
        115                 120                 125

Trp Tyr Pro Leu Leu Lys Asp Thr Asp Thr Lys Leu Asp Tyr Thr Cys
130                 135                 140

Tyr Ala Gly Thr Glu Thr Lys Leu Glu Gly Asn Tyr Leu Glu Phe Leu
145                 150                 155                 160

Glu Leu Leu Gly Ile Asp Lys Ser Arg Leu Ile Leu Ile Asn Arg Pro
                165                 170                 175

Thr Gln Phe Ser Glu Ile Ile Pro Glu Ser Ser Ile Leu Pro Gly
            180                 185                 190

Glu Tyr Tyr Thr Lys Glu Tyr Lys Met Leu Phe Asn Ser Leu Val Ala
        195                 200                 205

Asn Val Lys Leu Asp Asn Asn Leu Glu Ser Lys Lys Ile Tyr Cys Ser
210                 215                 220

Arg Ala Arg Leu Asp Leu Ala Lys Gly Lys Glu Phe Gly Glu Asn Gly
225                 230                 235                 240

Ile Glu Lys Val Phe Leu Lys Asn Gly Tyr Thr Pro Val Tyr Met Glu
                245                 250                 255

Thr Met Ser Leu Lys Glu Gln Ile Arg Thr Leu Leu Ser Ala Thr Thr
            260                 265                 270
```

```
Ile Val Leu Thr Ser Gly Ser Leu Ala His Asn Leu Phe Ile Asn
            275                 280                 285

Asn Lys Ile Asn Val Phe Ile Leu Asn Lys Thr Tyr Arg Val Asn Leu
290                 295                 300

His Gln Phe Leu Ile Asn Lys Ile Ser Glu Ala Ser Val Ser Phe Val
305                 310                 315                 320

Asp Ile Tyr Arg Ser Pro Leu Pro Ile Leu Tyr Gly Tyr Gly Pro Phe
                325                 330                 335

Leu Met Asp Ile Thr Lys Pro Leu Val Asn Phe Glu Asp Ser Gly
            340                 345                 350

Phe Thr Tyr Asp Ser Gly Thr Ile Leu Asp Lys Thr Asp Tyr Phe Lys
            355                 360                 365

Phe Tyr Leu Lys Trp Leu Trp Ser Tyr Lys Phe Phe Leu Phe Arg Leu
            370                 375                 380

Asn His Ile Lys Glu Gly Asn Ser Glu Phe Glu Lys Ser Phe Lys Ile
385                 390                 395                 400

Ile Arg Arg Tyr Tyr Lys Met Gly Arg Gln Tyr Glu
                405                 410

<210> SEQ ID NO 32
<211> LENGTH: 462
<212> TYPE: PRT
<213> ORGANISM: Streptococcus pneumoniae

<400> SEQUENCE: 32

Met Ser Lys Tyr Lys Glu Leu Ala Lys Asn Thr Gly Thr Phe Ala Leu
1               5                   10                  15

Ala Asn Phe Ser Ser Lys Ile Leu Ile Phe Leu Leu Val Pro Ile Tyr
                20                  25                  30

Thr Lys Val Leu Thr Thr Thr Glu Tyr Gly Phe Tyr Asp Leu Val Tyr
            35                  40                  45

Thr Thr Ile Gln Leu Leu Val Pro Ile Leu Thr Leu Asn Ile Ser Glu
        50                  55                  60

Ala Val Met Arg Phe Leu Met Lys Glu Asp Val Ser Lys Lys Ser Val
65                  70                  75                  80

Phe Ser Ile Ala Ile Leu Asp Ile Phe Leu Gly Ser Ile Ile Phe Cys
                85                  90                  95

Leu Leu Leu Leu Val Asn Gln Ile Phe Ser Leu Ser Glu Leu Ile Ser
                100                 105                 110

Gln Tyr Ser Ile Tyr Ile Met Ala Ile Phe Ala Phe Tyr Thr Leu Asn
            115                 120                 125

Asn Phe Leu Ile Gln Tyr Ser Lys Gly Ile Asp Lys Ile Gly Val Thr
        130                 135                 140

Ala Ile Ser Gly Val Ile Ser Ala Ala Val Met Leu Ser Met Asn Ile
145                 150                 155                 160

Leu Leu Leu Val Val Leu Asn Trp Gly Leu Leu Gly Phe Phe Ile Ala
                165                 170                 175

Asn Ile Cys Gly Tyr Val Ile Pro Cys Val Tyr Ile Val Lys Leu
                180                 185                 190

Lys Leu Trp Asp Leu Phe Glu Leu Lys Ile Asp Arg Ser Leu Gln Trp
            195                 200                 205

Glu Met Ile Tyr Tyr Thr Leu Pro Leu Ile Leu Asn Thr Leu Ser Trp
        210                 215                 220

Trp Val Asn Asn Thr Ser Asp Arg Tyr Ile Ile Thr Val Ile Ile Gly
225                 230                 235                 240
```

```
Ile Gln Ala Ser Ala Ile Ser Val Ala Tyr Lys Ile Pro Gln Ile
                245                 250                 255

Phe Ser Thr Ile Ser Ala Ile Phe Ile Gln Ser Trp Gln Ile Ser Ala
                260                 265                 270

Ile Lys Ile Gln Glu Glu Lys Glu Gly Asn Thr Phe Ile Ser Lys Met
            275                 280                 285

Leu Leu Tyr Tyr Asn Ala Leu Leu Ile Ile Ala Ser Gly Ile Ile
            290                 295                 300

Leu Phe Val Lys Pro Ile Ser Asn Ile Leu Phe Gly Ala Ser Phe Tyr
305                 310                 315                 320

Ser Ala Trp Thr Leu Val Pro Phe Leu Ile Ser Ser Leu Phe Asn
                325                 330                 335

Ala Ile Ser Gly Tyr Ile Gly Ala Ile Met Gly Ala Lys Met Asp Thr
                340                 345                 350

Lys Asn Ile Ala Lys Ser Ala Leu Val Gly Met Ile Ala Asn Val Phe
            355                 360                 365

Leu Asn Ile Val Leu Thr Phe Leu Met Gly Leu Gln Gly Ile Thr Ile
            370                 375                 380

Ser Thr Met Ile Ala Ser Phe Leu Ile Phe Tyr Met Arg Lys Asp Ser
385                 390                 395                 400

Val Glu Glu Ile Ala Pro Glu Thr Tyr Arg Ala Ile Tyr Leu Ser Trp
                405                 410                 415

Phe Leu Leu Val Val Glu Ala Ser Leu Leu Val Tyr Ile Asp Phe Ile
                420                 425                 430

Ile Gly Ala Thr Leu Val Thr Leu Ile Asn Leu Phe Leu Leu Lys Asp
                435                 440                 445

Thr Leu Lys Pro Leu Cys Leu Lys Leu Leu Lys Gly Phe Lys
        450                 455                 460

<210> SEQ ID NO 33
<211> LENGTH: 384
<212> TYPE: PRT
<213> ORGANISM: Streptococcus pneumoniae

<400> SEQUENCE: 33

Met Lys Met Asn Ile Leu Gln Tyr Ile Lys Ile Leu Ala Arg Thr Ile
1               5                   10                  15

Phe Met Leu Leu Ile Ser Thr Val Leu Leu Pro Val Arg Leu Lys Asn
                20                  25                  30

Asn Lys Ile Leu Phe Ile Asn Phe Asn Gly Lys Gly Tyr Gly Asp Asn
            35                  40                  45

Pro Lys Ser Ile Cys Glu Tyr Leu Arg Thr Thr Tyr Pro Asp Leu Asp
        50                  55                  60

Leu Val Trp Leu Ala Arg Asp Asn Glu Gly Pro Asp Gly Val Arg
65                  70                  75                  80

Val Val Lys Tyr Gly Thr Phe Gln Ala Phe Tyr Glu Gln Ala Ser Ser
                85                  90                  95

Lys Val Trp Val Tyr Asn Val Arg Ala Phe Arg Ile Leu Lys Lys
            100                 105                 110

Arg Gly Gln Ile Tyr Ile Gln Thr Trp His Gly Ala Ser Ser Phe Lys
            115                 120                 125

Leu Ile Glu Lys Gln Ala Asp Leu Pro Ile Asn Tyr Val Leu Glu Ala
        130                 135                 140

Lys Tyr Asp Ala Arg Val Thr Asp Ile Met Ile Ser Ser Arg Lys
145                 150                 155                 160
```

```
Gln Thr Glu Glu Phe Gln Lys Tyr Phe Trp Tyr Ser Gly Glu Ile Phe
                165                 170                 175

Glu Val Gly Met Pro Arg Asn Asp Ala Leu Phe His Tyr Lys Glu Asp
            180                 185                 190

Tyr Asp Lys Leu Asn Asn Ile Arg Lys Glu Leu Ser Ile His Ser Asp
        195                 200                 205

Asp Tyr Val Ile Leu Tyr Ala Pro Thr Phe Arg Asp Asp Gly Asp Ala
    210                 215                 220

Ser Tyr Leu Asp Ile Asn Phe Glu Arg Leu Leu Gln Cys Val Glu His
225                 230                 235                 240

Gly Ile Lys Lys Lys Cys Lys Phe Leu Ile Arg Leu His Pro Asn His
                245                 250                 255

Ser His Leu Cys Asn Asn Ile Ser Phe Asn Lys Asn Ile Ile Asn Ala
            260                 265                 270

Thr Phe Tyr Ser Asp Met Gln Glu Leu Thr Leu Leu Ala Asp Val Leu
        275                 280                 285

Val Thr Asp Tyr Ser Ser Ile Phe Asp Phe Met Leu Leu Asn Lys
    290                 295                 300

Pro Tyr Val Arg Tyr Val Asn Asp Leu Glu Lys Tyr Ala Glu Leu Arg
305                 310                 315                 320

Gly Val Ser Asp Thr Tyr Tyr Glu Leu Pro Asp Ser Ile Ile Lys Thr
                325                 330                 335

Ala Glu Glu Leu Tyr Asp Leu Leu Pro Lys Lys Ile Glu Asn Phe Asp
            340                 345                 350

Tyr Asp Ser Ile Lys Lys Tyr Arg Asn Glu Ile Leu Cys Pro Ile Phe
        355                 360                 365

Asn Gly Thr Ala Ser Glu Asn Val Gly Arg Arg Ile Ile Gln Glu Leu
    370                 375                 380

<210> SEQ ID NO 34
<211> LENGTH: 342
<212> TYPE: PRT
<213> ORGANISM: Streptococcus pneumoniae

<400> SEQUENCE: 34

Met Lys Asn Asn Asp Leu Lys Ile Gly Ser Gly Ala Ile His Gln Ile
1               5                   10                  15

Ser Ala Thr Leu Ser Gln Asn Ser Ile Ser Gly Lys Ile Leu Tyr Cys
            20                  25                  30

Ala Asp Pro Val Val Asp Leu Tyr Gly Ser Ile Val Arg Ser Gln
        35                  40                  45

Ile Glu Glu Ile Gly Arg Val Lys Glu Glu Ser Cys Asn Tyr Asn Thr
50                  55                  60

Ile Ala Tyr Ala Met Asn Ile Ala Glu Arg Ala Ile Ala Thr Asp Ile
65                  70                  75                  80

Asp Cys Ile Val Gly Met Gly Gly Gly Arg Val Leu Asp Val Cys Lys
                85                  90                  95

Tyr Ala Ser Phe Ile Ser Lys Arg Pro Tyr Leu Ser Ile Pro Thr Thr
            100                 105                 110

Ala Ala Asn Asp Gly Ile Ala Ser Pro Val Ala Val Leu Lys Arg Gln
        115                 120                 125

Asp Asp Arg Pro Lys Ser Leu Gly Ala Ala Ile Pro Ser Met Thr Leu
    130                 135                 140

Ile Asp Ile Asp Val Ile Ala Ser Gly Pro Ile Gln Asn Ile Lys Ala
145                 150                 155                 160
```

Gly Ile Gly Asp Thr Ile Ser Asn Tyr Thr Ala Leu Lys Asp Trp Glu
            165                 170                 175

Leu Ala Val Glu Arg Gly Lys Asp Glu Met His Gly Phe Ala Tyr Leu
        180                 185                 190

Met Ser Gln Asn Ser Leu Asp Ala Leu Met Lys Thr Lys Tyr Asn Ser
        195                 200                 205

Ile Thr Pro Asp Phe Ile Glu Val Leu Val Asn Ser Leu Val Leu Ser
    210                 215                 220

Gly Ile Ala Met Asp Phe Ala Gly Ser Ser Arg Pro Val Ser Gly Ser
225                 230                 235                 240

Glu His Leu Phe Ser His Ala Leu Asp Tyr Tyr Gly Ser Thr Arg Asn
                245                 250                 255

Leu His Gly Ile Gln Val Ala Leu Gly Thr Val Ala Val Leu Lys Leu
            260                 265                 270

Ile Glu Asn Ser Val Asp Thr Val Val Asp Tyr Leu Gln Arg Phe Glu
        275                 280                 285

Val His Ile Asn Pro Lys Leu Leu Gly Ile Asp Glu Glu Leu Phe Ile
    290                 295                 300

Tyr Cys Met Gln His Ala Thr Lys Met Arg Ser Asn Arg Tyr Thr Tyr
305                 310                 315                 320

Leu His Glu Val Asp Leu Ser Thr Asp Arg Leu Lys Gln Ile Tyr Lys
                325                 330                 335

Glu Leu Ile Ser Glu Leu
            340

<210> SEQ ID NO 35
<211> LENGTH: 234
<212> TYPE: PRT
<213> ORGANISM: Streptococcus pneumoniae

<400> SEQUENCE: 35

Met Lys Ala Leu Ile Leu Ala Ala Gly Leu Gly Thr Arg Leu Ala Pro
1               5                   10                  15

Ile Thr Asn Glu Val Pro Lys Ser Leu Val Pro Val Asn Gly Lys Pro
            20                  25                  30

Ile Leu Met Lys Gln Ile Glu Asn Leu Tyr Gln Asn Asn Ile Thr Asp
        35                  40                  45

Ile Thr Ile Ile Ala Gly Tyr Lys Ser Ser Val Leu Thr Asp Ala Val
    50                  55                  60

Thr Glu Lys Tyr Pro Glu Ile Asn Ile Asp Asn Val Asp Phe Lys
65                  70                  75                  80

Thr Thr Asn Asn Met Tyr Ser Ala Tyr Leu Gly Lys Ala Ala Met Gly
                85                  90                  95

Asp Ser Asp Phe Leu Met Met Asn Ala Asp Val Phe Tyr Asp Ala Ser
            100                 105                 110

Val Ile Lys Ser Leu Leu His Lys Ala Pro Asn Ala Ile Val Thr
        115                 120                 125

Asp Leu Gly Ile Tyr Ile Glu Glu Ser Met Lys Val Val Glu Lys Asn
    130                 135                 140

Gly Arg Leu Val Glu Ile Ser Lys Gln Ile Ser Pro Glu Glu Thr Leu
145                 150                 155                 160

Gly Ala Ser Ile Asp Val Tyr Lys Phe Ser Tyr Glu Ala Gly Ala Arg
                165                 170                 175

Phe Phe Glu Lys Cys Lys Glu Phe Ile Glu Asp Lys Arg Glu Leu Gln
            180                 185                 190

```
Met Trp Ser Glu Val Ala Leu Asn Ala Ile Leu Ser Glu Val Glu Phe
        195                 200                 205

Val Ala Cys Pro Leu Glu Gly Arg Trp Leu Glu Ile Asp Asn His Glu
    210                 215                 220

Asp Leu Val Ala Ala Glu Lys Leu Phe Ala
225                 230

<210> SEQ ID NO 36
<211> LENGTH: 283
<212> TYPE: PRT
<213> ORGANISM: Streptococcus pneumoniae

<400> SEQUENCE: 36

Met Asn Arg Ile Arg Arg Met Lys Leu Thr Asn Arg Val Asp Tyr Phe
1               5                   10                  15

Gly Ala Asp Ile Ser Glu Leu Gln Asn Lys Lys Leu Phe Leu Phe Asp
                20                  25                  30

Met Asp Gly Thr Ile Tyr Glu Glu Asp Arg Leu Phe Glu Gly Thr Leu
            35                  40                  45

Glu Leu Leu Asp Tyr Ile His Asn Ile Gly Gly Glu Tyr Ile Phe Ile
        50                  55                  60

Thr Asn Asn Ser Ser Lys Ser Val Val Asp Tyr Val Glu Lys Val Asn
65                  70                  75                  80

Arg Leu Gly Ile Lys Ala Glu Arg Asp Asn Phe Phe Thr Ser Ala Gln
                85                  90                  95

Ala Thr Ile Val Tyr Ile Lys Glu Asn Tyr Pro Lys Ser Lys Val Tyr
            100                 105                 110

Cys Gln Gly Thr Lys Ser Leu Ile Lys Glu Leu Ser Asp Ala Gly Ile
        115                 120                 125

Asp Val Thr Glu Gln Val Ser Ala Asp Ile Asp Val Val Leu Val Gly
130                 135                 140

Phe Asp Thr Glu Leu Thr Ser Asp Lys Ile Arg Asn Thr Cys Glu Ile
145                 150                 155                 160

Leu Ser Thr Lys Asp Val Pro Phe Ile Ala Thr Asn Pro Asp Ile Arg
                165                 170                 175

Cys Pro Val Ser Phe Gly Phe Ile Pro Asp Cys Gly Ser Ile Cys Asp
            180                 185                 190

Met Ile Ser Lys Ser Val Asp Arg Lys Pro Val Tyr Ile Gly Lys Pro
        195                 200                 205

Glu Pro Thr Met Val Asp Ile Val Arg Lys Lys Leu Asn Tyr Ser Leu
210                 215                 220

Phe Glu Thr Val Val Ile Gly Asp Arg Leu Tyr Thr Asp Ile Met Thr
225                 230                 235                 240

Gly Ile Asn Ala Gly Val Thr Ser Val Cys Val Leu Thr Gly Glu Ala
                245                 250                 255

Thr Val Asn Asp Ile Gln Gln Asp Ser Ile Lys Pro Thr Tyr Thr Phe
            260                 265                 270

Lys Asn Val Lys Glu Met Trp Lys Gly Ile Val
        275                 280

<210> SEQ ID NO 37
<211> LENGTH: 289
<212> TYPE: PRT
<213> ORGANISM: Streptococcus pneumoniae
```

<400> SEQUENCE: 37

Met Lys Gly Ile Ile Leu Ala Gly Gly Ser Gly Thr Arg Leu Tyr Pro
1               5                   10                  15

Leu Thr Arg Ala Ala Ser Lys Gln Leu Met Pro Val Tyr Asp Lys Pro
            20                  25                  30

Met Ile Tyr Tyr Pro Leu Ser Thr Leu Met Leu Ala Gly Ile Arg Asp
        35                  40                  45

Ile Leu Ile Ile Ser Thr Pro Gln Asp Leu Pro Arg Phe Lys Glu Leu
    50                  55                  60

Leu Gln Asp Gly Ser Glu Phe Gly Ile Lys Leu Ser Tyr Ala Glu Gln
65                  70                  75                  80

Pro Ser Pro Asp Gly Leu Ala Gln Ala Phe Ile Ile Gly Glu Glu Phe
                85                  90                  95

Ile Gly Asp Asp Ser Val Ala Leu Ile Leu Gly Asp Asn Ile Tyr His
            100                 105                 110

Gly Pro Gly Leu Ser Thr Met Leu Gln Lys Ala Ala Lys Lys Glu Lys
        115                 120                 125

Gly Ala Thr Val Phe Gly Tyr His Val Lys Asp Pro Glu Arg Phe Gly
    130                 135                 140

Val Val Glu Phe Asp Glu Asn Met Asn Ala Ile Ser Ile Glu Glu Lys
145                 150                 155                 160

Pro Glu Tyr Pro Arg Ser Asn Tyr Ala Val Thr Gly Leu Tyr Phe Tyr
                165                 170                 175

Asp Asn Asp Val Val Glu Ile Ala Lys Ser Ile Lys Pro Ser Pro Arg
            180                 185                 190

Gly Glu Leu Glu Ile Thr Asp Val Asn Lys Ala Tyr Leu Asp Arg Gly
        195                 200                 205

Asp Leu Ser Val Glu Leu Met Gly Arg Gly Phe Ala Trp Leu Asp Thr
    210                 215                 220

Gly Thr His Glu Ser Leu Leu Glu Ala Ser Gln Tyr Ile Glu Thr Val
225                 230                 235                 240

Gln Arg Met Gln Asn Val Gln Val Ala Asn Leu Glu Glu Ile Ala Tyr
                245                 250                 255

Arg Met Gly Tyr Ile Ser Arg Glu Asp Val Leu Ala Leu Ala Gln Pro
            260                 265                 270

Leu Lys Lys Asn Glu Tyr Gly Gln Tyr Leu Leu Arg Leu Ile Gly Glu
        275                 280                 285

Ala

<210> SEQ ID NO 38
<211> LENGTH: 197
<212> TYPE: PRT
<213> ORGANISM: Streptococcus pneumoniae

<400> SEQUENCE: 38

Met Thr Asp Asn Phe Phe Gly Lys Thr Leu Ala Ala Arg Lys Val Glu
1               5                   10                  15

Ala Ile Pro Gly Met Leu Glu Phe Asp Ile Pro Val His Gly Asp Asn
            20                  25                  30

Arg Gly Trp Phe Lys Glu Asn Phe Gln Lys Glu Lys Met Leu Pro Leu
        35                  40                  45

Gly Phe Pro Glu Ser Phe Phe Ala Glu Gly Lys Leu Gln Asn Asn Val
    50                  55                  60

Ser Phe Ser Arg Lys Asn Val Leu Arg Gly Leu His Ala Glu Pro Trp
65                  70                  75                  80

Asp Lys Tyr Ile Ser Val Ala Asp Gly Gly Lys Val Leu Gly Ser Trp
                85                  90                  95

Val Asp Leu Arg Glu Gly Glu Thr Phe Gly Asn Thr Tyr Gln Thr Val
            100                 105                 110

Ile Asp Ala Ser Lys Gly Ile Phe Val Pro Arg Gly Val Ala Asn Gly
            115                 120                 125

Phe Gln Val Leu Ser Asp Thr Val Ser Tyr Ser Tyr Leu Val Asn Asp
130                 135                 140

Tyr Trp Ala Leu Glu Leu Lys Pro Lys Tyr Ala Phe Val Asn Tyr Ala
145                 150                 155                 160

Asp Pro Ser Leu Gly Ile Glu Trp Glu Asn Ile Ala Glu Ala Glu Val
            165                 170                 175

Ser Glu Ala Asp Lys Asn His Pro Leu Leu Lys Asp Val Lys Pro Leu
            180                 185                 190

Lys Lys Glu Asp Leu
            195

<210> SEQ ID NO 39
<211> LENGTH: 349
<212> TYPE: PRT
<213> ORGANISM: Streptococcus pneumoniae (

<400> SEQUENCE: 39

Met Thr Glu Tyr Lys Asn Ile Ile Val Thr Gly Gly Ala Gly Phe Ile
1               5                   10                  15

Gly Ser Asn Phe Val His Tyr Val Tyr Glu Asn Phe Pro Gly Val His
                20                  25                  30

Val Thr Val Leu Asp Lys Leu Thr Tyr Ala Gly Asn Arg Ala Asn Ile
            35                  40                  45

Glu Glu Ile Leu Gly Asn Arg Val Glu Leu Val Val Gly Asp Ile Ala
        50                  55                  60

Asp Ala Glu Leu Val Asp Lys Leu Ala Ala Gln Ala Asp Ala Ile Val
65                  70                  75                  80

His Tyr Ala Ala Glu Ser His Asn Asp Asn Ser Leu Asn Asp Pro Ser
                85                  90                  95

Pro Phe Ile His Thr Asn Phe Ile Gly Thr Tyr Thr Leu Leu Glu Ala
            100                 105                 110

Ala Arg Lys Tyr Asp Ile Arg Phe His His Val Ser Thr Asp Glu Val
            115                 120                 125

Tyr Gly Asp Leu Pro Leu Arg Glu Asp Leu Pro Gly His Gly Glu Gly
130                 135                 140

Pro Gly Glu Lys Phe Thr Ala Glu Thr Lys Tyr Asn Pro Ser Ser Pro
145                 150                 155                 160

Tyr Ser Ser Thr Lys Ala Ala Ser Asp Leu Ile Val Lys Ala Trp Val
            165                 170                 175

Arg Ser Phe Gly Val Lys Ala Thr Ile Ser Asn Cys Ser Asn Asn Tyr
            180                 185                 190

Gly Pro Tyr Gln His Ile Glu Lys Phe Ile Pro Arg Gln Ile Thr Asn
            195                 200                 205

Ile Leu Ser Gly Ile Lys Pro Lys Leu Tyr Gly Glu Gly Lys Asn Val
            210                 215                 220

Arg Asp Trp Ile His Thr Asn Asp His Ser Ser Gly Val Trp Thr Ile
225                 230                 235                 240

Leu Thr Lys Gly Gln Ile Gly Glu Thr Tyr Leu Ile Gly Ala Asp Gly
            245                 250                 255

Glu Lys Asn Asn Lys Glu Val Leu Glu Leu Ile Leu Lys Glu Met Gly
        260                 265                 270

Gln Ala Thr Asp Ala Tyr Asp His Val Thr Asp Arg Ala Gly His Asp
    275                 280                 285

Leu Arg Tyr Ala Ile Asp Ala Ser Lys Leu Arg Asp Glu Leu Gly Trp
290                 295                 300

Lys Pro Glu Phe Thr Asn Phe Glu Ala Gly Leu Lys Ala Thr Ile Lys
305                 310                 315                 320

Trp Tyr Thr Asp Asn Gln Glu Trp Trp Lys Ala Glu Lys Glu Ala Val
            325                 330                 335

Glu Ala Asn Tyr Ala Lys Thr Gln Glu Ile Ile Thr Val
        340                 345

<210> SEQ ID NO 40
<211> LENGTH: 283
<212> TYPE: PRT
<213> ORGANISM: Streptococcus pneumoniae

<400> SEQUENCE: 40

Met Ile Leu Ile Thr Gly Ala Asn Gly Gln Leu Gly Thr Glu Leu Arg
1               5                   10                  15

Tyr Leu Leu Asp Glu Arg Asn Glu Glu Tyr Val Ala Val Asp Val Ala
            20                  25                  30

Glu Met Asp Ile Thr Asn Glu Glu Met Val Glu Lys Val Phe Glu Glu
        35                  40                  45

Val Lys Pro Thr Leu Val Tyr His Cys Ala Ala Tyr Thr Ala Val Asp
    50                  55                  60

Ala Ala Glu Asp Glu Gly Lys Glu Leu Asn Phe Ala Ile Asn Val Thr
65                  70                  75                  80

Gly Thr Lys Asn Val Ala Lys Ala Ser Glu Lys His Gly Ala Thr Leu
                85                  90                  95

Val Tyr Ile Ser Thr Asp Tyr Val Phe Asp Gly Lys Lys Pro Val Gly
            100                 105                 110

Gln Glu Trp Glu Val Asp Asp Arg Pro Asp Pro Gln Thr Glu Tyr Gly
        115                 120                 125

Arg Thr Lys Arg Met Gly Glu Glu Leu Val Glu Lys His Val Ser Asn
130                 135                 140

Phe Tyr Ile Ile Arg Thr Ala Trp Val Phe Gly Asn Tyr Gly Lys Asn
145                 150                 155                 160

Phe Val Phe Thr Met Gln Asn Leu Ala Lys Thr His Lys Thr Leu Thr
                165                 170                 175

Val Val Asn Asp Gln Tyr Gly Arg Pro Thr Trp Thr Arg Thr Leu Ala
            180                 185                 190

Glu Phe Met Thr Tyr Leu Ala Glu Asn Arg Lys Glu Phe Gly Tyr Tyr
        195                 200                 205

His Leu Ser Asn Asp Ala Thr Glu Asp Thr Thr Trp Tyr Asp Phe Ala
    210                 215                 220

Val Glu Ile Leu Lys Asp Thr Asp Val Glu Val Lys Pro Val Asp Ser
225                 230                 235                 240

Ser Gln Phe Pro Ala Lys Ala Lys Arg Pro Leu Asn Ser Thr Met Ser
                245                 250                 255

```
Leu Ala Lys Ala Lys Ala Thr Gly Phe Val Ile Pro Thr Trp Gln Asp
            260                 265                 270

Ala Leu Gln Glu Phe Tyr Lys Gln Glu Val Arg
        275                 280
```

<210> SEQ ID NO 41
<211> LENGTH: 481
<212> TYPE: PRT
<213> ORGANISM: Streptococcus pneumoniae

<400> SEQUENCE: 41

```
Met Ser Arg Arg Phe Lys Lys Ser Arg Ser Gln Lys Val Lys Arg Ser
1               5                   10                  15

Val Asn Ile Val Leu Leu Thr Ile Tyr Leu Leu Val Cys Phe Leu
                20                  25                  30

Leu Phe Leu Ile Phe Lys Tyr Asn Ile Leu Ala Phe Arg Tyr Leu Asn
            35                  40                  45

Leu Val Val Thr Ala Leu Val Leu Leu Val Ala Leu Val Gly Leu Leu
        50                  55                  60

Leu Ile Ile Tyr Lys Lys Ala Glu Lys Phe Thr Ile Phe Leu Leu Val
65                  70                  75                  80

Phe Ser Ile Leu Val Ser Ser Val Ser Leu Phe Ala Val Gln Gln Phe
                85                  90                  95

Val Gly Leu Thr Asn Arg Leu Asn Ala Thr Ser Asn Tyr Ser Glu Tyr
            100                 105                 110

Ser Ile Ser Val Ala Val Leu Ala Asp Ser Asp Ile Glu Asn Val Thr
        115                 120                 125

Gln Leu Thr Ser Val Thr Ala Pro Thr Gly Thr Asp Asn Glu Asn Ile
    130                 135                 140

Gln Lys Leu Leu Ala Asp Ile Lys Ser Ser Gln Asn Thr Asp Leu Thr
145                 150                 155                 160

Val Asp Gln Ser Ser Ser Tyr Leu Ala Ala Tyr Lys Ser Leu Ile Ala
                165                 170                 175

Gly Glu Thr Lys Ala Ile Val Leu Asn Ser Val Phe Glu Asn Ile Ile
            180                 185                 190

Glu Ser Glu Tyr Pro Asp Tyr Ala Ser Lys Ile Lys Lys Ile Tyr Thr
        195                 200                 205

Lys Gly Phe Thr Lys Lys Val Glu Ala Pro Lys Thr Ser Lys Asn Gln
    210                 215                 220

Ser Phe Asn Ile Tyr Val Ser Gly Ile Asp Thr Tyr Gly Pro Ile Ser
225                 230                 235                 240

Ser Val Ser Arg Ser Asp Val Asn Ile Leu Met Thr Val Asn Arg Asp
                245                 250                 255

Thr Lys Lys Ile Leu Leu Thr Thr Thr Pro Arg Asp Ala Tyr Val Pro
            260                 265                 270

Ile Ala Asp Gly Gly Asn Asn Gln Lys Asp Lys Leu Thr His Ala Gly
        275                 280                 285

Ile Tyr Gly Val Asp Ser Ser Ile His Thr Leu Glu Asn Leu Tyr Gly
    290                 295                 300

Val Asp Ile Asn Tyr Tyr Val Arg Leu Asn Phe Thr Ser Phe Leu Lys
305                 310                 315                 320

Met Ile Asp Leu Leu Gly Gly Val Asp Val His Asn Asp Gln Glu Phe
                325                 330                 335

Ser Ala Leu His Gly Lys Phe His Phe Pro Val Gly Asn Val His Leu
            340                 345                 350
```

```
Asp Ser Glu Gln Ala Leu Gly Phe Val Arg Glu Arg Tyr Ser Leu Ala
            355                 360                 365

Asp Gly Asp Arg Asp Arg Gly Arg Asn Gln Gln Lys Val Ile Val Ala
    370                 375                 380

Ile Leu Gln Lys Leu Thr Ser Thr Glu Ala Leu Lys Asn Tyr Ser Thr
385                 390                 395                 400

Ile Ile Asp Ser Leu Gln Asp Ser Ile Gln Thr Asn Met Pro Leu Glu
                405                 410                 415

Thr Met Ile Asn Leu Val Asn Ala Gln Leu Glu Ser Gly Gly Asn Tyr
            420                 425                 430

Lys Val Asn Ser Gln Asp Leu Lys Gly Thr Gly Arg Thr Asp Leu Pro
        435                 440                 445

Ser Tyr Ala Met Pro Asp Ser Asn Leu Tyr Val Met Glu Ile Asp Asp
    450                 455                 460

Ser Ser Leu Ala Val Val Lys Ala Ala Ile Gln Asp Val Met Glu Gly
465                 470                 475                 480

Arg

<210> SEQ ID NO 42
<211> LENGTH: 243
<212> TYPE: PRT
<213> ORGANISM: Streptococcus pneumoniae

<400> SEQUENCE: 42

Met Ile Asp Ile His Ser His Ile Val Phe Asp Val Asp Asp Gly Pro
1               5                   10                  15

Lys Ser Arg Glu Glu Ser Lys Ala Leu Leu Thr Glu Ser Tyr Arg Gln
            20                  25                  30

Gly Val Arg Thr Ile Val Ser Thr Ser His Arg Arg Lys Gly Met Phe
        35                  40                  45

Glu Thr Pro Glu Glu Lys Ile Ala Glu Asn Phe Leu Gln Val Arg Glu
    50                  55                  60

Ile Ala Lys Glu Val Ala Asp Asp Leu Val Ile Ala Tyr Gly Ala Glu
65                  70                  75                  80

Ile Tyr Tyr Thr Leu Asp Ala Leu Glu Lys Leu Glu Lys Lys Glu Ile
                85                  90                  95

Pro Thr Leu Asn Asp Ser Arg Tyr Ala Leu Ile Glu Phe Ser Met Asn
            100                 105                 110

Thr Pro Tyr Arg Asp Ile His Ser Ala Leu Ser Lys Ile Leu Met Leu
        115                 120                 125

Gly Ile Thr Pro Val Ile Ala His Ile Glu Arg Tyr Asp Ala Leu Glu
    130                 135                 140

Asn Asn Glu Lys Arg Val Arg Glu Leu Ile Asp Met Gly Cys Tyr Thr
145                 150                 155                 160

Gln Val Asn Ser Ser His Val Leu Lys Pro Lys Leu Phe Gly Glu Arg
                165                 170                 175

Tyr Lys Phe Met Lys Lys Arg Ala Gln Tyr Phe Leu Glu Gln Asp Leu
            180                 185                 190

Val His Val Ile Ala Ser Asp Met His Asn Leu Asp Gly Arg Pro Pro
        195                 200                 205

His Met Ala Glu Ala Tyr Asp Leu Val Thr Gln Lys Tyr Gly Glu Ala
    210                 215                 220
```

```
Lys Ala Gln Glu Leu Phe Ile Asp Asn Pro Arg Lys Ile Val Met Asp
225                 230                 235                 240

Gln Leu Ile

<210> SEQ ID NO 43
<211> LENGTH: 231
<212> TYPE: PRT
<213> ORGANISM: Streptococcus pneumoniae

<400> SEQUENCE: 43

Met Met Lys Glu Gln Asn Thr Ile Glu Ile Asp Val Phe Gln Leu Phe
1               5                   10                  15

Lys Thr Leu Trp Lys Arg Lys Leu Met Ile Leu Ile Val Ala Leu Val
                20                  25                  30

Thr Gly Thr Gly Ala Phe Ala Tyr Ser Thr Phe Ile Val Lys Pro Glu
            35                  40                  45

Tyr Thr Ser Thr Thr Arg Ile Tyr Val Val Asn Arg Asn Gln Gly Asp
        50                  55                  60

Lys Pro Gly Leu Thr Asn Gln Asp Leu Gln Ala Gly Thr Tyr Leu Val
65                  70                  75                  80

Lys Asp Tyr Arg Glu Ile Ile Leu Ser Gln Asp Ala Leu Glu Lys Val
                85                  90                  95

Ala Thr Asn Leu Lys Leu Asp Met Pro Ala Lys Thr Leu Ala Ser Lys
            100                 105                 110

Val Gln Val Ala Val Pro Ala Asp Thr Arg Ile Val Ser Ile Ser Val
        115                 120                 125

Lys Asp Lys Gln Pro Glu Glu Ala Ser Arg Ile Ala Asn Ser Leu Arg
130                 135                 140

Glu Val Ala Ala Glu Lys Ile Val Ala Val Thr Arg Val Ser Asp Val
145                 150                 155                 160

Thr Thr Leu Glu Glu Ala Arg Pro Ala Thr Thr Pro Ser Ser Pro Asn
                165                 170                 175

Val Arg Arg Asn Ser Leu Phe Gly Phe Leu Gly Gly Ala Val Val Thr
            180                 185                 190

Val Ile Ala Val Leu Leu Ile Glu Leu Leu Asp Thr Arg Val Lys Arg
        195                 200                 205

Pro Glu Asp Val Glu Asp Val Leu Lys Ile Pro Leu Leu Gly Leu Val
210                 215                 220

Pro Asp Phe Asp Lys Ile Lys
225                 230

<210> SEQ ID NO 44
<211> LENGTH: 229
<212> TYPE: PRT
<213> ORGANISM: Streptococcus pneumoniae

<400> SEQUENCE: 44

Met Pro Thr Leu Glu Ile Ser Gln Ala Lys Leu Asp Ser Val Lys Lys
1               5                   10                  15

Ala Glu Glu Tyr Tyr Asn Ala Leu Cys Thr Asn Leu Gln Leu Ser Gly
                20                  25                  30

Asp Gly Leu Lys Val Phe Ser Ile Thr Ser Val Lys Ile Gly Glu Gly
            35                  40                  45

Lys Ser Thr Thr Ser Ala Asn Ile Ala Trp Ala Phe Arg Ala Gly
        50                  55                  60
```

```
Tyr Lys Thr Leu Leu Ile Asp Gly Asp Ile Arg Asn Ser Val Met Leu
 65                  70                  75                  80

Gly Val Phe Lys Ala Arg Asn Lys Ile Thr Gly Leu Thr Glu Phe Leu
                 85                  90                  95

Ser Gly Thr Thr Asp Leu Ser Gln Gly Leu Cys Asp Thr Asn Ile Glu
            100                 105                 110

Asn Leu Phe Val Ile Gln Ala Gly Ser Val Ser Pro Asn Pro Thr Ala
        115                 120                 125

Leu Leu Gln Ser Lys Asn Phe Thr Thr Met Leu Glu Thr Leu Arg Lys
    130                 135                 140

Tyr Phe Asp Tyr Ile Ile Val Asp Thr Ala Pro Val Gly Val Val Ile
145                 150                 155                 160

Asp Ala Ala Ile Ile Thr Arg Asn Cys Asp Ala Ser Ile Leu Val Thr
                165                 170                 175

Glu Ala Gly Glu Ile Asn Arg Arg Asp Ile Gln Lys Ala Lys Glu Gln
            180                 185                 190

Leu Glu His Thr Gly Lys Pro Phe Leu Gly Ile Val Leu Asn Lys Phe
        195                 200                 205

Asp Thr Ser Val Asp Lys Tyr Gly Ser Tyr Gly Asn Tyr Gly Asn Tyr
    210                 215                 220

Gly Lys Asn Lys Lys
225

<210> SEQ ID NO 45
<211> LENGTH: 455
<212> TYPE: PRT
<213> ORGANISM: Streptococcus pneumoniae

<400> SEQUENCE: 45

Met Asn Glu Lys Ile Leu Arg Ser Ser Leu Ala Ile Ile Gln Ser Phe
  1               5                  10                  15

Leu Val Ile Leu Leu Thr Tyr Leu Leu Ser Ala Val Arg Glu Thr Glu
                 20                  25                  30

Ile Val Ser Thr Thr Ala Ile Ala Leu Cys Ile Leu His Tyr Phe Val
             35                  40                  45

Phe Tyr Ile Ser Asp Tyr Gly Gln Asp Phe Phe Lys Arg Arg Tyr Leu
 50                  55                  60

Ile Glu Leu Val Gln Thr Leu Lys Tyr Ile Leu Phe Phe Ala Leu Ala
 65                  70                  75                  80

Ile Gly Ile Ser Asn Phe Phe Leu Glu Asp Arg Phe Ser Ile Ser Arg
                 85                  90                  95

Arg Gly Met Ile Tyr Phe Leu Thr Leu His Ala Leu Leu Val Tyr Val
            100                 105                 110

Leu Asn Leu Phe Ile Lys Trp Tyr Trp Lys Arg Ala Tyr Pro Asn Phe
        115                 120                 125

Lys Gly Ser Lys Lys Ile Leu Leu Leu Thr Ala Thr Ser Arg Val Glu
    130                 135                 140

Lys Val Leu Asp Arg Leu Ile Glu Ser Asn Glu Val Val Gly Lys Leu
145                 150                 155                 160

Val Ala Val Ser Val Leu Asp Lys Pro Asp Phe Gln His Asp Cys Leu
                165                 170                 175

Lys Val Val Ala Glu Gly Gly Ile Val Asn Phe Ala Thr His Glu Val
            180                 185                 190

Val Asp Glu Val Phe Ile Asn Leu Pro Ser Glu Lys Tyr Asn Ile Gly
        195                 200                 205
```

```
Glu Leu Val Ser Gln Phe Glu Thr Met Gly Ile Asp Val Ile Val Asn
            210                 215                 220
Leu Asn Ala Phe Asp Arg Ser Leu Ala Arg Asn Lys Gln Ile Arg Glu
225                 230                 235                 240
Met Ala Gly Leu Asn Val Val Thr Phe Ser Thr Thr Phe Tyr Lys Thr
                245                 250                 255
Ser His Val Ile Ala Lys Arg Ile Ile Asp Ile Val Gly Ala Leu Val
            260                 265                 270
Gly Leu Ile Leu Cys Gly Leu Val Ser Ile Val Leu Val Pro Leu Ile
        275                 280                 285
Arg Lys Asp Gly Gly Ser Ala Ile Phe Ala Gln Thr Arg Ile Gly Lys
    290                 295                 300
Asn Gly Arg Gln Phe Thr Phe Tyr Lys Phe Arg Ser Met Cys Val Asp
305                 310                 315                 320
Ala Glu Ala Lys Lys Arg Glu Leu Met Glu Gln Asn Thr Met Gln Gly
                325                 330                 335
Gly Met Phe Lys Val Asp Asp Pro Arg Ile Thr Lys Ile Gly Cys
            340                 345                 350
Phe Ile Arg Lys Thr Ser Leu Asp Glu Leu Pro Gln Phe Tyr Asn Val
        355                 360                 365
Leu Lys Gly Asp Met Ser Leu Val Gly Thr Arg Pro Pro Thr Val Asp
370                 375                 380
Glu Tyr Glu His Tyr Thr Pro Glu Gln Lys Arg Arg Leu Ser Phe Lys
385                 390                 395                 400
Pro Gly Ile Thr Gly Leu Trp Gln Val Ser Gly Arg Ser Glu Ile Lys
                405                 410                 415
Asn Phe Asp Glu Val Val Lys Leu Asp Val Ala Tyr Ile Asp Gly Trp
            420                 425                 430
Thr Ile Trp Lys Asp Ile Glu Ile Leu Leu Lys Thr Val Lys Val Val
        435                 440                 445
Phe Met Arg Asp Gly Ala Lys
    450                 455

<210> SEQ ID NO 46
<211> LENGTH: 392
<212> TYPE: PRT
<213> ORGANISM: Streptococcus pneumoniae

<400> SEQUENCE: 46

Met Lys Lys Ser Val Tyr Ile Ile Gly Ser Lys Gly Ile Pro Ala Lys
1               5                   10                  15
Tyr Gly Gly Phe Glu Thr Phe Val Glu Lys Leu Thr Ala Phe Gln Gln
                20                  25                  30
Asp Lys Ala Ile Gln Tyr Tyr Val Ala Cys Met Arg Glu Asn Ser Ala
            35                  40                  45
Lys Ser Gly Thr Thr Glu Asp Val Phe Glu His Asn Gly Ala Ile Cys
        50                  55                  60
Tyr Asn Val Asp Val Pro Asn Phe Gly Pro Ala Arg Ala Ile Ala Tyr
65                  70                  75                  80
Asp Ile Ala Ala Ile Asn Arg Ala Ile Glu Ile Ala Lys Glu Asn Lys
                85                  90                  95
Asp Glu Asp Pro Ile Phe Tyr Ile Leu Ala Cys Arg Ile Gly Pro Phe
            100                 105                 110
Ile His Gly Ile Lys Lys Lys Ile Gln Glu Ile Gly Gly Thr Leu Leu
        115                 120                 125
```

Val Asn Pro Asp Gly His Glu Trp Leu Arg Ala Lys Trp Ser Ala Pro
        130                 135                 140

Val Arg Arg Tyr Trp Lys Ile Ser Glu Gly Leu Met Val Lys His Ala
145                 150                 155                 160

Asp Leu Leu Val Cys Asp Ser Lys Asn Ile Glu Lys Tyr Ile Gln Glu
                165                 170                 175

Asp Tyr Lys Gln Tyr Gln Pro Lys Thr Thr Tyr Ile Ala Tyr Gly Thr
            180                 185                 190

Asp Thr Thr Arg Ser Val Leu Lys Ser Ser Asp Glu Lys Val Arg Ser
        195                 200                 205

Trp Phe Lys Glu Lys Asn Val Ser Glu Asn Tyr Tyr Leu Val Val
210                 215                 220

Gly Arg Phe Val Pro Glu Asn Asn Tyr Glu Ser Met Ile Arg Gly Phe
225                 230                 235                 240

Leu Ala Ser Asn Ser Lys Lys Asp Phe Val Leu Ile Thr Asn Val Glu
                245                 250                 255

Gln Asn Lys Phe Tyr Asn Gln Leu Leu Ala Lys Thr Gly Phe Asp Lys
            260                 265                 270

Asp Pro Arg Val Lys Phe Val Gly Thr Val Tyr Glu Gln Glu Leu Leu
        275                 280                 285

Lys Tyr Ile Arg Glu Asn Ala Phe Ala Tyr Phe His Gly His Glu Val
290                 295                 300

Gly Gly Thr Asn Pro Ser Leu Leu Glu Ala Leu Ala Ser Thr Lys Leu
305                 310                 315                 320

Asn Leu Leu Leu Asp Val Gly Phe Asn Arg Glu Val Ala Glu Asp Gly
                325                 330                 335

Ala Ile Tyr Trp Lys Lys Asp Asn Leu His Glu Ile Ile Glu Thr Ser
            340                 345                 350

Glu Gln Lys Thr Gln Lys Glu Ile Asp Glu Lys Asp Ile Leu Ser Ile
        355                 360                 365

Lys Gln Val Thr Glu Arg Phe Ser Trp Glu Leu Ile Val Asn Glu Tyr
370                 375                 380

Glu Lys Leu Phe Leu Cys Glu Lys
385                 390

<210> SEQ ID NO 47
<211> LENGTH: 397
<212> TYPE: PRT
<213> ORGANISM: Streptococcus pneumoniae

<400> SEQUENCE: 47

Met Thr Ile Lys Ile Asn Asn Leu Phe Phe Val Cys Leu Ser Phe Phe
1               5                   10                  15

Gly Ile Val Leu Ser Ser Ser Gln Val Ile Val Asn Leu Gly Leu Ser
                20                  25                  30

Ser Ile Ile Gln Tyr Ile Ser Tyr Phe Met Leu Met Leu Cys Val Phe
            35                  40                  45

Leu Thr Leu Ile Lys Asn Thr Leu Asn Val Phe Ala Asn Arg Ile Ile
        50                  55                  60

Tyr Phe Leu Ile Ile Ser Phe Leu Phe Ile Ile Gly Ile Asn Leu Gln
65                  70                  75                  80

Asn Leu Pro Leu Ser Arg Lys Ile Tyr Leu Ser Phe Ser Met Leu Ile
                85                  90                  95

Ile Ser Ser Leu Ser Thr Leu Pro Ile Lys Leu Ile Asn Asn Leu Ser
            100                 105                 110

```
Asp Leu Arg Arg Ile Ser Tyr Tyr Leu Leu His Ser Ile Phe Leu Ser
            115                 120                 125

Val Phe Leu Gly Leu Val Phe Lys Ile Ser Leu Val Thr Val Ala Val
    130                 135                 140

Glu Gly Ile Gly Phe Ser Tyr Gly Phe Asn Gly Gly Leu Thr His Lys
145                 150                 155                 160

Asn Phe Tyr Ala Ile Thr Ile Leu Val Ser Tyr Ile Leu Leu Tyr Val
                165                 170                 175

Ser Arg Lys Tyr Asp Ala Lys His Gln Ile Asp Ser Phe Val Leu Trp
            180                 185                 190

Leu Asp Leu Phe Leu Leu Leu Ile Ser Asn Thr Arg Thr Val Tyr Ile
    195                 200                 205

Ile Leu Val Val Phe Trp Ile Ile Asn Arg Asn Phe Ile Asn Asn
210                 215                 220

Ile Lys Lys Glu His Arg Leu Val Val Thr Ala Thr Ile Val Ile
225                 230                 235                 240

Ser Leu Leu Ala Leu Thr Phe Phe Lys His Ile Ile Asn Asn Ser
                245                 250                 255

Glu Ser Tyr Ser His Arg Val Leu Gly Val Val Asn Phe Phe Lys Tyr
            260                 265                 270

Tyr Glu Ser Asp Arg Phe His Leu Phe Phe Gly Asp Ala Glu Leu Ala
    275                 280                 285

Phe Gly Asn Thr Thr Lys Gly Tyr Gly His Asn Ile Arg Ser Val Leu
    290                 295                 300

Gly Trp Asp Gly Thr Val Glu Met Pro Leu Leu Ser Val Met Ile Lys
305                 310                 315                 320

Asn Gly Tyr Val Gly Leu Val Gly Tyr Ile Ile Val Leu Phe Lys Phe
                325                 330                 335

Ile Ser Ser Ile Ile Ser Val Lys Asn Ser Thr Lys Lys Asn Ile Gly
            340                 345                 350

Leu Ser Ile Phe Ile Pro Leu Leu Ser Ala Thr Val Glu Asn Tyr
    355                 360                 365

Ile Val Asn Ile Ser Phe Val Phe Met Pro Val Cys Phe Cys Ile Leu
370                 375                 380

Cys Ser Ile Lys Asn Ile Lys Leu Val Asn Asn Arg Lys
385                 390                 395

<210> SEQ ID NO 48
<211> LENGTH: 323
<212> TYPE: PRT
<213> ORGANISM: Streptococcus pneumoniae

<400> SEQUENCE: 48

Met Glu Lys Leu Val Ser Ile Ile Leu Pro Val Tyr Asn Val Glu Gln
1               5                   10                  15

Tyr Ile Lys Asn Cys Leu Glu Ser Ile Gln Gln Gln Thr Tyr Ser Asn
                20                  25                  30

Leu Glu Val Ile Ile Val Asn Asp Gly Ser Thr Asp Lys Ser Val Glu
        35                  40                  45

Tyr Cys Glu Gln Ile Cys Lys Ile Asp Ser Arg Phe Ser Ile Thr His
    50                  55                  60

Lys Glu Asn Gly Gly Leu Ser Asp Ala Arg Asn Val Gly Ile Asp Lys
65                  70                  75                  80

Ser Lys Gly Asp Tyr Leu Ile Phe Val Asp Ser Asp Asp Phe Val Ser
                85                  90                  95
```

```
Gln Asp Met Val Ser Tyr Leu Val Ser Cys Met Glu Asn Asn Glu Ala
                100                 105                 110
Asp Ile Ala Ile Cys Asp Pro Val His Tyr Tyr Ser Asp Arg Gln Asn
            115                 120                 125
Asn Asp Leu Asn Ile Phe Ser Pro Ala Ser Asn Val Lys Val Tyr Glu
        130                 135                 140
Thr Thr Glu Ala Leu Cys Glu Met Phe Tyr Gln Lys Ser Phe Leu Val
145                 150                 155                 160
Ser Ala Trp Ala Lys Ile Phe Lys Arg Glu Leu Phe Asp Asp Ile Arg
                165                 170                 175
Phe Pro Val Gly Lys Leu Phe Glu Asp Ser Ala Ile Met Tyr Leu Leu
            180                 185                 190
Phe Glu Lys Cys Glu Thr Ile Ala Tyr Ser Asp Ala Glu Leu Tyr Ala
        195                 200                 205
Tyr Val His Arg Asp Asn Ser Ile Thr Thr Lys Lys Phe Ser Asp Arg
210                 215                 220
Asp Leu Asp Ile Leu Glu Ile Thr Asn Thr Ile Ile Asn His Tyr Gly
225                 230                 235                 240
Asp Asn Leu Arg Val Tyr Thr Ala Ala Val Ser Tyr Lys Val Ser Ala
            245                 250                 255
Cys Phe Arg Ile Leu Leu Asn Ser Pro Ser Gly Lys Tyr Lys Lys
        260                 265                 270
Val Gln Lys Glu Cys Leu Ser Tyr Ile Leu Gln Asn Trp Arg Asn Ile
            275                 280                 285
Leu Phe Asn Asn Val Arg Leu Lys Asn Lys Leu Ala Leu Ile Ser
        290                 295                 300
Ile Thr Ile Phe Asn Pro Phe Val Lys Phe Ile Tyr Ser Lys Val Asn
305                 310                 315                 320
Arg Trp Glu

<210> SEQ ID NO 49
<211> LENGTH: 410
<212> TYPE: PRT
<213> ORGANISM: Streptococcus pneumoniae

<400> SEQUENCE: 49

Met Asn Lys Tyr Glu Glu Arg Tyr Gln Glu Asn Leu Ser Lys Asn Asp
1               5                   10                  15
Phe Tyr Lys Leu Ile Asn Lys Ser Tyr Leu Ser Asp Lys Glu Leu Gln
                20                  25                  30
Val Gln Gln Val Lys Ala Gly Ile Val Leu Pro Pro Lys Ala Phe Glu
            35                  40                  45
Thr Lys Leu Ser Asn Lys Leu Gly Leu Gln Lys Ser Leu His Gly Lys
        50                  55                  60
Gly Gly Val Val Asp Ser Asn Gly Asn Tyr Ile Glu Leu Ser Ala Gln
65                  70                  75                  80
Lys Ala Val Gly Met Arg Asn Arg Val Tyr Gly Pro Tyr Lys Ile Asn
                85                  90                  95
Tyr Asp Asn Leu Pro Ile Arg Asn Glu Lys Val Ile Tyr Leu Asn Tyr
            100                 105                 110
Phe Ile Lys Gln Trp Gly His Phe Leu Leu Asp Val Val Gly Arg Leu
        115                 120                 125
Trp Tyr Pro Leu Leu Gln Asp Asn Asp Thr Lys Leu Val Tyr Thr Cys
    130                 135                 140
```

```
Tyr Ala Gly Thr Glu Thr Lys Ile Glu Gly Asn Tyr Leu Glu Phe Leu
145                 150                 155                 160

Lys Leu Leu Gly Ile Asp Gln Ser Arg Leu Ile Met Ile Asn Cys Pro
            165                 170                 175

Thr Gln Phe Ser Glu Val Ile Pro Glu Ser Ser Ile Leu Pro Gly
        180                 185                 190

Gly Tyr Tyr Thr Lys Glu Tyr Lys Gln Leu Phe Ser Ser Val Val Glu
            195                 200                 205

Asn Ile Lys Leu Asp Lys Tyr Asp Val Asn Ala Lys Met Ile Tyr Cys
        210                 215                 220

Ser Arg Ser Lys Leu Gly Ile Ala Lys Ser Lys Glu Phe Gly Glu Asp
225                 230                 235                 240

Gly Ile Glu Gly Ile Phe Lys Gln Asn Gly Tyr Thr Ser Val Tyr Met
                245                 250                 255

Glu Thr Met Ser Leu Glu Glu Gln Ile Lys Thr Leu Leu Ser Ala Lys
            260                 265                 270

Thr Ile Val Leu Thr Ser Gly Ser Leu Ala His Asn Leu Leu Phe Val
        275                 280                 285

Asn Lys Asp Ile Asp Val Phe Ile Leu Asn Lys Thr Tyr Arg Val Asn
290                 295                 300

Leu His Gln Phe Leu Ile Asn Glu Ile Ser Asp Ala Thr Val Arg Phe
305                 310                 315                 320

Val Asp Ile Tyr Arg Ser Pro Leu Pro Ile Leu Tyr Gly Tyr Gly Pro
                325                 330                 335

Phe Leu Met Asp Leu Thr Lys Pro Leu Ala Asn Phe Leu Asp Asp Asn
            340                 345                 350

Glu Phe Val Tyr Glu Lys Gly Thr Val Leu Ser Lys Lys Asp Tyr Phe
        355                 360                 365

Lys Tyr Tyr Leu Lys Trp Leu Trp Ser Tyr Arg Phe Phe Leu Phe Arg
    370                 375                 380

Leu Asn Gly Ile Lys Glu Gly Asn Ser Glu Phe Glu Lys Ser Phe Lys
385                 390                 395                 400

Ile Ile Arg Arg Tyr Tyr Lys Thr Gly Arg
                405                 410

<210> SEQ ID NO 50
<211> LENGTH: 461
<212> TYPE: PRT
<213> ORGANISM: Streptococcus pneumoniae

<400> SEQUENCE: 50

Met Ser Lys Tyr Lys Glu Leu Ala Lys Asn Thr Gly Ile Phe Ala Leu
1               5                   10                  15

Ala Asn Phe Ser Ser Lys Ile Leu Ile Phe Leu Leu Val Pro Ile Tyr
            20                  25                  30

Thr Arg Val Leu Thr Thr Thr Glu Tyr Gly Phe Tyr Asp Leu Val Tyr
        35                  40                  45

Thr Thr Ile Gln Leu Phe Val Pro Ile Leu Thr Leu Asn Ile Ser Glu
    50                  55                  60

Ala Val Met Arg Phe Leu Met Lys Asp Gly Val Ser Lys Ser Val
65                  70                  75                  80

Phe Ser Ile Ala Val Leu Asp Ile Phe Ile Gly Ser Ile Ala Phe Ala
            85                  90                  95

Leu Leu Leu Leu Val Asn Asn Leu Phe Ser Leu Ser Asp Leu Ile Ser
            100                 105                 110
```

Gln Tyr Ser Ile Tyr Ile Phe Val Ile Phe Val Phe Tyr Thr Leu Asn
            115                 120                 125

Asn Phe Leu Ile Gln Phe Ser Lys Gly Ile Asp Lys Ile Gly Val Thr
130                 135                 140

Ala Ile Ser Gly Val Ile Ser Thr Ala Val Met Leu Ala Met Asn Val
145                 150                 155                 160

Ile Leu Leu Val Val Phe Asp Trp Gly Leu Leu Gly Phe Phe Ile Ala
                165                 170                 175

Asn Val Cys Gly Tyr Val Ile Pro Cys Ile Tyr Ile Val Ser Arg Leu
            180                 185                 190

Arg Leu Trp Glu Leu Phe Glu Ile Lys Ile Asp Lys Lys Leu Gln Trp
        195                 200                 205

Glu Met Val Tyr Tyr Ala Leu Pro Leu Val Leu Asn Ile Leu Ser Trp
210                 215                 220

Trp Val Asn Asn Thr Ser Asp Arg Tyr Ile Val Thr Ala Ile Val Gly
225                 230                 235                 240

Ile Gln Ala Ser Ala Ile Ile Ser Val Ala Tyr Lys Ile Pro Gln Ile
                245                 250                 255

Leu Ser Thr Ile Ser Ala Ile Phe Ile Gln Ser Trp Gln Ile Ser Ala
            260                 265                 270

Ile Lys Ile Gln Glu Asp Lys Ser Asp Thr Thr Phe Val Ser Asn Met
        275                 280                 285

Leu Leu Tyr Tyr Asn Ala Leu Leu Ile Ile Ala Ser Gly Ile Ile
290                 295                 300

Leu Phe Val Lys Pro Ile Ser Asn Ile Leu Phe Gly Ile Ser Phe Tyr
305                 310                 315                 320

Ser Ala Trp Glu Leu Val Pro Phe Leu Ile Ile Ser Ser Leu Phe Asn
                325                 330                 335

Ala Ile Ser Gly Cys Ile Gly Ala Ile Met Gly Ala Lys Met Asp Thr
            340                 345                 350

His Asn Ile Ala Lys Ser Ala Leu Val Gly Met Ile Ala Asn Ile Ile
        355                 360                 365

Leu Asn Ile Val Leu Thr Phe Leu Met Gly Pro Gln Gly Ile Thr Ile
370                 375                 380

Ser Thr Leu Ile Ala Ser Phe Leu Ile Phe Tyr Met Arg Lys Asp Ser
385                 390                 395                 400

Val Lys Glu Ile Asn Ser Glu Thr Tyr Arg Ala Ile Tyr Leu Ser Trp
                405                 410                 415

Ile Leu Leu Val Val Glu Ala Cys Leu Leu Ile Tyr Met Asp Phe Ile
            420                 425                 430

Ile Gly Ala Leu Ile Ala Met Val Ile Asn Leu Phe Leu Leu Lys Asp
        435                 440                 445

Val Ile Lys Pro Leu Tyr Leu Lys Ile Phe Lys Arg Asn
450                 455                 460

<210> SEQ ID NO 51
<211> LENGTH: 382
<212> TYPE: PRT
<213> ORGANISM: Streptococcus pneumoniae

<400> SEQUENCE: 51

Met Ile Val Leu Gln Tyr Phe Lys Ile Leu Ala Arg Phe Val Phe Met
1               5                   10                  15

Phe Leu Ile Ser Ala Val Leu Leu Pro Phe Lys Ile Lys Pro Asn Lys
                20                  25                  30

```
Ile Val Phe Ile Asn Phe Asn Gly Lys Gly Tyr Gly Asp Asn Pro Lys
         35                  40                  45

Ser Ile Cys Glu Tyr Leu Arg Thr Thr Tyr Pro Asp Leu Asp Leu Val
 50                  55                  60

Trp Leu Ala Arg Asp Asn Glu Gly Phe Pro Asp Gly Val Arg Val Val
 65                  70                  75                  80

Lys Tyr Gly Thr Phe Gln Ala Phe Tyr Glu Gln Ala Ser Ser Lys Val
                 85                  90                  95

Trp Val Tyr Asn Val Arg Ala Phe Ala Arg Ile Leu Lys Lys Arg Gly
                100                 105                 110

Gln Ile Tyr Ile Gln Thr Trp His Gly Ala Ser Ser Phe Lys Leu Ile
            115                 120                 125

Glu Lys Gln Ala Asp Leu Pro Ile Asn Tyr Val Leu Glu Ala Lys Tyr
130                 135                 140

Asp Ala Arg Val Thr Asp Ile Met Ile Ser Asp Ser Arg Lys Gln Thr
145                 150                 155                 160

Glu Glu Phe Gln Lys Tyr Phe Trp Tyr Ser Gly Glu Ile Phe Glu Val
                165                 170                 175

Gly Met Pro Arg Asn Asp Ala Leu Phe His Tyr Lys Glu Asp Tyr Asp
                180                 185                 190

Lys Leu Asn Asn Ile Arg Lys Glu Leu Ser Ile His Ser Asp Asp Tyr
            195                 200                 205

Val Ile Leu Tyr Ala Pro Thr Phe Arg Asp Asp Gly Asp Ala Ser Tyr
210                 215                 220

Leu Asp Ile Asn Phe Glu Arg Leu Leu Gln Cys Val Glu His Gly Ile
225                 230                 235                 240

Lys Lys Lys Cys Lys Phe Leu Ile Arg Leu His Pro Asn His Ser His
                245                 250                 255

Leu Cys Asn Asn Ile Ser Phe Asn Lys Asn Ile Ile Asn Ala Thr Phe
            260                 265                 270

Tyr Ser Asp Met Gln Glu Leu Thr Leu Leu Ala Asp Val Leu Val Thr
275                 280                 285

Asp Tyr Ser Ser Ser Ile Phe Asp Phe Met Leu Leu Asn Lys Pro Tyr
290                 295                 300

Val Arg Tyr Val Asn Asp Leu Glu Lys Tyr Ala Glu Leu Arg Gly Val
305                 310                 315                 320

Ser Asp Thr Tyr Tyr Glu Leu Pro Asp Ser Ile Ile Lys Thr Ala Glu
                325                 330                 335

Glu Leu Tyr Asp Leu Leu Pro Lys Lys Ile Glu Asn Phe Asp Tyr Asp
            340                 345                 350

Ser Ile Lys Lys Tyr Arg Asn Glu Ile Leu Cys Pro Ile Phe Asn Gly
            355                 360                 365

Thr Ala Ser Glu Asn Val Gly Arg Arg Ile Ile Gln Glu Leu
            370                 375                 380

<210> SEQ ID NO 52
<211> LENGTH: 342
<212> TYPE: PRT
<213> ORGANISM: Streptococcus pneumoniae

<400> SEQUENCE: 52

Met Lys Asn Asn Asp Leu Lys Ile Gly Ser Gly Ala Ile His Gln Ile
 1               5                  10                  15

Ser Ala Thr Leu Ser Gln Asn Ser Ile Ser Gly Lys Ile Leu Tyr Cys
                20                  25                  30
```

```
Ala Asp Pro Val Val Asp Leu Tyr Gly Ser Ile Val Arg Ser Gln
         35                  40                  45

Ile Glu Glu Ile Gly Arg Val Lys Glu Ser Cys Asn Tyr Asn Thr
 50                  55                  60

Ile Ala Tyr Ala Met Asn Ile Ala Glu Arg Ala Ile Ala Thr Asp Ile
 65                  70                  75                  80

Asp Cys Ile Val Gly Met Gly Gly Arg Val Leu Asp Val Cys Lys
                 85                  90                  95

Tyr Ala Ser Phe Ile Ser Lys Arg Pro Tyr Leu Ser Ile Pro Thr Thr
                100                 105                 110

Ala Ala Asn Asp Gly Ile Ala Ser Pro Val Ala Val Leu Lys Arg Gln
            115                 120                 125

Asp Asp Arg Pro Lys Ser Leu Gly Ala Ala Ile Pro Ser Met Thr Leu
130                 135                 140

Ile Asp Ile Asp Val Ile Ala Ser Gly Pro Ile Gln Asn Ile Lys Ala
145                 150                 155                 160

Gly Ile Gly Asp Thr Ile Ser Asn Tyr Thr Ala Leu Lys Asp Trp Glu
                165                 170                 175

Leu Ala Val Glu Arg Gly Lys Asp Glu Met His Gly Phe Ala Tyr Leu
            180                 185                 190

Met Ser Gln Asn Ser Leu Asp Ala Leu Met Lys Thr Lys Tyr Asn Ser
        195                 200                 205

Ile Thr Pro Asp Phe Ile Glu Val Leu Val Asn Ser Leu Val Leu Ser
    210                 215                 220

Gly Ile Ala Met Asp Phe Ala Gly Ser Ser Arg Pro Val Ser Gly Ser
225                 230                 235                 240

Glu His Leu Phe Ser His Ala Leu Asp Tyr Tyr Gly Ser Thr Arg Asn
                245                 250                 255

Leu His Gly Ile Gln Val Ala Leu Gly Thr Val Ala Val Leu Lys Leu
            260                 265                 270

Ile Glu Asn Ser Val Asp Thr Val Val Asp Tyr Leu Gln Arg Phe Glu
        275                 280                 285

Val His Ile Asn Pro Lys Leu Leu Gly Ile Asp Glu Glu Leu Phe Ile
    290                 295                 300

Tyr Cys Met Gln His Ala Thr Lys Met Arg Ser Asn Arg Tyr Thr Tyr
305                 310                 315                 320

Leu His Glu Val Asp Leu Ser Thr Asp Arg Leu Lys Gln Ile Tyr Lys
                325                 330                 335

Glu Leu Ile Ser Glu Leu
            340

<210> SEQ ID NO 53
<211> LENGTH: 234
<212> TYPE: PRT
<213> ORGANISM: Streptococcus pneumoniae

<400> SEQUENCE: 53

Met Lys Ala Leu Ile Leu Ala Ala Gly Leu Gly Thr Arg Leu Ala Pro
 1               5                  10                  15

Ile Thr Asn Glu Val Pro Lys Ser Leu Val Pro Val Asn Gly Lys Pro
                20                  25                  30

Ile Leu Met Lys Gln Ile Glu Asn Leu Tyr Gln Asn Asn Ile Thr Asp
            35                  40                  45

Ile Thr Ile Ile Ala Gly Tyr Lys Ser Ser Val Leu Thr Asp Ala Val
50                  55                  60
```

Thr Glu Lys Tyr Pro Glu Ile Asn Ile Ile Asp Asn Val Asp Phe Lys
65                  70                  75                  80

Thr Thr Asn Asn Met Tyr Ser Ala Tyr Leu Gly Lys Ala Ala Met Gly
                85                  90                  95

Asp Ser Asp Phe Leu Met Met Asn Ala Asp Val Phe Tyr Asp Ala Ser
            100                 105                 110

Val Ile Lys Ser Leu Leu Leu His Lys Ala Pro Asn Ala Ile Val Thr
        115                 120                 125

Asp Leu Gly Ile Tyr Ile Glu Glu Ser Met Lys Val Val Glu Lys Asn
130                 135                 140

Gly Arg Leu Val Glu Ile Ser Lys Gln Ile Ser Pro Glu Glu Thr Leu
145                 150                 155                 160

Gly Ala Ser Ile Asp Val Tyr Lys Phe Ser Tyr Glu Ala Gly Ala Arg
                165                 170                 175

Phe Phe Glu Lys Cys Lys Glu Phe Ile Glu Asp Lys Arg Glu Leu Gln
            180                 185                 190

Met Trp Ser Glu Val Ala Leu Asn Ala Ile Leu Ser Glu Val Glu Phe
        195                 200                 205

Val Ala Cys Pro Leu Glu Gly Arg Trp Leu Glu Ile Asp Asn His Glu
210                 215                 220

Asp Leu Val Ala Ala Glu Lys Leu Phe Ala
225                 230

<210> SEQ ID NO 54
<211> LENGTH: 277
<212> TYPE: PRT
<213> ORGANISM: Streptococcus pneumoniae

<400> SEQUENCE: 54

Met Lys Leu Thr Asn Arg Val Asp Tyr Phe Gly Ala Asp Ile Ser Glu
1               5                   10                  15

Leu Gln Asn Lys Lys Leu Phe Leu Phe Asp Met Asp Gly Thr Ile Tyr
            20                  25                  30

Glu Glu Asp Arg Leu Phe Glu Gly Thr Leu Glu Leu Leu Asp Tyr Ile
        35                  40                  45

His Asn Ile Gly Gly Glu Tyr Ile Phe Ile Thr Asn Asn Ser Ser Lys
50                  55                  60

Ser Val Val Asp Tyr Val Glu Val Asn Arg Leu Gly Ile Lys Ala
65                  70                  75                  80

Glu Arg Asp Asn Phe Phe Thr Ser Ala Gln Ala Thr Ile Val Tyr Ile
                85                  90                  95

Lys Glu Asn Tyr Pro Lys Ser Lys Val Tyr Cys Gln Gly Thr Lys Ser
            100                 105                 110

Leu Ile Lys Glu Leu Ser Asp Ala Gly Ile Asp Val Thr Glu Gln Val
        115                 120                 125

Ser Ala Asp Ile Asp Val Val Leu Val Gly Phe Asp Thr Glu Leu Thr
130                 135                 140

Ser Asp Lys Ile Arg Asn Thr Cys Glu Ile Leu Ser Thr Lys Asp Val
145                 150                 155                 160

Pro Phe Ile Ala Thr Asn Pro Asp Ile Arg Cys Pro Val Ser Phe Gly
                165                 170                 175

Phe Ile Pro Asp Cys Gly Ser Ile Cys Asp Met Ile Ser Lys Ser Val
            180                 185                 190

Asp Arg Lys Pro Val Tyr Ile Gly Lys Pro Glu Pro Thr Met Val Asp
        195                 200                 205

```
Ile Val Arg Lys Lys Leu Asn Tyr Ser Leu Phe Glu Thr Val Val Ile
    210                 215                 220
Gly Asp Arg Leu Tyr Thr Asp Ile Met Thr Gly Ile Asn Ala Gly Val
225                 230                 235                 240
Thr Ser Val Cys Val Leu Thr Gly Glu Ala Thr Val Asn Asp Ile Gln
                245                 250                 255
Gln Asp Ser Ile Lys Pro Thr Tyr Thr Phe Lys Asn Val Lys Glu Met
                260                 265                 270
Trp Lys Gly Ile Val
            275

<210> SEQ ID NO 55
<211> LENGTH: 289
<212> TYPE: PRT
<213> ORGANISM: Streptococcus pneumoniae

<400> SEQUENCE: 55

Met Lys Gly Ile Ile Leu Ala Gly Gly Ser Gly Thr Arg Leu Tyr Pro
1               5                   10                  15
Leu Thr Arg Ala Ala Ser Lys Gln Leu Met Pro Val Tyr Asp Lys Pro
                20                  25                  30
Met Ile Tyr Tyr Pro Leu Ser Thr Leu Met Leu Ala Gly Ile Arg Asp
            35                  40                  45
Ile Leu Ile Ile Ser Thr Pro Gln Asp Leu Pro Arg Phe Lys Glu Leu
50                  55                  60
Leu Gln Asp Gly Ser Glu Phe Gly Ile Lys Leu Ser Tyr Ala Glu Gln
65                  70                  75                  80
Pro Ser Pro Asp Gly Leu Ala Gln Ala Phe Ile Ile Gly Glu Glu Phe
                85                  90                  95
Ile Gly Asp Ser Val Ala Leu Ile Leu Gly Asp Asn Ile Tyr His
            100                 105                 110
Gly Pro Gly Leu Ser Thr Met Leu Gln Lys Ala Ala Lys Lys Glu Lys
        115                 120                 125
Gly Ala Thr Val Phe Gly Tyr His Val Lys Asp Pro Glu Arg Phe Gly
130                 135                 140
Val Val Glu Phe Asp Glu Asn Met Asn Ala Ile Ser Ile Glu Glu Lys
145                 150                 155                 160
Pro Glu Tyr Pro Arg Ser Asn Tyr Ala Val Thr Gly Leu Tyr Phe Tyr
                165                 170                 175
Asp Asn Asp Val Val Glu Ile Ala Lys Ser Ile Lys Pro Ser Pro Arg
            180                 185                 190
Gly Glu Leu Glu Ile Thr Asp Val Asn Lys Ala Tyr Leu Asp Arg Gly
        195                 200                 205
Asp Leu Ser Val Glu Leu Met Gly Arg Gly Phe Ala Trp Leu Asp Thr
210                 215                 220
Gly Thr His Glu Ser Leu Leu Glu Ala Ser Gln Tyr Ile Glu Thr Val
225                 230                 235                 240
Gln Arg Met Gln Asn Val Gln Val Ala Asn Leu Glu Glu Ile Ala Tyr
                245                 250                 255
Arg Arg Gly Tyr Ile Ser Arg Glu Asp Val Leu Ala Leu Ala Gln Ser
            260                 265                 270
Leu Lys Lys Asn Glu Tyr Gly Gln Tyr Leu Leu Arg Leu Ile Gly Glu
        275                 280                 285
Ala
```

<210> SEQ ID NO 56
<211> LENGTH: 197
<212> TYPE: PRT
<213> ORGANISM: Streptococcus pneumoniae

<400> SEQUENCE: 56

| Met | Thr | Asp | Asn | Phe | Phe | Gly | Lys | Thr | Leu | Ala | Ala | Arg | Lys | Val | Glu |
|---|---|---|---|---|---|---|---|---|---|---|---|---|---|---|---|
| 1 | | | | 5 | | | | | 10 | | | | | 15 | |

| Ala | Ile | Pro | Gly | Met | Leu | Glu | Phe | Asp | Ile | Pro | Val | His | Gly | Asp | Asn |
| | | | 20 | | | | | 25 | | | | | 30 | | |

| Arg | Gly | Trp | Phe | Lys | Glu | Asn | Phe | Gln | Lys | Glu | Lys | Met | Leu | Pro | Leu |
| | | | 35 | | | | | 40 | | | | | 45 | | |

| Gly | Phe | Pro | Glu | Ser | Phe | Phe | Ala | Glu | Gly | Lys | Leu | Gln | Asn | Asn | Val |
| | 50 | | | | | 55 | | | | | 60 | | | | |

| Ser | Phe | Ser | Arg | Lys | Asn | Val | Leu | Arg | Gly | Leu | His | Ala | Glu | Pro | Trp |
| 65 | | | | | 70 | | | | | 75 | | | | | 80 |

| Asp | Lys | Tyr | Ile | Ser | Val | Ala | Asp | Gly | Gly | Lys | Val | Leu | Gly | Ser | Trp |
| | | | | 85 | | | | | 90 | | | | | 95 | |

| Val | Asp | Leu | Arg | Glu | Gly | Glu | Thr | Phe | Gly | Asn | Thr | Tyr | Gln | Thr | Val |
| | | | 100 | | | | | 105 | | | | | 110 | | |

| Ile | Asp | Ala | Ser | Lys | Gly | Ile | Phe | Val | Pro | Arg | Gly | Val | Ala | Asn | Gly |
| | | | | 115 | | | | | 120 | | | | | 125 | |

| Phe | Gln | Val | Leu | Ser | Asp | Thr | Val | Ser | Tyr | Ser | Tyr | Leu | Val | Asn | Asp |
| | 130 | | | | | 135 | | | | | 140 | | | | |

| Tyr | Trp | Ala | Leu | Glu | Leu | Lys | Pro | Lys | Tyr | Ala | Phe | Val | Asn | Tyr | Ala |
| 145 | | | | | 150 | | | | | 155 | | | | | 160 |

| Asp | Pro | Ser | Leu | Gly | Ile | Glu | Trp | Glu | Asn | Ile | Ala | Glu | Ala | Glu | Val |
| | | | | 165 | | | | | 170 | | | | | 175 | |

| Ser | Glu | Ala | Asp | Lys | Asn | His | Pro | Leu | Leu | Lys | Asp | Val | Lys | Pro | Leu |
| | | | 180 | | | | | 185 | | | | | 190 | | |

| Lys | Lys | Glu | Asp | Leu |
|---|---|---|---|---|
| | | | | 195 |

<210> SEQ ID NO 57
<211> LENGTH: 349
<212> TYPE: PRT
<213> ORGANISM: Streptococcus pneumoniae

<400> SEQUENCE: 57

| Met | Thr | Glu | Tyr | Lys | Asn | Ile | Ile | Val | Thr | Gly | Gly | Ala | Gly | Phe | Ile |
|---|---|---|---|---|---|---|---|---|---|---|---|---|---|---|---|
| 1 | | | | 5 | | | | | 10 | | | | | 15 | |

| Gly | Ser | Asn | Phe | Val | His | Tyr | Val | Tyr | Glu | Asn | Phe | Pro | Asp | Val | His |
| | | | 20 | | | | | 25 | | | | | 30 | | |

| Val | Thr | Val | Leu | Asp | Lys | Leu | Thr | Tyr | Ala | Gly | Asn | Arg | Ala | Asn | Ile |
| | | | 35 | | | | | 40 | | | | | 45 | | |

| Glu | Glu | Ile | Leu | Gly | Asn | Arg | Val | Glu | Leu | Val | Val | Gly | Asp | Ile | Ala |
| | 50 | | | | | 55 | | | | | 60 | | | | |

| Asp | Ala | Glu | Leu | Val | Asp | Lys | Leu | Ala | Ala | Gln | Ala | Asp | Ala | Ile | Val |
| 65 | | | | | 70 | | | | | 75 | | | | | 80 |

| His | Tyr | Ala | Ala | Glu | Ser | His | Asn | Asp | Asn | Ser | Leu | Asn | Asp | Pro | Ser |
| | | | | 85 | | | | | 90 | | | | | 95 | |

| Pro | Phe | Ile | His | Thr | Asn | Phe | Ile | Gly | Thr | Tyr | Thr | Leu | Leu | Glu | Ala |
| | | | 100 | | | | | 105 | | | | | 110 | | |

| Ala | Arg | Lys | Tyr | Asp | Ile | Arg | Phe | His | His | Val | Ser | Thr | Asp | Glu | Val |
| | | | | 115 | | | | | 120 | | | | | 125 | |

```
Tyr Gly Asp Leu Pro Leu Arg Glu Asp Leu Pro His Gly Glu Gly
            130                 135                 140

Pro Gly Glu Lys Phe Thr Ala Glu Thr Lys Tyr Asn Pro Ser Ser Pro
145                 150                 155                 160

Tyr Ser Ser Thr Lys Ala Ala Ser Asp Leu Ile Val Lys Ala Trp Val
                165                 170                 175

Arg Ser Phe Gly Val Lys Ala Thr Ile Ser Asn Cys Ser Asn Asn Tyr
            180                 185                 190

Gly Pro Tyr Gln His Ile Glu Lys Phe Ile Pro Arg Gln Ile Thr Asn
            195                 200                 205

Ile Leu Ser Gly Ile Lys Pro Lys Leu Tyr Gly Glu Gly Lys Asn Val
210                 215                 220

Arg Asp Trp Ile His Thr Asn Asp His Ser Ser Gly Val Trp Thr Ile
225                 230                 235                 240

Leu Thr Lys Gly Gln Ile Gly Glu Thr Tyr Leu Ile Gly Ala Asp Gly
                245                 250                 255

Glu Lys Asn Asn Lys Glu Val Leu Glu Leu Ile Leu Lys Glu Met Gly
            260                 265                 270

Gln Ala Val Asp Ala Tyr Asp His Val Thr Asp Arg Ala Gly His Asp
            275                 280                 285

Leu Arg Tyr Ala Ile Asp Ala Ser Lys Leu Arg Asp Glu Leu Gly Trp
290                 295                 300

Lys Pro Glu Phe Thr Asn Phe Glu Ala Gly Leu Lys Ala Thr Ile Lys
305                 310                 315                 320

Trp Tyr Thr Asp Asn Gln Glu Trp Trp Lys Ala Glu Lys Glu Ala Val
                325                 330                 335

Glu Ala Asn Tyr Ala Lys Thr Gln Glu Ile Ile Thr Val
            340                 345

<210> SEQ ID NO 58
<211> LENGTH: 283
<212> TYPE: PRT
<213> ORGANISM: Streptococcus pneumoniae

<400> SEQUENCE: 58

Met Ile Leu Ile Thr Gly Ala Asn Gly Gln Leu Gly Thr Glu Leu Arg
1               5                   10                  15

Tyr Leu Leu Asp Glu Arg Asn Glu Glu Tyr Val Ala Val Asp Val Ala
                20                  25                  30

Glu Met Asp Ile Thr Asp Ala Glu Met Val Glu Lys Val Phe Glu Glu
            35                  40                  45

Val Lys Pro Thr Leu Val Tyr His Cys Ala Ala Tyr Thr Ala Val Asp
50                  55                  60

Ala Ala Glu Asp Glu Gly Arg Glu Leu Asp Phe Ala Ile Asn Val Thr
65                  70                  75                  80

Gly Thr Lys Asn Val Ala Lys Ala Ser Glu Lys His Gly Ala Thr Leu
                85                  90                  95

Val Tyr Ile Ser Thr Asp Tyr Val Phe Asp Gly Lys Lys Pro Val Gly
            100                 105                 110

Gln Glu Trp Glu Val Asp Asp Arg Pro Asp Pro Gln Thr Glu Tyr Gly
            115                 120                 125

Arg Thr Lys Arg Met Gly Glu Glu Leu Val Glu Lys His Val Ser Asn
            130                 135                 140

Phe Tyr Ile Ile Arg Thr Ala Trp Val Phe Gly Asn Tyr Gly Lys Asn
145                 150                 155                 160
```

```
Phe Val Phe Thr Met Gln Asn Leu Ala Lys Thr His Lys Thr Leu Thr
            165                 170                 175

Val Val Asn Asp Gln Tyr Gly Arg Pro Thr Trp Thr Arg Thr Leu Ala
        180                 185                 190

Glu Phe Met Thr Tyr Leu Ala Glu Asn Arg Lys Glu Phe Gly Tyr Tyr
        195                 200                 205

His Leu Ser Asn Asp Ala Thr Glu Asp Thr Thr Trp Tyr Asp Phe Ala
        210                 215                 220

Val Glu Ile Leu Lys Gly Thr Asp Val Glu Lys Pro Val Asp Ser
225                 230                 235                 240

Ser Gln Phe Pro Ala Lys Ala Lys Arg Pro Leu Asn Ser Thr Met Ser
            245                 250                 255

Leu Ala Lys Ala Lys Ala Thr Gly Phe Val Ile Pro Thr Trp Gln Asp
            260                 265                 270

Ala Leu Gln Glu Phe Tyr Lys Gln Glu Val Arg
            275                 280
```

<210> SEQ ID NO 59
<211> LENGTH: 358
<212> TYPE: PRT
<213> ORGANISM: E. coli

<400> SEQUENCE: 59

```
Met Glu Glu Asn Asn Met Lys Thr Val Ala Val Val Gly Thr Val Gly
1               5                   10                  15

Val Pro Ala Cys Tyr Gly Gly Phe Glu Ser Leu Val Gln Asn Leu Ile
            20                  25                  30

Asp Tyr Gln Ser Asp Gly Ile Gln Tyr Gln Ile Phe Cys Ser Ser Lys
        35                  40                  45

Lys Tyr Asp Lys Lys Phe Lys Asn Tyr Lys Asn Ala Glu Leu Ile Tyr
    50                  55                  60

Leu Pro Ile Asn Ala Asn Gly Val Ser Ser Ile Ile Tyr Asp Ile Met
65                  70                  75                  80

Cys Leu Ile Ile Cys Leu Phe Lys Arg Pro Asp Val Val Leu Ile Leu
                85                  90                  95

Gly Val Ser Gly Cys Leu Phe Leu Pro Ile Tyr Lys Leu Phe Ser Lys
            100                 105                 110

Ser Lys Ile Ile Val Asn Ile Asp Gly Leu Glu Trp Arg Arg Asn Lys
        115                 120                 125

Trp Gly Thr Phe Ala Lys Lys Phe Leu Lys Ile Ser Glu Ala Ile Ser
130                 135                 140

Ile Arg Ile Ala Asp Ile Ile Ser Asp Asn Gln Ala Ile Ala Asp
145                 150                 155                 160

Tyr Val Glu Asn Lys Tyr Lys Lys Ser Val Val Ile Ala Tyr Gly
            165                 170                 175

Gly Asp His Ala Thr Asn Leu Ser Thr Pro Ile Asp Asn Asp Gln Lys
        180                 185                 190

Lys Glu Gly Tyr Tyr Leu Gly Leu Cys Arg Ile Glu Pro Glu Asn Asn
    195                 200                 205

Ile Glu Met Ile Leu Asn Ala Phe Ile Asn Thr Asp Lys Lys Ile Lys
    210                 215                 220

Phe Met Gly Asn Trp Asp Asn Ser Glu Tyr Gly Arg Gln Leu Lys Lys
225                 230                 235                 240

Tyr Tyr Ser Asn Tyr Pro Asn Ile Thr Leu Leu Glu Pro Asn Tyr Asn
                245                 250                 255
```

```
Ile Glu Glu Leu Tyr Lys Leu Arg Lys Asn Cys Leu Ala Tyr Ile His
            260                 265                 270

Gly His Ser Ala Gly Thr Asn Pro Ser Leu Val Glu Ala Met His
            275                 280                 285

Phe Asn Ile Pro Ile Phe Ala Phe Asp Cys Asp Phe Asn Arg Tyr Thr
            290                 295                 300

Thr Asn Asn Leu Ala His Tyr Phe Asn Asp Ser Glu Gln Leu Ser Leu
305                 310                 315                 320

Leu Ala Glu Ser Leu Ser Phe Gly Asn Leu Lys Cys Arg Val Leu Asp
                325                 330                 335

Leu Lys Asn Tyr Ala Glu Asp Met Tyr Asn Trp Arg His Ile Ala Ala
            340                 345                 350

Met Tyr Glu Ser Ile Tyr
            355

<210> SEQ ID NO 60
<211> LENGTH: 360
<212> TYPE: PRT
<213> ORGANISM: E. coli

<400> SEQUENCE: 60

Met Thr Glu Gln Phe Ser Glu Lys Lys Ile Asp Val Val Gly Ile Val
1               5                   10                  15

Gly Leu Pro Ala Cys Tyr Gly Phe Glu Ser Leu Val Gln Asn Leu
            20                  25                  30

Val Asp Tyr Gln Ser Gln Asn Ile Lys Tyr Asn Val Tyr Cys Ser Arg
            35                  40                  45

Lys Lys Tyr Lys Asn Thr Pro Lys Lys Tyr Lys Arg Ala Asp Leu Lys
    50                  55                  60

Tyr Ile Pro Phe Asp Ala Asn Gly Ser Ser Ile Leu Tyr Asp Ile
65                  70                  75                  80

Tyr Ser Leu Phe Leu Ser Leu Phe Asn Lys Val Asp Val Val Leu Ile
                85                  90                  95

Leu Gly Val Ser Gly Cys Val Phe Leu Pro Ile Tyr Arg Phe Phe Ser
            100                 105                 110

Ser Ser Lys Val Ile Val Asn Ile Asp Gly Leu Glu Trp Lys Arg Ala
        115                 120                 125

Lys Trp Lys Gly Ile Ala Lys Trp Tyr Leu Lys Ile Ser Glu Lys Ile
    130                 135                 140

Ala Val Lys Tyr Ser Asp Val Val Ala Asp Asn Glu Ala Ile Ala
145                 150                 155                 160

Lys Tyr Val Leu Lys Lys Tyr Gly Leu Glu Ala Lys Ile Ile Ala Tyr
                165                 170                 175

Gly Gly Asp His Ser Leu Val Lys Lys Pro Ile Ser Val Ile Lys Glu
            180                 185                 190

Asp Tyr Phe Phe Thr Val Cys Arg Ile Glu Pro Glu Asn Asn Ile Arg
        195                 200                 205

Met Ile Leu Glu Ala Phe Lys Asn Thr Thr His Ser Leu Lys Ile Val
    210                 215                 220

Gly Asn Trp Asp Ser Ser Leu Tyr Gly Arg Arg Leu Lys Glu Glu Phe
225                 230                 235                 240

Gly Asn Tyr Asn Asn Ile Glu Ile Ile Asp Pro Ile Tyr Asp Ser Asp
                245                 250                 255

Ile Leu Phe Asn Phe Arg Ser Leu Cys Arg Gly Tyr Ile His Gly His
            260                 265                 270
```

Ser Ala Gly Gly Thr Asn Pro Ser Leu Val Glu Ala Met His Phe Gln
            275                 280                 285

Ile Pro Ile Ile Ala Phe Asp Cys Asp Phe Asn Arg Phe Thr Thr Asp
290                 295                 300

Asn Tyr Ala Phe Tyr Phe Lys Asn Lys Asn Glu Leu Ser Phe Ile Val
305                 310                 315                 320

Asn Asp Ile Leu Asn Gly Asn Gln Asn Glu Gln Ala Glu Ile Cys Ala
                325                 330                 335

Lys Lys Met Lys Glu Ile Ala Thr Lys Lys Tyr Thr Trp Asp Thr Ile
            340                 345                 350

Ala Lys Met Tyr Glu Glu Leu Tyr
            355                 360

<210> SEQ ID NO 61
<211> LENGTH: 351
<212> TYPE: PRT
<213> ORGANISM: Cronobacter sakazakii

<400> SEQUENCE: 61

Met Lys Arg Ile Ala Val Val Gly Thr Val Gly Ile Pro Ala Cys Tyr
1               5                   10                  15

Gly Gly Phe Glu Ser Leu Val Glu Asn Leu Thr Lys Tyr Lys Gly Ala
            20                  25                  30

Gly Tyr Gln Tyr Tyr Ile Phe Cys Ser Ser Lys Asn Tyr Pro Glu Lys
        35                  40                  45

Ser Asp Ser His Asn Asp Ala Gln Leu Ile Tyr Val Pro Leu Lys Ala
    50                  55                  60

Asn Gly Ile Gln Ser Ile Leu Tyr Asp Ile Val Ser Leu Trp Lys Cys
65                  70                  75                  80

Leu Phe Leu Lys Val Asp Thr Ile Leu Ile Leu Gly Val Ser Gly Cys
                85                  90                  95

Ile Phe Leu Pro Val Phe Arg Leu Leu Ser Asn Ala Lys Ile Ile Thr
            100                 105                 110

Asn Ile Asp Gly Leu Glu Trp Lys Arg Glu Lys Trp Asn Tyr Pro Ile
        115                 120                 125

Lys Lys Phe Leu Lys Phe Ser Glu Leu Leu Ala Val Lys Tyr Ser His
130                 135                 140

Ala Ile Val Thr Asp Asn Arg Ala Ile Thr Asp Tyr Val Lys Lys Glu
145                 150                 155                 160

Tyr Asn Val Ser Ser Phe Thr Ile Ala Tyr Gly Gly Asp His Ala Val
                165                 170                 175

Arg Pro Ser Asn Asn Asn Asn Ile Lys Ser Ser Tyr Ala Leu Gly
            180                 185                 190

Leu Cys Arg Ile Glu Pro Glu Asn Asn Val Glu Leu Ile Leu Lys Ala
        195                 200                 205

Phe Thr Leu Ser Glu Asp Lys Leu Lys Phe Val Gly Asn Trp Asn Ala
    210                 215                 220

Ser Ser Tyr Gly Arg Met Leu Lys Lys Asn Tyr Ser Asn Tyr Ser Asn
225                 230                 235                 240

Ile Glu Leu Ile Glu Pro Ile Tyr Asp Ile Asp Lys Leu Tyr Ile Leu
                245                 250                 255

Arg Ser Gly Cys Asp Lys Tyr Ile His Gly His Ser Ala Gly Gly Thr
            260                 265                 270

Asn Pro Ser Leu Val Glu Met Met His Phe Gly Val Pro Ile Phe Ala
        275                 280                 285

```
Phe Asp Cys Glu Phe Asn Arg His Ser Thr Asp Asn Lys Ala Phe Tyr
        290                 295                 300

Phe Lys Asp Ala Gln His Leu Ala Asp Leu Val Lys Met Lys Asp Asn
305                 310                 315                 320

Thr Glu Leu Glu Lys Asn Ser Cys Asn Met Lys Val Leu Ala Gln Glu
                325                 330                 335

Asn Tyr Thr Trp Gln Lys Ile Thr Ala Ser Tyr Glu Ser Leu Tyr
                340                 345                 350

<210> SEQ ID NO 62
<211> LENGTH: 664
<212> TYPE: PRT
<213> ORGANISM: Campylobacter jejuni

<400> SEQUENCE: 62

Ile Ile Ser Asn Asp Gly Tyr Ala Phe Ala Glu Gly Ala Arg Asp Met
1               5                   10                  15

Ile Ala Gly Phe His Gln Pro Asn Asp Leu Ser Tyr Tyr Gly Ser Ser
                20                  25                  30

Leu Ser Thr Leu Thr Tyr Trp Leu Tyr Lys Ile Thr Pro Phe Ser Phe
            35                  40                  45

Glu Ser Ile Ile Leu Tyr Met Ser Thr Phe Leu Ser Ser Leu Val Val
    50                  55                  60

Ile Pro Ile Ile Leu Leu Ala Asn Glu Tyr Lys Arg Pro Leu Met Gly
65                  70                  75                  80

Phe Val Ala Ala Leu Leu Ala Ser Ile Ala Asn Ser Tyr Tyr Asn Arg
                85                  90                  95

Thr Met Ser Gly Tyr Tyr Asp Thr Asp Met Leu Val Ile Val Leu Pro
                100                 105                 110

Met Phe Ile Leu Phe Phe Met Val Arg Met Ile Leu Lys Lys Asp Phe
            115                 120                 125

Phe Ser Leu Ile Ala Leu Pro Leu Phe Ile Gly Ile Tyr Leu Trp Trp
130                 135                 140

Tyr Pro Ser Ser Tyr Thr Leu Asn Val Ala Leu Ile Gly Leu Phe Leu
145                 150                 155                 160

Ile Tyr Thr Leu Ile Phe His Arg Lys Glu Lys Ile Phe Tyr Ile Ala
                165                 170                 175

Val Ile Leu Ser Ser Leu Thr Leu Ser Asn Ile Ala Trp Phe Tyr Gln
                180                 185                 190

Ser Thr Ile Ile Val Ile Leu Phe Ala Leu Phe Ala Leu Glu Gln Lys
            195                 200                 205

Arg Leu Asn Phe Val Ile Ile Gly Ile Leu Ala Ser Val Thr Leu Ile
210                 215                 220

Phe Leu Ile Leu Ser Gly Gly Val Asp Pro Ile Leu Tyr Gln Leu Lys
225                 230                 235                 240

Phe Tyr Ile Phe Arg Ser Asp Glu Ser Ala Asn Leu Thr Gln Gly Phe
                245                 250                 255

Met Tyr Phe Asn Val Asn Gln Thr Ile Gln Glu Val Glu Asn Val Asp
                260                 265                 270

Leu Ser Glu Phe Met Arg Arg Ile Ser Gly Ser Glu Ile Val Phe Leu
            275                 280                 285

Phe Ser Leu Phe Gly Phe Val Trp Leu Leu Arg Lys His Lys Ser Met
290                 295                 300

Ile Met Ala Leu Pro Ile Leu Val Leu Gly Phe Leu Ala Leu Lys Gly
305                 310                 315                 320
```

Gly Leu Arg Phe Thr Ile Tyr Ser Val Pro Val Met Ala Leu Gly Phe
                    325                 330                 335

Gly Phe Leu Leu Ser Glu Phe Lys Ala Ile Leu Val Lys Lys Tyr Ser
                340                 345                 350

Gln Leu Thr Ser Asn Val Cys Ile Val Phe Ala Thr Ile Leu Thr Leu
            355                 360                 365

Ala Pro Val Phe Ile His Ile Tyr Asn Tyr Lys Ala Pro Thr Val Phe
370                 375                 380

Ser Gln Asn Glu Ala Ser Leu Leu Asn Gln Leu Lys Asn Ile Ala Asn
385                 390                 395                 400

Arg Glu Asp Tyr Val Val Thr Trp Trp Asp Tyr Gly Tyr Pro Val Arg
                405                 410                 415

Tyr Tyr Ser Asp Val Lys Thr Leu Val Asp Gly Lys His Leu Gly
                420                 425                 430

Lys Asp Asn Phe Phe Pro Ser Phe Ala Leu Ser Lys Asp Glu Gln Ala
                435                 440                 445

Ala Ala Asn Met Ala Arg Leu Ser Val Glu Tyr Thr Glu Lys Ser Phe
        450                 455                 460

Tyr Ala Pro Gln Asn Asp Ile Leu Lys Thr Asp Ile Leu Gln Ala Met
465                 470                 475                 480

Met Lys Asp Tyr Asn Gln Ser Asn Val Asp Leu Phe Leu Ala Ser Leu
                485                 490                 495

Ser Lys Pro Asp Phe Lys Ile Asp Thr Pro Lys Thr Arg Asp Ile Tyr
                500                 505                 510

Leu Tyr Met Pro Ala Arg Met Ser Leu Ile Phe Ser Thr Val Ala Ser
            515                 520                 525

Phe Ser Phe Ile Asn Leu Asp Thr Gly Val Leu Asp Lys Pro Phe Thr
530                 535                 540

Phe Ser Thr Ala Tyr Pro Leu Asp Val Lys Asn Gly Glu Ile Tyr Leu
545                 550                 555                 560

Ser Asn Gly Val Val Leu Ser Asp Asp Phe Arg Ser Phe Lys Ile Gly
                565                 570                 575

Asp Asn Val Val Ser Val Asn Ser Ile Val Glu Ile Asn Ser Ile Lys
                580                 585                 590

Gln Gly Glu Tyr Lys Ile Thr Pro Ile Asp Asp Lys Ala Gln Phe Tyr
            595                 600                 605

Ile Phe Tyr Leu Lys Asp Ser Ala Ile Pro Tyr Ala Gln Phe Ile Leu
            610                 615                 620

Met Asp Lys Thr Met Phe Asn Ser Ala Tyr Val Gln Met Phe Leu
625                 630                 635                 640

Gly Asn Tyr Asp Lys Asn Leu Phe Asp Leu Val Ile Asn Ser Arg Asp
                645                 650                 655

Ala Lys Val Phe Lys Leu Lys Ile
            660

<210> SEQ ID NO 63
<211> LENGTH: 257
<212> TYPE: PRT
<213> ORGANISM: E. coli

<400> SEQUENCE: 63

Met Met Val Phe Gly Lys Leu Tyr Leu Ser Ser Leu Gly Tyr Ile Phe
1               5                   10                  15

Gly Ser Trp Glu Met Val Leu Gly Pro Phe Gly Tyr Phe Leu Thr Leu
                20                  25                  30

```
Phe Ala Val Trp Ala Ala Ile Asn Ala Phe Asn Met Val Asp Gly Ile
         35                  40                  45

Asp Gly Leu Leu Gly Gly Leu Ser Cys Val Ser Phe Ala Ala Ile Gly
 50                  55                  60

Met Ile Leu Trp Phe Asp Gly Gln Thr Ser Leu Ala Ile Trp Cys Phe
 65                  70                  75                  80

Ala Met Ile Ala Ala Ile Leu Pro Tyr Ile Met Leu Asn Leu Gly Ile
                 85                  90                  95

Leu Gly Arg Arg Tyr Lys Val Phe Met Gly Asp Ala Gly Ser Thr Leu
            100                 105                 110

Ile Gly Phe Thr Val Ile Trp Ile Leu Glu Thr Thr Gln Gly Lys
            115                 120                 125

Thr His Pro Ile Ser Pro Val Thr Ala Leu Trp Ile Ile Ala Ile Pro
        130                 135                 140

Leu Met Asp Met Val Ala Ile Met Tyr Arg Arg Leu Arg Lys Gly Met
145                 150                 155                 160

Ser Pro Phe Ser Pro Asp Arg Gln His Ile His His Leu Ile Met Arg
                165                 170                 175

Ala Gly Phe Thr Ser Arg Gln Ala Phe Val Leu Ile Thr Leu Ala Ala
            180                 185                 190

Ala Leu Leu Ala Ser Ile Gly Val Leu Ala Glu Tyr Ser His Phe Val
        195                 200                 205

Pro Glu Trp Val Met Leu Val Leu Phe Leu Leu Ala Phe Phe Leu Tyr
    210                 215                 220

Gly Tyr Cys Ile Lys Arg Ala Trp Lys Val Ala Arg Phe Ile Lys Arg
225                 230                 235                 240

Val Lys Arg Arg Leu Arg Arg Asn Arg Gly Gly Ser Pro Asn Leu Thr
                245                 250                 255

Lys

<210> SEQ ID NO 64
<211> LENGTH: 207
<212> TYPE: PRT
<213> ORGANISM: E. coli

<400> SEQUENCE: 64

Met Ser Thr Ile Ile Met Asp Leu Cys Ser Tyr Thr Arg Leu Gly Leu
1               5                   10                  15

Thr Gly Tyr Leu Leu Ser Arg Gly Val Lys Lys Arg Glu Ile Asn Asp
                20                  25                  30

Ile Glu Thr Val Asp Asp Leu Ala Ile Ala Cys Asp Ser Gln Arg Pro
            35                  40                  45

Ser Val Val Phe Ile Asn Glu Asp Cys Phe Ile His Asp Ala Ser Asn
        50                  55                  60

Ser Gln Arg Ile Lys Leu Ile Ile Asn Gln His Pro Asn Thr Leu Phe
65                  70                  75                  80

Ile Val Phe Met Ala Ile Ala Asn Val His Phe Asp Glu Tyr Leu Leu
                85                  90                  95

Val Arg Lys Asn Leu Leu Ile Ser Ser Lys Ser Ile Lys Pro Glu Ser
            100                 105                 110

Leu Asp Asp Ile Leu Gly Asp Ile Leu Lys Lys Glu Thr Thr Ile Thr
        115                 120                 125

Ser Phe Leu Asn Met Pro Thr Leu Ser Leu Ser Arg Thr Glu Ser Ser
        130                 135                 140
```

```
Met Leu Arg Met Trp Met Ala Gly Gln Gly Thr Ile Gln Ile Ser Asp
145                 150                 155                 160

Gln Met Asn Ile Lys Ala Lys Thr Val Ser Ser His Lys Gly Asn Ile
                165                 170                 175

Lys Arg Lys Ile Lys Thr His Asn Lys Gln Val Ile Tyr His Val Val
            180                 185                 190

Arg Leu Thr Asp Asn Val Thr Asn Gly Ile Phe Val Asn Met Arg
        195                 200                 205
```

<210> SEQ ID NO 65
<211> LENGTH: 713
<212> TYPE: PRT
<213> ORGANISM: Campylobacter jejuni

<400> SEQUENCE: 65

```
Met Leu Lys Lys Glu Tyr Leu Lys Asn Pro Tyr Leu Val Leu Phe Ala
1               5                   10                  15

Met Ile Ile Leu Ala Tyr Val Phe Ser Val Phe Cys Arg Phe Tyr Trp
            20                  25                  30

Val Trp Trp Ala Ser Glu Phe Asn Glu Tyr Phe Phe Asn Asn Gln Leu
        35                  40                  45

Met Ile Ile Ser Asn Asp Gly Tyr Ala Phe Ala Glu Gly Ala Arg Asp
50                  55                  60

Met Ile Ala Gly Phe His Gln Pro Asn Asp Leu Ser Tyr Tyr Gly Ser
65                  70                  75                  80

Ser Leu Ser Ala Leu Thr Tyr Trp Leu Tyr Lys Ile Thr Pro Phe Ser
                85                  90                  95

Phe Glu Ser Ile Ile Leu Tyr Met Ser Thr Phe Leu Ser Ser Leu Val
            100                 105                 110

Val Ile Pro Thr Ile Leu Leu Ala Asn Glu Tyr Lys Arg Pro Leu Met
        115                 120                 125

Gly Phe Ala Ala Ala Leu Leu Ala Ser Ile Ala Asn Ser Tyr Tyr Asn
130                 135                 140

Arg Thr Met Ser Gly Tyr Tyr Asp Thr Asp Met Leu Val Ile Val Leu
145                 150                 155                 160

Pro Met Phe Ile Leu Phe Phe Met Val Arg Met Ile Leu Lys Lys Asp
                165                 170                 175

Phe Phe Ser Leu Ile Ala Leu Pro Leu Phe Ile Gly Ile Tyr Leu Trp
            180                 185                 190

Trp Tyr Pro Ser Ser Tyr Thr Leu Asn Val Ala Leu Ile Gly Leu Phe
        195                 200                 205

Leu Ile Tyr Thr Leu Ile Phe His Arg Lys Glu Lys Ile Phe Tyr Ile
210                 215                 220

Ala Val Ile Leu Ser Ser Leu Thr Leu Ser Asn Ile Ala Trp Phe Tyr
225                 230                 235                 240

Gln Ser Ala Ile Ile Val Ile Leu Phe Ala Leu Phe Ala Leu Glu Gln
                245                 250                 255

Lys Arg Leu Asn Phe Met Ile Ile Gly Ile Leu Gly Ser Ala Thr Leu
            260                 265                 270

Ile Phe Leu Ile Leu Ser Gly Gly Val Asp Pro Ile Leu Tyr Gln Leu
        275                 280                 285

Lys Phe Tyr Ile Phe Arg Ser Asp Glu Ser Ala Asn Leu Thr Gln Gly
290                 295                 300

Phe Met Tyr Phe Asn Val Asn Gln Thr Ile Gln Glu Val Glu Asn Val
305                 310                 315                 320
```

```
Asp Leu Ser Glu Phe Met Arg Arg Ile Ser Gly Ser Glu Ile Val Phe
                325                 330                 335

Leu Phe Ser Leu Phe Gly Phe Val Trp Leu Leu Arg Lys His Lys Ser
            340                 345                 350

Met Ile Met Ala Leu Pro Ile Leu Val Leu Gly Phe Leu Ala Leu Lys
            355                 360                 365

Gly Gly Leu Arg Phe Thr Ile Tyr Ser Val Pro Val Met Ala Leu Gly
        370                 375                 380

Phe Gly Phe Leu Leu Ser Glu Phe Lys Ala Ile Met Val Lys Lys Tyr
385                 390                 395                 400

Ser Gln Leu Thr Ser Asn Val Cys Ile Val Phe Ala Thr Ile Leu Thr
                405                 410                 415

Leu Ala Pro Val Phe Ile His Ile Tyr Asn Tyr Lys Ala Pro Thr Val
            420                 425                 430

Phe Ser Gln Asn Glu Ala Ser Leu Leu Asn Gln Leu Lys Asn Ile Ala
            435                 440                 445

Asn Arg Glu Asp Tyr Val Val Thr Trp Trp Asp Tyr Gly Tyr Pro Val
450                 455                 460

Arg Tyr Tyr Ser Asp Val Lys Thr Leu Val Asp Gly Gly Lys His Leu
465                 470                 475                 480

Gly Lys Asp Asn Phe Phe Pro Ser Phe Ala Leu Ser Lys Asp Glu Gln
                485                 490                 495

Ala Ala Ala Asn Met Ala Arg Leu Ser Val Glu Tyr Thr Glu Lys Ser
            500                 505                 510

Phe Tyr Ala Pro Gln Asn Asp Ile Leu Lys Thr Asp Ile Leu Gln Ala
            515                 520                 525

Met Met Lys Asp Tyr Asn Gln Ser Asn Val Asp Leu Phe Leu Ala Ser
        530                 535                 540

Leu Ser Lys Pro Asp Phe Lys Ile Asp Thr Pro Lys Thr Arg Asp Ile
545                 550                 555                 560

Tyr Leu Tyr Met Pro Ala Arg Met Ser Leu Ile Phe Ser Thr Val Ala
                565                 570                 575

Ser Phe Ser Phe Ile Asn Leu Asp Thr Gly Val Leu Asp Lys Pro Phe
            580                 585                 590

Thr Phe Ser Thr Ala Tyr Pro Leu Asp Val Lys Asn Gly Glu Ile Tyr
            595                 600                 605

Leu Ser Asn Gly Val Val Leu Ser Asp Asp Phe Arg Ser Phe Lys Ile
        610                 615                 620

Gly Asp Asn Val Val Ser Val Asn Ser Ile Val Glu Ile Asn Ser Ile
625                 630                 635                 640

Lys Gln Gly Glu Tyr Lys Ile Thr Pro Ile Asp Asp Lys Ala Gln Phe
                645                 650                 655

Tyr Ile Phe Tyr Leu Lys Asp Ser Ala Ile Pro Tyr Ala Gln Phe Ile
            660                 665                 670

Leu Met Asp Lys Thr Met Phe Asn Ser Ala Tyr Val Gln Met Phe Phe
            675                 680                 685

Leu Gly Asn Tyr Asp Lys Asn Leu Phe Asp Leu Val Ile Asn Ser Arg
        690                 695                 700

Asp Ala Lys Val Phe Lys Leu Lys Ile
705                 710
```

<210> SEQ ID NO 66
<211> LENGTH: 378
<212> TYPE: PRT
<213> ORGANISM: Salmonella typhimurium

<400> SEQUENCE: 66

```
Met Pro Ser Leu Asn Val Lys Gln Glu Lys Asn Gln Ser Phe Ala Gly
1               5                   10                  15

Tyr Ser Leu Pro Pro Ala Asn Ser His Glu Ile Asp Leu Phe Ser Leu
            20                  25                  30

Ile Glu Val Leu Trp Gln Ala Lys Arg Arg Ile Leu Ala Thr Val Phe
        35                  40                  45

Ala Phe Ala Cys Val Gly Leu Leu Ser Phe Leu Leu Pro Gln Lys
    50                  55                  60

Trp Thr Ser Gln Ala Ile Val Thr Pro Ala Glu Ser Val Gln Trp Gln
65                  70                  75                  80

Gly Leu Glu Arg Thr Leu Thr Ala Leu Arg Val Leu Asp Met Glu Val
                85                  90                  95

Ser Val Asp Arg Gly Ser Val Phe Asn Leu Phe Ile Lys Lys Phe Ser
            100                 105                 110

Ser Pro Ser Leu Glu Glu Tyr Leu Arg Ser Pro Tyr Val Met
        115                 120                 125

Asp Gln Leu Lys Gly Ala Gln Ile Asp Glu Gln Asp Leu His Arg Ala
130                 135                 140

Ile Val Leu Leu Ser Glu Lys Met Lys Ala Val Asp Ser Asn Val Gly
145                 150                 155                 160

Lys Lys Asn Glu Thr Ser Leu Phe Thr Ser Trp Thr Leu Ser Phe Thr
                165                 170                 175

Ala Pro Thr Arg Glu Glu Ala Gln Lys Val Leu Ala Gly Tyr Ile Gln
            180                 185                 190

Tyr Ile Ser Asp Ile Val Val Lys Glu Thr Leu Glu Asn Ile Arg Asn
        195                 200                 205

Gln Leu Glu Ile Lys Thr Arg Tyr Glu Gln Glu Lys Leu Ala Met Asp
    210                 215                 220

Arg Val Arg Leu Lys Asn Gln Leu Asp Ala Asn Ile Gln Arg Leu His
225                 230                 235                 240

Tyr Ser Leu Glu Ile Ala Asn Ala Ala Gly Ile Lys Arg Pro Val Tyr
                245                 250                 255

Ser Asn Gly Gln Ala Val Lys Asp Asp Pro Asp Phe Ser Ile Ser Leu
            260                 265                 270

Gly Ala Asp Gly Ile Ser Arg Lys Leu Glu Ile Glu Lys Gly Val Thr
        275                 280                 285

Asp Val Ala Glu Ile Asp Gly Asp Leu Arg Asn Arg Gln Tyr His Val
    290                 295                 300

Glu Gln Leu Ala Ala Met Asn Val Ser Asp Val Lys Phe Thr Pro Phe
305                 310                 315                 320

Lys Tyr Gln Leu Ser Pro Ser Leu Pro Val Lys Lys Asp Gly Pro Gly
                325                 330                 335

Lys Ala Ile Ile Ile Ile Leu Ala Ala Leu Ile Gly Gly Met Met Ala
            340                 345                 350

Cys Gly Gly Val Leu Leu Arg His Ala Met Val Ser Arg Lys Met Glu
        355                 360                 365

Asn Ala Leu Ala Ile Asp Glu Arg Leu Val
    370                 375
```